US007553491B2

(12) United States Patent
Litman et al.

(10) Patent No.: US 7,553,491 B2

(45) Date of Patent: Jun. 30, 2009

(54) BIVM (BASIC, IMMUNOGLOBULIN-LIKE VARIABLE MOTIF-CONTAINING) GENE, TRANSCRIPTIONAL PRODUCTS, AND USES THEREOF

(75) Inventors: Gary W. Litman, Gulfport, FL (US); Noel A. Hawke, Durham, NC (US); Jeffrey A. Yoder, St. Petersburg, FL (US); Donna D. Eason, Bradenton, FL (US)

(73) Assignee: University of South Florida, Tampa, FL (US)

( * ) Notice: Subject to any disclaimer, the term of this patent is extended or adjusted under 35 U.S.C. 154(b) by 114 days.

(21) Appl. No.: 11/415,536

(22) Filed: May 2, 2006

(65) Prior Publication Data

US 2006/0205689 A1 Sep. 14, 2006

Related U.S. Application Data

(62) Division of application No. 10/417,476, filed on Apr. 16, 2003, now Pat. No. 7,038,030.

(60) Provisional application No. 60/373,146, filed on Apr. 16, 2002.

(51) Int. Cl.
*A61K 39/002* (2006.01)

(52) U.S. Cl. ............... 424/191.1; 424/265.1; 435/320.1

(58) Field of Classification Search ....................... None
See application file for complete search history.

(56) References Cited

U.S. PATENT DOCUMENTS 5,645,995 A 7/1997 Kieback 6,639,063 B1 10/2003 Edwards et al.

OTHER PUBLICATIONS

Hawke, N.A. et al. "Expanding our Understanding of Immunoglobulin, T-cell Antigen Receptor, and Novel Immune-Type Receptor Genes: a Subset of the Immunoglobulin Gene Superfamily" *Immunogenetics*, 1999, 50:124-133.

Abbaszadega, M. "Advanced Detection of Viruses and Protozoan Parasites in Water" *Rev. Biol. Biotech.*, 2001, 1(2):21-26.

McArthur, A.G. "The *Giardia* Genome Project Database" *FEMS Microbiol. Lett.*, 2000, 189:271-273.

Christian, S.L. et al. "An Evaluation of the Assembly of an Approximately 15-Mb Region on Human Chromosome 13q32-q33 Linked to Bipolar Disorder and Schizophrenia" *Genomics*, May 2002, pp. 635-658, vol. 79, No. 5.

*Primary Examiner*—Stacy B Chen

(74) *Attorney, Agent, or Firm*—Saliwanchik, Lloyd & Saliwanchik

(57) ABSTRACT

The subject invention provides polynucleotide sequences, designated BIVM, and transcriptional/translational products obtained from the polynucleotide sequences of the invention. The subject invention also provides polynucleotide and polypeptide sequences provided by SEQ ID NOs:1-28. Also provided are methods of detecting the presence of BIVM nucleic acids or polypeptides in samples suspected of containing BIVM genes, BIVM transcriptional products, or BIVM translational products. These methods are also useful for the detection of BIVM orthologs. Other embodiments provide polypeptide and/or nucleic acid vaccines for the induction of an immune response to in an individual. Kits for detecting the presence of BIVM genes, orthologs thereof, BIVM polypeptides, or BIVM transcriptional products are also provided.

Figure 3B:
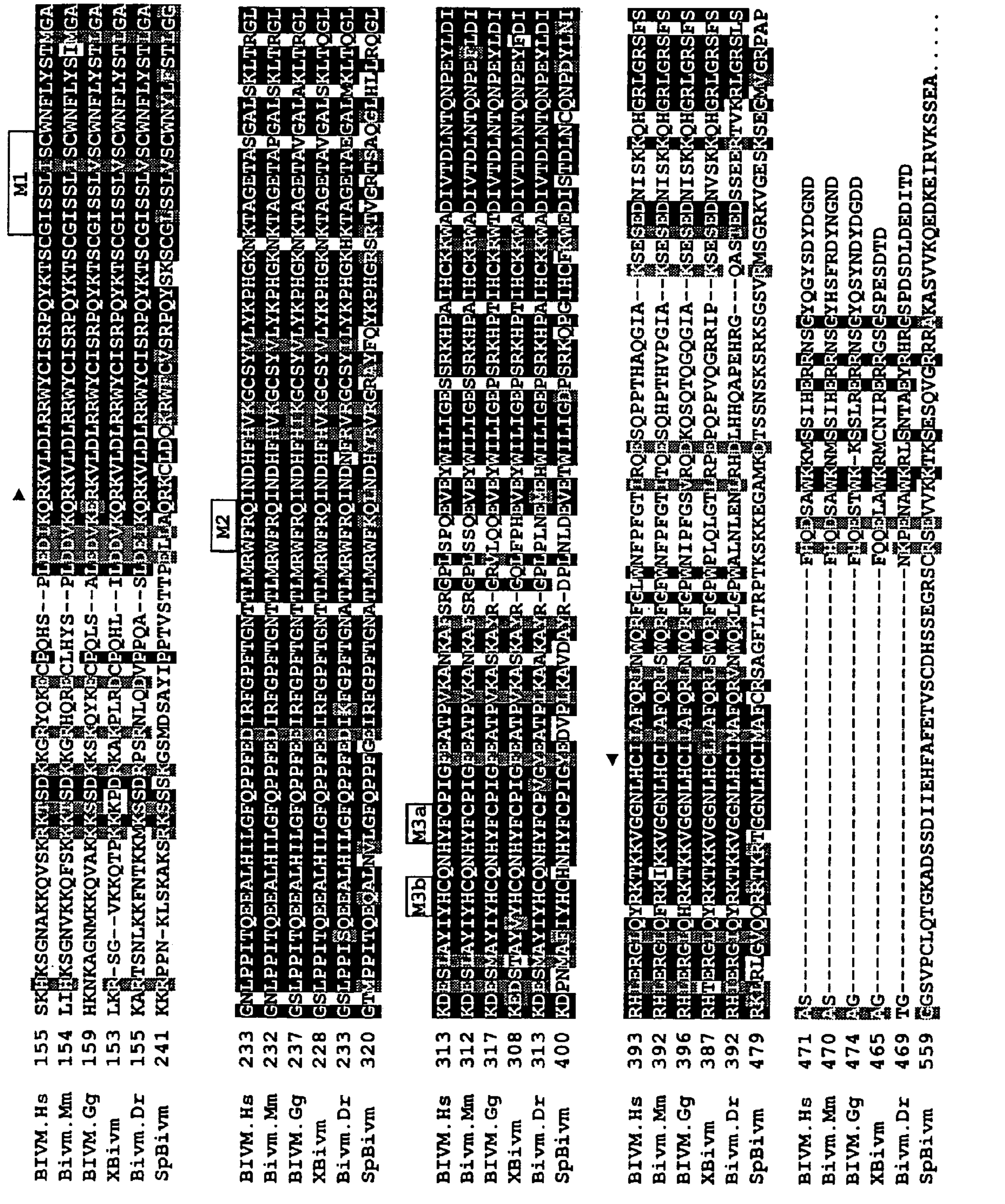

9 Claims, 15 Drawing Sheets
(2 of 15 Drawing Sheet(s) Filed in Color)

FIG. 1A

```
    AGTAACGCCTTCTCCAAGTGGATGGCGGGGTGGACACGCGTCCCGGCGCCCCGGGCTCCC   60
    TGGGATATGTAGTTCGCGACAGGACGAGCGGAAATACTGCCAGGATTTTACCACCTCTCG  120
    CCCATTTTATTTACTTCTCGGTCACCGCTTTCGGGGACAGATAAACACCACAGATGCCCA  180
    TCAAAGGGGCGCACGGGTCTGGAGGCGCAGCTCAGGTTTTTGCGTTGGTCACCCTGCCCT  240
    CCGCACGTGGAGAGGGCAGGCATAAAGCACCTTGAAAGGAAGGTGCTGTCAATGCTATCC  300
    GACGACCTGTCGCCGGGCACCGCAGCATCCTCGCTCGCTCCGATGGGACGAGGGACGCCG  360
    GCCCCAGGGTAACAGGAGGCGCCTCGCCGGCCGCGCGCTGGATGCTGTGATCCAGGTCCG  420
    GAGCCGGGTTCCGCCGCGGCCGCAGCGACCCGACCCCACCCGACAGGCCAGAGGAATCAG  480
    TTTAGACTTGAAATTCAGTTTTTCCTGAAACTGATCAGAAGTTAGTGACACCTTGATTGG  540
    ATCCGTTTTTCTGTCAGGAGCTCATTTTGCAGCTCTCAAGCTTTTATAGCATGCTGTAAA  600
    CAATTGTCAAAGTTGTTTATCAAGAAACAGATAGAGTTGCAACTTGTTTCTAGTAATAGA  660
    AACTTTTACACTGCATTCAATGCCTAACGTTGCAGAAACAGAAAGGTCAAATGATTCTGG  720
1                          M  P  N  V  A  E  T  E  R  S  N  D  S  G
    AAATGGTGAGCACAAATCTGAGAGAAAGTCACCTGAAGAGAATCTACAAGGTGCTGTAAA  780
15   N  G  E  H  K  S  E  R  K  S  P  E  E  N  L  Q  G  A  V  K
    ATCTTTCTGCACAAGTGCCTCAGGAGCACCCTTGGGTCCCAAAGGAGATGGTCATTATCC  840
35   S  F  C  T  S  A  S  G  A  P  L  G  P  K  G  D  G  H  Y  P
    ATGGAGTTGTCCAGTGACTCATACACGGGAAAAAATTTATGCCATCTGTTCGGACTATGC  900
55   W  S  C  P  V  T  H  T  R  E  K  I  Y  A  I  C  S  D  Y  A
    CTTTCTCAACCAGGCGACCTCAATCTATAAAACTCCAAATCCATCCCGCTCTCCTTGCCT  960
75   F  L  N  Q  A  T  S  I  Y  K  T  P  N  P  S  R  S  P  C  L
    CCCTGATAGTACCTCTTTATCTGCTGGAAATAATTCATCAAGATACATTGGTATCCCGAC  1020
95   P  D  S  T  S  L  S  A  G  N  N  S  S  R  Y  I  G  I  P  T
    TAGTACATCGGAAATTATCTACAATGAAGAAAATAGCTTGGAAAACTTATCCAACAGCCT  1080
115  S  T  S  E  I  I  Y  N  E  E  N  S  L  E  N  L  S  N  S  L
    GGGCAAGCTACCTCTCGCATGGGAAATTGATAAATCTGAATTTGATGGGGTGACCACAAA  1140
135  G  K  L  P  L  A  W  E  I  D  K  S  E  F  D  G  V  T  T  N
    TTCGAAACACAAATCAGGCAATGCAAAGAAACAAGTTTCCAAGAGAAAAACTTCAGATAA  1200
155  S  K  H  K  S  G  N  A  K  K  Q  V  S  K  R  K  T  S  D  K
    AAAGGGAAGATATCAGAAGGAATGTCCTCAGCATTCTCCTCTTGAAGATATTAAACAGCG  1260
175  K  G  R  Y  Q  K  E  C  P  Q  H  S  P  L  E  D  I  K  Q  R
    GAAAGTATTAGACCTCAGACGATGGTACTGCATAAGCCGACCACAGTATAAGACTTCTTG  1320
195  K  V  L  D  L  R  R  W  Y  C  I  S  R  P  Q  Y  K  T  S  C
    TGGCATCTCTTCATTAATTTCTTGTTGGAATTTCTTATACAGCACAATGGGAGCTGGAAA  1380
215  G  I  S  S  L  I  S  C  W  N  F  L  Y  S  T  M  G  A  G  N
    CCTTCCACCTATTACCCAAGAAGAAGCTTTACATATTCTGGGCTTTCAACCTCCATTTGA  1440
235  L  P  P  I  T  Q  E  E  A  L  H  I  L  G  F  Q  P  P  F  E
    AGATATTAGGTTTGGTCCTTTCACGGGGAATACAACACTTATGAGGTGGTTTAGACAAAT  1500
255  D  I  R  F  G  P  F  T  G  N  T  T  L  M  R  W  F  R  Q  I
    TAATGACCACTTCCATGTAAAAGGATGCTCTTATGTTCTATATAAGCCTCATGGGAAGAA  1560
275  N  D  H  F  H  V  K  G  C  S  Y  V  L  Y  K  P  H  G  K  N
    TAAAACAGCAGGAGAAACTGCTTCAGGGGCCCTGTCAAAGTTAACCCGTGGATTGAAAGA  1620
295  K  T  A  G  E  T  A  S  G  A  L  S  K  L  T  R  G  L  K  D
    TGAATCGCTGGCTTATATCTATCATTGCCAAAATCATTATTTTTGTCCAATTGGCTTCGA  1680
315  E  S  L  A  Y  I  Y  H  C  Q  N  H  Y  F  C  P  I  G  F  E
    AGCAACCCCTGTTAAAGCTAATAAAGCATTCAGCAGGGGACCTCTCTCACCACAGGAAGT  1740
335  A  T  P  V  K  A  N  K  A  F  S  R  G  P  L  S  P  Q  E  V
    TGAATATTGGATCTTAATTGGAGAATCAAGTAGAAAACATCCTGCCATTCACTGTAAAAA  1800
```

FIG. 1B

335 A T P V K A N K A F S R G P L S P Q E V
TGAATATTGGATCTTAATTGGAGAATCAAGTAGAAAACATCCTGCCATTCACTGTAAAAA 1800
355 E Y W I L I G E S S R K H P A I H C K K
ATGGGCAGATATTGTTACTGATCTAAACACTCAAAATCCAGAATACCTGGATATCCGGCA 1860
375 W A D I V T D L N T Q N P E Y L D I R H
CTTAGAGAGGGGACTGCAGTATAGAAAAACAAAGAAGGTTGGGGGAAATTTGCATTGCAT 1920
395 L E R G L Q Y R K T K K V G G N L H C I
CATAGCATTCCAGAGACTTAACTGGCAAAGATTTGGCCTTTGGAACTTTCCATTTGGAAC 1980
415 I A F Q R L N W Q R F G L W N F P F G T
CATTAGACAAGAATCACAACCTCCAACACATGCCCAGGGAATTGCCAAATCTGAGAGTGA 2040
435 I R Q E S Q P P T H A Q G I A K S E S E
AGACAATATTTCCAAGAAGCAGCATGGGCGTCTGGGCCGGTCTTTCAGTGCTAGTTTCCA 2100
455 D N I S K K Q H G R L G R S F S A S F H
TCAGGACTCGGCATGGAAAAAGATGTCTAGTATCCATGAGAGAAGGAACAGTGGTTACCA 2160
475 Q D S A W K K M S S I H E R R N S G Y Q
GGGTTACAGTGATTACGATGGGAATGATTGACTATGCTTGCTACTGAACAGCTGGCATTA 2220
495 G Y S D Y D G N D
TATATGAAACTGCTATATACAGGACTGTATAAAGACAGTAGAAGATTTTAGTAAGCCTAC 2280
ATTAAATAGGAGCAGATCTTGTGGTATAAAAAATAACCTTGTAGTTCTCCAGATACTAAG 2340
CTTGTATATGATTATGGTGGGTGATTTCAGATATATAAGCAGATAAGCACAGATTATTGT 2400
CCTTTCAAGTTAAGAGTATATAATCTGGACAGAAAATTTCACAAAATTCAATAAAATTAC 2460
AACTGTTGTCTAAATAAGTGAAACACAAATTCACTTAATAGCATCAAGATTTGAAATACT 2520
TAAGCATGAAGTGACTTTTATAATGACTCGATCCCTAGACATTTGTTACAGATAGTTTTA 2580
TGCCTAAGACCAAGATGTAAAGTACCATCTGCCCTTAAAAAAAATTGGGGCTGTCAATTT 2640
CTAGTTTTCACTCATGGTTAACACGCATTTAAAATTATTTCATGAGTCTAGTAGTTCTTT 2700
GATTTATAGCAGGATCTTGCTTGCCTCATTTGTTTCCTGGTTATGTTCTTAGGATTCTGA 2760
CTAAGAGGCAAAAGAGAAAAGACTCAAGAAACTGATCCTGgagatcgagaccatcctggc 2820
taacatggtgaaaccccgtctctactaaacatacaaaaaattagccgggtgtagtggtgg 2880
gcacctgtagtcctagctactcgagaggctgaggcaggagaatggcgtgaacccgggagg 2940
tggagcttgcagtgagcggagatcgcgccactgcactccagcctgggcgacagggcaaga 3000
ctctgtctcAAAAAAAAAAAAAAAAAAAAGACGGATCCTTTTTTTTTGGTGCAAATGGGT 3060
GACTTAGTGCATTGATTCAGATTTTTAAAATTTCTTGATGTGGTTTGTAATAATCAAATA 3120
TTGACAAGAACCTTAGGTCTCGAAAGACTTTTATAAGTCTAGATGACGTTTGCCTTAGGG 3180
GTAAAGTAAAAGAACAATTGGCACCTTAAGTTTCTATACCCAAGGTTATCTGTGAAATGA 3240
GATCTCCTGATATTTGATTGCTTTCTCAGTATGGAGTCATATGTTGATAACAGTACTGAA 3300
GATGCATAAGAAATGCCCAAGTCACTCAGAGGACAACTACCCATATTCCAGACTCTGAGC 3360
TGTTTCCTTTTTAAAAATCATATAGACAATTAGCTGTTTGAAGTGAGTATTAAATATTTC 3420
AGAAGTGTGAATTTCATGTATTTGAGCTCCTCTAGTTGCTGTTGGTTTTTCTTCTGCTGC 3480
CAACCTGTGACTCACAAATGACTAGGATCTCTTGTTCTTTAATTTTAGGGTCTTGTTCCA 3540
GGACTCAAATCAGTAACTTGGTGATTACAAGGTGCTGAATGTGTTGGTAACCATATCGCA 3600
ATACACCTCAAGGAAAAGGTTCAGATTTTTATTTTTAAAATATTTTCATTTTTTTCTTGA 3660
ATTTTATATCCGTTTGTTCACTCGTACATGCCTAGCCTACAGAAGGGGATATATATTATG 3720
AAATGGTCATTTTTCTGAAGAGAATATTTTGCTTGAAATGCAAAGGACTGAAAGAGATTT 3780
GTAGGTTGTTGATTTTGTTACTTCATACTGGAACTTTTAAAAAGATTTCATCAAATAAAG 3840
TTTTGTTTTCTACTTTT 3857

FIG. 1C

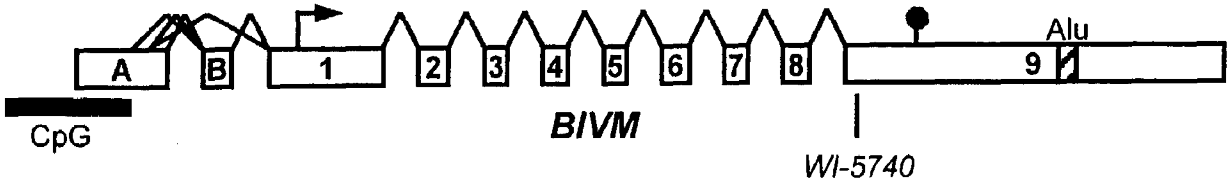

FIG. 2

```
BIVM.Hs    1 ---MPNVAETERSNDSGNGEHKSERKSPEEN-------------------------------------------------
Bivm.Mm    1 ---MPNATEAGKATDPGHGEHTSENKSPEEG-------------------------------------------------
BIVM.Gg    1 ---MPHISEDEKENGSGNNGNTEKKPGKESSEA-----------------------------------------------
XBivm      1 ---MPNIEADRVTSVPENNDCKSKSQPLRNN-------------------------------------------------
Bivm.Dr    1 ---MPNTVESEGAKVSASTDQEAPSRAPGRED------------------------------------------------
SpBivm     1 MGNWPSVLSGEGSEDSSSESNNESNNQETSDQENTRHHLCGSEESYFSEEELLPIVYPDDDDDAAARDDVLGDFLSVKED

BIVM.Hs   29 -------LQGAVKSFCTSASGAPLGPKGDGHYPWSCPVTHTREKIYAICSDYAFLNQATSIYKTPNPSRSPCLPDSTSLS
Bivm.Mm   29 -------LQGAVPSFYTSASEAPIAPRGDGHYPSSCPVTHTREKIYAICSDYAFLNQATSVYKTPSLTRSACLPDNTSLS
BIVM.Gg   31 -----SLRDPIKSYCISDASTVSLVSRGDGHYPWGCPVTHTREKFYTICSDYAFLNRVTSICKSPSASVNACLSGSAALN
XBivm     29 ------LHETVKSYSIQGAATANIEPPAERPYPWGCPVTHTKEKFYTICADYAFLNQATSLCKSSS---SVCSSSSEDKS
Bivm.Dr   30 -----ERERSFLSPMMRDALRVRRASSAELQLPWTCPVTHSREKFYTVCSDYALLNRARPVITSEDAS--QTNPDSGTSL
SpBivm    81 GEFTTDEVDGSRYDLAPEYYPTSLHEDVTARESDLASPVDRKESSYSSTDDYDDNDSDDEEEEEDDHYYQRRRNDKYSLM

BIVM.Hs  102 AGNNSSRYIGIPTSTSEIIYNEENSLENLSNSLC---------------------------KLPLAWEIDKSEEDGVTTN
Bivm.Mm  102 AG-NTTRYIGISTSTSEIIYNEENNLENLSTGMG---------------------------KLPLAWEIDKSEEDGVTTN
BIVM.Gg  106 VGNNTPSLLGIQTGASEIIYSEDANLETLSGSLC---------------------------KLPLAWEIDKSEENSVTAN
XBivm    100 ALSNTINYIDLQTSESDSVYNEDASLESLSSNLC---------------------------TRPLAWEIDKSDESTMTSK
Bivm.Dr  103 AKSNTATSSQSHSGGISVSLDGNCDMEVVSSSN----------------------------KPVLAWEIDTSDEDAVLTR
SpBivm   161 KEDDDDNELSSIPLPPPSSLYEVASAEQMQGVTAYLNADRPDTLQETIVPFESRAEECSAPERVVAWEIDVSDMTGSKKT
```

FIG. 3A

```
    GCACATCTTGCAGGTCAAAACGAACACCCCCTCCTTCGATATCCTCTCAGACCCTACACT 60
    CTCAATTGTGTTACAGACCGGGCATGGGAAGAACTTGCTACGGCCGGCTTTCTTAGGGGG 120
    CGCCGCCCCTTGTCCTCTTCTTCTTTCCCATCCTCCTGTCCTCTTTTTGTGACTGTTTGTG 180
    ACTAGACGCCGTTTCTAACAAAATTGCCAAGCATGTATGCAAAATTAAAATGGAAAGATA 240
1                                                   M  E  R  Y
    CCCCAGACAACGGTTAGACGACGGCAGGTGGCAGTGCGTGGCAGCGCAGTACAGATACTC 300
5    P  R  Q  R  L  D  D  G  R  W  Q  C  V  A  A  Q  Y  R  Y  S
    CTGCGCCATCTCATGCCTTGTGAGCATATTCAATCATCTCTTCAACAGAGACATGACCCT 360
25   C  A  I  S  C  L  V  S  I  F  N  H  L  F  N  R  D  M  T  L
    GGACGAGTGTATTGCTATTCTCTTTCCAGACCTGAAAGAAGACCCACGACACTATGATTT 420
45   D  E  C  I  A  I  L  F  P  D  L  K  E  D  P  R  H  Y  D  F
    TGGACCTCAGGCTTCTAACAGTGCTGTTCAAAGCTGGTTCAAGACCCTCTGCATGCACTA 480
65   G  P  Q  A  S  N  S  A  V  Q  S  W  F  K  T  L  C  M  H  Y
    TGGCCTTTCTGGCACCTCTTGCACGATATACAAGGAGCAGGGCAGAACGAGAACTGCGTG 540
85   G  L  S  G  T  S  C  T  I  Y  K  E  Q  G  R  T  R  T  A  C
    TAGCAAGCAAGAGGCACTTAAGAATATCATCACTGCTTTGAATACGCCAAGATGTGCGTT 600
105  S  K  Q  E  A  L  K  N  I  I  T  A  L  N  T  P  R  C  A  L
    ACTGTATCACTGCTTGAACCATTACTGCATAATCGTAGGCTATATAATAAGTCCATCTAC 660
125  L  Y  H  C  L  N  H  Y  C  I  I  V  G  Y  I  I  S  P  S  T
    GCCTAATAGACCAAGTAATCATTGCGTCTTCAGCGGGGATGATGGATGCACCCTCAAGCT 720
145  P  N  R  P  S  N  H  C  V  F  S  G  D  D  G  C  T  L  K  L
    CCTGTGTGCAGACGGCACAGAAGCCGAGGACGTGGACGATAGTAATATTTGGTTAATAGT 780
165  L  C  A  D  G  T  E  A  E  D  V  D  D  S  N  I  W  L  I  V
    GGCAGACTGTGGGAAAGGAACTGCTCCCCTTAGGTCACTGACCTGGGAATTTGTACATAA 840
185  A  D  C  G  K  G  T  A  P  L  R  S  L  T  W  E  F  V  H  K
    AGATATATCTACCCGACCTCCGTATGCATATAACGCTAGGTGCCCTGAGAGAGGACTGCT 900
205  D  I  S  T  R  P  P  Y  A  Y  N  A  R  C  P  E  R  G  L  L
    AAGGAAAAACAGAATCAAAGGGATATATACCAGTTGAGATAGACTCAGTGCTTGTTAACAG 960
225  R  K  T  E  S  K  G  Y  I  P  V  E  I  D  S  V  L  V  N  S
    CACGGGAGTATCCACCTGTGTTAGATCTGGTGGCGTCATCAAGGGATCGTCGCACTGCAT 1020
245  T  G  V  S  T  C  V  R  S  G  G  V  I  K  G  S  S  H  C  I
    CATTGGATTTGTTAGTGACTAGAGCCCCGTTTATTACTCCCGGACGAAAGTATAACTATT 1080
265  I  G  F  V  S  D  *
    AACACCACAAGCACAACGATAGCTCCAGTAGAGCAGAGCCGAAGCACTTGAGGCAGCGAG 1140
    GCCTCCAAATACCCACATAGAACGTCACAGATGATAGCTGTCCATGTCGCAATTGACAAG 1200
    GTTAACGGGAAGGTTGAAACAGGCGAGGGCGTCCATCTGGTACGTTGTACTTTGGTTGTT 1260
    GAATATTGAACTGTTGTAAGTGTTGATTTGCTGGGTATATCTATTGCTTATGTACCGAAA 1320
    AAGGGCATTGCAAACGTCATATATTGCATCTATCTGATGAACACAGACCCCAGTTTTTTG 1380
    AAGATTTGCAAGTCTTCTTTGTGGTGGGGCATTCATATATGAATAAGAGCAGACTTCTCC 1440
    GCAGGCAAAGGACATGGACTGAATGGCATGCTCGTAACCAGTTAGGTCCAGTGCTTTGGT 1500
    TCGTGCATAGTATTTAAAGACCTTCTGAAGAAGGATGGTTTGAAATAGGGTCGTCCTGTC 1560
    CACACAGTCCAGGCAGTTTATCCGCGGATAGCACTTCTGAACAAAGTCAGGAAGAGCAAC 1620
    TCCGACATCACCGCTAGGAACTAGAACTGTGCTTGTGGCTATGTCATCTGCTAACTGGTG 1680
    ATACTCTGTGTTGCTGTGTCTACGTATGTTGTAGTTCATCAACTTAACGTTGAGGGAGTT 1740
    CTTGCGGCGAGAATCAGCAGTTTTTCTCATAGACTCGGTAAAGAACGCCGTCAGAGCCGC 1800
    TCATCGGCGGTCTCAAGGCTTTTCTTTTCACTGGCAGCAATGGAGTCATCCAAAAGATCG 1860
    ACTTCATTTTTGAGGAGGTTGACGATAAGTATCTCTGCGTCTGCAGTCACTAAGTTACCC 1920
    AATAGAAGGCTTATATGCCTTTGCAAGAGACTACTAAACTGAGCGAGGCCCTGCTCTTCA 1980
    TGAGCCCCATCTGGGAAGCGTATGGCAGGAGTGAACTTGTAAGTAAAAAAAAAAAAAAAA 2040
```

FIG. 7A

```
BIVM    189 EDIKQRKVLDLRRWYCISRPQYKTSCGISSLISCWNFLYSTMGAGNLPPI
BIVML     1 MERYPRQRLDDGRWQCVAA-QYRYSCAISCLVSIENHLENRDMT-----L

                                            M2
BIVM    239 TQEEALHILGFQPPFEDIRFGPFTGNYTLMRWFRQINDHEHVKGCSYVLY
BIVML    45 DECIAILFPDLKEDPRHYDFGPQASNSAVQSWFKTLCMHYGLSGTSCTIY

                                             M3b
BIVM    289 KPHGKNKTAGETASGALSKLTRGLKDESLAYIYHCQNHYFCPIGFEATPV
BIVML    94 KEQGRTRTACSKQE-ALKNIITALNTPRCALLYHCLNHYCIIVGYIISPS

BIVM    339 KANKAFSRGPLSPQEVEYWILIGESSRKHPAIHCKKWADIVTDLNTQNPE
BIVML   119 TPN-------------------------RPSNHCVFSGDDGCTLKLLCAD

BIVM    389 YLDIRHLERGLQYRKTKKVGGNLHCIIAFQRLNWQRFGLWNFPFGTIRQE
BIVML   166 GTEAEDVDDSNIWLIVADCG---KGTAPLRSLTWEFVHKDISTRPPYAYN

BIVM    439 SQPPTHAQGIAKSESEDNISKKQHGRLGRSFSASFHQDSAWKKMSSIHER
BIVML   212 ARCP-ERGLLRKTESKGYIPVEIDSVLVNSTGVSTCVRSGGVIKGSSHC-

BIVM    489 RNSGYQGYSDYDGND
BIVML   264 -IIG--FVSD
```

FIG. 7B

SEQUENCE LISTING

```
<160> NUMBER OF SEQ ID NOS: 65

<210> SEQ ID NO 1
<211> LENGTH: 3857
<212> TYPE: DNA
<213> ORGANISM: Homo sapiens
<220> FEATURE:
<221> NAME/KEY: misc_feature
<222> LOCATION: (1)..(473)
<223> OTHER INFORMATION: Exon A - untranslated
<220> FEATURE:
<221> NAME/KEY: misc_feature
<222> LOCATION: (474)..(557)
<223> OTHER INFORMATION: Exon B - untranslated
<220> FEATURE:
<221> NAME/KEY: misc_feature
<222> LOCATION: (558)..(1157)
<223> OTHER INFORMATION: Exon 1
<220> FEATURE:
<221> NAME/KEY: misc_feature
<222> LOCATION: (680)..(682)
<223> OTHER INFORMATION: Translation initiation codon (ATG)
<220> FEATURE:
<221> NAME/KEY: misc_feature
<222> LOCATION: (1158)..(1284)
<223> OTHER INFORMATION: Exon 2
<220> FEATURE:
<221> NAME/KEY: misc_feature
<222> LOCATION: (1285)..(1380)
<223> OTHER INFORMATION: Exon 3
<220> FEATURE:
<221> NAME/KEY: misc_feature
<222> LOCATION: (1381)..(1485)
<223> OTHER INFORMATION: Exon 4
<220> FEATURE:
<221> NAME/KEY: misc_feature
<222> LOCATION: (1486)..(1580)
<223> OTHER INFORMATION: Exon 5
<220> FEATURE:
<221> NAME/KEY: misc_feature
<222> LOCATION: (1581)..(1713)
<223> OTHER INFORMATION: Exon 6
```

-continued

<220> FEATURE:
<221> NAME/KEY: misc_feature
<222> LOCATION: (1714)..(1800)
<223> OTHER INFORMATION: Exon 7
<220> FEATURE:
<221> NAME/KEY: misc_feature
<222> LOCATION: (1801)..(1897)
<223> OTHER INFORMATION: Exon 8
<220> FEATURE:
<221> NAME/KEY: misc_feature
<222> LOCATION: (1898)..(3857)
<223> OTHER INFORMATION: Exon 9
<220> FEATURE:
<221> NAME/KEY: misc_feature
<222> LOCATION: (2189)..(2191)
<223> OTHER INFORMATION: Translation termination codon (TGA)
<220> FEATURE:
<221> NAME/KEY: misc_feature
<222> LOCATION: (2801)..(3009)
<223> OTHER INFORMATION: Alu sequence

<400> SEQUENCE: 1
agtaacgcct tctccaagtg gatggcgggg tggacacgcg tcccggcgcc ccgggctccc 60
tgggatatgt agttcgcgac aggacgagcg gaaatactgc caggatttta ccacctctcg 120
cccatttatt tacttctcgg tcaccgcttt cgggggacag ataaacacca cagatgccca 180
tcaaaggggc gcacgggtct ggaggcgcag ctcaggtttt tgcgttggtc accctgccct 240
ccgcacgtgg agagggcagg cataaagcac cttgaaagga aggtgctgtc aatgctatcc 300
gacgacctgt cgccgggcac cgcagcatcc tcgctcgctc cgatgggacg agggacgccg 360
gccccagggt aacaggaggc gcctcgccgg ccgcgcgctg gatgctgtga tccaggtccg 420
gagccgggtt ccgccgcggc cgcagcgacc cgaccccacc cgacaggcca gaggaatcag 480
tttagacttg aaattcagtt tttcctgaaa ctgatcagaa gttagtgaca ccttgattgg 540
atccgttttt ctgtcaggag ctcattttgc agctctcaag cttttatagc atgctgtaaa 600
caattgtcaa agttgtttat caagaaacag atagagttgc aacttgtttc tagtaataga 660
aacttttaca ctgcattcaa tgcctaacgt tgcagaaaca gaaaggtcaa atgattctgg 720
aaatggtgag cacaaatctg agagaaagtc acctgaagag aatctacaag gtgctgtaaa 780
atctttctgc acaagtgcct caggagcacc cttgggtccc aaaggagatg gtcattatcc 840
atggagttgt ccagtgactc atacacggga aaaaatttat gccatctgtt cggactatgc 900
ctttctcaac caggcgacct caatctataa aactccaaat ccatcccgct ctccttgcct 960
ccctgatagt acctctttat ctgctggaaa taattcatca agatacattg gtatcccgac 1020
tagtacatcg gaaattatct acaatgaaga aaatagcttg gaaaacttat ccaacagcct 1080
gggcaagcta cctctcgcat gggaaattga taaatctgaa tttgatgggg tgaccacaaa 1140
ttcgaaacac aaatcaggca atgcaaagaa acaagtttcc aagagaaaaa cttcagataa 1200
aaagggaaga tatcagaagg aatgtcctca gcattctcct cttgaagata ttaaacagcg 1260
gaaagtatta gacctcagac gatggtactg cataagccga ccacagtata agacttcttg 1320
tggcatctct tcattaattt cttgttggaa tttcttatac agcacaatgg gagctggaaa 1380
ccttccacct attacccaag aagaagcttt acatattctg ggctttcaac ctccatttga 1440
agatattagg tttggtcctt tcacggggaa tacaacactt atgaggtggt ttagacaaat 1500
taatgaccac ttccatgtaa aaggatgctc ttatgttcta tataagcctc atgggaagaa 1560
taaaacagca ggagaaactg cttcaggggc cctgtcaaag ttaacccgtg gattgaaaga 1620
tgaatcgctg gcttatatct atcattgcca aaatcattat tttgtccaa ttggcttcga 1680

-continued

```
agcaacccct gttaaagcta ataaagcatt cagcagggga cctctctcac cacaggaagt   1740

tgaatattgg atcttaattg gagaatcaag tagaaaacat cctgccattc actgtaaaaa   1800

atgggcagat attgttactg atctaaacac tcaaaatcca gaatacctgg atatccggca   1860

cttagagagg ggactgcagt atagaaaaac aaagaaggtt gggggaaatt tgcattgcat   1920

catagcattc cagagactta actggcaaag atttggcctt tggaactttc catttggaac   1980

cattagacaa gaatcacaac ctccaacaca tgcccaggga attgccaaat ctgagagtga   2040

agacaatatt tccaagaagc agcatgggcg tctgggccgg tctttcagtg ctagtttcca   2100

tcaggactcg gcatggaaaa agatgtctag tatccatgag agaaggaaca gtggttacca   2160

gggttacagt gattacgatg ggaatgattg actatgcttg ctactgaaca gctggcatta   2220

tatatgaaac tgctatatac aggactgtat aaagacagta gaagatttta gtaagcctac   2280

attaaatagg agcagatctt gtggtataaa aaataacctt gtagttctcc agatactaag   2340

cttgtatatg attatggtgg gtgatttcag atatataagc agataagcac agattattgt   2400

cctttcaagt taagagtata taatctggac agaaaatttc acaaaattca ataaaattac   2460

aactgttgtc taaataagtg aaacacaaat tcacttaata gcatcaagat ttgaaatact   2520

taagcatgaa gtgactttta taatgactcg atccctagac atttgttaca gatagtttta   2580

tgcctaagac caagatgtaa agtaccatct gcccttaaaa aaaattgggg ctgtcaattt   2640

ctagttttca ctcatggtta acacgcattt aaaattattt catgagtcta gtagttcttt   2700

gatttatagc aggatcttgc ttgcctcatt tgtttcctgg ttatgttctt aggattctga   2760

ctaagaggca aaagagaaaa gactcaagaa actgatcctg gagatcgaga ccatcctggc   2820

taacatggtg aaaccccgtc tctactaaac atacaaaaaa ttagccgggt gtagtggtgg   2880

gcacctgtag tcctagctac tcgagaggct gaggcaggag aatggcgtga acccgggagg   2940

tggagcttgc agtgagcgga gatcgcgcca ctgcactcca gcctgggcga cagggcaaga   3000

ctctgtctca aaaaaaaaaa aaaaaaaaaa gacggatcct tttttttggt gcaaatgggt   3060

gacttagtgc attgattcag atttttaaaa tttcttgatg tggtttgtaa taatcaaata   3120

ttgacaagaa ccttaggtct cgaaagactt ttataagtct agatgacgtt tgccttaggg   3180

gtaaagtaaa agaacaattg gcaccttaag tttctatacc caaggttatc tgtgaaatga   3240

gatctcctga tatttgattg ctttctcagt atggagtcat atgttgataa cagtactgaa   3300

gatgcataag aaatgcccaa gtcactcaga ggacaactac ccatattcca gactctgagc   3360

tgtttccttt ttaaaaatca tatagacaat tagctgtttg aagtgagtat taaatatttc   3420

agaagtgtga atttcatgta tttgagctcc tctagttgct gttggttttt cttctgctgc   3480

caacctgtga ctcacaaatg actaggatct cttgttcttt aattttaggg tcttgttcca   3540

ggactcaaat cagtaacttg gtgattacaa ggtgctgaat gtgttggtaa ccatatcgca   3600

atacacctca aggaaaaggt tcagattttt atttttaaaa tattttcatt tttttcttga   3660

attttatatc cgtttgttca ctcgtacatg cctagcctac agaaggggat atatattatg   3720

aaatggtcat ttttctgaag agaatatttt gcttgaaatg caaaggactg aaagagattt   3780

gtaggttgtt gattttgtta cttcatactg gaacttttaa aaagatttca tcaaataaag   3840

ttttgttttc tacttt                                                   3857
```

<210> SEQ ID NO 2
<211> LENGTH: 503
<212> TYPE: PRT
<213> ORGANISM: Homo sapiens -continued

<400> SEQUENCE: 2

```
Met Pro Asn Val Ala Glu Thr Glu Arg Ser Asn Asp Ser Gly Asn Gly
1               5                   10                  15

Glu His Lys Ser Glu Arg Lys Ser Pro Glu Glu Asn Leu Gln Gly Ala
            20                  25                  30

Val Lys Ser Phe Cys Thr Ser Ala Ser Gly Ala Pro Leu Gly Pro Lys
        35                  40                  45

Gly Asp Gly His Tyr Pro Trp Ser Cys Pro Val Thr His Thr Arg Glu
    50                  55                  60

Lys Ile Tyr Ala Ile Cys Ser Asp Tyr Ala Phe Leu Asn Gln Ala Thr
65                  70                  75                  80

Ser Ile Tyr Lys Thr Pro Asn Pro Ser Arg Ser Pro Cys Leu Pro Asp
                85                  90                  95

Ser Thr Ser Leu Ser Ala Gly Asn Asn Ser Ser Arg Tyr Ile Gly Ile
            100                 105                 110

Pro Thr Ser Thr Ser Glu Ile Ile Tyr Asn Glu Glu Asn Ser Leu Glu
        115                 120                 125

Asn Leu Ser Asn Ser Leu Gly Lys Leu Pro Leu Ala Trp Glu Ile Asp
    130                 135                 140

Lys Ser Glu Phe Asp Gly Val Thr Thr Asn Ser Lys His Lys Ser Gly
145                 150                 155                 160

Asn Ala Lys Lys Gln Val Ser Lys Arg Lys Thr Ser Asp Lys Lys Gly
                165                 170                 175

Arg Tyr Gln Lys Glu Cys Pro Gln His Ser Pro Leu Glu Asp Ile Lys
            180                 185                 190

Gln Arg Lys Val Leu Asp Leu Arg Arg Trp Tyr Cys Ile Ser Arg Pro
        195                 200                 205

Gln Tyr Lys Thr Ser Cys Gly Ile Ser Ser Leu Ile Ser Cys Trp Asn
    210                 215                 220

Phe Leu Tyr Ser Thr Met Gly Ala Gly Asn Leu Pro Pro Ile Thr Gln
225                 230                 235                 240

Glu Glu Ala Leu His Ile Leu Gly Phe Gln Pro Pro Phe Glu Asp Ile
                245                 250                 255

Arg Phe Gly Pro Phe Thr Gly Asn Thr Thr Leu Met Arg Trp Phe Arg
            260                 265                 270

Gln Ile Asn Asp His Phe His Val Lys Gly Cys Ser Tyr Val Leu Tyr
        275                 280                 285

Lys Pro His Gly Lys Asn Lys Thr Ala Gly Glu Thr Ala Ser Gly Ala
    290                 295                 300

Leu Ser Lys Leu Thr Arg Gly Leu Lys Asp Glu Ser Leu Ala Tyr Ile
305                 310                 315                 320

Tyr His Cys Gln Asn His Tyr Phe Cys Pro Ile Gly Phe Glu Ala Thr
                325                 330                 335

Pro Val Lys Ala Asn Lys Ala Phe Ser Arg Gly Pro Leu Ser Pro Gln
            340                 345                 350

Glu Val Glu Tyr Trp Ile Leu Ile Gly Glu Ser Ser Arg Lys His Pro
        355                 360                 365

Ala Ile His Cys Lys Lys Trp Ala Asp Ile Val Thr Asp Leu Asn Thr
    370                 375                 380

Gln Asn Pro Glu Tyr Leu Asp Ile Arg His Leu Glu Arg Gly Leu Gln
385                 390                 395                 400

Tyr Arg Lys Thr Lys Lys Val Gly Gly Asn Leu His Cys Ile Ile Ala
```

-continued

```
                405                 410                 415

Phe Gln Arg Leu Asn Trp Gln Arg Phe Gly Leu Trp Asn Phe Pro Phe
            420                 425                 430

Gly Thr Ile Arg Gln Glu Ser Gln Pro Pro Thr His Ala Gln Gly Ile
        435                 440                 445

Ala Lys Ser Glu Ser Glu Asp Asn Ile Ser Lys Lys Gln His Gly Arg
    450                 455                 460

Leu Gly Arg Ser Phe Ser Ala Ser Phe His Gln Asp Ser Ala Trp Lys
465                 470                 475                 480

Lys Met Ser Ser Ile His Glu Arg Arg Asn Ser Gly Tyr Gln Gly Tyr
                485                 490                 495

Ser Asp Tyr Asp Gly Asn Asp
            500


<210> SEQ ID NO 3
<211> LENGTH: 96898
<212> TYPE: DNA
<213> ORGANISM: Homo sapiens
<220> FEATURE:
<221> NAME/KEY: misc_feature
<222> LOCATION: (466)..(702)
<223> OTHER INFORMATION: Inverse complement of MGC5302 Exon 6
<220> FEATURE:
<221> NAME/KEY: misc_feature
<222> LOCATION: (823)..(997)
<223> OTHER INFORMATION: Inverse complement of MGC5302 Exon 5
<220> FEATURE:
<221> NAME/KEY: misc_feature
<222> LOCATION: (2904)..(2985)
<223> OTHER INFORMATION: Inverse complement of MGC5302 Exon 4
<220> FEATURE:
<221> NAME/KEY: misc_feature
<222> LOCATION: (3164)..(3366)
<223> OTHER INFORMATION: Inverse complement of MGC5302 Exon 3
<220> FEATURE:
<221> NAME/KEY: misc_feature
<222> LOCATION: (6395)..(6570)
<223> OTHER INFORMATION: Inverse complement of MGC5302 Exon 2
<220> FEATURE:
<221> NAME/KEY: misc_feature
<222> LOCATION: (8013)..(8312)
<223> OTHER INFORMATION: Genomic fragment identified as part of CpG
      island (Genbank Z59762)
<220> FEATURE:
<221> NAME/KEY: misc_feature
<222> LOCATION: (8059)..(8572)
<223> OTHER INFORMATION: Inverse complement of MGC5302 Exon 1
<220> FEATURE:
<221> NAME/KEY: misc_feature
<222> LOCATION: (8233)..(8235)
<223> OTHER INFORMATION: Inverse complement of MGC5302 translation
      initiation codon (ATG)
<220> FEATURE:
<221> NAME/KEY: misc_feature
<222> LOCATION: (8614)..(9086)
<223> OTHER INFORMATION: BIVM Exon A - untranslated
<220> FEATURE:
<221> NAME/KEY: misc_feature
<222> LOCATION: (9019)..(9033)
<223> OTHER INFORMATION: BIVM Exon A alternative splice donor site
<220> FEATURE:
<221> NAME/KEY: misc_feature
<222> LOCATION: (9077)..(9091)
<223> OTHER INFORMATION: BIVM Exon A splice donor site
<220> FEATURE:
<221> NAME/KEY: misc_feature
<222> LOCATION: (14862)..(14876)
<223> OTHER INFORMATION: BIVM Exon B splice acceptor site
<220> FEATURE:
<221> NAME/KEY: misc_feature
<222> LOCATION: (14872)..(14955)
<223> OTHER INFORMATION: BIVM Exon B - untranslated
```

-continued

<220> FEATURE:
<221> NAME/KEY: misc_feature
<222> LOCATION: (14946)..(14960)
<223> OTHER INFORMATION: BIVM Exon B splice donor site
<220> FEATURE:
<221> NAME/KEY: misc_feature
<222> LOCATION: (16309)..(16309)
<223> OTHER INFORMATION: n = a, c, g, or t.
<220> FEATURE:
<221> NAME/KEY: misc_feature
<222> LOCATION: (16701)..(16715)
<223> OTHER INFORMATION: BIVM Exon 1 splice acceptor site
<220> FEATURE:
<221> NAME/KEY: misc_feature
<222> LOCATION: (16711)..(17310)
<223> OTHER INFORMATION: BIVM Exon 1
<220> FEATURE:
<221> NAME/KEY: misc_feature
<222> LOCATION: (16833)..(16835)
<223> OTHER INFORMATION: BIVM translation initiation codon (ATG)
<220> FEATURE:
<221> NAME/KEY: misc_feature
<222> LOCATION: (17301)..(17315)
<223> OTHER INFORMATION: BIVM Exon 1 splice donor site
<220> FEATURE:
<221> NAME/KEY: misc_feature
<222> LOCATION: (25983)..(25997)
<223> OTHER INFORMATION: BIVM Exon 2 splice acceptor site
<220> FEATURE:
<221> NAME/KEY: misc_feature
<222> LOCATION: (25993)..(26119)
<223> OTHER INFORMATION: BIVM Exon 2
<220> FEATURE:
<221> NAME/KEY: misc_feature
<222> LOCATION: (26110)..(26124)
<223> OTHER INFORMATION: BIVM Exon 2 splice donor site
<220> FEATURE:
<221> NAME/KEY: misc_feature
<222> LOCATION: (30592)..(30606)
<223> OTHER INFORMATION: BIVM Exon 3 splice acceptor site
<220> FEATURE:
<221> NAME/KEY: misc_feature
<222> LOCATION: (30602)..(30697)
<223> OTHER INFORMATION: BIVM Exon 3
<220> FEATURE:
<221> NAME/KEY: misc_feature
<222> LOCATION: (30688)..(30702)
<223> OTHER INFORMATION: BIVM Exon 3 splice donor site
<220> FEATURE:
<221> NAME/KEY: misc_feature
<222> LOCATION: (31298)..(31312)
<223> OTHER INFORMATION: BIVM Exon 4 splice acceptor site
<220> FEATURE:
<221> NAME/KEY: misc_feature
<222> LOCATION: (31308)..(31412)
<223> OTHER INFORMATION: BIVM Exon 4
<220> FEATURE:
<221> NAME/KEY: misc_feature
<222> LOCATION: (31403)..(31417)
<223> OTHER INFORMATION: BIVM Exon 4 splice donor site
<220> FEATURE:
<221> NAME/KEY: misc_feature
<222> LOCATION: (31620)..(31634)
<223> OTHER INFORMATION: BIVM Exon 5 splice acceptor site
<220> FEATURE:
<221> NAME/KEY: misc_feature
<222> LOCATION: (31630)..(31724)
<223> OTHER INFORMATION: BIVM Exon 5
<220> FEATURE:
<221> NAME/KEY: misc_feature
<222> LOCATION: (31715)..(31729)
<223> OTHER INFORMATION: BIVM Exon 5 splice donor site
<220> FEATURE:
<221> NAME/KEY: misc_feature
<222> LOCATION: (41120)..(41134)
<223> OTHER INFORMATION: BIVM Exon 6 splice acceptor site
<220> FEATURE:
<221> NAME/KEY: misc_feature
<222> LOCATION: (41130)..(41262)

-continued

<223> OTHER INFORMATION: BIVM Exon 6
<220> FEATURE:
<221> NAME/KEY: misc_feature
<222> LOCATION: (41253)..(41267)
<223> OTHER INFORMATION: BIVM Exon 6 splice donor site
<220> FEATURE:
<221> NAME/KEY: misc_feature
<222> LOCATION: (44021)..(44035)
<223> OTHER INFORMATION: BIVM Exon 7 splice acceptor site
<220> FEATURE:
<221> NAME/KEY: misc_feature
<222> LOCATION: (44031)..(44117)
<223> OTHER INFORMATION: BIVM Exon 7
<220> FEATURE:
<221> NAME/KEY: misc_feature
<222> LOCATION: (44108)..(44122)
<223> OTHER INFORMATION: BIVM Exon 7 splice donor site
<220> FEATURE:
<221> NAME/KEY: misc_feature
<222> LOCATION: (48198)..(48212)
<223> OTHER INFORMATION: BVIM Exon 8 splice acceptor site
<220> FEATURE:
<221> NAME/KEY: misc_feature
<222> LOCATION: (48208)..(48304)
<223> OTHER INFORMATION: BIVM Exon 8
<220> FEATURE:
<221> NAME/KEY: misc_feature
<222> LOCATION: (48295)..(48309)
<223> OTHER INFORMATION: BIVM Exon 8 splice donor site
<220> FEATURE:
<221> NAME/KEY: misc_feature
<222> LOCATION: (49127)..(49141)
<223> OTHER INFORMATION: BIVM Exon 9 splice acceptor site
<220> FEATURE:
<221> NAME/KEY: misc_feature
<222> LOCATION: (49137)..(51096)
<223> OTHER INFORMATION: BIVM Exon 9
<220> FEATURE:
<221> NAME/KEY: misc_feature
<222> LOCATION: (49428)..(49430)
<223> OTHER INFORMATION: BIVM translation termination codon (TGA)
<220> FEATURE:
<221> NAME/KEY: misc_feature
<222> LOCATION: (50039)..(50248)
<223> OTHER INFORMATION: Alu sequence
<220> FEATURE:
<221> NAME/KEY: misc_feature
<222> LOCATION: (55216)..(55975)
<223> OTHER INFORMATION: ERCC5 Exon 1
<220> FEATURE:
<221> NAME/KEY: misc_feature
<222> LOCATION: (61682)..(61860)
<223> OTHER INFORMATION: ERCC5 Exon 2
<220> FEATURE:
<221> NAME/KEY: misc_feature
<222> LOCATION: (63321)..(63437)
<223> OTHER INFORMATION: ERCC5 Exon 3
<220> FEATURE:
<221> NAME/KEY: misc_feature
<222> LOCATION: (63851)..(63939)
<223> OTHER INFORMATION: ERCC5 Exon 4
<220> FEATURE:
<221> NAME/KEY: misc_feature
<222> LOCATION: (65614)..(65678)
<223> OTHER INFORMATION: ERCC5 Exon 5
<220> FEATURE:
<221> NAME/KEY: misc_feature
<222> LOCATION: (67834)..(67984)
<223> OTHER INFORMATION: ERCC5 Exon 6
<220> FEATURE:
<221> NAME/KEY: misc_feature
<222> LOCATION: (71070)..(71283)
<223> OTHER INFORMATION: ERCC5 Exon 7
<220> FEATURE:
<221> NAME/KEY: misc_feature
<222> LOCATION: (71592)..(72669)
<223> OTHER INFORMATION: ERCC5 Exon 8
<220> FEATURE:
<221> NAME/KEY: misc_feature -continued

```
<222> LOCATION: (75231)..(75477)
<223> OTHER INFORMATION: ERCC5 Exon 9
<220> FEATURE:
<221> NAME/KEY: misc_feature
<222> LOCATION: (75826)..(75944)
<223> OTHER INFORMATION: ERCC5 Exon 10
<220> FEATURE:
<221> NAME/KEY: misc_feature
<222> LOCATION: (76194)..(76411)
<223> OTHER INFORMATION: ERCC5 Exon 11
<220> FEATURE:
<221> NAME/KEY: misc_feature
<222> LOCATION: (77677)..(77822)
<223> OTHER INFORMATION: ERCC5 Exon 12
<220> FEATURE:
<221> NAME/KEY: misc_feature
<222> LOCATION: (81763)..(81965)
<223> OTHER INFORMATION: ERCC5 Exon 13
<220> FEATURE:
<221> NAME/KEY: misc_feature
<222> LOCATION: (82824)..(82908)
<223> OTHER INFORMATION: ERCC5 Exon 14
<220> FEATURE:
<221> NAME/KEY: misc_feature
<222> LOCATION: (84870)..(85560)
<223> OTHER INFORMATION: ERCC5 Exon 15

<400> SEQUENCE: 3

ctagacagag aaagcaaacc ctaattccca gacagaacat ttggatgagt ttcacgtcat     60

tcccccaccag aaggcctggt aagaaacaag tagtttatat cttccttatt ctgttgtgat    120

aacatggctc tgggaaaaag tatttgtaaa atgacttaca tgtaagtatt aataaaaaca    180

tatttggagg tgacatgtgc ttatctcaag ggttagctgg aaaaaaatta tagctctatc    240

caggctccaa actcccttga tgcgcattta atatcaagac tgggcagtga gggcagaccc    300

tggttgccaa aacagtcccc agcaccccca tgtctcaata ttcgctcaat tttgtgctaa    360

cttctcccac ctcttgaaat ttgcaggcct taatttccct tcccaaagca ctatgtacaa    420

atacattaga aaaacaaaaa agattagcta ctgattaagt cataccttga agaaatcaaa    480

aaatgaaata tgtttcacaa tgggaccata caggttttca tcgtgtttaa agaagaaaaa    540

gttggtgaaa gcagcgtcta tgagttctgg gtgttttcta ctgagtttaa ccagctcgag    600

tctctctttg cggctgtctc gccctctcca gacggcagtg gaatttttgc tttcccaggg    660

aggacccgtg ttagcttgca cggacatcat atccagactt accctagaag acaaagtgca    720

acagattttc ctcccaaatc atcatatcac aaaggttgtt gcaaaagaac tcaccaaaga    780

aagaaaacca aggctctggg ccaaccctga cttatctctc accggcccat ggtttccaga    840

acagaatcag tcaaatcgta cgtaggcatc acgatatcct tggaatctgt ggagccacac    900

caggaaaaga tcggatggat gtttgaattg gatttctttt tttccaaagg ccagtctccc    960

aaattaacaa agagctccac atctggcatc ttcacctaga aaaaacaaaa cgaggagctt   1020

attcacattt cctgcattgg ataatacatt gtatttatca atttaaattt gaaattgcat   1080

taatgaaagg ccaatgttac atgtttcagg taataataat taccttggtt tgaatagtgg   1140

gcaatgtttc agaatatggt cacatgtata agtattctat gctccctatg aaagggatga   1200

aactgcaaaa gtaatctctg ttctaatact gcgaacagcc tctaagatga tcaaagagaa   1260

ggagaattat tggaaaataa tttaaaaaat agcacttggg actctaaccc tagtttcctg   1320

ctagtgagcc agatggttcc attttaaaaa acatacacca ggtaggtggt gggaccagga   1380

tttgaactca ggaagcccaa caccaacagc aacgtagtaa gtttcaagct atgcttcctt   1440

cctctactgg caaatggcat gaatatgtaa agaggatatg ttttatctag tcacagaaaa   1500
```

-continued

```
tgtttagagt atttacaaaa caacagatat acatttttaa ggccagaaaa gcactgacca   1560
gtctgagaag catcttgaga aaccgaagtc ctgaagaaca ttctcatttt cccatggatt   1620
gacaaagagg agcaagagaa gtatgacggt actctgatgt cttagtttaa aggaggctta   1680
atattgatgc tatataacta cctacattca gaattaacag actgtaagtg ctttgaaatc   1740
ttgaaaaaaa ggcattatga ttttccatga gtagtttaat caagatatac atgcaaatta   1800
ttcaacaaat aaatataata gattacaaat aaatatacat ttggtaaaaa tgttggtaga   1860
gtctttcaca tccaccattt taacattact ttcaaaccat tccactagaa cccaacaaaa   1920
gcccattatc ccaaggaatg ggattcagta caaggcaagt catctttgga ctcagagtta   1980
gtttagtacc aaaataattt tatgataagg catttttctt tcctctataa aatattgtgt   2040
ccctgcaaaa gatatgctga agtcttaaat cccagtgtct cagaatgacc ttatttggaa   2100
atagggttgt tgcagatatt agttagcatg aggtcatact ggagtaggct gggccattaa   2160
tccactatgc tgtgtcctta taagaagaga cccagagaca tgaggggaga agcccacgtg   2220
atgacagagg cagagatggg aggatgcagc tgcaaaccaa ggaacaccaa agatggaggg   2280
ccactgacag cagccaggaa gaggcaggaa aggaaaggaa aggatcatct cagagggagc   2340
tggcctcctg acactttaat ttttttggg gggggacagg atctcactct tgtcacccag   2400
gccttgggag tgcagtggcg tgatctcggc tcatgcagcc tcgacctcct aggttcaagc   2460
gatcttcctg cctcagctcc ccattagctg aaactactac aggctaattt ttgtattttt   2520
tgtagagaca ggtcttcacc atgttgccca gcctggtctc aagctcctgg gctcaagtga   2580
tccacccgct ttgacctcct aaagtgctag gattacaggc gtgagccatg gcacctagct   2640
gacactttga ttttggacat ctggcctcca taactgccag agaatacatt tctgttattt   2700
taaggcttcc agtttgtagc actttgttac ggcagcccta ggaaacaaac gcaggtacct   2760
gaaataacag aaagcttcag aatagtatta tcataaggct ccagaagaga ataccctgat   2820
agtgtataat ttgtattttg aaaaattatc ctgtaaaatc tgggcttaaa ttatctatta   2880
cagctaagag aaaatatata cttacctttc tagtcaaaga aagtagtatg gcatccatga   2940
aaattctaaa acctacatgt tcaccatgag tcttgatata aacctaaaag agaatttacc   3000
atttattatg ttagtctaaa gacgctggca gacttcactg aggaaaagct tgtcacagtg   3060
ctcattcgaa tgatgtttat aaaatgattt agctaattgt agccaaatgt tcaaaacaag   3120
aaaaaaaatc actaaaacaa acaagcaaaa aatcatgtgt tgtaccttgt tatcctttaa   3180
ggtgtagtga catagctct gcctctgtcc aaatcttttt gggatttcta ctgcaatctt   3240
ttctggatcc acagcaggga aatgtgccag atctctctga atctgagcaa tggtttcagg   3300
gcagttcatc tcccgtagcc aggctgcact atcttgcaga ggacagtcac agttctcatg   3360
gtaaaccggc cctatttaca taagaataac aaagtacaac agtgatcatt tcactcagca   3420
ttcgaaactt gtaataaaca tctataatgt ggcttcatga attttgctta gttacatagg   3480
aagagcattt tcattgaaaa cacattttaa gagaattaca ggccagcaag gttggctcat   3540
gtcggtaatc ccagcacttt gggaggctga ggcaggaaga cagcctgagc ccaggagttc   3600
gggagcagcc tgggcaacac agggagacca tgtctctaca aaaaataaaa aattagctgg   3660
gtgcgttggc atgcacctgt ggtttcagct acttgggagg ctgacgtggg aggatcactt   3720
gagcccagga ggttgaagct gcagtgagcc atgtttgcgc cactccatcc tgggcaagac   3780
agtgagagcc cgtttcaaag aaaaaaaaag taatacattt ttactatact ggggcattgc   3840
aagtaagtca gccttctact ctgacagctc ttcacagtga agttttgtga tattttcata   3900
```

-continued

```
ataataaggt ctactttgca tgagttcaaa agaaaggaaa tagaggctgg gtgcagtggc   3960
tcacgtctgt aataccagca ctttgggagg ctgaggtggg tggataactt gaggtcagga   4020
gtttgagacc agcctggcca acatgttgaa accccatctc tactaaaaat acaaaaaagt   4080
ttagctgggt atggtggtgt gtgcctgaaa tctcagctac tcaggaggct gaggcatgac   4140
aatagcttga atctgggagg tgaaggttgc agtgagcgga gattgtgcca ctgtgctcca   4200
gcttggggga cagagtgaga ctcttgtttc aaaaaataaa agaaagacaa cagatacttg   4260
gtttatgtct atggtaatat tacagctcat tattccttat gttttgcaga ctgaagaata   4320
accaaatact ggtaaaaggg tatcagagga gcatacctat tttaatgaaa gacaaaagtg   4380
atatgattta ctattttgat ggtctgttat acaaacaggt tcttaaagtg tctaaggtac   4440
ttttctcaat aagtaaatca tcaataacag caaaaataaa caaggaactg ctattctttt   4500
tttttttttt tttaagaatt attaaggagg aaaagtaggc tgggttcttg gctcatgcct   4560
gtaatcccag cactttggga ggctgaggcg ggcggatcac gaggtcagga gatcgagacc   4620
atcctggtca acatggtgaa accccgtctc tactaaaaat acaaaaatta gccaggtgtt   4680
gtggcgcgtc cctgtagtct cagctatttg ggtggctgag gcagcagaat cgcttgaacc   4740
cgggaggcag agcttgcagt gagccgagat tgcaccactg cactctaggc tagtgacaga   4800
gcgagacatc gtctcaaaaa aaaaaaaaaa aaaaaaagca aaagtagctg ggtacagtgg   4860
ctcacgcctg taatcctagc actttgggag actgaggtgg gcagatcact tgagctccag   4920
ggttcgggac cagtctgagc aacatggcaa aaccctgttt ctacaaaaaa tacaaaaatt   4980
agtggggcat ggtggtgagt gcctgtagtc ccagctactc atgcagctga ggtgggagga   5040
ttgcttgaac ccaggaggtc gaggctgcag taagcagtga ttgcaccact gcactccagc   5100
ctgggcaaca gagcgagacc ctgtctcaac aacaacggca acaaaaagaa gcaaaagtaa   5160
ttctcaaaac agtccacttc actaatttta taacaaatta attacagtct gcactgaggt   5220
ttttactgtt attccttttt ataattctca gatcccacct aacccaggca gtggctgaca   5280
atggaatatc tttttaaggt ttagtgggtg atactgtacc aggctgtact ggcagaatgt   5340
aggaaaggaa cctagacact cttgaaaagt gtttaccttt tcttacttct ctgcagagtt   5400
cacaaaaata aaaaaaaaaa agtttacttt tcttggggtt gttaaggggg ggacaagatt   5460
tctgcctttg tatatacact gcttccctac tgtcttgtgg tactgtcgcc tgtaagaggg   5520
aaggagatgg ctctaggtaa taaaactgta ctctcatcct atataagaaa catcagaatg   5580
gccgagcatg gtggctcaca cctgtaatcc cagcactttg ggagactgag gcaggcagat   5640
catgaggtca agagatcgaa accatcctgg tcaacatggt gaaatcctgt ctctactaaa   5700
aatacaaaaa ttagcctggc atggtggtgc gtgcctgtaa tcccagctac atgggaggct   5760
aaggcaggat aatcgcttga acccggaagg cggagcttgc agtgagccaa gactgcgcca   5820
ttgcactcca gccttgtgac agagcgagac tctgcctcaa aaaaaaaaaa aaaaaaataa   5880
ataaataaat aaataaataa atgtcagaga atttctctgg gaaaatggca ttggaacaaa   5940
gacaaaaaaa caaccaccag tgcgctcctt gtctttcgag ctatctccct tcctgaagtg   6000
atctacctaa tttcaataac acttatcagt tacttaagtc atatatttcc aattaagaaa   6060
gtatcatata tgagcatgaa cacagcttga ttattcttgc taatgtatgt cttcgcggag   6120
taaattctct actaatatgt tccttgctct ttagcaaatc agaatttccg ttcaaatctt   6180
gaatgtcttt ttaccaggac tcataactta gctttcaagt agaaagcctt tatttttctt   6240
```

-continued

```
ctttcagtaa aaaaaaaaaa aaaaatatat atatatatat atatatcatg ccaagttgtt   6300
tttgttgatg gaataacata tattatttta ttcaaatact gctgttataa aattatattc   6360
caaattacct tttaaaatat atggggattt ggccacatgt tgcccttgga atttaatttc   6420
caccttcaga tttttgtagc ttgcatacat tctgtatctt actatgaagg acccatcttt   6480
tcggtctaaa acctggactc caactctagt gaattgctcc tctggtgctg agactttcac   6540
ctggaagacc ttttcgcctg gagaagatgt gaatctgtga tgaaaaggca atgggggaga   6600
taaacagatt ttaacgaaca aacacacaaa ggttatgctc ttcagtctgg aaacttgatt   6660
attctcctcc acattcttcc tctaacatat gattgcttct tcttctctta tgcttttagt   6720
accagaatga atatgatgga tcagagattt aaaaaaatga ggatgacaat ggccaagata   6780
acatgaaaca gtttcattaa acagtcacaa tggagtatgt taagactatt aatctatata   6840
agcacagaac atactcatgc attccatatg gaaaaatatt cttactaact tatttcatgc   6900
tatcacatct ggatatttgt gatcaaatga tgctcccaaa gataatgatc ttattttgaa   6960
aaatctctgc caatgaatct ttacaatatc agtattataa atcacgctca ggcctggcac   7020
tgtggcccat gcctactatc tcaacatctt gggaggccaa ggagggaaga ctgcttgagg   7080
ccaggagttc gagatcagcc tgggcaacaa ggtgagatcc tgtctctaca aataataata   7140
ataataataa aaaacaaata gccaggcgag gtggcacacg cctgtagtcc caactactag   7200
ggaggctgag gtgggaggat agcttcagcc tgggaggttg agggtacagt gagctgtgat   7260
tgcaccactg cactccagac taggctagga agtgaaaccc tgtcttaaaa aaaaaaaact   7320
cacgctcagc catgggcaaa agcaaagtag taggtagtgt atcatctttt gccaaataac   7380
aaaatttaca acctgccttt tacttgacaa ccttttattc cagtattttt ttctgtatga   7440
aatacacaca gtcagcatcc accaataata gagacaatca tttcagaagt ataggaatta   7500
taaaaataag ttttaagtat gatgttaaag tattaaattc attggaacaa aatatttgtt   7560
acaatcatat aggagattaa tacttcgata ctttccttcc gaactctgaa gtttcaaata   7620
gtacttcatt tttctttttc agtttcaaaa catgcttacc tgcagatgtc tccttgaaaa   7680
ttgagggccg caccagagaa agatgaagcc catcaagtct ctaacaacta ggtttaaatc   7740
ccttataata gcttatgcga aaagtagtta gaaacagtat ttccagcaaa gtggagggac   7800
tttgtcttgc cctgataatg tgggaatctg aatcaaaatt gctaggagat tattttatat   7860
gttatataca atacattata ttgcatatat tataattcgg aacaatttct acagctacag   7920
agaaaaatgg gtaaccaaat atcctggaat ataaactgct gtggagaaac gagttcttgg   7980
aaagaaaaat cttaaaggga gaaacagatt taaccgccat ccaaaatagg taaggagccg   8040
tttctcgact tacttattcc ctgatgtatc cactgcctga atatagaaat agcgggcggg   8100
aaggacgacg tctgctttta gcccgggtcc ccatatttcg ctcttctccg ggctcagctg   8160
cctttctccg ccggtctcgg cgagtgctgg aactgtcgcc agaaagaagc aataaagtag   8220
caaagtgcca aacatttaca agacggactc tcgaaatgat ccaccgataa atgaagaagt   8280
gtaagaggtg gacagaagca gccgagcctt cggcagggac ccgccggccg atcgcagcag   8340
ccaacgcgac tgcaaaggtt gccgcccggc gtgcagggca ggcgcgcggg tctccgcgac   8400
cccaggacaa tcaaagcccg tgccccggcg cgcccaggtg agggtcccct ggcgttctgc   8460
tgtcccggcc gagaaccgcg ctgctcctct ctctcaggac aatgatgaac ttgagttgct   8520
cctgccactg gagcatcatt tgggagcgaa tccgtctcag gttccagcca aggtgtaggg   8580
cgaggggatt ggcccgtgcg tcgggccagg ctcagtaacg ccttctccaa gtggatggcg   8640
```

-continued

```
gggtggacac gcgtcccggc gccccgggct ccctgggata tgtagttcgc gacaggacga   8700
gcggaaatac tgccaggatt ttaccacctc tcgcccattt atttacttct cggtcaccgc   8760
tttcggggga cagataaaca ccacagatgc ccatcaaagg ggcgcacggg tctggaggcg   8820
cagctcaggt ttttgcgttg gtcaccctgc cctccgcacg tggagagggc aggcataaag   8880
caccttgaaa ggaaggtgct gtcaatgcta tccgacgacc tgtcgccggg caccgcagca   8940
tcctcgctcg ctccgatggg acgagggacg ccggccccag ggtaacagga ggcgcctcgc   9000
cggccgcgcg ctggatgctg tgatccaggt ccggagccgg gttccgccgc ggccgcagcg   9060
acccgacccc acccgacagg ccagaggtac cccggggcgg ggggcagggg ccgaggtggc   9120
ggccggctgt gcgctctgag cgcctggccc tccgctgggc acctgggcgc cgccagcccg   9180
gcctgctgcc gctctacgcg cagccacctg ggcattcaaa atttttactt aattcgatac   9240
cggcctgggc tgccaggggt catcgcctct ccgagccccg tggcgtccag atggaggcca   9300
ctgcatgggt gcgcgctctc ccgggaagga gtagggggaa gagctgtgtc gcggggggaa   9360
gagaagcgcc agggaaagaa gggcctagcc ctctggtgaa caaagctcga ttaggaggtg   9420
tccatgtgga taccggtgac ccctgtgcgg ccgtcggtct ccacgccacg ctgggcaggg   9480
tccgggaacc agcgcgcagc ggccgtcgcc ttcccctgca cgccagcacc cgggtctggg   9540
ccgccgccag gagtcacggg ctcaccgccc tggtcagctt ggcagtcgga cccggagccg   9600
cctcctctgc ctgcctccct cttgccagct gccccgaaaa cccagaagag ccggtggctc   9660
cgagccaagg cgggcctggt tcggcgccag gaaagggggt ttctttccta ttttcttttg   9720
tgcaattgtc attattaatg ataccgactc gtttactcaa acagtcgaat cggagcccca   9780
gctcttagcc cggatgcagc aattgcccgt gggccccctt taacaccaac agcgtccccg   9840
gggcccgggg caagcatgtt cgaggcggtc acccccgggc ctcggcgcgc tccccctggc   9900
ggagagcctc gtcttccggc cggtgaggga aggtagagga gggagtaggg gcgaggaggc   9960
ctcggcggcc cttgggctct gcgggctggg gactcggggt gcccgcgaca cgcgcggagg  10020
cgcgggctgg gttggccacg ggcagggagc gcagccgcgc tccttcctct ctgcccgcgt  10080
cgcctccgcg cgcactggtt ctgcgcggcg gggcttggcc tgcgcgactg tctactccgt  10140
cccggcggcc tcggagcccg gccgagcggc gagcttgtca gaggacggtg gtggaaacgc  10200
tcccggcctc cccaggggcg cgggctggag gctggcgcca ggcgcggagg actcccggta  10260
tcttttgaca ggctggcgcc tcggctctgg ggacccgcag gtctgaaggg gaggaagggg  10320
cctggagggc gcgggaggac accgggtggg aagggtggca ttagctcggc cgggggctat  10380
gcgcctctgg tttcgccctc ccgcgcatat tcgaccctta cgaggtcacc ggaatgcccc  10440
tgctcctcag ttgccttcta tacaggatat cgatcagggt attttgttat acgaaaaggc  10500
tttactgaag aggtttttag agatgtttgg ttctctcata aacttgatac ttgagaatac  10560
agacaaaata taacctgaaa agactacaac ctaggcgatg aagattggct ttacaaatgg  10620
acgtttattt tacagaacac ttcgttcagt gactttgaac aatcatgact ctggcggtgc  10680
tttttaaact tgccatttta taaatttttg ctttgcatac gagcaaacca tatttctatt  10740
gcttatgaca tgattttatg agtaagctat tagttgagcc tgaggtcctg cagtcattct  10800
tagtagtaaa tttttttttt tttttttttg agacggagtt ttgctctgat cgcccaggct  10860
ggagtgcaat ggtgcaactg taacctccac ctctggtgtt cagcgattct ccagccttgc  10920
ctcctgagta gctgggccta cacgcatgcg ccaccatgca cggctaattt tgtatttttt  10980
```

-continued

```
tattttttat ttttttttag tagaaacggg tctcaccatg ttggccaggc tggcctcaaa  11040
ctcctgacct cagatgatcc acccgcctca gcctcccaaa gtgctgggat tacaggtgtg  11100
agccaccacg ccggcttagt aaatcttaat atagcaacac ctcacttgcc tggaagaggg  11160
aaccgcaatc aatcaaaatg agggcctaca gtaatgcctg gcatgatgca aacacttaaa  11220
aattatctgt tgaatgagac gtctacaaat cctaggccct ggggatacaa taatctggaa  11280
aaccagactt gcaggatgca gacgttgatc atatgaacag atatgcacag aagtaagtgt  11340
aaaattgcca cctggtaaga cctgtgtgag gaaggtacta gagtctgtac cgggtcacct  11400
ggcctagttt gagaagccaa gaaggtttcc cccagaaagt gacatttgag ctgacattgg  11460
aaagatgaat gggaatgagc taagtaaggg agacagtatt gggagaacca aaaagtaatg  11520
tggagcttgg ggggtggggg aaaggaatga gatggagcta accagataga tctagggacc  11580
atcaggagtt ggccttttgt tctaagagca gaggctttca ggcagaggag ttctgtgatc  11640
atatatatgt agcaaacttt attttctaat atctctgcac aggtcaggtt agaagtgtca  11700
actcactggg aatagtttat aaatagagaa acaaaaggag ataaaagatg agtcaaaaca  11760
gtgacagctg cagcctatta agtggaggga caaactgcct ctctatagct cagtattgtc  11820
tataatgatt ctgttattag tattatcagt aataaattgt gcttagtgta ctttaagaaa  11880
gctagaatct gagcatgcaa taatagaagc cccccttggcc tcttggggct ctcactatag  11940
tggagagaat agacgtgaga cagtgtggaa agaaagtaaa cactagcagt gtttgggtcg  12000
tgggatttgg gtaatttcca ttttcctgta atatcttttg gtactttgca tttttttgta  12060
atgtttttact tataaaatct atgaatatta cattttcaaa gagaaattta catatagttt  12120
ccaatgagaa tgtttcatgc ccttggattt tagtgacagt caatataaaa tgcatcctta  12180
tattgatgat cttcattttt tttttgctaa aacttcgacc aaataaatca tcttgttccg  12240
tgaccattat ttaaaagcaa acaaactaaa aacacaaaca aaccagactg ttactttttt  12300
ctctctttcc tttttttttt ttttttttga gacagagtct tgctttgttg cccaggctag  12360
agtgcagtgg tgtgatcata gctcactgca gcctcaaact cctggcctca agtgattctt  12420
ttgcctcagc ctcccaaagc atagatatta caggtatgag ccactgtgcc tggctcacac  12480
tgttactctt tttattaatc tagtgctgtg ttctatcttt agcgtccagg aagcttaccc  12540
ccaacttttg tgcttaaatg cagtcatttc cctttgccta tgtttttgat aagaatattc  12600
tccatggctg ggcatggtgg cttgtgcctg taatgccagc aatttgggag gctgaggcgg  12660
gaggattgct tgaagccaag aggtcaagac cagcctaggc aacatagcaa gaccctgttt  12720
cttaaaaaaa aaaaaaaaaa aggttattct atatatgttc caaatgagca tacttttaca  12780
atccctgcca ggtgcagtgg ctcattccta taatcccagc actttggggg gccgaggcca  12840
gcagatcacc tgaggtcagg agttccagac cagcctggcc aacgtggtga aaccccatct  12900
ctactaaaaa tacaaaaatt agccaggcat ggtggcacct gcctgtaatt ccagctactc  12960
cagaggctga ggcaggagaa tctcttgaat ccaggagaca gaggttgcag tgagctgaga  13020
tccggccatt gcactccagc ctgggcaaca gagtgagatt ccatttaaaa aaatcaaatc  13080
aaatccctac actgtcacac agagagctgg tcccacaggc aaaattccat tcagtgtgag  13140
gaaggaagcc ctgggaaagt ggaagccaag tctgagatga ggatataaaa ggggcagggc  13200
ctggaacatt tccgtctcgc caccaaactc actctaataa cctttgtcta ttgcctctca  13260
ccgagactat atgctctttc attcctcacc tcgcacagcc cacccccacg accccaatac  13320
cacaaatacc tacctctctg tccaccacac tgatgtagag aaaggcatga aggtcacaga  13380
```

-continued

```
tgagaagtag aaaatgctat gttaggacat ctgctgagaa tcagagcaac tctgtcttcc  13440
aaaaagacaa gagtttggtc tgaacaacgc caggtactga gcttccctct gccatcaccg  13500
ttgcaccacc agatgaataa ggagagagca ccacttccac ttgaggaccc actacaacta  13560
ctccaagaat tttttttacc aaaagaaagt gaaagttttc aaagtgaaac cacaggaggt  13620
tccacctttc gtggtaatat tcctatccaa ctgaccctct tgcaaacaac tataaactct  13680
gcacaaatta ttttaaaact gaagagtttt ttgtttgttt gttcgtttcg agacaagatg  13740
gagtgcaggt cacccaggct ggagtgcagt ggcgcgatct tggctcaacg caacctccac  13800
cttcgagcct caagcaattc tgcctcagcc tcccgagtag ctgggattac aggcatgcgt  13860
cactaccgcc tggctaattt ttatcttttt tttgagatgg agtttcactc tgtcacccag  13920
gctggagtgc aatggcagga tctcagctca ctgcaacctc cacctcctgg gttcaggccg  13980
ttctcctgcc tcagcctcgc aagtagctgt gattacaggt gcgcgccatc atgcccagct  14040
aatttttttg tgtttttttag tagagacagg gtttcaccct gtgtgccagg ctggtctcga  14100
actctgacct catgatccac ccgcctcggc ctcctacagt gctgggatta caggtgtgag  14160
ccactgcacc cggcccttac tgtctggcta atttttaaat tttcagtcga gatggggttt  14220
caccatattg gccaggctag tcttgaactc ctgacctcaa atgatccacc cgcctcagcc  14280
tcccaaagtg ctgggattac aggcatgagc caccacacca ggcctaaaaa ctgaaggttt  14340
gaatagagaa aaagcatgct ttaaaagtaa agaaaatgga attttgccta gcatatgtgg  14400
agtcctaata tgcagctctg tttccttaaa ttccatgaaa gccatgcagt acctttgcta  14460
gtttctcctc acagatcagg ataacctagg gggctcttgt gtgaatcgtc ttctatttct  14520
tgcagcctaa ctcataggct ttcgttgttc aatatttgta tgatggtttt gatactattt  14580
ttggtaaccc atgacagtta tttttatttc taatttttta agtaagcaaa tgggcagaga  14640
tattaactgg taaaagtcca actgatcacc cagggtggac tgaatctctc aactgatgct  14700
ctgttgctgg agccctgaga aacccgcata ccctgcccgg gcacctgcct ggggttgtct  14760
gctgcgtgtc ctgggatggt tcaattcacc aaggacttcc tctggtataa atcttcagct  14820
tccttgcatg ccctcagttg ctatttaagc tttctgtttt cttccctaaa ggaatcagtt  14880
tagacttgaa attcagtttt tcctgaaact gatcagaagt tagtgacacc ttgattggat  14940
ccgtttttct gtcaggtgat gaatctttgg aaaatttact ttctgtattc tgtgtttatt  15000
taaatctgtg gccgttattc atcatgtatc ctttatgcct atgtacgtaa aaaatcttgc  15060
taatacatta ttttttagac aactttatgg aggtataatt cacacaccat ataatttacc  15120
cattaagtta tgcaattcat tggcttttag ggtatttaca agttgtgtgt tcattgccac  15180
aatcatttat agaatattat cattattaca aaaagaaact ccatcacccc caaaccccaa  15240
gccctaggaa accatgaatc tactttctgt ctgcatagat ttgcctgttc tggacatgtt  15300
atataaatag aataatacac tatctggtcc tttgtgacga tcttctttta ctcactataa  15360
tgttttcggg gttcatccat gttgtagcat gggtcagtac ttcatttctt tttattgcca  15420
aataatattc cattgtatgg atataccaca ttttatttat acattcctca gttggtggac  15480
atttgggttg tttccatttt ttggccatta tgaataatgc tgctattaac atttgtgtga  15540
agatgtattt tcatctgtca cggatatata ccttggcatg aaattgctgg accatatggt  15600
aactctgttt aattgttgga agaactgttt tccaaagcaa ctggaccatt ttacatttcc  15660
attagcaatg tatgagggtt atgatttctc cacgtcctca ccaacatttt tgattatagc  15720
```

-continued

```
cattctagcg tgtgtgaggt gttaatctca ttgtggtttt gatttgtatt tccatgatgg  15780
ctaatgatac tgagcatctt ttcatgtgct tattggccat ttatttttat ttttgataca  15840
gtctcgctct gttgcccagg ctagagtgta gtggcgcgat ctcggctcac tgcaacctct  15900
acctcccagg ttcaagtgag tcttatgtct cagcctcctg agtagctggg actacaggca  15960
tgtgccacca tgcctggcta atttttgtat ttttagaagg gacggggttt caccatgttg  16020
gccaggctgg tctcgaactc ctgaccccaa gtgatccacc tgccttggcc tcccaaagtg  16080
ctggattaca ggtgtgagtg actgcgcctg gccttattgg caatttctgt actgattttg  16140
gagaagacac tattcagata ctttgcccat ttttaaaaat tgggctattt gctggccggg  16200
catggtggct cacatctgta attccagcac tttgggaggc agaggtgggc agatcacttg  16260
aggtcgggat tttgagacca gcctgaccaa gatggagaaa aaacatctnt actaaaaata  16320
caaaattagc cgggcgtggt ggcgcatgcc tgtaatccca gctacttggg aggctgaggc  16380
aggagaatca cttgaacccg ggaggcggag gttgcggtga gccgagattg tgccattgca  16440
ctccagcctg ggcaacaaga gtgaaactcc atctcaaaaa aaaaaaaatt gggctatttg  16500
ctttttaatt atttttttaat tatttgaaaa taatttaatg catattttag actaatttaa  16560
aaaataagat agtgattgtg actccagtca tatagtagtt gtaaaattaa tatagaatga  16620
aggcatatgt atgcataaaa cttgctatgc tttttagtgg ctctttgtgt atctggtgga  16680
ttgttgatca ttctttttcc ttcctcttag gagctcattt tgcagctctc aagcttttat  16740
agcatgctgt aaacaattgt caaagttgtt tatcaagaaa cagatagagt tgcaacttgt  16800
ttctagtaat agaaactttt acactgcatt caatgcctaa cgttgcagaa acagaaaggt  16860
caaatgattc tggaaatggt gagcacaaat ctgagagaaa gtcacctgaa gagaatctac  16920
aaggtgctgt aaaatctttc tgcacaagtg cctcaggagc acccttgggt cccaaaggag  16980
atggtcatta tccatggagt tgtccagtga ctcatacacg ggaaaaaaatt tatgccatct  17040
gttcggacta tgcctttctc aaccaggcga cctcaatcta taaaactcca aatccatccc  17100
gctctccttg cctccctgat agtacctctt tatctgctgg aaataattca tcaagataca  17160
ttggtatccc gactagtaca tcggaaatta tctacaatga agaaaatagc ttggaaaact  17220
tatccaacag cctgggcaag ctacctctcg catgggaaat tgataaatct gaatttgatg  17280
gggtgaccac aaattcgaaa cacaaatcag gtaaggaggg agccatgaag ttcatatgtg  17340
aaaataatga gaaaacaaac actatgtctt gtttaatctt gccattacac atagtttcct  17400
tgtataatac tagataagga acatggctat catcttgtct gtcaatgtag ttttaggaaa  17460
gtaaccttga cgtagggcat gtagttcatt gcggggcttc cactggaaac ttcaagcata  17520
agctttgtat caaatatttt gagagatttg aaaatctaat aatgtaaaat attataaaca  17580
gatggtagct tagaaaatga aatgttaata acatggctag aataacttac tactgtttca  17640
tagttttata ggcacatgaa gttgtatttc ctgaccaaac atcttttttt cctgctatat  17700
aatgttttag ctttttttgt tgttaaaatt ttttaggcac ccagcaaagc ctccatgtac  17760
caccaagtgg gttgtgtact gctcaattta agaggatgct gtttaccgag gttgtgcata  17820
actttcacag ttgcaatggg gtggtcctat ggcagataga aatactttac acttctttct  17880
tttgaattca aagtaataca ggaattttat gaggcaggta ctgttagccc catttgtagg  17940
tgaagaaatt gaggcttaga agggataaat ctctagaccg aagttgcaga gttaataaga  18000
ggaggtcaaa ctaggatttg tatttacttc tagtcttctc tgatgatttt ataaaacctt  18060
aatgcttctg cttgtttatc tgcaaaatca atttgtttca tagaatttta ggtaaatttg  18120
```

-continued taattcttaa gggtaggagg gggattttgc tttttttgtc taaatttgta ggtaatgagt 18180
ctgcaatttt ctttttgtct aatgcctttg gccagttttg gaattagggc tatgcaaatc 18240
ttctaagaaa agttgggaag tgtttttttcc tcctgttttc tgaggatttt cagagagata 18300
ttaaaatctg tatttataat tatggagttg tcttgatttc tgttaatttc tgacaaattt 18360
taatttgtcc atgtcattta agttgtcaaa tttgggggct taaagttaat gttatccctc 18420
taacatctaa ggaatctttg ttgacaactc cttttgcatc ctaatactgg taattaattt 18480
atttctctta tttttttttaa aactgatcaa tctagctagg agtttatcaa ttttgttaat 18540
cttttcaaat aactagcttt tgttaatttt ctcaattgtt tgttttctat ttcattggtt 18600
tctgctcttt attatttgct tcctctgact tactttgggt ttattttgtt cttcattttc 18660
tgacttctta agatggaagc ttagatcatt gattttagac ttttctacca taagcataga 18720
atactccaaa ttgctaagta ctgctttagc tgcagctcac aaattttgat atgcttatta 18780
ttattactta attggaaata ttttctaatt tcctttgcaa tttattcttt gatacatgta 18840
ttacttagat gtatgctgtt taatttctag atattaatag tttttctaaa tattgatttc 18900
tagtttagtt ccattgtgga cagagggcat atgctctcag tctttttaaa tttactgaga 18960
cttgttttat gacccaacat atggtctatc ttggtgaatg tgccatgtgc acttgaaaag 19020
aatgtgcatt ctgcagtcat tgggagtatc tataaatatt aattatgtcg aagtgtttga 19080
aagtgtcatt cacatctttt gtgtctccgc ttaacttgtg tcttgttcta tcaattacca 19140
aaagaagggt gttaaaaatc ttcaactatg attgtgaagt tgtcttttct ccatttaatt 19200
tcttttttaa aaactaatac atgtctaata acagaaaatt tactgtctta accattttta 19260
cgtgtacagt ttagtggcat taagtacatt tacgttgttg tgcaaccatc atcactattc 19320
atctccaaat ctctttcctt ttctttttctt tctttttttt ttttttctga gacagagtct 19380
cgctctgtcg cccaggctgg agtgcagtgg cgcgatctcg gctcactgca agctccgcct 19440
cccgggttca caccattctc ctgcctcagc ctcccgagta cctgggacta caggcgcctg 19500
tcaccgtgcc cggctacttt tttgtatttt tagtagggtc ggggtttcac cgtggtctcg 19560
acctcctgac ctcgtgatcc gcccgcctcg gcctcccaaa gtgctgggat tacaggcgtg 19620
agccaccccg cccagccctt cttttcatct tacaaaataa actttgtacc cattaaacaa 19680
taaatcctca ttccttctcc tcacagtccc tggaaaccac aattttactt tttgtcactg 19740
tgaatttgac tattctaggt accttatgta agtgaaatca tatagtattt gtctttttat 19800
gactggttta tttatagcca cccctgctct cttctgggtg ctatttgctt tggaatactt 19860
atttccatcc ttttactttc agcctatttg tatctctaga tctaaagtga gtgtttcaga 19920
gacagcatat agttagctaa ttttttctgt ttctgttttt gtgtgtgaac ccacgtatac 19980
aaaaacatat ttttaaaaaa atgcattctg ccagtctcta tgttttgagt ggagaattta 20040
atccatttac atttgaagta atcactgata aggagagact tgtcatttta gtacttgtta 20100
tttatatgta aacactctgt tcctatactg cttcgtccac acttaacttt cagttattga 20160
tgttatcaaa ttacaaattt atatattgtg tgtctgaaaa cataaactaa taatttttat 20220
gtattaatct cttaaataat gtggaaaaca aaatgtggag ttacaaacca aagttattat 20280
aataatagct tttttatttt tattttttat tttgaaatag ggtcttgctc tcttgcccag 20340
gctggagtgc agtggcacga ccatggctta ctgcagcctt gacctcaggc ttaagcaatc 20400
ctcccacttc agccttctga gtagctggga ctacaggtgc acatcaccac gactggctaa 20460

-continued

```
tttttaatat ttttttgtag agatagagtc tcactatgtt gccaggggtg gtcttgaact  20520
cctgggctca agcaatcctc ctgcctcggc cttccaaagt gctgggaata caggcatgag  20580
ccactgctcc tggcctacta ctagctttta agctaataat aatttctcaa aaatgtatta  20640
gtctcataaa tcatatagaa tacaaaaact ggagttgcaa actaacaaaa taacactggc  20700
ttttataatt gttcgtgtat taccttcact gaggtaaatt tatttcttcc tatggctttg  20760
aggtactagc taatgtcctt tcatttcaac cagcaggaat ccttttagca ttccttacag  20820
ggcaagtcta gtggtaataa actccttcag tttttgtttg tctgggaatg tctgagtttc  20880
ttcttcactt ttgaaggaca gttttgctgg atttagaatt cttgtttgaa tttttttttt  20940
atttcagcac tttgaatata tcagcccact tccttctggc ttccaaagtt tctgatgaga  21000
aatctgttga tattcttatt aacagtccat tgtatgtgat gagttgcttc tcttgtgttg  21060
cttttaagag tctttgtctt tttgcaattt ttaaattttt tatttgatac ggagttttgt  21120
tcttgttgcc caggttggag tgcaatggca cgatcttggc tcaccacaac ctccaccttc  21180
tgggttcaag caattctcct gcctcagcct cccaagtagc tgggattaca ggcgtgcgcc  21240
accatgcctg gctaattttg tatttttagt agagacggag tttctccatg ttggtcaggc  21300
tggtcttgaa ctcctgacct caggtcatcc gcctgcctca gcctcccaaa gtgctgggat  21360
tacaggcgtg agccaccgtg cccagccttg caattttatt ataacatata ttggtgtggg  21420
tctttctaag ttcatcctat ttggaatttg ttgagtttct tggatgttta tattcatgtt  21480
ttttaaatca aatttggaaa gtttttaggc attatttgtt tggataatct cctacccctt  21540
tttcagtgtc ttctccttct ggaacttctg caatgtatag gttggtccac tcgatggtgt  21600
ccccaggtcc cttaaggtct gtttactttt cttcagacct tttttttct gttcctcata  21660
ctcaattatt tcagttttcc catcttcaag gtcactaatt tttctgcctg ctcaaaactg  21720
cctttgaatc actctagtga gtttttcatt tcagttatta tatttttcag cccaagaatt  21780
tatttttggt tttaagtttt ctatctcttc attgatattt ccatgttctt catacataca  21840
tctttcgtta gttcttttgg catctttaag atagtggttt taaagtcctt gtctagcaag  21900
tctgccattt ggtctttcca ggatggtttc tgttggttta tatatttttt tgtttctttg  21960
aatgggcctt attctgtttc ttgtgatttt ttgttgttgt tgttgttgga aactagacat  22020
tcaaatatta tttaataatg cagtaactct ggaaatcaat acccatcttt cccagagttt  22080
gttgatttta gtttttgttt tttgattgct ataggctgtt tctatgctgg taatcaacct  22140
gaggtataca tttaagggct tctcagggaa aagcccctgc ctttctctga gtgtgtacag  22200
tgattttcta catttccctg tataagtgat tgcttttgaa tatactgttt ttgaaatgtc  22260
tggctcccca aacagaaaat ggagaggaaa aaaaacagaa caaaaaaacc acaccaaagg  22320
tgctggcccc ttaagtcctc tggaagttgc ttctgttgta gtgggagggg cttgcaacat  22380
tggagggaga gttgcaacaa tggctgcccc cctgtatctg tgctttcaag atcagaagca  22440
gcagtcagca atcagaacac agatttccaa ttttcatagg acatggacct ttttgcccac  22500
catggttccc acaaactgcc tgaagcttct ccaggagcat atgcacagtt tcttggactt  22560
ggggataggt agttgtacct tgctatgtgc tgaaattgac caaaatttgc atttactgtt  22620
caggacttcc tctgaaagtt gcaatccttt gaatagactc tggaattcca aaataattac  22680
atcagacaga ttctgccagt gcagttgtct aggtggggag acagattcct ggtgcctcct  22740
acactgcact taattctgtt aatttttta aaaatgtaat ttgaagctct gttattaagt  22800
tcacatacat ttatgagatt taggccttct tcctgaattg acccttttat cattatgaaa  22860
```

-continued

```
tatatttcgt tattcctgga agtatttctt gttctgaaag ttactttgtt tgatattaat  22920
aaagctcctc agctttattt tgattatatt tgcatggtat atatttttcc atctatttat  22980
tttagttcta gaatttacat ttttatagct tctatttctc atctgagatt tgctatattt  23040
ttcatttatt acaagagcat tttatctatg tcataatgca gagttataat atctacttta  23100
atttcttatc tgcaaatttc aaaatctggc taatctcaca gtaggcctta tctttttttct  23160
tgagaatgag tcatattttt cactttcctt atatgttcta taattttgca ttgtatccta  23220
gagagtggga ctattatgtt atggcaactc tggtatattc cttcaaagtg ttgatttttt  23280
tttggttttg ggaggcagtt aatttggttg aactaaaact gtaaattctg tctccttggt  23340
acagctccaa ccatctcagt tcagctcttt tagctgtgtt gcttgaattt gctccttaca  23400
tgcatggtcc aggggtcagt ccaaggtttg ggccaaattt atacacagaa tttgggcccc  23460
ctcttctctg tggctctctt ctttctgggt ttcctctcac ctcactttca gtgatggtga  23520
ttgcacagga ctctgtcctt tggttcttcc agtaaaaaaa gacagtggat tttctgcttt  23580
tgtttgctct tctcatacct ttttctaaaa gtcagtgtgg tgaatacata tatttgtgtg  23640
tgtatgtgtc tgtgtgtgtc tgtctgtctg tgtgtgtgtt tggtgttgag gctgtgtgtg  23700
tgtgctgtgg gtagggtgag gaatggaaga aggaactcag taatgagaag gagcagtggg  23760
cgaaggttct tgaagctgat gtgatggaag gcagaaggtg caggtgttgc tcttctatgt  23820
tcccatctca aacggcgctt tcactttgat gtggcttctt tccctcaagt caaatgaact  23880
tttgcctgtg ggaccagctc tttctgtggc agtgcgggca ttttatgaag tacgctcatt  23940
tgggccgtat atgctaattg atcccagggg caatccgaga ttcaacaaaa agagaatagg  24000
gggcaaggtc atggaaccct agaggaaagt gtgagtacag actgttggca gagcctatca  24060
aggtcacaca tttctatgtt tcattagctt taacatttta agtggctggg aaaactactt  24120
agggaattaa gtcattatta ggcagtgaag acatctcaag aaatgttaga aactaattct  24180
tctgttatct gactctgtaa gagtcatttt accagtcaag gaaatttggc acaatgagat  24240
ttggcacagt tgctcacctt tgccagtgat gttcagctct gtgaaaagtg tgttctctgt  24300
aaaaacttag aaaaaaataat taaaagggtc acgcatgatg gctcacactt gtaatcccag  24360
cattttgtga ggctgaggca ggtggattgc ttgagctcag gagtttgaga ccaacctggg  24420
caacatagtg agaccctgac tttgttaaaa atacaaaaat tagctgggca tggtcgcacg  24480
cacttgtggt cccaggtact cctgaggctg atgtaggagg attgcttgag ccccggaggc  24540
agaggttgca atgagtggag attgcgtcac tgcactcttg tctgggcaac aaagcaagac  24600
cttgtctcaa aacaaacaaa caaacaaaca aacaaaaaga ataattaaaa ggaaggcgaa  24660
acattgtttc ttgactttat agtcttcatt attattacat ttttacagaa attccctgtg  24720
taataatagt tcctgagttc cagctgttcg taggtgtcaa atggtttctc tgtatagtat  24780
cttgaaggaa taaaactgat ctctttccat gtttgcttac taggcatata tgtatataat  24840
ctattttata atttatgaat gactcataaa aatgaaatat tagccttcag ttaattttta  24900
taacagaact gttttaaaat agaatatgtg tgaaatatta aagtatttga gcatagctat  24960
ctgaaatctt aatagtattt taatgaaatg aggcttggat gttatttatt gatattttac  25020
tttatataat tttttactag atacttcact aacgatttag aaataaaact tataaaaata  25080
aaaagtatag ggatggatac cccattctcc atgatgtggt tatttcacat tgcatgcttg  25140
tatcaaaaca tcttatgtac ccctaagcat gtacacctac tatgtactct caaaaattaa  25200
```

-continued

```
aaaaaattaa aaagtacaaa ttctcactct tacttttggc ttccttttgt ctagctccca  25260
attctccctt ccccagtagt aaccactgtt gtttgccttg agggtctttt ggagaatgtt  25320
tgtatgtgtg tgcatgtatg agtgtgtgtg cacatgcata catagatgca tacatgcaca  25380
caggaggctt gcttttcatt ctagtttctg tgctagagtt gcattttagt aatgtatatg  25440
tgtgcatcat tcttcattca ttctgtcgtc tctgtcggtc cagagatatt tttaaacatc  25500
acatcatcac attaatggat ctggtgcttt tactttctta acagagttgc tttaatttgg  25560
ttttattgtt ttatagaaag ccttcatttt ctggaaagtg gtctagttaa attttttac  25620
tgtcgataat ttgattttcc ggatgtggct aaagatttag tgattgactg ttccaccagc  25680
taagtgacta gctctggaat tggagtataa gaacctgaca cgaaatagga ttcatggttg  25740
tttaaatttg tttttattat ttctctttaa ggtaggggac tattattgaa aatacatgta  25800
ttacttcatt gtgtttgcaa atatcacttt tagaacctgt ggcagttatt tatttgttat  25860
tatttttct ttgcactttc tcagcagaat tattaaggca gttacttctt aattttggtg  25920
cataattaat ttttgtcatt tcagtttact tcatcttaag cattttgctt attttatact  25980
cttgtattct aggcaatgca aagaaacaag tttccaagag aaaaacttca gataaaaagg  26040
gaagatatca gaaggaatgt cctcagcatt ctcctcttga agatattaaa cagcggaaag  26100
tattagacct cagacgatgg tgatgttatc agtttttatt tttttcattt ttgaaatatg  26160
taatatatgt tggcaataac gtagcagttt acaaattaat acattatatg tatcataaat  26220
atttttattt ctaaaattat taccaggatt tctgaatatt taaagtcacc acaaatgttt  26280
gaagtagatt aataatgagt tatgctggtc tttcccaaac tcggcttatt attagagtca  26340
tctgtgtgac tccacgtaac tgccatgtag atttaacaat gattaacctt ttgatgtagt  26400
taaatactta gcttttcatt gctgaagaat tttcaagtaa gtgactgatt tttattatat  26460
ttcatctcaa gttacctaag tatgcatctc taaaaaatga cttttttcta cttaaccaca  26520
atacttttgt catacttaat aagattaacg atatttccct agtgtctaat tcccaggcta  26580
aattcacgtt tcccagattg ttctgaaaag gtcttcacat ctgtttgttc aaagtgggac  26640
ccagttgtga accacatgtt tgcttgtcat gacccataat tctctcaatc taggtcagtc  26700
tccaccccac tttccccctt gtcttttaaa aattctatta ttttaatcga caaatgagaa  26760
taataaagat tgacttattg aagagacttg gccagatatt ttatagaatg tcctacattc  26820
cagatttgta ttttcctttt agtttcctaa attatgcatc taacctcaat atttcctgta  26880
aactggaagt tgaatacaaa gacttgatta aattccagta caacatttta tgcaagaaca  26940
ctgcttaagt gggccctcat acttcaaagg tttcacatca gaaggcacat ggtatctgat  27000
tatccagtat tagcaattct aagtgattac tgggttaagg tggtgacagc tgtattctac  27060
attgacgagt tctttctttc tcctctggta ccctcaagta atcagtagag tgacagagtg  27120
gcattaggta atagccaggt tccatcagct ttttacctta tggttttagc caaatgtatt  27180
gacaacccaa acccattgat gatccttgtc tgaatatttg ttgcaaaatg gttatatttc  27240
aaaattccaa ttttttttt tttttacttt tattacccag ccttcttctg tagctttcac  27300
tgatcaactg gggctatttg gttatcttaa aatacagttc ctagtctaat gaaaacaagt  27360
ttaattcatg acaactttta tgtattactg accctgattt gggtttttaa aattcctttg  27420
tatgacattt tagaaatata tttttatcac ttatttaata aatattggac cctttgctgt  27480
aggctgagaa acagagatgc acacaacatt gtctttgttt tcccaaggtt tacaatccag  27540
ttgaggtgag gggactaaac agaaaaatgt taaatatctt aggcagtttg tcatgtgatg  27600
```

-continued ggtatgaatc actaattaac catgaaagga ggtaatgatc accagaatgc tttactaagg 27660
tcctgggtct taagggagga aatatgaagg gttggagggt gaagggtctt tgaaagaatt 27720
acagcaaagt gtctctggaa tgtgggtaat gaagagtaga gtagcttgtc taaagtgagg 27780
ctcagagagg ccaagaaacc tgccagtgtc acatggctaa taagtagaag atcttgtatt 27840
gaagctgaag agtcagactc aacattcatg ctgtttgcgt ataatacatg tcatgatctg 27900
tttcttagat atcaggctca atatttagat ttttttctg agttaaagat aagccatgga 27960
cgatttctta acaaaaggaa cttttatcaa gataaatttg gaatagttag tatgtaggga 28020
ataatggaga agagacatta aagtcacaaa cattcatttt agtttctttg aaaagaaggt 28080
tttgctcgtt tgtgcttcta atcacttaga tttaagcttt gtttcaacaa caaatctgtg 28140
taactacata ttaatagtat aacatgtgag gccatgaagg ctaggactag gaaggataga 28200
tgggagaaat gccctgaggg gaaaacatca ccaggactat aagcctgttt tccactgaga 28260
atattacaag attaggttag aatggaaagt cccgtagaag atagtagaat gttggtaagc 28320
attttaacct ggtcataaac aagactagga aacaagttta gattgatgaa aaagtatgaa 28380
aaatcttaag agaaattccc ctttccctct cctttttaaa aattctttca ggccaaattt 28440
agtgttatga gaaaaactat atacatgcat gcaatacttt gttagtaaat atatgtaaag 28500
ataaatgttg taaaatataa aacactgtta gtattggact tgtaaaataa tccccaaaat 28560
tgaactctgg caaaaatatt cacagcagaa aaaaaaaatc agtaaatgaa tgagttgctt 28620
gtgttttatc agcaagggcc atatagctta tgatgacaga actgttaata atcacttgtc 28680
cacaaaggtc tcttaggttg gagttcacac tcatatttaa acaactaggg cagattactt 28740
gaataaggac attagtaaat tgctcatgtt tccagggata ggggaaaggg gtaaaaggga 28800
gttgtgttgt tcagtgggta aagagtttca tttttgcaag atgaaaaagt tctgttgcct 28860
aacaatttgc atatagttga cactactgac ctgtacactt aaaaatagtg tacatgataa 28920
atttgatgtt gtatgttttt atcacaatta aagaacaaag caaaactgag ggaggactca 28980
atagatttga cagtaaggtg ttgaagacag cacttagtat gttaagtgat agttattagc 29040
ttttgtgtgt cattttgtgt agtctacaga tttagggctc gtggcacacg ttctcactga 29100
taagtgagag ccgaacaatg tgaacacatg gacgtaggga gggaacaaca cacactgggc 29160
cctgtcgcgg ggtgggaacc ggggacagga gagtatcagg aaaaatagct aatgcacaca 29220
gagtgtaata cctaggtaat gggttgatag atgcagcaaa ccaccatgac acacatttat 29280
ctatgtaata aagctgcaca tcctgcatgt ataccctgga acttaaaaaa aaatattgaa 29340
gggtcatggt taacttgtat gtgtgccaat atgcatagta tatatacata tacaaatgca 29400
tatatgtaca catgcatatg tctaattttt cattttgtaa ttaattttta gaccacacta 29460
aagttgctct tagtgatgat agggcttgtt tctttgtttc attgtggcta cttcttagca 29520
ccttctttag aaagcagtta ggagaagatc atttgaaggc caacgagtgt tgtgggttat 29580
tgttaagctg atttaacatt atctcccccc acaaccacgc ttgactagct tcacatttgg 29640
ccaggtgcag tggctcacgt ctgtaatcca gcactttggg aggctgaggt ggaagatcac 29700
aaggtcaaga gattgagacc atcctggcca acatagtgaa accctgtctc tactaaaaat 29760
acaaaaatta gctggttgtg gtggcgcacg cctgtcgtcc cagctactcg ggaggctgag 29820
gcaggagaat tgcttgaaca cgggaggtgg aggttgcagt gagccaagat tgcaccacag 29880
cactccagcc tgggcgacag agtgagactc tgtctcaaaa aaaaaaaaaa aaaaaaaaaa 29940

-continued

```
gagaaagcaa acgtatttct tcttaaaaca gaataaataa atagtctgtc tctttctcct  30000
tctgttcaca tttgccccag tttcttctct tgaatcatga cagtttggaa aattgtctgg  30060
attgcttagt gccactgaat catgccatgg aaggattttg tatttcactt ttaaacttct  30120
ctgtgacagg agaagcactg cttcatggct tcttgcccaa ggattttaga tggacacagt  30180
gggtaataaa tggatgaatt tttgtttggg ttgaagaatc tctctgagaa gttgacacgt  30240
gggggcaatg gtttgtttct cttgtatttc tgaagttgca aataatcatg taagcagttc  30300
aaccaggagt ttacaccaaa cttttaatag gcgatatatc attatttttt ttcccattgg  30360
tttggataac atccacttta actggcagtt agtcatactt agctattttt gttaaagcag  30420
gtgatttatt gttattttat atttatgaca tgattaataa gtgaatatgg aagattttac  30480
attgacttag gggatcaaag ttttcattat attaacacct ttaattgcca tgagttttct  30540
atttctagca tgcatatttt gtgttcattc aagtgaagaa aacagtcttt tgtgttctca  30600
ggtactgcat aagccgacca cagtataaga cttcttgtgg catctcttca ttaatttctt  30660
gttggaattt cttatacagc acaatgggag ctggaaagta agtatgtcaa tttatcagta  30720
cccccaaact ccaaagtaat ttgatgttgc tttttctata acagaaaaaa atttaagaat  30780
agatttttta taaatttaac aaaaccctgc tgtattttag tgtaagtctt ttagcttaaa  30840
atatatacat gtattatttt cagtgaaata aaaatgggct gggtacagtg gcccacactt  30900
gtaatgtcag cactttggaa ggccaaggcg ggagtattgc ttgaagccaa ggagtttgag  30960
accagcctgg gcaacaaagc aagaccccac ctctacaaag taaaaaaata aaaacaacta  31020
gccaggcaca atggcatgta cttgtatttc tagtctctta ggagactgag gcaagaggat  31080
cacttgagcc caggagttta aggctgcagt gagctatgat cacgccactg cactccagcc  31140
tgggccacag agtgagaacc tgtctctaaa aaaataaata aaataaaata atgaaaaata  31200
ttactaatat tatttgcaaa tcagacaagc atattaacat tgagacaggc tgtatttgcg  31260
tatgactgga attgaaaaat gaaaggcaat gaatgtttct tttgtagcct tccacctatt  31320
acccaagaag aagctttaca tattctgggc tttcaacctc catttgaaga tattaggttt  31380
ggtcctttca cggggaatac aacacttatg aggtatgaag accctcttag aggcaatatc  31440
gtgtttctag ttttgcaaaa taataatgat gtagatgtgt gttgatagta aaccatgtat  31500
ccagctgctg ggcttcaacc tctcataggt ataccaactt tgggctatgc ctgaatttct  31560
ttagaattgg aataatgcca tctttgttgt agaattgttg ccatgaacaa atcttcttgt  31620
tactttcagg tggtttagac aaattaatga ccacttccat gtaaaaggat gctcttatgt  31680
tctatataag cctcatggga agaataaaac agcaggagaa actggtaggt aaacatatag  31740
aagatttaca tacacacata cacacatgca cacacacaca tacacacaca cggtttagag  31800
ttcgtctcaa agactgcctg tttagcttcc tgggacatta tgtaaaccct cagcacagtc  31860
tgttacttgc atgtaatctg tagggcactt tttaataagc agtttaatat tttacctctt  31920
ctaacctttt tatgtagaac ctttagaact ttaaggtata tcacaaacac tactctaaca  31980
cattgtattg tttgggtccg tggtgtgtgt gtgtgtttgt gtgtgtatgt atgtgcgtgt  32040
gtacgcgcac atgctagtaa aactctaagg aagcagcatg gagttagcag ttttcttcct  32100
aagaaggaat gtaaggattt gagaatattt gatgttagac ctgtgtggtg acatataatg  32160
gcaggaaaat agactgttga agtgacaaag ttctgctata aaatagtctt gtttataaca  32220
gaaatattaa tggagttgat ctcaaggatt attttagtta tgtgctaatt aaataatttg  32280
tactatttag caatttccat ttttaaaatt gttacaatct tttgactgtg taaatcagaa  32340
```

-continued

```
aattgtaata cattgttaaa gaaaaaatta ttctgacact tgttaatagg gtgagaagac  32400
tttattttaa acttgtgaaa ggcctattgt agtaggaatg agagatcagg ctcagctctg  32460
aatacagcaa agacaacaaa gacaactggg actttatagc caagggacac agcgaggggt  32520
ttgggggtgg gatattacta agagggtcaa gggtatgggg attcttgcta aagcctaaca  32580
gacttcttgc taaaggcagg tcaagggctg agacatcagg agttggcagg ggacgtccgt  32640
aaggaacttg attagatatt aagggttgtg ggttctctct aaactgactt agcaggattc  32700
atgctaaaac tggacacaga agtctaaggt ccaggcctgt ttgagaagag gactcaagga  32760
ttaatcagga agagaattgt tatcaataga gggtatatgg tttaccaagg taaaagactg  32820
agcacaaagt cagatatatt tctgttgacc tatattgggt atatcaggtt ggttacttgg  32880
aggcaggctt ggagattaca tgttgctttc tacacatact agttttgtga ccttgaacaa  32940
gtcacttgct gagccttgat gtagaccttt tatctttcta tatttgtata gggtcagtgt  33000
gaggataaaa ggagacatac ttgtaatgta cttagcacgc tgtgttacag agtaaggact  33060
cagtaagtgc tagcatttat tcctactgac taaattctat gcattcacat ggggcctgtc  33120
tatccttctg gaaaacacag ctttaaatgc tgtgttgcta tttatttctg tttctagtga  33180
gactgtcacc acactactct cagtaagtga tcaggcaacg aaaaactaag aaaggatata  33240
ttatcctgtt tggtaatttt ctcttcagct gtgtctagtt tgctttttat actgcctatt  33300
gagtttgagt tttttaaaag aggttttcaa tcatttttat tctaaaatat gtagttcttt  33360
taaaaatctg cttttaaaaa taacctcatt ccttactcat attttcaaac ccttttattt  33420
tttaaatcta ttgaaacttt ttcctctgta tttggtgtaa tgtaggaaat gtgtatatat  33480
ctgattttgc tgtctcttgt ttcttctgga tcttatttga ggtgtcttcg tgtgccatga  33540
aaagaaaatg cataatttgg cattgtcttt tatagttctt gaatgtttac ttccacagga  33600
tgtgccaaac ctttttctgg tccaaaagat ttttatggtc attctccagt tattagaagg  33660
tataataatg attctgtcag ttgtgttcat taaaagtttt ataaaatgtc tgccaatgac  33720
attttgcacc ctgtaaactg aatacatagc agttcagtga aagcaagtga gagggtaagg  33780
ggtgtcaagg cacagtaatt agcaacctga gctggcacca ccatgtggag ttcctgcccc  33840
tctctcagga tagcacatgt gtgacctggg acctttggat gtagggttgt atagtgtaga  33900
cagcatccac actcaatcca cagaataaat actagtaaag cttaatttct ttttaaaata  33960
tgagggtcac tataaataaa tgttctaata ttttgtttct gtgcccacaa agggggtcat  34020
cttgtataac cacctggatg tgtcggtact gaaaatcatt aacctagagg agcagtagtt  34080
ggcaaatgtt tttacataaa aggcttgata gtaaatattc ttggctttga gagacacatg  34140
gttctggggc agtcacagct gcttgatgca gctgcttgga tcttgaaggc agccatagac  34200
aacatgtaaa caaatggata tggtggtgtc ctgggaaaac cttactgatg gacctgaaat  34260
ttgaatatca cataattttc acatgtcaca aaatattatt tttcttttga acttttaaaa  34320
attttattat ttattttta gagatgaggg tctcattccg tccactaggc tggaatgcag  34380
tggctgtgat catggcttac tgcagccttg aactcctagg ctcaagcgat cctttcccct  34440
tagcctccca agtagctagg actacaggtt catgccactg cacctggcta atttttaatt  34500
taattaatta attaattttt tttttgagac ggagtctcgc tctgttgccc aggctggagt  34560
tcagtggcgc gatcttggct cactgcaagc tccacctgct gggttcacgc tattctcctg  34620
cctcagcctc ccgagtagct gggactacag gcgcccacca ccatgcccgg ctaatttttt  34680
```

-continued

```
gtattttttt tagtagagat ggggtttcac catgttagcc aggatggtct cgatctcctg  34740
accttgtgat ccgcccgcct cggcctccca aagtgctggg attacaggtg tgaaccactg  34800
tgcccagact aattttattt tttaattttt ttcaattaaa tttttagaga tgggggctca  34860
ctatattgcc caggctagtc ttgaactcct ggccttaagt gatcctccta cctcggcctc  34920
ccaaagtgct gggattacag gcatgagcta ctgtgcctgg cccaattttc ttttgatttt  34980
taacaatgta aaaaccattt tagcttgctg cccatttcaa cacaggctgc agtctggaga  35040
ctggatttac ctgttggtgg gagtttgcca aaccctaacc tagaggatga agcctaaatt  35100
cctgagcatg gtgtttgagg gactggcttt cgaatatcct gcttcagcct acctcccctg  35160
gtgttcagcc atgctgggct cctcgatgtt tccctgttct tcacaagata caggtcatcc  35220
ttaggcctat gtgcctcact gatgggatgc cctgctgtgg agcatgtgga atgtgggatt  35280
tcatatcttt gtgattggtg gattcctatt tatttgtcca tcctggactt cagcgtaaca  35340
aatggatatg gtggtgtccc gtgaaaacct ggggggatgg ctttttcttc tgcttgccag  35400
gcaggattca atcccttcgt ctcctgggtt gtcacagcac catgtgtgcc tctggtagaa  35460
ctttgatttc attgcgaggt aattcttggt gcaccgtatg gtttcatgca gaaaaactag  35520
agttgccttt cttgaggatt aggccaagtt cttactcatt tgtgcatcac agtgcctgat  35580
acttaggtgc tcagtaggag ttaatttaat gaattcgcaa ttgaggatat gagtcaggag  35640
gaattcagga gattggggtt acgaaacttc taagagagaa ttttgttgtc cattccaaag  35700
ctggcattct tcctttgcaa gagctctctc ttgtgatgtg gaaaggaaaa tgtttctctt  35760
ttccctttct gtagctcatc tttccttctg gctcctacct gctctcccct ccccacactc  35820
ccagacacac actcacctgc acctgtgtgc tagatctgcc ctgctttcca tcagaaccca  35880
gtgcgtcctc cttctgtctt ctggagtctc tcagttgaca gtttttcgtg tgttcctaag  35940
gacaggaaat gagccaactc attgaatctg aagttttcaa ctttacatct tagcagtgcc  36000
ttgaacattg ccttttacat tataaatagt aagagattaa gattgtctca gaatcacttc  36060
ctaactgatt catagggtgg ctttatatct cttttaatgg ggtgtggacc aaaatgcatg  36120
tctgggagta tagaaataat cactggaacg aatgtcatac ttacgtgtcg gatataatgg  36180
aaagctatta caatacagtt ctcagtcttg tgtcccaaga ctgcattatg agtaaggccc  36240
tgggagacac cagaacaagt ctcataattc cttttacttg ttttcttttt gcctgctgat  36300
tagaagagga cttcatttga gtagttaatg gctttttcta ttaatatcag cagtatctag  36360
atggagtgag aggatagatg aagagatggg tcagtcaaag taaaggaaat taagggaagc  36420
aggaagaccc agagaaatta gaataagaga gaaaatctat caaagaaact ctgggtatcg  36480
aggaaacatc agctatatac atttaatcaa attcccaaag taagaacata tacttttata  36540
attaatggaa tggaataaaa cactaaaagg gccatggaga gagttgactt aggaatcact  36600
attctggaat tttaaaagat ttttgatcaa ctgtcttgtc caactttaag attttatact  36660
ataattttgc tagaaattct catttgtaga tcttttgaat atctgtactt tatttatttt  36720
attttccaat agtctggtac ctcccaagtt ctttgtgact tatttaaatg taatgatttg  36780
gtgcatgtgt taaccagttc ccttaataat ctaggatgtg tagcattggg tcccaatgac  36840
tttttttttt tttttaacct atttgtttaa atttcctcca gcatacatcc aaacttttca  36900
ttgaggaatg ggataaacta cctattttcc ttaaatttgt tttcttttgt tagggggttg  36960
aggtgcttac tgtaatttga gtaagtttta atatattttt caagttttat tcctactttc  37020
aatttttttt ttccagaata ttcgactttt tactgctttt ctgtgtgcat ttcctgaagg  37080
```

-continued

```
ataattaatc tgcgtacgcc tcctggaata tttttgtctt tacctttgct aattgggggga  37140
cccagttaag ccctgcttca tctctgatat gttccttggc caccttagcc ctggattcct  37200
ctaaattcct ctagtactga tttttcacac ccatcatttt ccatttgcta tgtgctatgt  37260
tttattatgt ttcacctgtt caatgtgagt gtccagctcc ttgaccatag ggactgttct  37320
gagtagccct tacatgctag atatgatgcc cacgacatta cacgttaccc tatgaattct  37380
gatggtattc aggcggtagg gtggttcatg tgtaaagcag acgtctcttc cgttctctcc  37440
cattgtggaa gaaagagttg cagagatagg ctttctgatt tctctctggg atgttcactg  37500
gtgaaaacca ttgtcagtgg cgctatttgt ttaaaaacac ttttaaatct atcttctctt  37560
tgtgcttaaa ttgtttttta aggaccacta agcctgtttt tcacaatggg ctttacgttt  37620
tcctggggac cacgctgttg tgattcaggg actccccggt gcttatgtcc agtgggctct  37680
tagtaactgt aaactaagca cactaatgga ataaaagtga agtccaggga ttttgataag  37740
acttagctgt taatatcagt attttttca gagatgtcac tagtcacaat gaaaatttat  37800
tctaggagtt gccaacatta ggtctctgtt cagataactt ccgagtatgg gttcacttag  37860
ccaccaacat ttgcaccagg caagtccaga ctcatttttt taatcagcta gcttgaaaat  37920
tgcatttata ttcatgtatt tagtttttttc tagtgggtat tgcagttcat aacttttgct  37980
taacagagaa gacccgtctc tggcctcatt cctgtataac tcacacatcg cttcaccatg  38040
attgttgtta ccagcttact gaagcacctc agtacatctc cggtggacaa tacattagta  38100
ttctgttttc ctcatgtact ggttttctcc aattaatatt agacacaaat aataaatctc  38160
ttgaacatgc agtgctaaca taccccttc ctctttagga gctgtttggt gcttgcttac  38220
agcataaact gcttagtgtc attccaagct gacacaaatt ggccttcccc tgctgtcctc  38280
catgtaccag ttgtatttaa gatgtcaggg gaagctggca tagtggctca cgcctgtaat  38340
cccagcaggt tgggaggccg aggtgggtgg attccttgag gccaggagtt tgagactatc  38400
ctggccaaca tagtgaaacc ttttctctac taagaataca aaaaattacc tgggcatggt  38460
ggcgtgcacc tgtaatccca gctacttggg aggctgaggc acgagaattg cttgaacccg  38520
ggaggtggag gttgcagtga gctgagattg tgccatgcac tccagcctgg gcatcttttt  38580
ttttttttt aaaataaaaa agatgtcagg ggaataagga ccttgcagag taatgttaga  38640
ttgctggatt acctatcaga gtttcagaag ctattcttgt ctttgaaggt gtaaaaatat  38700
actctataag ttcttatgga gttatctagc attcctctat agatgatcag ggtctacagg  38760
acaagctcat actaagcaaa ctcagaatgt cagaatgtta acagagtaac ttgaagtaag  38820
aaacataatc tcaaagggac cagaattctc ttattggctg ctcagaatac ctgctcttct  38880
ccatgcagca ggccagtgga ttcctgtagt tttttctcc tttctctatg ccgtgcagat  38940
catggctctg catttggtgg tggttgcttt gttgcttaag tttcagattt taaagctata  39000
ctgaagtaca gactcaactt cattctgaat ttagcttccc tcagtaatac atttgtgtct  39060
tctcatacac agaattactt tcttggacaa ctaccttaat gtgttgaatg ctgtatttac  39120
tggctcggca cagtggctca cacctgtaat cccagcactt tgggaggctg agaggggcgg  39180
gacacttgat tttgggaatt tgagaccagc ctggccaaca tagtgaaacc ccgtctctac  39240
taaaaataca aaaattagct gggcgtggtg gtgagtgcat ggaatcccaa ttacttggga  39300
ggctgaggca tgaggattgt ttgaaccggg gaggtagagg ttgcagtgag ccgagatcat  39360
gccactgcac tccagcctcg gcgacagagc aaggccctgt ctcaaaaaat aaaataaaat  39420
```

-continued

```
aaaataaata attaaataaa tgctgtattt actatctttt atttcagagg gtgatctttt  39480
tcttattttg gcctgaaatt gttggattgt cccacagtag gctcctctat accatcctac  39540
cctgtattct ataaactaga tcacgggctg ttccctgagt atattccttt tccccagtgg  39600
ttttgttttc tcctaatgct ctttcctctg tctagattgt tgaaatcctg acacttcatt  39660
aagtttcatc ttgaatgcta cttcttcttg actcctcaaa cctgatgtgc tctttctcct  39720
ttgaattcta tgccccttt gtggcactat cttattccac cttatataaa agttacttgt  39780
tccatcttcc ctactaatgc acttgaggga ccgtgcatca ctccttggct ctcttctgcg  39840
gccgtggacc tgctgctctt agtggtcttc agctatttca gtggccagaa agtcgatcac  39900
tgaaactatg acttgcaagc tttcatctgc ttcatctatt tttaggattt ctagttttaa  39960
tgggctgttt atgaataaat aatttagctt cttctaggac atgccagtta atgaaacctc  40020
agttaatggc tttgagtact aagtgctggt gaaaagtcat ttcttatggt aatacttttg  40080
aaattgacca ctattatagt tatggcaaat gtccagggaa gagtgggcat aagaggttgt  40140
ggtggtacta ccagcctgtc tctgtagaga tgttatcttg tcacttggct tgtgaagact  40200
actcctctag cctccataag ttttgtgtaa agattaaagt gtgtgtagaa aaatctgggt  40260
tcttatcaca caacaaggaa agattaggct cacagatact ttgaagggtg aaggggaaca  40320
gaatttattg ggtgaaaagg aaaaaactca gcaaagcgag aagggttcct gctaacaggc  40380
ccccatctca cagattgaat cccaggttgc cacacaggga caggagaggc caaggtcctc  40440
ccctctgcaa acagcgggca cttcctgagg cccaacccca tcctcccagc acgcaggcca  40500
gctggagatt ctccaggaag ccgtttttac ttggctgtct cattagtagg agaagtttgc  40560
atttttagaa cttgattatt acctggagtt tatttttatt catatacatc agtagttttt  40620
taagttggga tgtgtgtact gcatatatat tagaacttct atattttaac ctaattttaa  40680
attccaactt tttgtatatc ttttataaag acatattagt acagtggtat atgtatatac  40740
tttataaatg catgtgctaa cattgggcat gcttgttcag aattttaagt gacagctgtg  40800
tacaaccaga aaagttgaaa ccattgctga atacactagg taaatttcat agacaagtat  40860
gtgtgttatt agaaggtttt ggtaagcaag gacatatttt agttctttag tttgctaatg  40920
agcttacctg aatttcagtt taaagagtaa aacagaatac atttattaac attttttgta  40980
cctatcaata gcttcttgtt tttccccagc agtgtcagtg tattccaagt aatgtctttt  41040
ctgtccttaa gcccttaacc ggtcctttgt gtaaagcatg gacactgctt tatgggcttt  41100
cagtttgtgt gtttgtttgt ttttaatagc ttcaggggcc ctgtcaaagt taacccgtgg  41160
attgaaagat gaatcgctgg cttatatcta tcattgccaa aatcattatt tttgtccaat  41220
tggcttcgaa gcaacccctg ttaaagctaa taaagcattc aggtaagcat tgacgtgttt  41280
tagaaagtgc attttaagaa atattaaaaa atagatgggt gcggtagctc acgcctgtaa  41340
tcctagcact ttgggaggcc gaggtgggcg gatcacgagg tcagaagatc gagaccatcc  41400
tggctaacac ggtgaaaccc cgtctctact aaaaatacaa aaaaaaaaaa aaaaaaaaaa  41460
ttagccgggc gtggtggcag gcgcctgtag tcccagctac tcgggaggct gagggaggag  41520
aatggcgtga acccgggagg cagaacttgc aaaaaaaaaa ttaaaaaaat taaaaaatat  41580
tcaaagtctg tgatattggg aggcttggcc atctgctttc ctgacatcaa gttagactat  41640
tctttaaaca ttatgactta ttcttctgca gaattgcatt tagttaattg tgctgttgaa  41700
aatatccatt tagatactgt tgttcagtca ttataggaaa aagtcatttg aaaagtcact  41760
tgtttttctc ttagagacag ggtctcactc tgtcatccag gctggagtgc aatggtgtaa  41820
```

-continued

```
ttataggtca ctgctgcctc aaactcctgg cctcaagcaa tccttctacc tcagcctcct  41880
gagtggctag aactacaggc atgcaccacc atgcccagct cataaaattt tttaatttgt  41940
gttttctata gagacggggt cttgctatgt tgtgcaggct ggtctcaaac tcctggcctc  42000
aagtggtcct tattcctggg cctcccaaag tgctgggatt acaggtgtga gccaccacac  42060
ccttcctgaa aagtaatttt tacatttatt ataaaacagt tgcaaaggat tttatagact  42120
atgtcacagt gcctcatcca acgtcccaca tgaacaatat attacagaat ctagtgtcaa  42180
gaagattgtc acaactgagt aaattaaaaa gcatcttctt ttcttaaagt gaagaatatg  42240
gaatttgtct gggttccccc tttgtcctga ttgcaaggaa gctctgagcc aatttttatt  42300
tccaatgtca gaaactacat gactttcatg gttatatttc ttttttgcct aatctagagt  42360
ttctgtttta ttaactatat aactttactg gtaaacttgc atctttgtgg aagagatgat  42420
ccctaagaaa gagaaggtga ctaagtttta atggtttttt tcctgtttag ccacttttcc  42480
ttatgatggg ttgagataat accaggatgg ttgaaagcca agggagaagt atctagttaa  42540
gaattggtgg gtggggtgca gtggtgtaat cccagcattt tgggaggctg aggcaggcag  42600
attgcttgca cccaggagtt caagaccagc ctgggcaaca tagtgagacc ctgtctctta  42660
aaaaaataca aaagttagct gagtgtgttg gtatgcacct gtagtcccag ctacttggga  42720
ggctgagacg ggaggatcgc ctgagctgag aacatgccac tgcactccag cctgggcaac  42780
agagcgagat cctttctgta aaaaaagaaa gaaagaaaga aagaattggt gaaaacacaa  42840
gccatgagta ctttgagcaa agggattggc ttggtcatgg ggataggatg ggtttttttt  42900
tttttttttt gagacaaggc cttgctgtgt tgcccagact ggagtgcagt ggtgagatca  42960
tagctcactg cagcctcgac ctcctgggct taagtgatcc tcccacctca gcctcctgag  43020
tagctggaac tacaggtaca caccaccata cttggctaat tttgagatgg ggtttcaggg  43080
tttcaccatg ttacccaggc tggtcttgaa ctcctgggct ccagtgatct gaccatgtca  43140
gtctcccaaa gtgcttggat tatagacgtg agccaccaca cccagccagg atgggttatt  43200
tggggctgga ggccatgtgg ctttggagtc ccactcaaag gcccctcggg tttggggaag  43260
agagggattc tgagacaggt tggaatgacc tgggagaacc aggaagctgg aagttgtgtt  43320
ttgtgaataa ggagcaagag ggaactctct tgttctctcc caatgctgaa atgctttatt  43380
catctttctg gaggtggaat ttcttgtaag tgaggtatac tgtatgtttc ttttatgatt  43440
tcatcctgca gcttcacctt atttctgaca tttatcaaat ataaatcatg gttttaaacc  43500
aactttgtac cctttaaaag agagtccctc acttctgcct gtacctaaga atcatgtgag  43560
atttcttaa aaaactatat aaatccccag gctctactcc agacctattt gaattagaat  43620
gtccagggat gggtttagga catcagtgtg tttaaagact tcattgcttt agggtttcat  43680
ttttaggatg cgttttgaga tgtcttgaat tcatagtgaa aggagaagag tagtggaaaa  43740
atgcagatag cattccagga tttttttttc ctcctagaat tttagaggtg gtatattaaa  43800
acattttata gccctagatt ttgaatagag gattaaggct gaaattttaa tttgtgagtt  43860
ctctttaatg gcctgtagaa atttgccctc acctaagctc taatgtctgt tcttgatgaa  43920
tgaatgccag gtttgaatac actctagtat gccttttatt aatatatatt tgaagcaata  43980
tactcaaggg agtaactatt aaacgtactg tgaatgtatt ttatatttag caggggacct  44040
ctctcaccac aggaagttga atattggatc ttaattggag aatcaagtag aaaacatcct  44100
gccattcact gtaaaaagta tgttaacttc cctttatttt ctttaattga ggtaacattt  44160
```

-continued

```
agatacagtg aaatgcacag atcttagttg tatataatta gtttgataaa tgaatgcacc  44220
tgtataatca ccacccaaac aggatatggt acacattcat tgccatggaa aatactctca  44280
ctctctactc ctatcaatct ccatagaaag cccctcttct gatttctgtc actacagatt  44340
tgctttgcct cttcttgaat tccatgtaaa gagaatcaga caatattatt tttgcatcaa  44400
tatcttaagt aacatttttg agattcctcc attgtgtcat gtgtatcaag agtttattat  44460
tttttattg ctgagtagta ttctgttgca taagcatgct gcaatttgtt ttccattttc  44520
ctgttgatgg gcatttggat tgctttgagg tttggtctct tgtcaatgaa gctcttggga  44580
acattcatgt acaagccttg aaacaaatta tataaaaatt ttattaaaat ataattcaca  44640
taccataaag ttcactgcac ccaccatgcg cggtggctca tgcctgtaat cccagcactt  44700
tgggaggctg aggtgggagg atcgcttgag cccaggagtt caaggccaac ctgggcaaca  44760
tagtgagacc ctgtctctac aaaaaaatta aaaaatgagg caagaggatt gcttgagcct  44820
aggagattga ggctgtaata agctgtgatc gtatcgctgc actctcatct gggtgacaga  44880
acgagatcct gcctcaaaaa aagggaaaaa agtgtacaat tccatagatt ttattatagt  44940
tacagggttc tgcaccaatc accactatat aattgcagaa cattttcatc actccagaaa  45000
gaaaccccat accccttggc agtcactccg tattccctga gccctggcaa ccactgatct  45060
accttctgtc tctagggatt tgcctattct tgtttgtttg tttgtttggt tttttaaga  45120
cagagtctct ttctgtcact taggtgggag tgcagtggtg tgatgtcagc tcactgaacc  45180
ttcatctccc aggttcaaga gattctcctg ccgtagcctc ctgagtagtt gggcttacag  45240
gcgcccacta tcacgcccag ctaatttttg tgtttttcgt agagacgggg tttcgccatg  45300
ttggccaggc tggtctcaaa ctactgatat caagtgatcc accctcctca gcctcccaaa  45360
gtgttgggat tacaggcgtg agccaccacg cctggctggg atttgcctgt tcttgacatt  45420
tcgtataaat ggtgtcatac agtatgtagc attttgtacc tggcttcttt cacttaatac  45480
agtgttttca atgtcatcca tgttttagca tggattagaa cttcattcct ttatatggcc  45540
aaatcatttc ctttgtatgg agaagtcact tttgttgtac aagtctttta gaggacatat  45600
gttttgttct cctggaagac acctaggact agaattgctg attcatagta tagatgtata  45660
tttaagaaac tgtgagaaaa ttctccaaag tggttgtaaa ccttctgatg aacagaagtt  45720
ctgattctaa ttaatcttaa ttaaatttat tttatcaatt ttcttctttt atatgttttg  45780
tgcctctata agaaattttt gcctacccca cgacctcaaa gatgctttcc tgtttttttc  45840
tagaagcttt atagatttta tgtttagatt tctgatccct ttctattatt gttttgagac  45900
agggtctctc tctatcaccc aggccagaga acagcggtgt gatcatggct cactaaagcc  45960
tcgacctcct gggttcaagt gatcctccca tctcagtctc ctgagtagct gagaccacag  46020
atgtgtgccc ccatgcccta ctaattttaa aactttttttg tagagacaga gtcttgctgt  46080
gttgtccagg ctggtttcaa actcctggac tcaagtgatc ttacttcctt ggcctcccaa  46140
agggccggga ttacagatgt gagccaccat gcctggcctt aattaccttt tgtgtgtggt  46200
atgtggtaga gctcaacttt gatttttttcc cccagtgttt atctagttat tctagcacta  46260
tttgtttaca aagattttcc tttccgtatt taacttcttt ggtgcctctg ctgaaaactg  46320
tatgtgtggg ctgtttctgg accctgtcct actaatctgt ctgtcctttt accgatgcca  46380
cactctcaat tgttgtttat actaaatcct gaaattagat agcacgaatt ctctgaattt  46440
ttctttttct taaagattgt tttggctctt ctaggacctt ggcttttcca taaaaatttt  46500
agaatttgtc cttttaatta gagtttgtaa agattttgat gaggatagaa tctatagaat  46560
```

-continued

```
tcataatttt ggctgggcgc ggtggctcat gcttgtaatc ccagcgctta ggtgggagga  46620
tcacttcagc tcaggagttc gagaccagcc ttggcactat ggcgaaaccc catctctact  46680
aaaacgacaa aaattagcca ggcatggtgg catgtgcgtg tagtttcagc tactcgggag  46740
gctgaggggg gaggatcaac tgagcctggg aggtcgaggc tgcagtgagc tgagattgca  46800
ccactgcact cctccctaag tgataaggtg agaccctgtc tcataaagaa agaaagaatt  46860
catagtttag ttttggaaga attgacatca taacaacatg gactatatct ttacttaatt  46920
agagctttaa tttcaacttt ttaaaaaaat tttttcagta tggagtttta tgtcttttat  46980
taaacatttt ttctctatgt gttctattac actgctggtg ggaatgtaaa ttagtacaat  47040
cactatgaca aacagtatgg agattcctta aagaactaaa agtagatcta ccatttgatc  47100
cagcaatccc actactgagt atctgcccaa aggaaaataa gtcatatgaa aaacacacag  47160
gcacacacgt ttatagtggt acaattcgca gttgcaaaga tggagaatca acctaagtgc  47220
ccatcaacca atgagtggat aaagaaaatg tggtatgtat attaccacgg aatactactc  47280
agccataaaa aggaatgaaa tgatgtcttt tgcaacaact tgggtggagc cggaggccgt  47340
tattctaagt gaagtaactc aggaatggaa agccaaatat catatgtttt cactttaagt  47400
gggagctaag ctatgcggat gcaaaggcat aagaatgata taatggactt tggggactcc  47460
tgagggcagt ctgggaggcg ggtgagagat aaaagactac atattggatt cagtgtacac  47520
tgcttggatg atgggtgcac taaaatctca gaaatcacca ccgaagaact tattggtata  47580
accaaaaccc agctgtaccc caaaaacaat tgaagtaaaa cttaaaaaag atattgcaat  47640
aaaaaggttt tcctcagtgt gttatacttt ttgatgctat tgtaaattga tttttttaaa  47700
atttcatttc ttcattattt gctggttgaa tacaaaaata caattgattt tcctatgtag  47760
accttgaatc ttccatcttt accaaatcct tttagttcta gtagttgttt tgtaattccc  47820
ttggattttc tgcacaattg tgttgtctcc taatagagac atattaactt tacattcttt  47880
taaaagtgga cttgactgta attgaaaagg aaatatagca tattgctgct ttagcatgca  47940
ggatgtcatc taacatgttg gtatttattt attctgtagg aagagtaacc aattgtacac  48000
tgaaaacctt ggcaacggtt ggataaacag aattgtcata aaactagaag ttattacagt  48060
ttagtagatg aaacaatgtt gagataagag aattactgcc aattattgct gtgataatat  48120
tgcagcaact tgctcatgaa aaattccatt gcaatgatac tttagaccta aagaaaattg  48180
tgctttatcc tttcttctta actatagatg ggcagatatt gttactgatc taaacactca  48240
aaatccagaa tacctggata tccggcactt agagagggga ctgcagtata gaaaaacaaa  48300
gaaggtaaga agaacaccat tgtgtttgaa ggcatttccc agctgaccaa aatgtggtgt  48360
tttacttagc actctttagg ttgcaagtaa cagaaaccta tatttgatag aggagtgaaa  48420
attattttaa ggacacacgg ctgtctttaa aacccaaggg caaggggtat aacctggagt  48480
cataaaggaa tggtagatgg tagcaggtat tggaatgaca gcaagggcca agtagctggt  48540
agtctgcttc actcttttgg gggctatata ttgttcttag ctttcctttt gtctgattac  48600
tttcttcgta agatcatcat ctttccattt atgtgtcgtt tttagatgaa cagtctagac  48660
tgagactgac ctgtcttggg ttcagttccg tagtcttagc ccagcttggg ccagattaac  48720
tgtggccttg tggcagagtc atgtgtacaa acaaggcttt gggagaggct ctcaggaaat  48780
gatatcttat tgatgcaatc ttactcatat aactatatga agaataggag agagaggaaa  48840
aggaatgatc ttggtgtttg aattaggcag atggggaagt tctctagtat gtgttgggag  48900
```

-continued

```
tgagtagtag agaggcatgg ggaggaaggt gttttggctc cggtgggcat tgttatattt  48960
tgtaaaggca gctgttagaa aaggtgcagg atgaggtgct ctgatgatgc ctggaaggaa  49020
agtaccattc tgaggccggt gaagtaaaaa aagaaagaag ggagttcata gggacctaca  49080
aattagtaca attaatttcc ctttattttc ttcagccaac atttttttct tctcaggttg  49140
ggggaaattt gcattgcatc atagcattcc agagacttaa ctggcaaaga tttggccttt  49200
ggaactttcc atttggaacc attagacaag aatcacaacc tccaacacat gcccagggaa  49260
ttgccaaatc tgagagtgaa gacaatattt ccaagaagca gcatgggcgt ctgggccggt  49320
ctttcagtgc tagtttccat caggactcgg catggaaaaa gatgtctagt atccatgaga  49380
gaaggaacag tggttaccag ggttacagtg attacgatgg gaatgattga ctatgcttgc  49440
tactgaacag ctggcattat atatgaaact gctatataca ggactgtata aagacagtag  49500
aagattttag taagcctaca ttaaatagga gcagatcttg tggtataaaa aataaccttg  49560
tagttctcca gatactaagc ttgtatatga ttatggtggg tgatttcaga tatataagca  49620
gataagcaca gattattgtc ctttcaagtt aagagtatat aatctggaca gaaaatttca  49680
caaaattcaa taaaattaca actgttgtct aaataagtga aacacaaatt cacttaatag  49740
catcaagatt tgaaatactt aagcatgaag tgacttttat aatgactcga tccctagaca  49800
tttgttacag atagttttat gcctaagacc aagatgtaaa gtaccatctg cccttaaaaa  49860
aaattggggc tgtcaatttc tagttttcac tcatggttaa cacgcattta aaattatttc  49920
atgagtctag tagttctttg atttatagca ggatcttgct tgcctcattt gtttcctggt  49980
tatgttctta ggattctgac taagaggcaa aagagaaaag actcaagaaa ctgatcctgg  50040
agatcgagac catcctggct aacatggtga aaccccgtct ctactaaaca tacaaaaaat  50100
tagccgggtg tagtggtggg cacctgtagt cctagctact cgagaggctg aggcaggaga  50160
atggcgtgaa cccgggaggt ggagcttgca gtgagcggag atcgcgccac tgcactccag  50220
cctgggcgac agggcaagac tctgtctcaa aaaaaaaaaa aaaaaaaaag acggatcctt  50280
ttttttggtg caaatgggtg acttagtgca ttgattcaga tttttaaaat ttcttgatgt  50340
ggtttgtaat aatcaaatat tgacaagaac cttaggtctc gaaagacttt tataagtcta  50400
gatgacgttt gccttagggg taaagtaaaa gaacaattgg caccttaagt ttctataccc  50460
aaggttatct gtgaaatgag atctcctgat atttgattgc tttctcagta tggagtcata  50520
tgttgataac agtactgaag atgcataaga aatgcccaag tcactcagag gacaactacc  50580
catattccag actctgagct gtttcctttt taaaaatcat atagacaatt agctgtttga  50640
agtgagtatt aaatatttca gaagtgtgaa tttcatgtat ttgagctcct ctagttgctg  50700
ttggtttttc ttctgctgcc aacctgtgac tcacaaatga ctaggatctc ttgttcttta  50760
attttagggt cttgttccag gactcaaatc agtaacttgg tgattacaag gtgctgaatg  50820
tgttggtaac catatcgcaa tacacctcaa ggaaaaggtt cagattttta tttttaaaat  50880
attttcattt ttttcttgaa ttttatatcc gtttgttcac tcgtacatgc ctagcctaca  50940
gaaggggata tatattatga aatggtcatt tttctgaaga gaatattttg cttgaaatgc  51000
aaaggactga aagagatttg taggttgttg attttgttac ttcatactgg aacttttaaa  51060
aagatttcat caaataaagt tttgttttct acttttaatt atatgaatgt ttttaaacct  51120
ttgttttagg tagaaggtac cattgtgtct ttgaagtaca tgataatttg tcaattctgc  51180
tcaactggta cattgtaaga aaccatcttg agccttttat aattaatgaa acaatatgca  51240
ttatgatgac tgtaatttta gatttctaat ttaataggaa atagaaaatt tgattctttt  51300
```

-continued

```
attagcttga accaaatgaa gttgtcatct ttgtaggtca aaaatggttg aatattagca  51360
atttcataca gttcaactga atatttcaga gaagacgtag gtaggaagaa ccaagaggaa  51420
aggagaaaaa tgcaaaataa aataagaaat taaaggatag ggagacacct agaaaaacag  51480
gatgagttat tcagactatt gaccataatc aatttttata aaagtcttga tctgttctaa  51540
gtttggcttc caagtttggc tttccagtta ttaagagcac aatgaggttt gagtttagtg  51600
agattatctt tcccgcagaa gctgtaagca agagttactg catacttctc ttagaagatt  51660
agtaaaattc ccttgatatt tgatttcttg gtcagctctt aggaatccta tagatacagt  51720
gaaagttcaa atactggctc tgcacttaca agctatatca cctatagtga tataggcaag  51780
ttaaggttaa ttttttttct gtgcctattt cctcattagt aaagtggggg taatagtatc  51840
tactttataa atgaatttga agaataagct aatacatgta gtgtttagaa cagtgctttg  51900
tagataggaa gtgctattta agagcttgct attattccaa aagatgtgaa ttttactatt  51960
cagagtcttt agagagagcc ctttagatag catcttaagg agctaattcc ttttaaatca  52020
catatgcacc ccttagttgc tgtttcttca aaagaatatt tcatattcaa gaatgttgct  52080
ttattttttt gagacagagt ctcgctctat tgccaaggct ggagtgcagt ggtgctctct  52140
gcaacctccg cctcccgggt tcaagtggtt ctcctgcttc agcctcccga gtagctggga  52200
ttacaggcat gcaccaccat gcccggctaa tttttgtatt tttagtagag actgggtttc  52260
accatgttgg ccagggtggt ctcgagctcc cggcctcaag tgatctgcct gcctcggcct  52320
cccaaagtgc tgggattaca ggcgtgagcc accatgccca gcctttgctt tggttttaaa  52380
agtacttaca atactcaaat gcctatgttg gctatttatt tttacccagc tcacaggcag  52440
aaaaaaaaaa gtttatttag atcaaattct gcagcaattc ctttccctac tgctattact  52500
gttaaagaac tgtgtgccat cattaggcca agttggtgca gcacccaaaa tacttgccaa  52560
cttgtcttct cccagactgg aggggctcag gcagctcttc taggatccat cacattctgc  52620
atctcaactt taccaataac actcccaccc ctcctgtacc agcgattcac tcaacaaact  52680
aaattataca ccattaccag gtcagttctt aaatagctca gcagcaacaa gaacaacaag  52740
atgttggtcg cattctaatt ttactggcag aaactgaggg tttcattggt gaagaaacct  52800
gcctaggatc acagtgtctt agtttctcag ggctaccata acaaaacacc acagacaggg  52860
tggcgtaaac aacagaaatt tgttttctca tggttctgga aactagaagt ccaggagcag  52920
gcaggtttgg tttcttctga ggcctgtctc cttcacctgc agagggccgc cttctcactg  52980
tgtcctcaca aggcctttcc tctgtgccta tcatccctgg agtctctccc tgtggcccaa  53040
tttcctcttt ctacaaagac accagtcaaa ttggatttag ggcctatcct aatggcctcg  53100
tttcaattta atcattttta aacgctgtgt cttcagatag tcacattctg aggtactcag  53160
gcttccacag atgaattttg gaggacacaa ttcagaccat aacacaaggc aacatatggt  53220
tcagatgaga tctgaatgaa tgatcagcct aacctccaag cagattcttt cagcagactg  53280
caaggtgcac tggagagctt tagactagag gcttaagagg tcatttaggc aatatttaca  53340
gaactgctaa gtgccaggat tgggggatgt agcagtcacg aaaatcgttc ttcgtttcag  53400
taagtttaca gtttaccatg gggaagagac aaatactgaa caggcagtta tattactctc  53460
agtaaaataa caactgggaa cagtttctgg ggattacttt acatatggag gaaatgcaaa  53520
aaacactttg tcaggattat tcctgtagca aattagatgt gactaggtca accaaacatg  53580
gccactgtga accatcttat tgagcataga agtggttttg ctaaaaatgg atttctccac  53640
```

-continued

```
ggagcacggt ggctcatgtc tgtaactcca gcactttggg agactgaggc aggaggattg  53700
tttgagacca gtttgggcaa caaagcaaga ccctgtctca aaaaaaaaaa aatcagggcg  53760
tggtggtggg ggcctgtaat ctcaactact cgggaggctg aggcaagagc atcacttgag  53820
cctgagaggt ggaagttgca gtaagctgag actgcactac tgcactctag cctgggcgac  53880
agagtgagac cctgtcaaaa aaataaaaaa taaaaaaata aaaaaaatca atttcccgta  53940
tacttctgtt ataaagaagt ctttaaaaaa ttgcctgctc ccttaagtca gccttttcac  54000
tgagtttaaa tttcgttcca atttgaacaa atatggatgc taatactatc ctttatagtt  54060
actagtgcta agtgcgttgc atgtaacacc ttgaatactt actgaagtct gcaaggttgg  54120
ttttatgccc tgattactga tggagacaca aattctgaac aactgtgact tcagggatgc  54180
taaacaccat agtgaggcac gatgcgggga tttgaatctt ggcctgaggg ttccagagct  54240
gtggcctttt ctggggttac tctgttaatt gatttctagt cctttctgat ctacaagccg  54300
cggcattata acttttagat gctgaagaaa actaaactat atgtcaagga ttaaggcttg  54360
tgaaccccca aaatttggga caggtctcag ttaatttaga aagtttattt tgccaacgtt  54420
aaggacgcgc agctgtgaca cagccccagg aagtccagat gacatgtgcc caaggtggtt  54480
ggggcacaga ttggttttat acattttagg gagacaggag acatcaatca acatatgtaa  54540
gtacactggt tccttccaga aaggtgggga caactcggaa gcaggaaggg cttctaggtc  54600
acaggtagat gagagacaaa aggctgcata cgagtttctg ataagccttt ccaaaggaga  54660
caatcagaat atgcatctat ctcagtgagc agaaggatga ctgactagaa tgggaggcag  54720
gttttgccct gagcagttcc cagcttgact tttccctttt gcttagtaat tttgggaccc  54780
taacattttc acaggcttta aattttatta ttctttagtt actacgtgct agcatataaa  54840
taaatagtac aaaaccaaga aggcatccac cttttggttg tctcttcacg tgtaaaacaa  54900
cactttgtgt taagtatctt cacacacggc ggcgcaaagg tagaaaccga tactaaaaaa  54960
gcgtgtagaa aatagttccc agcctgggca acacagggag acctcatttc tacaaaaata  55020
attcgccaag catagtggtg cgcacctgcg gtcccagcta cttgagaggc tgagatggga  55080
aagttgcttg agctcgggca gcaggagttc caggctgcag tgagctaaga atgcgccact  55140
ggactccagt atgggcgaca gcgtgagacc ctgtctcaaa caaaaacaaa agcccgttac  55200
tccaccaaga aggcgctttt gcacattgtt ttaatgctta acgccttcag gatgccagcg  55260
tgacggaagc aagtaaccac caaggcatca ccactggcgc taaacttctc acttccggag  55320
tgctgcaagc gcagaaaata tacgtcatgt gcggaggcgg agcttccgcc ctgcgcgtcg  55380
tattagacgg aaaccgagcg ggcccatttt tcatgggttt gcggacccac cagcgaaggc  55440
gggaggtgtc gcagggacat cttctggctg tttccgtcgc ctgcgtggcc cttgcacccc  55500
ggtcttccat tagcggcgca gacgtttggg cctaagcgct gggcgaggcg aggccctgcc  55560
cctccccgcc aacggccatt ctctggacct gtctttcttc cgggaggcgg tgacagctgc  55620
tgagacgtgt tgcagccaga gtctctccgc tttaatgcgc tcccattagt gccgtccccc  55680
actggaaaac cgtggcttct gtattatttg ccatctttgt tgtgtaggag cagggagggc  55740
ttcctcccgg ggtcctaggc ggcggtgcag tccgtcgtag aagaattaga gtagaagttg  55800
tcggggtccg ctcttaggac gcagccgcct catgggggtc caggggctct ggaagctgct  55860
ggagtgctcc gggcggcagg tcagccccga agcgctggaa gggaagatcc tggctgttgg  55920
tatccttaac gccgcgttgg gacttggggt gcagggattc ggggctggat tcctcgcggg  55980
gctctgcctt gggcacagtg gcatctgcag gatgatggtc ttgggtcggg gtcggggtcg  56040
```

-continued

```
ctatagaatc tctgtcacta ggttttctaa gtacagtcgt ccctcggtat ccccggggct  56100
ttggttccag cccctcctcc gtataccacg atgttcaagt tccttcaact cccttatata  56160
atggcgtggt atttgcatat aaactaccca cttccgtaat cttttaaatc gtttctagct  56220
tacttgtaat gccgaatgca atgtaagtga tctgtaaata gttgttatac tgtattttaa  56280
aatttttgt agtttttatt ggtatgtttt atttatttat ttttttccat cgcaaatatt  56340
tttgatccgt ggtaggttga ttgcggaatc gggtgatgag gcgggccgcc ctgtctgctt  56400
tccccagctt tgcagtctta gcggcctgtg catcctggtt tgtcactttg tggcagtgct  56460
ttatgttcct ctctgcctta gttctctcat ctgcaaagta gaggtggtga tagtatctac  56520
acacaggatt ggaatgagga ataaagaaat tgcctacatg agagaagttt agtgcgatta  56580
atacagtaaa tcttaaagtt attatcctgt ccgggaggtc agtaaggaga gcagagtaga  56640
cttcgacgat tagttttgct tgagtcttgc cccatttatg tttcttagag gaaggatagt  56700
gtggacaggt gttttaccca tttttaaat tgacttttta aggactattg tttctgtaca  56760
tgtttggctg gttttgtttg tcattggaat taaattcttt tttcattagc aaaacgtgat  56820
actgcttttg aaatttttat ctttttcttt gttatgtagt catttttttt tttttttga  56880
gtatctattc tggctcagaa tctggtgata ccttacacca atttcctaaa tggggatcta  56940
tgagtctagg ggctcgtggg cttgtggaaa gagtcctgta aatgattgcg gggggattgg  57000
ggacgggaaa tggagtgcaa gagtgtgtgg gcgttcagca aaggaatccc tgactgtgga  57060
gccctaattc ttcagtaggt acaaaactta taaataaaac gacattgata agttttaaaa  57120
cataatgaga ttatcatttt ttgcaagtga ataatcttta aataaatctg taattgattt  57180
ttggcttaaa agtttttata cagggtactt tgaattgggg aaagccaaag gatttttgtt  57240
ttgttttgtt ttgtttttg tttttagag cacatgcgct gttgctgccc tcaagctgtt  57300
gcttagtatc attgcagtct aaagattttc tcagaaataa agggtaaagg ttagttttca  57360
gtgacaagaa cccttaaaac ttcagcaaag atttagatca ttttatgtag cagcccttgt  57420
gaagaattac taaagaggac tgtggccagg ctcagtggct tacgcctgtc atcccagcac  57480
tttgggaggt caaggcagga ggatcatttg agcccaggag ttcaagacca gcctgggcaa  57540
catagtgaac ccctgtctac acacagtcaa aaaattagct ggacgtggtg gcctgcacct  57600
ttggtcccag ctacacggaa ggctgaggca ggaagattgc ttgggcccag gcggtcaagg  57660
ctgcaatgag ccgtgttcat gtctgtctct gaataaataa ataaaaagga ctgtgaaaga  57720
cattctagtc atgacaacct catatattta taataaactc gtttatgtca aaggagtata  57780
tctgattact tgttctacaa tcggttttgc tttatttcat tttcacggga attcagacac  57840
ctgaaattat ttagatttta ttgtattgtt tgttaatgac aaacttaccc gttattatac  57900
tagtttcata atttactctt gtatctctat actaaattgt ttggtcttta aaccatctat  57960
atagcttagt gtcttattta tacagtctaa atgtctgtgt caaataatgc agaagtaagt  58020
taaacttttg tctcttatag attttaatgt ttgtaatatg cgtttaagtg tattagcaag  58080
atattaccat ctctttaggc tatgtatact aatggagatt tttaagtcac ctaactaaag  58140
aactaaagaa acttattttt tgtattgaaa tgttattggt ctttgggtct tataccgaaa  58200
gtgatttttg gctttgctgc agattttaac ttttctgtcc gcagaaattt aattttgcgt  58260
atataaactt actgaaatta gacaagtcaa attatacaaa tattttcaga ttgtctcatt  58320
tttcatattt cttgtctaac aatttatgtg aatattttca ggtcgtctaa ttttacatat  58380
```

-continued

```
ttcatctcta agaattcaag ccaaaattct caaccctagc tgagaattgg cattacctgt  58440
agttaattga aaaataaaaa ataaaagaag tcctacctca gtctctatga tttagaattt  58500
taggcccatg ggtttaata atccgtatgt ttcagaagct tcatatccta ttctaatgga  58560
tagcagggat gagagccact gatctgaaac tagatttcct cactgaagtt aaagtttaaa  58620
gtagtgggcc aagtagaaac taatttaatc ctatgtaata gtgagcttca tggcttttcc  58680
agactatact tgtagcaagc agaaacatcg atctaataca agacagatgc acatcaacac  58740
caagttctac ctctgagatg tatcttttat ccgatctctt ctcgtggtct ccaccactac  58800
tgtctgcgtt aacttgggct attgtaactc attttagaac tggtttcctt ataatctgtt  58860
cttcacatgt tcatcaaagt tatccttaaa tcatgttcta gaaacttccc agtggccgta  58920
tcacctcctg ccattccttt tgtcctgctg cactggcttc ctggagatag ggaccgtctc  58980
tgttttgttc atggctgaat tgtttggtgt atatccctag ggtcttggat atgcctggcc  59040
catggtattg ctaaatatta tagaaataag catagcagta gcttgctttc cactaggtat  59100
tttgttacat agtgttttgt aaattaattg ttgatggacc tacatttttt tttatgttag  59160
taaaagttag gcagtgtaca ttcatttaaa tactaaactg ttcaacttat ttaatagcag  59220
atatttattg tgtataagag tccctgtgaa agggagtgca gtgcacaaat tgcccgggca  59280
agccatggag cacacaggct gggtttttc cctgctagat tataaactcc atagggccaa  59340
tactgtgttt tgttcagtgc actggatatg ccagtgcata gaaaaaatgc tgccacataa  59400
taaaaacaga aataacgtga taggtggccc cttcaatgtt cttttcctat gttagaaatt  59460
tacctgcaaa tattagcatc agtccaggtt tctctctgtt tttttttct ttttgttttt  59520
ttttgagaca gagtctccct ctgttacgca ggctcgagtg cagtggcgtg atcttggctc  59580
actgcaacct tcgcctccca ggttcaatcg attctcctgc ctcagcctta taggcacacg  59640
ccaccatgcc tggctaattt ttgtattttt agtagagaca ggatttcacc attttggcca  59700
ggatggtctc gatctcctga cctcaggtgg tctgcccgcc ttggcctccc aaagtgctgg  59760
gattacaagt gtgagctacc gcactcggcc tcaatatatt ttttaaatag gaatgtatac  59820
aaggaggatg tcttcatcta gactgaggag gggacccctg gactgagacc ttagagtagg  59880
agagaactag gcggagagag ggagaaactg tttcaggcag aggaagcagc atgtgagaag  59940
aacctggagg caggaaggag cttagtgatt tctgggtttg aggaaagccc agtagcagga  60000
agtgagcaga ggccagatca ttcaaggctt cctagaccag gagaagaagt tttagatagt  60060
atcttgaagg cagtgggaag ctttggaggg ttttcaccaa agatacgttg gtgaaatcta  60120
gtatatacct tcaagataca ttagaagata gaattgatag acctggtaat agctataggt  60180
ggtgatgccc agcattctgg ctcaggtgaa tggcagggac attcactgag atgggggcat  60240
gagcagctga gtggagaaga catggagttc agttttgatc atgttaagtt tgaaatgtct  60300
atgaggtatg gggtagagac gtcatctggg ctctctgttc tggggtcagg agcgtgctct  60360
gggccagaca tatacatgga gtcagggcgt ggtgtatgtg gaggggagtg gaggttgata  60420
gttcagacag gaggaaagaa gagggcctga gaaagatcac tgatgaagtg aatactttaa  60480
cagtgttaca ggagctggca aagagtctga gagcaggaaa accagcagag cgcggtgtca  60540
ctctttcttt tggacaaata taacattttt tgagaagcac tttttagaaa agtttaaaaa  60600
tataagaaaa cttcaagatg aaaatataag ttatctttag tctcagcaga cataatatct  60660
actttaatat tttggtatgt gaactagttt tttatattta acatatatac tgtatcagaa  60720
aatggagtta tactttatat ggttttatag cctgttttac tatctttaat aatatttaat  60780
```

-continued

```
gactatcttc cttatcacac atgctcctgc aacttccatt tttaagggct ttttggtatt  60840
ccagcaaata ggtctgccat aattagtttt tctttttga gacggagtct tgctctgtca  60900
ccaggctgga gtgcagtggc gcgatctcgg ctcactgcaa cctctgcctc ctgggttcaa  60960
gcgattctcc tgcctcagcc tcctgagtag ctgggactac aggtgcgcac caccatgccc  61020
agccaatttt tgtattttta gtagagatgg ggtttcacca tgttggccag gatggtctcg  61080
atctcttgat ctcgtgatcc acctgcctcg gcctcccaaa gtgctgggat tacaggtgtg  61140
agccaccgcg cccggcctat gattagtttt ttaaaaagac ctgctggaaa acttttaagt  61200
tgatttttat attttcatta ttataaacaa gcattctgta aataactctc attatatatc  61260
catgatgatt ttctgaggat caatgtctgg aagtggtaaa atagactgca aagttttaaa  61320
aagtttttt cactatgaat tgtcaaattg tcctccagaa aatttgtgct aattcatgaa  61380
aattctttag caatcactta ttttttttta aagaagcaat tctttgcaat gagacttctt  61440
aaaaggatat gtctgtcttt gtatgatttt aaaatgcagt atgtgaatag gggtaacaag  61500
agttcaacta aaagttaact gactttaggt agatcccatg agagctaaat gtttttcaat  61560
tttaaatgaa tagtgataag tatttagtgt tcaacgtttg gataatatca gttattagga  61620
aattgaagtt gtgaggatga agagaaaaat cccggagttt tttccattaa caattctccc  61680
agatattagc atttggttaa accaagcact taaaggagtc cgggatcgcc atgggaactc  61740
aatagaaaat cctcatcttc tcactttgtt tcatcggctc tgcaaactct tattttttcg  61800
aattcgtcct atttttgtgt ttgatgggga tgctccacta ttgaagaaac agactttggt  61860
aagtgtcgta tagtttttag taagtgtcaa ataatttttt tctttctgca ttcttagaaa  61920
aattcacata aaatttttgt tttctcttta gaattttaga aacagactta ttttgacaca  61980
tacttaatta catctacttt tttatcttga acaattaatt tttcttttaa aaagttttat  62040
gagagttcat catgggtaca atgataaaat ttaactttta aataaaacta actactaaaa  62100
accttgctgt tgagagtttt cccttcagag gatcttgtta ggtgttttat atttatttca  62160
aggatgcggc catcactcag aacactgtgg aaaccctctt ttgggaagtg cctccctgaa  62220
tctgagatca agtatcctcc gtgatagcaa gccttctttt aaggggaatt ggattttagg  62280
agtaagcaat gttatgtggt gccaagtggt gactaaagtg gattatctag gaaggaaatt  62340
gaccatgata tagaagagtc agaatgagtt gctgctttat tgttctggaa gtagttttaa  62400
aaaatgtttt tggaaggccg gggcaggag gattgcttga gcccaagtcc agcctgggca  62460
acacagggag accccatctc taaaaaaatg acataaaata atgtttaaac agtccaaatg  62520
acagcaccca tttggatata tgacttttat ttgttgaaaa taccaaagta atgaaatgat  62580
gactttgtaa tcataccaga tactctctaa atgaggatat aggataaaag taaggatata  62640
ggataaaaat aaaaagcatt tataaatgct gggggacctt tgttgcctca gtaagagtgt  62700
ctagtcttga atgttgcagt tttcagttac ccaaggcata ctgtaaatca ggtactttgt  62760
ggaaggatta gaaaggaaaa gagaatatct tggttatttt tatccgatat tcagccataa  62820
gcacagggac tatccatttg tcactacttg aacatttctt acaagatatt tctatacatt  62880
ttagaatttc tcatgatata taatcttgaa tattgaaggg cagaattaca tgtaagtaat  62940
gcatgtttat aaaaagcaat attagaaatt gtttttggtg tcactgtgac attttataga  63000
ataaataaat aatttctttt gggaagcatt taagctttcc acttcttggg catattaaaa  63060
gacatttaaa agaaactgaa agtaaattaa gtttcccaaa tatattgtgt agtagcccat  63120
```

-continued taagtaatag atggaaactc tgggtgtcct ttacgtagca gcaacctgaa gatatacact 63180
gatatggcaa ttaggaggaa atgctaaagc agccatagtc tgaaaactca gacaaaccaa 63240
attctctgga aaataaatca cagcaatgtt tctagtggtc taatatcctg aagtgagatc 63300
ttacatcctt tcttctcata ggtgaagaga aggcagagaa aggacttagc gtccagtgac 63360
tccaggaaaa cgacagagaa gcttctgaaa acatttttga aaagacaagc catcaaaact 63420
gccttcagaa gcaaaaggca agaggaaaat tatagtcgtg ttagagatga agttttaaaa 63480
aagtgatttt tgtcttgatt tcctgcgatt ctctttccct atctaatttt gactctcaac 63540
agaaaataga gagtgaaatg agacaagtag gctgccattt tgacctggta atttggagtt 63600
gtggcaattc tccgttctgt gagaatcaac tttgctaatg agaaaaaaaa gctgtcgtgt 63660
tgcgtcatgt acacttttta ctttgattat ggtcttcttg actctaggtg agcagccccg 63720
ccaaggttcc ttcctttctc tcggctgcat ttattttcca cagcagtggc ctgagagcag 63780
ccaggtcagg tccctgttca ccatcctgag cagggtctgc ataatctgtt taaagatttg 63840
tgtactttcc agagatgaag cactacccag tcttacccaa gttcgaagag aaaacgacct 63900
ctatgttttg cctcctttac aagaggaaga aaaacacagg taaatgttta actatttaag 63960
aatattattt tagtcattgc tacattcaga cacatttaaa ccttgatgtg ttatctacat 64020
gataaggcat gtgaacattt cttaatgcat ctgaaatagg catgctctat acctttcaga 64080
atatttttca aagactaaat tttttattta ctattctttg tgttttggtg attcatgatt 64140
cttattcctc ttcattctaa agaacttctg ccagggctgt ggattctaaa ttctccaagg 64200
catgaatttt agttttgctt acactttgct tacacatgct gtctctagct gcttttcaat 64260
ccagtatggt ctctctcacc atgatgctaa aataccacaa cccatgacat tcttgttgct 64320
aaatctagca gacgctttgc acgtcttagt gtgctcgact tctctgcact aaacaccatg 64380
ccacactgcc ccgctccccc ggcatctctc tggcgctttc tgctcagcct ctctgtggac 64440
tcctcttcct ctgtctctct cttaatggtt ggtggtttct gtgtttgaag tgaaggtgga 64500
gaaccggaag cttggcagtt tgcctttgtc ccctgtcctt ccctccacct cttcctttcc 64560
caggagttcc caagagacaa cttagctttt gtatcagctc agttctattt gtctccattg 64620
ctaccactgt catttttcct ccaggttaca ttattagctt ttaaacttct ttctgtcttt 64680
gtctttgatc ataccctttt tgtaatagtt cctcccacca agcccaatct ctgttttgtg 64740
ttatagtctg tttaaaatcc aaatctgata ttgtcatttc cttacttaaa acactttcta 64800
gcttctcctt ctcatttttt tctttctttt ttttttgaga tggagtctct gttgcccaga 64860
ctggagtgca gtggcacaat ctcagctcac tgcaacccct gcctcctggg tttaagcgat 64920
tctcctgcct cagcctccgg agtagctggg attacaggca cgtgccacca cacctggcta 64980 atttttgta tttttagtag agacgaggtt tcaccatgtt gtccaggctg gtctcgaact 65040
cctgacctca agtgatccac ctgcctcggc ctcccaaagt gctgggattg caggcgtgag 65100
ccaccacacg cagcttagct tctcatttct ttaggataaa actttaactc cttaattaca 65160
ctttccagtc ttatccctgc ctttcttcac atcatccaca ggcaggcttt cttttccttg 65220
tttctatatg gtcatacaac ttagttcttt tgcctggaac actcttctcc atgaaccttc 65280
ccgctcccta caactacact cattaattcg tggctaactc caaccagtgt aattgcagga 65340
gatcctggaa agcttttgtg actcctaaat tgggtgaggt gactccctat tgcatctcta 65400
gtgacctgcc cttcccttgt ggtggaagtt attagatccc actctaattg cttacttaca 65460
cgtgtccccc accagaccat gagaccagta gtggcacaga tcttgctgtt ttattcacca 65520

-continued

```
ctgtagcccg tataacgagc agagccttgc atacaagtat ttttgtaagg ggtccttaaa  65580
aatcatagat atcgtaaaag tatgtttgac tttcagttca gaagaggaag atgaaaaaga  65640
atggcaagaa agaatgaatc aaaaacaagc attacaggta tttagatcat ttttgaattc  65700
agaatgtatt ctgttatttg aaatgaatga catgaaaatg aatattaatg aggtatatca  65760
aactgtgaaa gttcctgata aaaagtaaag acagatggct ttttggttgt gcatatatat  65820
gtgtacatgt atgtatttaa aacacactca cctacacacg tgtatatata tatatatgga  65880
atttgccatt atgcacatct atatattcaa aacaagctat ttttctttta caaccaacca  65940
accaatagta atatgtgctt acatagaaaa tatagaaaac atatcattca taaataactt  66000
gtaataacag tttgatatat tttcatccat tctttgcctg ccccatatag ttgaatatct  66060
gtgtgtgtat ttgtatatat gtatcaaatg tgcatgtgta catatatatg tgtacacata  66120
tgtgtgtatg ttctagttat ctgtcgctgt gtaacttagt ggttaaaaca tcatttgtta  66180
tcgtcatctg tctgggttcc aggggtagat gagctcagac aggcagttct ctctggggtc  66240
tcttgtgtag atgcagccag tctgtagctg gggctggagt gattaacgag gtttccttgc  66300
tgccatgggc ggtggttgat gctggctgtc agccagtctt ccatgcggcc agcaccagag  66360
cacctacttg tggcctctcc acgtggcctg ggcattttcc cagcatgatg actgtattcc  66420
cagtgtgggc atcccaagag aaagttctaa gcagaagccc tgttgccttt ctgacctagc  66480
tttggaagtt gtgcagcatc cttcccacta catcctgttc ctcagaagct agttactgcc  66540
ctatggaagg ggcagagagt tagacaagaa gaatgtccca cacatatttt catgaataac  66600
atttttacaa attgagatta tgctgtatat atacattttt ttcataaaca tttttcaagt  66660
ttcttagtgt cacagatagc attttttgat tcccaaattc actgtttctt gtttgttcat  66720
atggttttgt tctatcaggt agaaactttt gagctaaaac ctcgagatcc ttcaggttgc  66780
ggaggtgctg tgctattaat gcagctagtg agagcaatct tagttaagac catgggcctc  66840
gtggtcaaaa agacctgcgt ttcagtccag gctccactgt tcactagctg tgtgatctta  66900
cacagattaa attctccaag gctttatttt tttttgtaaa acgaaattga tatcaatgcc  66960
ttcctgatgg gggtgatggg agcattagtg agggaaagca caggaaatgc tgagcgcagt  67020
gacaggtctg tcctacgtgt ttgctggttg gtacgtacac atgtaacata cagacatgca  67080
ggacatcagg ttgtattagc ttatcttttt tactaatgaa ggattttaaa gtacttttgg  67140
taatgagtta aagttgagaa aagttttaca cttttccatg tcttctgtga atttctttta  67200
atttcatttc ttatgttata agcaaaataa aactaactta attatgggaa tgatatatat  67260
tgcttgaatt cctaaggcac attctgtctt gggttcttgc attttctgtt ctctcagcct  67320
gaaatgctct atcctcagtg aggctctttg atatcttcca agtccctgct cacacatcct  67380
ctttttagtg gggtcttctt tatctatcaa atagatcttt ttttccacgt tctgttcatg  67440
taatcactct catatcagat aaatctgctt tattttacca ttatcttgtt catttattta  67500
tttatttatt gtcttctctc ctctgctcct aagagcaggg accttatctg gcaccttatc  67560
cgatctcaca gtaccttagc acctagaaca gtgcctggtg ccttagaggt acctgctaag  67620
tatttttttc ttttgaatga attaaagagt gaatggctac attccctaat ttgcctactc  67680
actttgttgc ctgtcacaga ttatatgcaa ctgtgtttag ccaattgttg attatgtaga  67740
actgtgttta ttatataaac ataatacata tccttaatgt tgaatagaac taagtgtatg  67800
aaatgtaaat ttcatggtgc tgtgatttta tctttacagg aagagttctt tcataatcct  67860
```

-continued

```
caagcgatag atattgagtc tgaggacttc agcagcctgc cccctgaagt aaagcatgaa  67920
atcttgactg atatgaaaga gttcaccaag cgcagaagaa cattatttga agcaatgcca  67980
gaggtgaaat atgcaacagt acattcatgc ttagaattaa gaacttcagc aaaacttttt  68040
attagaaaga agagaaaatt gataagcaat acttacacga tatctcagtt aacagtaaac  68100
agcatttcta catctcagat tctaagaagc atcgtatatt tatacgtttg agcctataga  68160
catttactct aagaagtttt tcttgacttt tgacccgaga ctaggtcttt tttcctggtc  68220
tttgttctca cagcaccctg taatatcact tcatagttct tagttccaaa acacgcttat  68280
cttgctcacc tctgtatttt cagtgtctag ctcagtattt ttcacatggt atgtgtccag  68340
tagatgctta ctgactcaat tcttaggtta ggtcataaaa gttattgtaa cctataatat  68400
acattgtcta taaaaactaa tagtcatata gaatctaatc acaatggaaa aataagttct  68460
aaattgaaat tccaggtata tcttcctctg ctgcagccct agagatgcca ttggctctcc  68520
acattccctt gccctcttcc tggacagtgc gaatggggct tcttcacctt ggaacatctt  68580
gtagcttggc aggcccagaa agctagagtg gaggtggtat gtgcagttgg gtgctagcaa  68640
atgtgtctcc tgatcatgct gccattgata cttaattcat gttactattg atgactccct  68700
gtcttagttg ccagtgagtg agttcttttt ctctttctgt tgctgctacc tgttatttct  68760
accgtagttc tccattcacc cactatagga cagaatcgaa attttgcagc atcatcgacc  68820
ttagtgcata gatggagtgt ttttttattt tctacaattt ttgaatattg cttaaattga  68880
tagcagaaat atgaaaaagg aagggtaaat ttcttttctc atcactccct gtttttttcca  68940
caaagaatgt gcagtagcac acactaaggt gcacagaagt gacattcttg ggtctttgga  69000
tatacaaagg acagaagtaa attgattttt atttcaggag aaaaatccag gctcagtctg  69060
tctatcaggc attttatttc ttgagtatga aaggatctct ggctggcagt tgaggaagta  69120
gaattttggt tgtgtaaaca ataacaggaa gaaatgggag aaagagagac agtccctaat  69180
gatttactgt tctttatttt ctttctgcaa ccatgaagtc tctggaagtg gtggactgta  69240
gggtggtgtg gagtagcagc ttactggatc tgtaattttg atagagatgt tctaagtcat  69300
ccatgttggg cctttgtgtg atctgtatgt cgtgcaaatg taatattgat aatagtagtg  69360
atggtaggta ataatagcag tagtaataat cataatacca tagttccact ttactcacgg  69420
tttgcagttt tcagtgacct gtggtaaact gtggtctgaa aatattaaat ggaaactttc  69480
agaaataaac aattcataag ttttaagttg cacaccattc tgagtagagt gatgaaatct  69540
cacaccctcc tgctccatct tgcctggaac gtgaatcctc cctttgtcta gcatctccgt  69600
gctgtagatg cttcctgcct gttaatcact gagtagctgt cgcggtgatc agatcaactg  69660
tcgcgatatt gcagtgcttc tcctcaagtc actcttattt gacttaatga tggcacaaca  69720
gtgcaagagt atgatgctgg caatttgaat atgccaaaga gaagctgtaa agtgcctcct  69780
ttaaatgaaa aggtgaaagt tcttgaatta ataaggaaag aaaaaaatcg tattctggct  69840
gaggttgctt agatctgcat aaaaatgact tttctatctg tgatattgtg aagaagcgaa  69900
aagaaattgg tgctagtttt gctgccgtac cataaactgc aaaagtcatg acctcagcgt  69960
gtgataagtg ctcagttagg atggaaaagc cattacattt tggggtggaa gacatgaaga  70020
gaaacatgtt ctgattgatg acaatcaggt ttggtacttc tgcagtttca ggcatcctct  70080
gggggtcttg gaacataccc caaggatgag ggggctgtct actatgttaa tagaatcaat  70140
tgtagtaaat tgacatgctt ttgatcccag atctaccact tattagccct gtgactctag  70200
ggaggttacc taacctattt aagtcccaat ttcttcattt ataaaatgga ggtgatatct  70260
```

-continued

```
gtttcatagg atgattgtga gaataaaatg aggtattata tgtaaaagca cttagaaaaa  70320
tgccctccat gggaaatgcc ttataatgtt aagtattact gttaataact gtgattactg  70380
tgatttattg tgtcttttat gggataaggt tgtgcaggac acttcacttg catatttacc  70440
tacattctag aagattgtta agccataatc agatgtcata gtgactgcta tgcattacat  70500
gctcaataca tgtttattga ataatgatta aatcataaac agtattcatg attttttttt  70560
ttttttttt gaggggaagt ctcgctcttg tccctcaggc tggagtgcaa tggcacaatc  70620
tcggctcact gcaacctctg cctccccggt tcaagtgatt ctcctgcctc agtctcctgg  70680
gtagctggga ttacaggtgc ctgccatcac acccggctaa tttttgtatt tttagtagag  70740
acagggtttc accacgttgg ccaggctggt ctcgaactcc tgacctccgg tggtccaccc  70800
atctcggcct cccaaagtgc taggattaca ggcatgagcc accgcacctg gccatagtat  70860
tcatgatttt tttttgccca actctttcga agattatttt tttaaaagga agctgtagtt  70920
tttcttgtta ttcacctttt ataatatgaa actaccatca atgaaaaaag ccaattgttc  70980
tttgttccct gttggggaaa gggtggaaat atggtaatat tatctgtatt taatataaaa  71040
cagtaatttt gtttgtttat tttgccttta ggagtctgat gacttttcac agtaccaact  71100
caaaggcttg cttaaaaaga actatctgaa ccagcatata gaacatgtcc aaaaggaaat  71160
gaatcagcaa cattcaggac acatccgaag gcagtatgaa gatgaagggg gctttctgaa  71220
ggaggtagag tcaaggagag tggtctctga agacacttca cattacatct tgataaaagg  71280
tatcaggcac catcatttat atatttacat taaaaaatca aagatatatc atgactctga  71340
attctataaa ctagcacccc tggataatat taatgaaatt ctatttatgt aataactgta  71400
tactgctatt aatggattaa ctactatagt gccaaaccac tttaaaatta gctaatgaat  71460
taactcctag ttgccgatta aatgaaaatg tatatactta tttatgagaa ccagtgttct  71520
cttatccatc ttactagaag cgtattgtca cactgtaaaa ctgaatggtg agaagtgttt  71580
taattcttct taaggtattc aagctaagac agttgcagaa gtggattcag agtctcttcc  71640
ttcttccagc aaaatgcacg gcatgtcttt tgacgtgaag tcatctccat gtgaaaaact  71700
gaagacagag aaagagcctg atgctacccc tccttctcca agaactttac tagctatgca  71760
agctgccctg ctgggaagta gctcagaaga ggagctggag agtgaaaatc gaaggcaggc  71820
ccgtgggagg aacgcacctg ctgctgtaga cgaaggctcc atatcacccc ggactctttc  71880
agccattaag agagctcttg acgatgacga agatgtaaaa gtgtgtgctg gggatgatgt  71940
gcagacggga gggccaggag cagaagaaat gcgtataaac agctccaccg agaacagtga  72000
tgaaggactt aaagtgagag atggaaaagg aataccgttt actgcaacac ttgcgtcatc  72060
tagtgtgaac tctgcagagg agcacgtagc cagcactaat gaggggagag agcccacaga  72120
ctcagttcca aaagaacaaa tgtcacttgt tcacgtgggg actgaagcct ttccgataag  72180
tgatgagtct atgattaagg acagaaaaga tcggctgcct ctggagagtg cagtggttag  72240
acatagtgac gcacctgggc tcccgaatgg aagggaactg acaccggcat ctccaacttg  72300
tacaaattct gtgtcaaaga atgaaacaca tgctgaagtg cttgagcagc agaacgaact  72360
ttgcccatat gagagtaaat tcgattcttc tcttctttca agtgatgatg aaacaaaatg  72420
taaaccgaat tctgcttctg aagtcattgg ccctgtcagt ttgcaagaaa caagtagcat  72480
agtaagtgtc ccttcagagg cagtagataa tgtggaaaat gtggtgtcat ttaatgctaa  72540
agagcatgag aattttctgg aaaccatcca agaacagcag accactgaat ctgcaggcca  72600
```

-continued

```
ggatttaatt tccattccaa aggccgtgga accaatggaa attgactcgg aagaaagtga  72660
atctgatggt acgtgtctgt gcttttgtag aaatctggaa cggtaggatt tcccctctgt  72720
aggaattcag agatcggtta gtgtagtccc gttttaactt tttacagata aggaacgaga  72780
gacgtagaaa gaaagatgaa atgactttcc cagggagtca cagctggtca tggaatcttg  72840
accttccctg tgttgctctg ctttttgtta tcatttttaa aggcatgaag tgccctattt  72900
ggggaaggta aagttgagtt tccctctagt ttttaaaaac tttttatttt gaaataatta  72960
tgaactttaa aaagttggaa gaatattata aaacactggt tccttcatcc agtacctcag  73020
tggctagcat gttaccacat tagcttagaa tttctcttgg tctctctgtg gccctctata  73080
tgtatatcat atatctccaa atctgtatac atatgtatac cattgatcct cattatttgt  73140
agattccata tttgcaaaat tgcctgatca ctaaaattta tttataactc caaaatcagt  73200
actcaccgca atgtctttgt ggtcatttgt ggacatttgc agagttgggg aaaagcttga  73260
gttgccacac tgtcccctgc tgaggttaag caaggtgaca ctctgcctgg ttcccgtgtt  73320
ctgagagaga tgaccagagg gtggggacag taggggatta tgcaatggag agagagcaag  73380
aagctccggc cccaggccag ttggaccaga tttgaatccc tattctggca cctgttagcg  73440
tggcagcttc acacaggtca ctaatttgtt tcttgaactt tgtttcttgt ttataaaata  73500
aatggaatct attaagatgg tggtttttta ggatttaaga taatatatat gaaatgtgtt  73560
catatatatg ttatatatgc atatgtgtgt atatgcacat agatatgttt aggagcaatg  73620
actcggtatt ggctaattta gtgttcacag agacttcata cgtgatggcc actttgaata  73680
agagaatcaa ccacacacac acacacacac acacacacac acacacacac aatttgttcc  73740
tggtatctgc tagttttctt cattcaaatg ttactatttc ccttttgtaa ttaataagta  73800
ttttgtggaa aaggaatttt tggagctata taaatatgct gttcctgaac aaacttccac  73860
ccacttgtta gcatccattg atgtttacct gaataatttg ttactacgtt ggttgccaaa  73920
tgatggtttt tctaactcca tcattcctta tatattatta cttgacatcc tcctatgagg  73980
aagatctttt ccttctcccc atttattttt attattttta atcagtgtag actcctgtat  74040
tcctatttag tgagttataa tccaatactg tcataattta ctttgttact caaattatca  74100
cagctttggc cattgggggct ccttctaatg gctttcagca gtttttcat tatattttga  74160
gcttttcctt gctttctggc caagctgttt caggcatatg ttgtactttc tctgccctgg  74220
tcctggaacc agccatttca ccagggagct ctggttcctt tcagtggagc atggggttta  74280
gacaccacaa gctggatgtg agtgtgctta tggatcctga ggtataactg tctcaggcct  74340
tttcagcaac agtgccagga agtatattta tgtatacata tacatgcaca cacacatcta  74400
tatttatttc tatgtctatc tgtactaaaa tccatgagtt tatactgaca tctgcaattc  74460
catggggttc agtctagcct cctgcttctt tatagtttcc ctaacaatga gaaacattgc  74520
tccccttatc ctcaatacat ttacatctgc ttattctccc tggatatgta accatctccc  74580
cctcccactg gcctcctcct tggccctgct ctcttctttg cttcagctgt gtccttggtg  74640
ccagctccca gtccctgaga gccccctcct ctgttctgat tgtctcctta aacccagctg  74700
gacaggcctt gccagccctc tccacctaca gggaaggaag gcaaccatta aatatatttt  74760
aaggagaagg aaagacagta agacagtaag agaggagaga agggaagtgg aagaggaaga  74820
actatttctt agtcacagct ttattctgtg ctgtgtaaat agcataaaaa catactgagc  74880
aacttccatg attgtttata tactttgata atcctccttt ttgaattttt aaaacaatgt  74940
cagttaactt agaacatatt tatataaagc gaatatacaa atcttaagag agtttcctac  75000
```

-continued

```
tttcaaagac agtgccagtt tacctaattg aaaaggcttg ttttgaagtt acaggcattt  75060
gtgattacat ttatttatta ataacgctac tattacatgt attctgttat agtcatatct  75120
ttccttttta ggatgtagca tttttcaggt tcctccagaa agctcttgat gattgcagga  75180
tcattttaat gttttgattg tagatgaagt gaccttttaa ttttggtaca ggaagtttca  75240
ttgaagtgca aagtgtgatt agtgatgagg aacttcaagc agaattccct gaaacttcca  75300
aacctccctc agaacaaggc gaagaggaac tggtaggaac tagggaggga gaagcccctg  75360
ctgagtccga gagcctcctg agggacaact ctgagaggga cgacgtggat ggtgagccac  75420
aggaagctga gaaagatgcg gaagattcgc tccatgaatg gcaagatatt aatttggtaa  75480
taccgtaaca ttgtgtttcg acttcttgct gaggaagcca ggttaagtag gttttgagtt  75540
ttaaggagtt ggtggatgag tatttagtag ctatttgcag tacatcttgt ggttgctgat  75600
ggcttcattt ttgtgtaggt tactggctgg gatagactcc gttttccatg tggtttagtg  75660
atgaatctct aaagatatta cagagtcttg gttagacatc cagtggagta cttcctaagg  75720
agaaagagct tattggtaat ttcagtcaga ctaaatgcag gctttttgta aacaaaactc  75780
atttggatta ttaatataaa tctataaatg aaaaaacatt ttataggagg agttggaaac  75840
tctggagagc aacctcttag cacagcagaa ttcactgaaa gctcaaaaac agcagcaaga  75900
acggatcgct gctactgtca ccggacagat gttcctggaa agccaggtgg gtgcaggcag  75960
cttgggtttc ctttaccacc ttcttcagac ccctggggga atgcactgca tgaagggggt  76020
atgcactgtg ccccctggtg ctcagggcct ggtgatgccg ttccctgggg gtcactgtgt  76080
gtccctaact ctgcaggaat gaatgcatta catgaagtgg taggcactgc tccccctgtg  76140
ctcagggcct ggcggtgccc ttccctgggc gtcactgtgt acccctcact ctgcaggaac  76200
tcctgcgcct gttcggcatt ccctacatcc aggctcccat ggaagcagag gcgcagtgcg  76260
ccatcctgga cctgactgat cagacttccg gaaccatcac tgatgacagt gatatctggc  76320
tgtttggagc gcggcatgtc tatagaaact tttttaataa aaacaagttt gtagaatatt  76380
atcaatatgt ggactttcac aatcaattgg gtaagacttc agagtctttt tgattacttt  76440
ctgacattta ccttcagagt ttgtcctagg aagttttctt tccaaggaac tagtttgatg  76500
cattgatgga aattgcaggt ctatgcaaat ttttatatga gtgatctttg gcttatatag  76560
aggaatagga ttttaaacat ttgaattaag gaattaaagt cctagtatgt ttaggtagtt  76620
aatcaactga cttagttaaa ctttgactag ttacccgaga tctccacagt gaacaaaagg  76680
tggtggagag gggaagcagg ccgcgcctgg gcctgtattc gggtttctgg cactgatctt  76740
cttctgttca tccagcaaat atatgtttgg tgactcctat atgccagttg ttcttaacaa  76800
gagggaagga acagagagta aaatagtagg agaaacagat gataagcaga tacataaatc  76860
ataatttgac agttggtggt aagtgccaaa tagaaaaata taacagtaaa ggagaggaga  76920
gagtgaactt caggcatcga gagtgcaggt gctgtttcag agagttgttg ggaaaggctt  76980
tactcgtgta acttcaaggc agggacctgc aggaaatagg aagcaagcac tgtagataga  77040
tacctcggga ctagtgagtg aaaggggctg aggcagaagc ttgtgggctg tgttctaggg  77100
aagcaaggag gccagtgtga gaggaggagg gaggaaatgg caagggttaa tcttagagaa  77160
taggaagaag ctgaaaccca ccagggtctg gtgtgctagg gtatgcaggc agattgaatg  77220
tggggtggga gaagaatgaa gtcgaggagg attccagata ctgagcagct ggtcgagtgg  77280
acctgccttc agtaagacaa ggagggagca cagtggagga ggagaaacga agtgttcagg  77340
```

-continued

```
tttggatatg ataaattggg gatgctcatt ggatacccag tggaggtgtt gagttgatag  77400
ttgaatatat gtgactgtgg ttcagagaga ctcaggctag atagctaact ttgggggtca  77460
gcgtatagag ggtatttaaa gctatgagaa tggatgaaac tttaaaaata ttaacagaat  77520
gccattgaat aaaataattt attttcaaat aataagatat ttttggtggt tggatataga  77580
tatagatata cacacgtaca tgatttatat aataaaatgt ttataaatgt catataagaa  77640
atcttgataa aaattaaaaa atattgttac tctttaggat tggaccggaa taagttaata  77700
aatttggctt atttgcttgg aagtgattat accgaaggaa taccaactgt gggttgtgta  77760
accgccatgg aaattctcaa tgaattccct gggcatggcc tggaacctct cctaaaattc  77820
tcgtaaggtc ttttatttct ttaatttgga taattgtgta aatacccaaa taagcaaata  77880
gaactattat ttacagcatg aactgtcatg ctgtaacatg tgaacaatgg ttcactgaga  77940
aagcagcaga aagtattggt tgttttccat tttctagaga tgatgaaatc agagtcagtt  78000
cttagtggtg ctgggcttat cctagttcaa gggtacaaag ccagtcctgt ggatttcaca  78060
ggaatgtaga agttgccttt tcatccattg acatacttat agagcagcta tgatgtgtca  78120
gacactgtgc tggccctggg gaaaggagag atgagtaagg cataggccat accctcaagg  78180
actcccccca tatacttgga ggtgatggag aagcaaagca aattgtactt gtctgtgtgt  78240
ttggtgtcct gagagaggtc agccaggaag cgacttggaa atataatgcc aggaatgtta  78300
catccagcac tcctgtcctg tttctcacca tgtgaatccc gtgacgtgtt cagtggtgaa  78360
gtcttgctcc atccagaacc cagagtcgtg ctatactcgg ggtacattta tcattttgaa  78420
gattctgaga tggtaggagt tatgagtatg tctgggaaag tagttttttc tttgtccttg  78480
atggcatctt tttaaaaaat tgaaatatag tcacatacca cagagttcac cgatttaaag  78540
tgtacagttc attggttttt agtgtattca caagattgtg gtggcatctt ttaaccgtca  78600
ctatgtcgtg agatgctgtt tggtggtggc tgatttaatg atccttgagt gttctctcca  78660
gttacatatc ctgtgtttga aagatgctag gatgctctga cctgaagagt cagtgactgg  78720
aatcactgaa atgaacggcg aaactgttgt agtgatcatg gtcttccagt catagcacac  78780
tcaccaatgt gttgtatttt atactttctt catttatctt tttctgattt tcttattgtt  78840
gaggaaattt atataccggg aatgagttat gaggtagaca tacgtcatgg taggtaaata  78900
acttgaaaac ctacaaataa ctttattata caaataaagt aaatacatca tagaaaatta  78960
taaatatgta ttaaaaagat gattacagtt tacaatttgt ttatgtaatt ttagacttca  79020
cacatatata tgcatataca ttgcatatat atgtatactc atttgagtgt gtgtatgatt  79080
ttttttataa gaatgggatg atgctatata ctttttattt tacctgtaac ccatttggta  79140
ttagaacaag acctattatc aacgatgata tagatttata tcgtttttaa tggctacagg  79200
tagtatcttt ttgcgtctat cagggctagt ttaatcaagt gtcttttgtt atttctattt  79260
ttagaaaggt attaacagac attgatttga gtgtccttaa tcttcgggtt cttatctaat  79320
gattatttta gaataagtga aatagtatct gacttttcca tttggtttct tgataactat  79380
tgagagtgaa ttttttatgt tcatagacgg tttgtgtttc tgatttagtg aatgacctgt  79440
ttatgctgtt ccacttttct ttgttcagca gtttttgctc gtttgttgcc tgctgaatca  79500
ttttcatatt tgagcagttt ctgcctttgg tcctccagct cgttgatgcc agataggagc  79560
agccttcgct ctgcctggct caggacattt aggatgaata cagagtaaag agcaggaagg  79620
atggtgggaa accagtaaaa tcagaatgtg gcctcacttt gttttctgtt ctcctcttct  79680
gagggcaccc tggctggtga atcattctta gagtggggct gcattgggcc tgcaggttga  79740
```

-continued attgagctgt agtcacattt ggtttggact acacggtgta ttcttctctt gagctttaat 79800
tttcaattgg ctaccaacat ttacctttgg gagattttac acaaaattat ggattctgtt 79860
gggggaaaaa ggagagctga aaatactggg cctgaatttc tggatagccc caaaatagct 79920
ggcatggagc aacagcagtt cccctcccct accccaaggc cttggactgg gcatgaatcc 79980
ttcagtttca tcacagttgc ctccactccc ccagctcagc tgattgacag acaccttcct 80040
cctttcatct ttatgtgaag tgccaggccc tcctgcttga aggagtaacc atagctttgg 80100
cttgatgagc tcacaagtgc actgattcta actgccagtc atgattacag tttcaaaaac 80160
gaaaatctgc aagtaaagta gaggagaatt atcggtattc tctcagtgca ctcctggaaa 80220
gaatgttgta aaagtaatga agaaaaatta ttttttcctt tttgcatttt gttgttataa 80280
tactttgaag accgcaatta gtaatttcca acgctagatg gcactcctgc atcggtgagg 80340
cggaccctgg ccctgacagc cggtctgagt gggttcctaa tgctgcacta gcaagcttgt 80400
gaagcggggg agcctgagct gcgggcgttt tttcaggttc cattgagtac atagattggt 80460
gaggattatg ttagtaactt tgatggcatt tattttttcc taattgtgta aatgtttctg 80520
gtcagtcgtc actgcattac aaactacctt cagccttagt ggcttcacac agcagtagtc 80580
actgattttg ctcatgcctc tgaagctcgc tcaggcctgg tgggggtgtc ttgtctctgt 80640
tccatgtcgg ctaggacagc tcagctgggc taggacccct taagatggct cgcggggctg 80700
atgaggtggc ttcggcctcg gggcctgggt ggacacttgg tgagcttggc ttcctcatag 80760
catgttggag ccaagagcag gaggtccagg ggacaggaag tggcgagggc ctcccctagg 80820
cctggcacgg cttgagtcac actggtcagc catggccgcc ctgctcaaga ggaggccaca 80880
gggacccccct tcgtgatggg aggagggtcc aagagtgtgt cgctgtcttt atccggccga 80940
tttaggctta gaatggaaaa cattgaaaaa tgaataaaat ataaagaaga aaatgaatgg 81000
ctgtgtgctc acgtagaata ttgcctagca cacagcgaaa taatagttgt tagtgttatt 81060
tattttaagt atctgtttac ttttctcata tatgtgtttt ttccaaaact ggaatcatac 81120
tttaagtaga gttctattat ctctgttttt gtatatattt atttgtttta catacatatg 81180
tatttatata tatataaaat gttaaatttt aaaaacagat acatgtatct gtttttacag 81240
attttttaaa caaatttaac attttcttgg catatttaca ttttattaaa tattcttcga 81300
tccattattg tatttgattt gaggtaaata atacagatac attacttcca ttttactgct 81360
gagaaagaga cccagagaag ttgtaacttc tgtggtataa ttatgagtgt gggctctaga 81420
ggaagactgt accaattcca gctgtgaaat cttgagccag ttacttattt ttgagttcag 81480
ttccctcctc tgtgaggtga gggtaacgat agggcatggc ttgtgtgatg attgggcatg 81540
tgaaatattt aacacagtgc caagcacaga ggaagacttc cataaatgtt tgccatcatt 81600
atacattgtg gctaatagta ctaaaattaa taaaatattc tatatagcat acaatttgag 81660
ttagaacttg agtttacatg ttctaagttt agttcttcat ccatagtgta tgaactataa 81720
tgtctcattg ctgtgtaagt aattgtttcc tttattttac agagaatggt ggcatgaagc 81780
tcaaaaaaat ccaaagataa gacctaatcc tcatgacacc aaagtgaaaa aaaaattacg 81840
gacattgcaa ctcacccctg gctttcctaa cccagctgtt gccgaggcct acctcaaacc 81900
cgtggtggat gactcgaagg gatcctttct gtgggggaaa cctgatctcg acaaaattag 81960
agaatatcct ttgcttctta aaagagaagg aaacaccttg tcaaatatgt gtttggttta 82020
aaacttatgg aagagaaact tggatcattt ttttcttata tcccgttaat cccattttct 82080

-continued

```
taatatcccg ctctcctttt cactctttct tccctctcct cagttgttgt tttttgtttg  82140
tttgtttgtt ttaaaggaac agtgtatcac tctgtcaccc agcctggagt gcagtggtgc  82200
aatcatagct cactgcagcc accacttcct gggctcaagg aatcctcctg cctcagcctc  82260
ctaagtagca caagccactg catctggccc ctctccttag ttttaaagag ggtctttgtt  82320
tgaataagca gtgataagca ttcatagata taaccacata cttaaatatt attgattctg  82380
aaagaaggaa agatgactaa tcttgtcctt tttattactg gttgtccttt ccgtgtatat  82440
ttaagtaatc atttggatag atgtttcaaa acttgcacta gaattaatcc aactacgttt  82500
gatttttttct cttaatgaaa taggcaagat atctgaaact tgtttttatt ccagttaacc  82560
tttttcata gtcacaagtc tttgatgtcc taaagtgaga gctaaatatg ttttatttta  82620
tagaattgaa aagaacatag tgccagatga ttatgctgga gtcatttatt ttgttagtac  82680
tttcttttag cactctaatc tttataaata ggaaaatctt aggagataca gggaatggaa  82740
tcaagaatgg gttctttgga cctttttatt tgtcacttgt ttaaatatct ttcaaaatat  82800
ttataagtct taactgcatg catattttgt cagcggtatt tcggctggaa cagaacgaag  82860
acagatgaat ctctgtttcc tgtattaaag caactcgatg cccagcaggt aatcatggtg  82920
gacccttctc ctaagttcag gatgaagggt aggctgtggt tgacagctgt taaagaccag  82980
ttaactctta ttttggggca tagagcagac attttgaaat taggataatt tagatgagag  83040
aatagaagaa aatagaaaaa gaaaagttag actttggctt cattttctat gatcactctt  83100
agggctgaac tttggagtcc tttcatattc attttttttct ttgaaaaaac cagtctaata  83160
actgatttca cactaaggtg tttctgatta aatacattac cccttgggat ttactttcat  83220
tttttaacga aaggaagtct tcaaagcaat tctgatcatt taagttttta taagtactaa  83280
tatttttaaa ttctataaac gaatcttgaa aggtagaagt tcagtcatta ttgtgtatca  83340
gtaggagagg tttttgtggg aaggagccct tttgtatgac ctttagttcc tctaggtacc  83400
tacttcttgc tttatctgtg agtatgttct gactcacaca aaacaagctt tcgcccacac  83460
tagaaacaac ccacaaaaca tacatacaaa taaaccactt agcagaaatg agaatgtagc  83520
ttttgtgata atatatttaa attaaaccca ttttcattag gcttggataa ttttgaaaaa  83580
catgaacaaa actaagacag catttctatg agtttctctt tgttttttgg atgactatct  83640
actggaaaca ttataaacca accaaaaagg aaagctattt gtcttagtgt ctggtgattt  83700
cttaatttca gataaatttt gttgtaatat ttatctcctt tttcattcta aaacttaatg  83760
tgtttatttt tccaaaatta gaaaatgaag aaaatgaatt aaaactactc attagttacc  83820
tcctctaata cagttgttaa catttaggtt aaaaaatttt cctgcattta tttgtggcca  83880
tactaaatgt aacttaatag atctaatcct cccccccaac ttattagcat attttcttct  83940
atgtattgtg tggttttctt aattccagat gactagatta tatttcatga aagatattta  84000
aataattagt tcagtttact tgttagacct ttaattttca agtttgttat agtaatgctg  84060
tgatgaacat taggcatata gctttaccca tatatttttt ttttgagacg gagtctcact  84120
ctgtctccca ggctggagtg cagtggtgag aactcggctc actgcaagct ccgcctcccg  84180
ggttcacgcc attctcctgc ctcagcctcc cgagtagctg ggactacagg cgcccgccac  84240
cacgcctggc taatgttttg tattttttta gtagagacgg ggtttcaccg tgtaagccag  84300
aatggtctcg atctgacctc gtgatccacc cacctcggcc tcccagagtg ctggggttac  84360
aggcgtgagc caccatgccc ggccaaagaa tatcttctta aaagtgaatt tactgaataa  84420
aaggcatgaa tatttcttac agttgctaat atatactgtg aacttgcctc tcaaaggtat  84480
```

-continued tgtatgatga taatgttttt aaaagaaaga tatagtagga cttagaaaca ggccccatga 84540
agtcgtgttg ctcctgagga agatgaaatg tttagctaca gaaaaatatt taacgctctt 84600
tgaatatctt aggaagagat ttctcatttg agatgtggac taaagactta gttgacagag 84660
atggtacaag tactgcttta ggtatgattt agaaagtgaa aattactgtc agtaattcac 84720
tgggagagaa ctgggttttg ggagataatg aattaatatt ctctgacata gtaatccaat 84780
gtgagtgatc aaggttgagc ttgttgattt ggtttagaaa cttgacttac ttgtctgatt 84840
tattattatt attcttttgt tattttttta gacacagctc cgaattgatt ccttctttag 84900
attagcacaa caggagaaag aagatgctaa acgtattaag agccagagac taaacagagc 84960
tgtgacatgt atgctaagga aagagaaaga agcagcagcc agcgaaatag aagcagtttc 85020
tgttgccatg gagaaagaat ttgagctact tgataaggca aaaggaaaaa cccagaagag 85080
aggcataaca aataccttag aagagtcatc aagcctgaaa agaaagaggc tttcagattc 85140
taaaggaaag aatacatgcg gtggattttt gggggagacc tgcctctcag aatcatctga 85200
tggatcttca agtgaagatg ctgaaagttc atctttaatg aatgtacaaa ggagaacagc 85260
tgcgaaagag ccaaaaacca gtgcttcaga ttcgcagaac tcagtgaagg aagctcccgt 85320
gaagaatgga ggtgcgacca ccagcagctc tagtgatagt gatgacgatg gagggaaaga 85380
gaagatggtc ctcgtgaccg ccagatctgt gtttgggaag aaaagaagga aactaagacg 85440
tgcgagggga agaaaaagga aaacctaatt aaaaaatatg tatcctctat aattagttat 85500
gacagccatt tgtaatgaat ttgtcgcaaa gacgtaataa aattaactgg tggcacggtc 85560
tttgtattta gtgtgtggtt cctaaaaaca aatgctaaat ctgacatttg tttttaatg 85620
ttttactttt ctagtatttt ttagctgaat atttcaagta tcattggata ttatcttgta 85680
ttcacaggct ttgtcttttc atgttttcat tatcttaaca atgtctgatc cttcctggtc 85740
acatgttaaa aaagcgaaaa agatttctat tgatcagcac tcactctcaa taggctttcc 85800
ctctgacatt cagacgtagc tgagaagaaa tacgtgcatg tttctaattc cacaatagtg 85860
gcagttttac acaactgttt agccctgctg cccacggctt tgcattttcc ctcaggttcc 85920
acttaaaagc atagcaggag ggagcctcac tgctggaaca tatttcaata tgtttgctgt 85980
ggttttagca aacaattagg aaacctaaat ggggtgcatc attctacctg tgaacattaa 86040
gtgtatggga acctctgtac cgttatgttt ggcttttaaa ccagacttca cttattagaa 86100
gctgacttct gtgtaaatgg atttggaggc tgggggctgg agttgaactg gtgtaggtgg 86160
gtcagcttta ggagtggcct gcaggggatg attgttgttg acacagtgtt tgttcagagt 86220
ggacaaagaa ggttatttta agactgctcc tgtggagacg tctcccaaga acaacccccca 86280
agctcctatt tgcttcgagt taagaatgat tggaggagag tactaccaat tactttgagc 86340
gtgggtcctc tgccttcaga gctaccttcc caagtctgtg tccttttggc atctttagta 86400
tttccatctt tcctgacttt ttccttcagc cttcaaattg aaaatcttca ccaatgaaaa 86460
caaaatccaa atagataatc tccagcagtc tttgaacgac tcctagatgt gttgtttttt 86520
aggctctcat ttatattgac ttggccagcc aaacttctcc agtacttgga ctacagcagc 86580
tgcttttctt tgcacactat tttttcctaa tttcaaatac gtcttctgca tccatcattc 86640
ttctctagca gctccttcta aagtcaacaa tgatttccac ataaactcaa atcttttctt 86700
catgcttctt ttctctggag gtacttggag cagaacattt ttggaggcaa ggggagggga 86760
aaattaactt tttcgtgttt ttctcatttc tcagaattac ttgtcactgg gagttttctg 86820

-continued

```
catatatatt tgcaggtaga ataattgtct tgctaacaaa tttaatttga tgcctttaat  86880
agatatttac atttgttttt cactgcgtta gctttgggaa aggataagct actgtaacaa  86940
aagatgctca tatacagtgg tctgaataag ctagaacatt acttctctct tactcaacag  87000
tctggccagt ctgagctggt gaagcagttg tgcaccatga ggtcatgcag tcctgtgttc  87060
agccaacccc tagggtgcta tcttgcctga gtggtctata ctgggtgatt acttcatctg  87120
cattgcatcc tgccagaagg ggaaagaacc aaagtccagg gcaagcagaa ggggaaatgg  87180
atggtcagga ccatgagaaa cctgttctgt aacactattt atatgagagt ttgatattgt  87240
atcttctttt tctcttaacc ctgtgaccaa gacataatgc ttttacaagg ggagaaacac  87300
gtttagagac attaaccagt tttgccaaat tcacccatgt agtaggtaaa acttctcacc  87360
tgaaccaaaa tcttctaact caaaattcca gggtgctatt ttacctatga aagaggttgc  87420
ctgtttaaaa taatcagcag ctgaacaaat tctttattat tcacatcaag ttggtgtacc  87480
tagagcttat ttaggatgat gaccatcata cgccttttcg attatcttcc agctcattaa  87540
tattttgttt agctttatct atacttgctg ttaaacccat atattgagta ttttatttca  87600
ttgattgtta tttttcagtt ttatttgact cttttttttt ttcaatttga ctcattttta  87660
tagattccag ttccctggtg tacttcttgt catctgtttt tgagtatctt aatcacagtt  87720
actttaaagt ctgtcgaata actccaatat ctaagtcacc tatgagttta tttctattgt  87780
ctgtttcttg gtatgcatgg gtaaatttta actgaatgtt ggacagtcta tgggaaaaat  87840
tataggtacc ctgtaccttc ctctagagag gattccagaa tgtatttgga caggcagcag  87900
aggggaagat cacctcagtg cagccagcga ggacaaagta gattgaaggc tagtttgcag  87960
tttttctgt aagactccag cttctagttt cacccgtatt ccaggaaagt cactttccag  88020
gagtgccctg atgtttcttc ttttgcgctt ggatctgctt ttgccactga atgcttcaaa  88080
aattagcctc ttgccctaaa cagcttaatc agtcaattct tcgactgaat agtcagcact  88140
aagcgtcagg cttctctctc cctttttct gggatcttgg gcccacaaat ctgactgtct  88200
tggcagccac actcttcttt tgtctccaca gttctgtgag attgcctgat gctccgctgc  88260
tatccttaca tgcggtcttc tctttggctt cctcaggaaa cagcaatgcc tggaattctt  88320
ggctgccttg acagctctct gatactttat aacagaggca tgtttgtgtg gggtgtgtgt  88380
gtgtgtttaa aaatctattt ttctcattgt taatagaagc tgaggtttgc tataagctac  88440
ttacagctgg aggcagaagt ctgtatgtat ttgttaaaca gtcatgttgg ttaagatgct  88500
tgattgaggg attctgcctc ttaagagatc taacagtgag gattgcatga tctttcaaaa  88560
aaatccttaa aaaagacaat ggtttttatt cgtcatttat tttgttttta aaaaagcccc  88620
aaagaaagag tatcctctgc cccaagttaa ctgcctatga ataatagttc acattgctta  88680
ggattttgaa ctttccagaa tgtttttacc tataatattc accccacaaa tatatgttgt  88740
atgacttttg tatcattttt aaaagacatt tatatttttt tgagataggg tcttgctctg  88800
ctacccaggc gggagtttgg tggtgtgacc acggctcact gcagcctcca tttcctgggc  88860
tgagtggtcc tcctgccttg gtctcccaaa ggctaaggca ccctgccgat atatacttgt  88920
tctatagatg atgaaaccaa gaaacatact aagtaaatgg cttaaaatca caatctaatt  88980
ataggcagga ataactaaaa tcaggcttcc caactcctag ccctttccaa tacattaaag  89040
tgacctcgat tcatctgtgt atacattatg gacctgtagt cacactccta agtttaactt  89100
tccaatattg ctttatctta actctgtaac tttctatcag ggatctttcc agtggcatgg  89160
gaaatgtgta tgtcctctga gaggcacaca tacatgcact tgggcaggtg cacagatgga  89220
```

-continued

```
tctatgttcg gagcctgccc attcagtctg aataaaaagg aatcatggta gtttgatttc  89280
tgggtgcaga gcaatgctac agacattcta gtatggttgt tggagtctaa agacagtgtt  89340
cccatgcaga taggtgacat gaaaaatatg tagcgttcat ttcctagaat gtcatagcca  89400
cggagtctta gaataactct tggcatccaa gttaaaagct ggatcacttc ctccaaatag  89460
tcttcactca cttccgggag tgggttgtat tcacctttag ctctgttcac gagacactcg  89520
tgggatattc ctagccttct gccccttag ttacgggcat tgccgtctca ctgctgtata  89580
accagaggcg tgggagctgc agctgtcaga atcctaatcc cttctgcctg gactcgttac  89640
cagtggtagc gagtgtgtat agtagtaaac tgtgctgcga tgctagcctt tcagtcacta  89700
ccagaggtcc cagcagcaaa aacaaaaatt gtggatgata cattttaacc ttctagaaac  89760
tcagctaact cctttaggta tgtccaggct ttccatttaa atatcagcct taaggcagac  89820
atgtctttct ttaatggaag agatctaaat tgggagcaaa acatgtgacc acttttgcta  89880
tcgttttagc tgtgtagcct caatgacata atttaacctt ggttttcctg atttgcaaac  89940
tgtagggaaa ataatgtctt ctaacttgct gaagtatgct gtaaaagaaa atgtggtggc  90000
tgtaaaatgt gctttgggat tctcggaaga aaggagtgct atattaattc atggtactgc  90060
aattgttatt ttaccccaga ttgagaagta aaatatcaaa tcgttatttt ctaaagtttg  90120
aataactgtt aaatttattc agataatctg ctctattcaa gaggcataaa tagtttcttc  90180
agttttaaat atatcggctg tgatggtatg gactccttaa ggtagacgct gctcaaaaga  90240
ttatctggca atgaggctgt ttgacattgc ataggtgcta atgatgcatt gatggtaaca  90300
agtgaacttt caatgtttta atcgcctctt aaattttagg attgcagtct tactagtcaa  90360
tatgaagatg atgcctttct ttgttacaac tgaggtagtc tctggtgaag aatatgtttt  90420
ctttctgtag tagcttttta aaatttctga ctcagaagct tttgttctga ttttaatttg  90480
ttctagatag tgtttagatg gtctttctta agtcacgctt cgttaatata tgatatttta  90540
atataatttt gtctgctgta tttgaagtta agctttatta agaaactata aaagcactcc  90600
atacatattt tgaattatta ccatttgata ttttaatgta ttatctatct agttttcaag  90660
aaataatgaa gaaaacatca atatatcacc taccatcatt tcattacttg atggattcag  90720
aagctcaaga aggtaagtca ttttatgttt atgtagctta ccaattctaa gaagacaaat  90780
aactaataga atataaagtg tcacctttgt agtattcatt aatgtcttaa atggagctga  90840
cacttttatc aatggcatat tatgtcttgg tttatatttg tgagcctgca aacatcttga  90900
atcatgttta agtctattac tataccatga tcttgatgat atgttaaaga tacttttgac  90960
agattaaatt aaatatatag acttactaag catgtacagg gtttttgatc ttcaaataag  91020
gaatacattt ttttctcaag tgctgtacac taaatgtatg atgtgatttc taagcaaatt  91080
ttatttcaga taagaagctt gcaagaaaga taaaaatagt tttatgtgaa aactataagt  91140
ttttactggt ggttggatga aaggtgaatt taggctatac agacatctgt agcctgagtt  91200
tatggttcct ctaactattt attagaggca aatacataat gtaatttgac ctctggatgt  91260
aaagagatta agtttgaatt ctactatcag tgtggttatt tgaaattgaa ccatcatttt  91320
tatatagtct taagtatcaa gcgtgacttt gcatgggtta tgtaatataa ctgtccccat  91380
tgtcttgaga tcaaaagtac agacatacac tcttgacaga ctagaaaaat taccatattt  91440
ttgtagagca gttgtaatac aaatctaaat atcttgattt cttttgttct ctccttatct  91500
gcacacactg tagatgtttt ctgaacacta tagttctggt ttttctgttt ttggccattc  91560
```

-continued

```
caggtggctt ctacctagga gaacacatct ttaggccaag aaagctgggt gtatgcccag  91620
tgttggcagc ctacctggct taaacacaaa tagttttacc aagcgattct tgcaaaccta  91680
accatttaag tcgatcactt agagaaccca gccatttaga tgatttgaat gaagacgcaa  91740
tttctgtatg gtttatgaat aaaattatat cattatcatt accattagta acaattcttg  91800
gtttcaactg tgtagaagat aatttggcaa attacaaagg aagtggaaga agttcaaggt  91860
aaggttgaga cggaactagc attacaatgt tttacaacac aaacaaacac actctgtaat  91920
catctatata gccaaatgaa gctttaaaaa tgtgttcaca cacacagagc taagggaatt  91980
aaggatgtgc ccttggagca gatcaggtgg catttagttg gaaagccatc accaagtaga  92040
ggaacactca gttctcaagt actgaaggat actgactttt cctgccctct tttatactta  92100
gaatcctgtg cttggaaagg atggagcaaa cccatagctc agtgctcata tttcaacact  92160
ggcatgaaga tccaagaact ataggatgtc acttatttat acacagatta aaattagggc  92220
tatggtgggt gctaaaaaat tcttctgtat gtgtttctaa ggctatattg taatctaagg  92280
tgtctaaaac cttacccaca ttaactattc taaatatcct atgttgcctg cctcatgcca  92340
gcagcctctc tccagctgtt agtacacgta gcaatctgtt atagaatagt agggtcaccg  92400
gaggacctgc agccttgggg cagattcatc cttgcccaag gctcagtgat tctggctctc  92460
aatgaccctc gagtctgtca cgtcagctgc ttacttgaca tcctacttac tacctcttgt  92520
cagtttaggg ccttcaagac atagatgcca aaatggggct aagcatgtaa gggatttact  92580
gggggaaatg tttgtggagg ataaggaaga aaacagaagt aggctagggg agccttcaga  92640
gcccaacatg ggtccagtgc ccgtgagagg agacagaaga cagattggat gggaagagtc  92700
tccaattgca acacaattct gagacagtct caggtgggct gatgaaaatc cctgagcagg  92760
agttgcccac tagaggagtg tcctatatgg aacaggaact ggctggcttg agtaggcagc  92820
ctcaggagga acatggtctc ccaggagcca caggtgcagc aatgggcagt gttgggcaac  92880
tctgctcctt gtggcaggtt ctcttaatct gagtggcaca ccagggtaat atgtatttaa  92940
aataattttc ctttacaggt ttgcccttcc acctatattt tcgatctcac tcaatggcaa  93000
catcactccc caggctaccc agaaacctgg aatcatcctg attttctccc tttccttcac  93060
acccttcatc attacatctc attgatttta cattcctgat atgtttccct acgccttgtt  93120
ccatttccac catcacttac cttgattctt cattatctct gctcctgact gctgttaacc  93180
accttctaat tggctgtctc gctctgggcc aactcccttt ctttacccte tctagttctt  93240
ttcccacact gtaacctgca ctgcatgatc ttttaaaaat ccaaatcttg tcacatttgt  93300
cttctgcttg aaattcttca gtgcctcatt atttcttaca ggataaaatc aaggcttctt  93360
agtatggtgt aatgtgtttt accttgtgct actatcctca tttatcctat attctggttc  93420
tcagggtttc caaaattggt caggagactt tttgccagtg ggcttttgca catgtcattt  93480
cctgtatatg gcaggtcttc ccttctccta tttgacaaac tcataattag gaaggctcag  93540
ataattcttt cctgagctct ctgagaggtg gaactttcca tttttgcatt gcctactgaa  93600
gtctctgtta tagcactttt actgaacctc tcttatatag cacttggtct gccttctaat  93660
tcatagtgcc caggtactta ataagtgagt gaatgaatga atgaatgaat tagctataac  93720
ataaccgtat tggctgactt aaatttgctc atgagtgatg atcttgtatt tctgatcata  93780
agtcagttga ctcccttcag gacctaatat aatgttctcc tcaaggcatc acattaaaaa  93840
ttttcaggag catcttcata aatctttgca gaattggatt aatgggtaat atggttttta  93900
taaacagtat tgcattaata tatatggaaa tttatgtaat tctaccactg ttttaagaaa  93960
```

-continued

```
cctatcaaac tacagtctga ggcaatatat ttaatatact agttggagta ctatagcaca  94020
tataattact aaagtgagaa taatttatta acacatttta aacattttac aagtaacatg  94080
aataattatc ttccagataa gactaataaa ttttctacat gttgaataaa aataactctt  94140
gaatatacca gtctacttca gatgtcttca aaactcagat ttgaacgtca agtttgaatg  94200
tcaattgtcc acccctaggg gaggcatacc accactttga aagcacacac gttcatactt  94260
ggctccttga cccaaggcct tcatttagac tcttgtcatt tttcatctag actgttccaa  94320
taatcttcta attagcttgt aaggtcacca gttcttcagc tcctgctgtc agatgtagtt  94380
cttaaatatc aaatctgatc atgtcaattc ctgttctaat aatctttatt agctcctcct  94440
caccttatag aacaaaggtc aatgttgcac ataaatttaa tcccaaccta cttcttcagg  94500
cttattttct atagttcccc tccatgcacc ttgtgtaata ttcattataa tccctaaaga  94560
cacaatccaa aatgccatga tcctgaatgt tgaaatcccc aaagaacaaa tgcccttaca  94620
gctaattgaa ttcccaaacc ataatgatag atttggaatt aggtgccatc aaaacttcta  94680
aaggtggatt tcaaggtgtt agcaacagtt tctttttcca ttcagcccaa tacatttgcc  94740
ggaaaattca gatgaatgga ttgcctgtag aatatagtaa catggaaaac ttcagtttat  94800
aacgcattat ttgtctgcat tggcattcct tctagctgat gaaattctag gaggtcttaa  94860
tgagttaaag ctgaatttgc ctgatgaagc cagcaaagtt actgactcta aaataactat  94920
gtgcatggta ggataagaaa gcacacaatg atgttgctgt tcgatcacca gtattgtttc  94980
agccaaatct gtggtctgta tatgagtgca tgagcaaagg atttccatgt acccaaaaca  95040
acacagaagc atgacacaga gataggaaat ttaatagaaa atgctcatgt cagtgtgtat  95100
tgaataaaac tagaatttca aaaagagcag catcatgtag aaaatcaatg tgaatgtatt  95160
cttcaagaag agccatgtcc taaaagaaaa gaaacagtta ctcatctcca cgcaagactt  95220
cagaatacag ttaatgattg tggaagtcgg ccagctctta tgggctacct ccgtgcagtt  95280
gcccataatt tatccctgta atgcgctttt tcatatgttg aattttcttt ttagtttctt  95340
tgggaaggtt ttgtttttct ttttcctttt ttaaagtttt tttcctcacc attttaaatc  95400
atcagcatta tttttacaa ctcactatgg tatgctacgt gtttcatctt tacatttcca  95460
aaactagagg cataaattgt atgagctttt agagagttct aatttgtttt atgcactttt  95520
tgtttttgc aaaattgact ccatggaagt gcattttaat aacactgacc ttgtgtgtaa  95580
gcattgtgca tatatatgta aaaaccttaa aacttcctca ataaataaag ggatatcctt  95640
tttctgcatc tgcatttgtg aaagataaca tttttcaata tctcagctct ttaggcaact  95700
gtatatgact gtatatgtgg tggtgaccca ttgttggtat ttaattttaa tttttttagc  95760
aaggggcgtc tcactatgtt gcccaggctg ggctctaacg atccttccac ctcagcttcc  95820
tgagtagcgg ggactacagg cgtgagccac tgcattcagc tccactgtag gtttggatct  95880
gtttcatcag aagacttagg ttgttcatca ggatatttca agtgaccaaa ctatataagt  95940
gatttcttta tgaatacaat ttctctgctc ataactgtta tgcctgtgta actgtgggta  96000
gcacacctga gtgcttatca ttgcaaaatt atgtatatac aattttattg tataaagtag  96060
cccacaaagt gttctgttgt gtttttatgt ttctaaactc ttttaaaaat gtaaatatgt  96120
tttaaagaac ttttagaatt atttttatca gaattatgta tttggggttt tgatctttca  96180
ggattcaaca ctggggatta tggcatcaga aactatcttt tgggattctg gcccaaacct  96240
ctagccttgt accctcgctc catagatctt ctaacagctc ctgggcttaa atatctcctc  96300
```

-continued ttttatgatg cttctcctga ttcaaccaac cagtggtgct tcccatagca ttttagaaag 96360
acctgtttta tagcatttat caaggtattg acatttgttc agttgtctgc cccttccgtg 96420
atctcagtag caaacttgta gtacaactaa tttaggttct ttatttttcc acttgcatcc 96480
tgagcaacct caataaaagg tgcattttct ttcttttgta aacacaaagt gtagcattgt 96540
ttggtctact tgattagagt tacaacctct gtacattctt gaaactaaga agaccagcag 96600
acagagaata tctgtagaat cttctcagga attggtttca acataagggt ccaagacctt 96660
ggcattgctg aggttttcag aattctatct tttaagttaa gcctgtgact atttactaat 96720
ctgaaaatat ctttaacttc ttttttttaa tctgtaggca tttctaagaa gcacatgaca 96780
ttcagctttg aatagaagat tcatttgaat gacagtttct ttcatttagt agaggggatt 96840
ttactttaaa ttttgctgac aggttttcgt gacagccctc aaatggaagc ttgaattc 96898

<210> SEQ ID NO 4
<211> LENGTH: 2129
<212> TYPE: DNA
<213> ORGANISM: Xenopus sp.
<220> FEATURE:
<221> NAME/KEY: misc_feature
<222> LOCATION: (74)..(74)
<223> OTHER INFORMATION: n = a, c, g, or t.
<220> FEATURE:
<221> NAME/KEY: misc_feature
<222> LOCATION: (292)..(294)
<223> OTHER INFORMATION: Translation initiation codon (ATG)
<220> FEATURE:
<221> NAME/KEY: misc_feature
<222> LOCATION: (1771)..(1773)
<223> OTHER INFORMATION: Translation termination codon (TGA)
<220> FEATURE:
<221> NAME/KEY: misc_feature
<222> LOCATION: (1810)..(1884)
<223> OTHER INFORMATION: Repeat
<220> FEATURE:
<221> NAME/KEY: misc_feature
<222> LOCATION: (1888)..(1962)
<223> OTHER INFORMATION: Repeat

<400> SEQUENCE: 4
gaagaagagg agaatggtag gacggagcca gcagctttat gacaaaatag gttgaaaatt 60
gttgattgag gcanccgctg tgggatgtgc aaagattgta agctgttgtg agtggcagag 120
atctctggcc ccatttggat ccccgtacct atgtttgtta cgtaattgtt ttactggcga 180
acaaggtctc agttaaagga tgaagctcat tcggtgagac ttttattgac caaaacatag 240
tcaatatttt tgttgtgatt tgcaccgaac tgcattgttc atcttcattc aatgcctaac 300
atagaagcgg acagagttac aagcgttccc gaaaataacg actgcaaatc caagagtcag 360
cctctgagga ataatctcca tgaaactgta aaatcctaca gtatacaagg tgctgccaca 420
gcaaatatcg agcctcctgc agaaagacct tatccctggg gatgtcctgt gacacacaca 480
aaggaaaagt tctataccat ctgcgcagac tacgcctttt tgaatcaagc aacatctctt 540
tgcaaatcgt ctagttctgt ctgcagctca agctcagagg acaaatctgc tctgagcaat 600
acaataaatt acattgatct tcagaccagc gaatcagatt ctgtatacaa cgaggatgca 660
agcttggagt ctttatctag caatcttggt acacgtccgc ttgcctggga aattgataaa 720
tcagacttca gcacaatgac ttccaagtta aaaagatcag gtgtaaaaaa acaaacacct 780
aagaagaaac ctgacaggaa ggcaaaacca ttaagggact gtcctcaaca cttaatcctg 840
gatgatgtta aacagcggaa agttctagac ctcagacgat ggtattgtat cagtcgaccc 900
cagtacaaga cctcgtgtgg catttcttct ctggtatcat gctggaactt tctttacagt 960

-continued

```
actctgggag caggaagcct cccaccaatt actcaagagg aagctttaca tattttgggc   1020

tttcaaccac cctttgaaga gattaggttt ggtcctttta ctgggaacac aactttgatg   1080

agatggttca gacaaatcaa tgatcatttc catgtaaaag gatgctccta tgttctgtat   1140

aagccgcatg gcaagaacaa gacagcagga gaaactgctg ttggggcact atcaaagtta   1200

acacaagggt taaaagaaga ctcaacagcc tacgtctatc attgtcagaa tcattatttt   1260

tgcccaattg gttttgaggc aacccctgtg aaggcatcca aagcatacag ggccaacttt   1320

ttcccgcatg aagtggagta ctggatttta attggtgagc caagcagaaa acaccctaca   1380

attcactgca aaaagtgggc agatattgtt actgacttaa atactcaaaa tccagaatat   1440

tttgatatta gacacactga aagaggcctt cagtacagga aaacaaaaaa ggttggagga   1500

aaccttcact gccttctggc atttcagaga ctcagctggc aaagatttgg tccatggccc   1560

ttacagcttg gaacccttag gccagaaccc cagccacccg tacaaggaag aagaatccct   1620

aaatctgaaa gtgaggataa tgtctccaag aaacagcatg ggcgtctggg gaggtcattt   1680

agtgctggat ttcagcaaga gcttgcatgg aaaagaatgt gtaatatacg tgaacgcagg   1740

ggcagtggct cacctgaaag tgatacggac tgagaaggaa atgattaaat tatacaaagt   1800

cagtgttact tgtagttttg ggttcatggc actacgatta aactaaacat tagtcatata   1860

atgctggaca tggttggcag acattatttg tagttttggg ttcatggcac taccattaag   1920

ctaaacatta gtcatataat gctggacatg gttggtagac atctatagtg ctctcccatt   1980

aatcataaaa cctttgcaaa ctttttacaa tcatttatga acttattgct caaatgccat   2040

tcctgatcta cagtatactg ggtattgtat actgccatgt caggagtatt ttcattaatt   2100

aataaaattg gagtttaaaa tcaaaaaaa                                     2129


<210> SEQ ID NO 5
<211> LENGTH: 493
<212> TYPE: PRT
<213> ORGANISM: Xenopus sp.

<400> SEQUENCE: 5

Met Pro Asn Ile Glu Ala Asp Arg Val Thr Ser Val Pro Glu Asn Asn
1               5                   10                  15

Asp Cys Lys Ser Lys Ser Gln Pro Leu Arg Asn Asn Leu His Glu Thr
            20                  25                  30

Val Lys Ser Tyr Ser Ile Gln Gly Ala Ala Thr Ala Asn Ile Glu Pro
        35                  40                  45

Pro Ala Glu Arg Pro Tyr Pro Trp Gly Cys Pro Val Thr His Thr Lys
    50                  55                  60

Glu Lys Phe Tyr Thr Ile Cys Ala Asp Tyr Ala Phe Leu Asn Gln Ala
65                  70                  75                  80

Thr Ser Leu Cys Lys Ser Ser Ser Ser Val Cys Ser Ser Ser Ser Glu
                85                  90                  95

Asp Lys Ser Ala Leu Ser Asn Thr Ile Asn Tyr Ile Asp Leu Gln Thr
            100                 105                 110

Ser Glu Ser Asp Ser Val Tyr Asn Glu Asp Ala Ser Leu Glu Ser Leu
        115                 120                 125

Ser Ser Asn Leu Gly Thr Arg Pro Leu Ala Trp Glu Ile Asp Lys Ser
    130                 135                 140

Asp Phe Ser Thr Met Thr Ser Lys Leu Lys Arg Ser Gly Val Lys Lys
145                 150                 155                 160
```

-continued

```
Gln Thr Pro Lys Lys Lys Pro Asp Arg Lys Ala Lys Pro Leu Arg Asp
                165                 170                 175

Cys Pro Gln His Leu Ile Leu Asp Asp Val Lys Gln Arg Lys Val Leu
            180                 185                 190

Asp Leu Arg Arg Trp Tyr Cys Ile Ser Arg Pro Gln Tyr Lys Thr Ser
        195                 200                 205

Cys Gly Ile Ser Ser Leu Val Ser Cys Trp Asn Phe Leu Tyr Ser Thr
    210                 215                 220

Leu Gly Ala Gly Ser Leu Pro Pro Ile Thr Gln Glu Glu Ala Leu His
225                 230                 235                 240

Ile Leu Gly Phe Gln Pro Pro Phe Glu Glu Ile Arg Phe Gly Pro Phe
                245                 250                 255

Thr Gly Asn Thr Thr Leu Met Arg Trp Phe Arg Gln Ile Asn Asp His
            260                 265                 270

Phe His Val Lys Gly Cys Ser Tyr Val Leu Tyr Lys Pro His Gly Lys
        275                 280                 285

Asn Lys Thr Ala Gly Glu Thr Ala Val Gly Ala Leu Ser Lys Leu Thr
    290                 295                 300

Gln Gly Leu Lys Glu Asp Ser Thr Ala Tyr Val Tyr His Cys Gln Asn
305                 310                 315                 320

His Tyr Phe Cys Pro Ile Gly Phe Glu Ala Thr Pro Val Lys Ala Ser
                325                 330                 335

Lys Ala Tyr Arg Gly Gln Leu Phe Pro His Glu Val Glu Tyr Trp Ile
            340                 345                 350

Leu Ile Gly Glu Pro Ser Arg Lys His Pro Thr Ile His Cys Lys Lys
        355                 360                 365

Trp Ala Asp Ile Val Thr Asp Leu Asn Thr Gln Asn Pro Glu Tyr Phe
    370                 375                 380

Asp Ile Arg His Thr Glu Arg Gly Leu Gln Tyr Arg Lys Thr Lys Lys
385                 390                 395                 400

Val Gly Gly Asn Leu His Cys Leu Leu Ala Phe Gln Arg Leu Ser Trp
                405                 410                 415

Gln Arg Phe Gly Pro Trp Pro Leu Gln Leu Gly Thr Leu Arg Pro Glu
            420                 425                 430

Pro Gln Pro Pro Val Gln Gly Arg Arg Ile Pro Lys Ser Glu Ser Glu
        435                 440                 445

Asp Asn Val Ser Lys Lys Gln His Gly Arg Leu Gly Arg Ser Phe Ser
    450                 455                 460

Ala Gly Phe Gln Gln Glu Leu Ala Trp Lys Arg Met Cys Asn Ile Arg
465                 470                 475                 480

Glu Arg Arg Gly Ser Gly Ser Pro Glu Ser Asp Thr Asp
                485                 490
```

<210> SEQ ID NO 6
<211> LENGTH: 2841
<212> TYPE: DNA
<213> ORGANISM: Gallus sp.
<220> FEATURE:
<221> NAME/KEY: misc_feature
<222> LOCATION: (235)..(237)
<223> OTHER INFORMATION: Translation initiation codon (ATG)
<220> FEATURE:
<221> NAME/KEY: misc_feature
<222> LOCATION: (1750)..(1752)
<223> OTHER INFORMATION: Translation termination codon (TAG)

<400> SEQUENCE: 6

-continued

```
ggacactgac atggactgaa ggagtagaaa gcaggtgagc gctcgtcgtg gcttctcccc     60
cccctgcgtc gcgcactgcg tctgtttccg gcgcgggcac attccccgct ccgccgcggg    120
cccgcgcagg tacctcacct tgcagtaaca atggaggcag cgatgcaaac tatgtggtaa    180
ttaaaaataa gcaaaaccat tcctcgcagt acaagacgct tccaatatta ttcaatgcct    240
cacatctcag aagatgaaaa ggagaatggt tctggaaaca atggaaacac tgaaaagaaa    300
cctgggaaag aatcctcaga agcttctctt cgtgatccta taaagtcgta ctgcatctca    360
gatgcctcca ctgtgtcttt ggtgtccagg ggagatggac attacccatg ggatgtcct     420
gtgactcaca cacgagagaa attttatacc atttgctcag actatgcttt tttaaacaga    480
gtaacatcta tttgtaaaag cccaagtgct tcagttaacg cctgcctgtc aggcagtgct    540
gccttaaacg ttggaaataa cacacctagc ttactgggca ttcaaactgg tgcttcggag    600
ataatctaca gtgaagatgc taacttggaa accttgtctg gcagccttgg aaagcttcca    660
ctggcatggg aaattgacaa atcagaattc aacagcgtga ctgcgaatca taaaaacaaa    720
gcaggcaaca tgaagaaaca agtggcaaag aaaaagtcct cagacaaaaa aagcaaacag    780
tacaaggagt gtcctcagct gtctgctctt gaagatgtga aggagaggaa agtgttggac    840
ctccgaagat ggtactgtat tagccgacct cagtacaaga cttcttgtgg aatttcttca    900
ttagtgtctt gctggaattt cttatatagt acgctgggag ctggcagttt accacctatt    960
actcaagaag aagctttgca tatattgggt tttcaacccc catttgagga gatcaggttt   1020
ggtcccttca ctggaaatac gactttaatg agatggttta ggcaaataaa tgatcacttc   1080
catatcaagg gttgctcata tgttctgtat aaacctcatg gaaagaacaa gacagctgga   1140
gaaactgctg tgggggccct tgcaaagcta acacgtggac tgaaagatga atcaatggcc   1200
tacatctacc attgccaaaa ccattatttt tgcccaattg gatttgaagc aactccagta   1260
aaagctagta aagcgtatag aggtcgtgtt ttgcagcaag aagtagaata ctggatctta   1320
attggagagc cgagcagaaa acatccaacg atacactgta aaaggtggac agatattgtc   1380
actgacctaa acacccaaaa tccagagtac ctagatattc ggcacctaga gagaggactg   1440
cagcatcgga aaacaaagaa ggttggagga aatcttcatt gcatcatcgc ctttcagaga   1500
cttaactggc aaagatttgg tccttggaat attccatttg gaagtgtcag acaggataaa   1560
caatcccaaa cacaaggaca aggtattgcc aaatctgaga gtgaagacaa tatctctaaa   1620
aaacaacatg gacgactggg tcgatctttc agtgctggtt tccatcaaga atctacatgg   1680
aaaaagtcta gtcttcgtga gaggaggaac agcgggtatc agagctataa tgattatgat   1740
ggagatgatt agaattaact ttaggtaata gagtttatat atcaaagtta gttttaatca   1800
acacagaata ggggtttatt agtcctagga tacatgtgaa tagaaaatat ggcataagat   1860
acagctttgt aatccttaaa tcaattatga attatatggt tgcagtggat aaaagagcag   1920
attgaaatta gccaatgtaa taaacagatt tcattgaaaa tacttgatat tcagaagcat   1980
gaaaatgtat tatatgactt tataaaaagg gttatactgc atatggtgta aggataaaag   2040
taaacatttg ccttcctttt tagcactcca ttttgttaag gctgctgata tccagtgaga   2100
agaaagaaat tgaataggtt agaaaacctt gtcagattaa caaaattgaa tgtatattct   2160
caatctagtt gtcagtagaa ttctgtgagt cagataatcc tgttttgtag gtagatccca   2220
gttatttttc ccatagctag atacctgttt taaactgaga agaattgctg gtggcaagga   2280
aggtttgaag atggacattt actgcttttg ctctgtggat atggtagcag attttctatc   2340
ctgtgagctc tggtgagcag tgactgcata acacaggctt gtgaaaatca tttttataaa   2400
```

gctgcattta acctgagccc aatgaactgg ctgaacagtg tgttctgctg gcaattcttt 2460
tccttgttca gtctcaaaac tcctgttgtt tttgtgctgc tctcttgatt ttgtatgaag 2520
gtgatgcaag tgccgacaac tgctggcagc ccttatgata tacctctatg ccagcaaaca 2580
atccaagtct tttcaggtgt ccatgtgcag ttttttttt ttcctttctg gtttattcag 2640
ttgtttgccc aaatgcatct cgacagttgt aactttgtgt gcgaatgtcc acacctgctc 2700
aaggattttt tttttttac ataaaacaat ttgtcatgta atgcagggtt tttgtaggtt 2760
gatgctgttg ttaaccaaaa atggagggag acttttggac tttcgttcat tcaataaaat 2820
ttgttttatt taaaaaaaaa a 2841

<210> SEQ ID NO 7
<211> LENGTH: 3038
<212> TYPE: DNA
<213> ORGANISM: Gallus sp.
<220> FEATURE:
<221> NAME/KEY: misc_feature
<222> LOCATION: (235)..(237)
<223> OTHER INFORMATION: Translation initiation codon (ATG)
<220> FEATURE:
<221> NAME/KEY: misc_feature
<222> LOCATION: (1281)..(1352)
<223> OTHER INFORMATION: Sequence of alternative splicing
<220> FEATURE:
<221> NAME/KEY: misc_feature
<222> LOCATION: (1822)..(1824)
<223> OTHER INFORMATION: Translation termination codon (TAG)
<220> FEATURE:
<221> NAME/KEY: misc_feature
<222> LOCATION: (1982)..(2106)
<223> OTHER INFORMATION: Sequence of alternative splicing

<400> SEQUENCE: 7
ggacactgac atggactgaa ggagtagaaa gcaggtgagc gctcgtcgtg gcttctcccc 60
cccctgcgtc gcgcactgcg tctgtttccg gcgcgggcac attccccgct ccgccgcggg 120
cccgcgcagg tacctcacct tgcagtaaca atggaggcag cgatgcaaac tatgtggtaa 180
ttaaaaataa gcaaaaccat tcctcgcagt acaagacgct tccaatatta ttcaatgcct 240
cacatctcag aagatgaaaa ggagaatggt tctggaaaca atggaaacac tgaaaagaaa 300
cctgggaaag aatcctcaga agcttctctt cgtgatccta taaagtcgta ctgcatctca 360
gatgcctcca ctgtgtcttt ggtgtccagg ggagatggac attacccatg ggatgtcct 420 gtgactcaca cacgagagaa attttatacc atttgctcag actatgcttt tttaaacaga 480
gtaacatcta tttgtaaaag cccaagtgct tcagttaacg cctgcctgtc aggcagtgct 540
gccttaaacg ttggaaataa cacacctagc ttactgggca ttcaaactgg tgcttcggag 600
ataatctaca gtgaagatgc taacttggaa accttgtctg gcagccttgg aaagcttcca 660
ctggcatggg aaattgacaa atcagaattc aacagcgtga ctgcgaatca taaaaacaaa 720
gcaggcaaca tgaagaaaca agtggcaaag aaaaagtcct cagacaaaaa aagcaaacag 780
tacaaggagt gtcctcagct gtctgctctt gaagatgtga aggagaggaa agtgttggac 840
ctccgaagat ggtactgtat tagccgacct cagtacaaga cttcttgtgg aatttcttca 900
ttagtgtctt gctggaattt cttatatagt acgctgggag ctggcagttt accacctatt 960
actcaagaag aagctttgca tatattgggt tttcaacccc catttgagga gatcaggttt 1020
ggtcccttca ctggaaatac gactttaatg agatggttta ggcaaataaa tgatcacttc 1080
catatcaagg gttgctcata tgttctgtat aaacctcatg gaaagaacaa gacagctgga 1140

-continued

```
gaaactgctg tgggggccct tgcaaagcta acacgtggac tgaaagatga atcaatggcc   1200

tacatctacc attgccaaaa ccattatttt tgcccaattg gatttgaagc aactccagta   1260

aaagctagta aagcgtatag gttgctggat ttggactcgg gagacctggg ttcggttccc   1320

agttcaaccg cagacttcca ttgtgatttt agaggtcgtg ttttgcagca agaagtagaa   1380

tactggatct taattggaga gccgagcaga aaacatccaa cgatacactg taaaaggtgg   1440

acagatattg tcactgacct aaacacccaa aatccagagt acctagatat tcggcaccta   1500

gagagaggac tgcagcatcg gaaaacaaag aaggttggag gaaatcttca ttgcatcatc   1560

gcctttcaga gacttaactg gcaaagattt ggtccttgga atattccatt tggaagtgtc   1620

agacaggata aacaatccca aacacaagga caaggtattg ccaaatctga gagtgaagac   1680

aatatctcta aaaaacaaca tggacgactg ggtcgatctt tcagtgctgg tttccatcaa   1740

gaatctacat ggaaaaagtc tagtcttcgt gagaggagga acagcgggta tcagagctat   1800

aatgattatg atggagatga ttagaattaa ctttaggtaa tagagtttat atatcaaagt   1860

tagttttaat caacacagaa taggggttta ttagtcctag gatacatgtg aatagaaaat   1920

atggcataag atacagcttt gtaatcctta aatcaattat gaattatatg gttgcagtgg   1980

atgacatctg atacatgaac tgacagataa gcacagatta ttgtactttt gtaatcaaaa   2040

gcagatatga cagctaaatc aatcacttat tttgaagtta ctatactata tcctgatctg   2100

tgagaataaa agagcagatt gaaattagcc aatgtaataa acagatttca ttgaaaatac   2160

ttgatattca gaagcatgaa aatgtattat atgactttat aaaaagggtt atactgcata   2220

tggtgtaagg ataaaagtaa acatttgcct tcctttttag cactccattt tgttaaggct   2280

gctgatatcc agtgagaaga aagaaattga ataggttaga aaaccttgtc agattaacaa   2340

aattgaatgt atattctcaa tctagttgtc agtagaattc tgtgagtcag ataatcctgt   2400

tttgtaggta gatcccagtt atttttccca tagctagata cctgttttaa actgagaaga   2460

attgctggtg gcaaggaagg tttgaagatg gacatttact gcttttgctc tgtggatatg   2520

gtagcagatt ttctatcctg tgagctctgg tgagcagtga ctgcataaca caggcttgtg   2580

aaaatcattt ttataaagct gcatttaacc tgagcccaat gaactggctg aacagtgtgt   2640

tctgctggca attcttttcc ttgttcagtc tcaaaactcc tgttgttttt gtgctgctct   2700

cttgattttg tatgaaggtg atgcaagtgc cgacaactgc tggcagccct tatgatatac   2760

ctctatgcca gcaaacaatc caagtctttt caggtgtcca tgtgcagttt tttttttttc   2820

ctttctggtt tattcagttg tttgcccaaa tgcatctcga cagttgtaac tttgtgtgcg   2880

aatgtccaca cctgctcaag gatttttttt tttttacata aaacaatttg tcatgtaatg   2940

cagggttttt gtaggttgat gctgttgtta accaaaaatg gagggagact tttggacttt   3000

cgttcattca ataaaatttg ttttatttaa aaaaaaaa                           3038
```

```
<210> SEQ ID NO 8
<211> LENGTH: 505
<212> TYPE: PRT
<213> ORGANISM: Gallus sp.

<400> SEQUENCE: 8

Met Pro His Ile Ser Glu Asp Glu Lys Glu Asn Gly Ser Gly Asn Asn
1               5                   10                  15

Gly Asn Thr Glu Lys Lys Pro Gly Lys Glu Ser Ser Glu Ala Ser Leu
            20                  25                  30

Arg Asp Pro Ile Lys Ser Tyr Cys Ile Ser Asp Ala Ser Thr Val Ser
```

-continued

```
        35                  40                  45

Leu Val Ser Arg Gly Asp Gly His Tyr Pro Trp Gly Cys Pro Val Thr
    50                  55                  60

His Thr Arg Glu Lys Phe Tyr Thr Ile Cys Ser Asp Tyr Ala Phe Leu
65                  70                  75                  80

Asn Arg Val Thr Ser Ile Cys Lys Ser Pro Ser Ala Ser Val Asn Ala
                85                  90                  95

Cys Leu Ser Gly Ser Ala Ala Leu Asn Val Gly Asn Asn Thr Pro Ser
            100                 105                 110

Leu Leu Gly Ile Gln Thr Gly Ala Ser Glu Ile Ile Tyr Ser Glu Asp
        115                 120                 125

Ala Asn Leu Glu Thr Leu Ser Gly Ser Leu Gly Lys Leu Pro Leu Ala
    130                 135                 140

Trp Glu Ile Asp Lys Ser Glu Phe Asn Ser Val Thr Ala Asn His Lys
145                 150                 155                 160

Asn Lys Ala Gly Asn Met Lys Lys Gln Val Ala Lys Lys Lys Ser Ser
                165                 170                 175

Asp Lys Lys Ser Lys Gln Tyr Lys Glu Cys Pro Gln Leu Ser Ala Leu
            180                 185                 190

Glu Asp Val Lys Glu Arg Lys Val Leu Asp Leu Arg Arg Trp Tyr Cys
        195                 200                 205

Ile Ser Arg Pro Gln Tyr Lys Thr Ser Cys Gly Ile Ser Ser Leu Val
    210                 215                 220

Ser Cys Trp Asn Phe Leu Tyr Ser Thr Leu Gly Ala Gly Ser Leu Pro
225                 230                 235                 240

Pro Ile Thr Gln Glu Glu Ala Leu His Ile Leu Gly Phe Gln Pro Pro
                245                 250                 255

Phe Glu Glu Ile Arg Phe Gly Pro Phe Thr Gly Asn Thr Thr Leu Met
            260                 265                 270

Arg Trp Phe Arg Gln Ile Asn Asp His Phe His Ile Lys Gly Cys Ser
        275                 280                 285

Tyr Val Leu Tyr Lys Pro His Gly Lys Asn Lys Thr Ala Gly Glu Thr
    290                 295                 300

Ala Val Gly Ala Leu Ala Lys Leu Thr Arg Gly Leu Lys Asp Glu Ser
305                 310                 315                 320

Met Ala Tyr Ile Tyr His Cys Gln Asn His Tyr Phe Cys Pro Ile Gly
                325                 330                 335

Phe Glu Ala Thr Pro Val Lys Ala Ser Lys Ala Tyr Arg Gly Arg Val
            340                 345                 350

Leu Gln Gln Glu Val Glu Tyr Trp Ile Leu Ile Gly Glu Pro Ser Arg
        355                 360                 365

Lys His Pro Thr Ile His Cys Lys Arg Trp Thr Asp Ile Val Thr Asp
    370                 375                 380

Leu Asn Thr Gln Asn Pro Glu Tyr Leu Asp Ile Arg His Leu Glu Arg
385                 390                 395                 400

Gly Leu Gln His Arg Lys Thr Lys Lys Val Gly Gly Asn Leu His Cys
                405                 410                 415

Ile Ile Ala Phe Gln Arg Leu Asn Trp Gln Arg Phe Gly Pro Trp Asn
            420                 425                 430

Ile Pro Phe Gly Ser Val Arg Gln Asp Lys Gln Ser Gln Thr Gln Gly
        435                 440                 445

Gln Gly Ile Ala Lys Ser Glu Ser Glu Asp Asn Ile Ser Lys Lys Gln
    450                 455                 460
```

-continued

```
His Gly Arg Leu Gly Arg Ser Phe Ser Ala Gly Phe His Gln Glu Ser
465                 470                 475                 480

Thr Trp Lys Lys Ser Ser Leu Arg Glu Arg Arg Asn Ser Gly Tyr Gln
                485                 490                 495

Ser Tyr Asn Asp Tyr Asp Gly Asp Asp
            500                 505


<210> SEQ ID NO 9
<211> LENGTH: 529
<212> TYPE: PRT
<213> ORGANISM: Gallus sp.

<400> SEQUENCE: 9

Met Pro His Ile Ser Glu Asp Glu Lys Glu Asn Gly Ser Gly Asn Asn
1               5                   10                  15

Gly Asn Thr Glu Lys Lys Pro Gly Lys Glu Ser Ser Glu Ala Ser Leu
            20                  25                  30

Arg Asp Pro Ile Lys Ser Tyr Cys Ile Ser Asp Ala Ser Thr Val Ser
        35                  40                  45

Leu Val Ser Arg Gly Asp Gly His Tyr Pro Trp Gly Cys Pro Val Thr
    50                  55                  60

His Thr Arg Glu Lys Phe Tyr Thr Ile Cys Ser Asp Tyr Ala Phe Leu
65                  70                  75                  80

Asn Arg Val Thr Ser Ile Cys Lys Ser Pro Ser Ala Ser Val Asn Ala
                85                  90                  95

Cys Leu Ser Gly Ser Ala Ala Leu Asn Val Gly Asn Asn Thr Pro Ser
            100                 105                 110

Leu Leu Gly Ile Gln Thr Gly Ala Ser Glu Ile Ile Tyr Ser Glu Asp
        115                 120                 125

Ala Asn Leu Glu Thr Leu Ser Gly Ser Leu Gly Lys Leu Pro Leu Ala
    130                 135                 140

Trp Glu Ile Asp Lys Ser Glu Phe Asn Ser Val Thr Ala Asn His Lys
145                 150                 155                 160

Asn Lys Ala Gly Asn Met Lys Lys Gln Val Ala Lys Lys Lys Ser Ser
                165                 170                 175

Asp Lys Lys Ser Lys Gln Tyr Lys Glu Cys Pro Gln Leu Ser Ala Leu
            180                 185                 190

Glu Asp Val Lys Glu Arg Lys Val Leu Asp Leu Arg Arg Trp Tyr Cys
        195                 200                 205

Ile Ser Arg Pro Gln Tyr Lys Thr Ser Cys Gly Ile Ser Ser Leu Val
    210                 215                 220

Ser Cys Trp Asn Phe Leu Tyr Ser Thr Leu Gly Ala Gly Ser Leu Pro
225                 230                 235                 240

Pro Ile Thr Gln Glu Glu Ala Leu His Ile Leu Gly Phe Gln Pro Pro
                245                 250                 255

Phe Glu Glu Ile Arg Phe Gly Pro Phe Thr Gly Asn Thr Thr Leu Met
            260                 265                 270

Arg Trp Phe Arg Gln Ile Asn Asp His Phe His Ile Lys Gly Cys Ser
        275                 280                 285

Tyr Val Leu Tyr Lys Pro His Gly Lys Asn Lys Thr Ala Gly Glu Thr
    290                 295                 300

Ala Val Gly Ala Leu Ala Lys Leu Thr Arg Gly Leu Lys Asp Glu Ser
305                 310                 315                 320

Met Ala Tyr Ile Tyr His Cys Gln Asn His Tyr Phe Cys Pro Ile Gly
```

-continued

```
                325                 330                 335

Phe Glu Ala Thr Pro Val Lys Ala Ser Lys Ala Tyr Arg Leu Leu Asp
            340                 345                 350

Leu Asp Ser Gly Asp Leu Gly Ser Val Pro Ser Ser Thr Ala Asp Phe
        355                 360                 365

His Cys Asp Phe Arg Gly Arg Val Leu Gln Gln Glu Val Glu Tyr Trp
    370                 375                 380

Ile Leu Ile Gly Glu Pro Ser Arg Lys His Pro Thr Ile His Cys Lys
385                 390                 395                 400

Arg Trp Thr Asp Ile Val Thr Asp Leu Asn Thr Gln Asn Pro Glu Tyr
                405                 410                 415

Leu Asp Ile Arg His Leu Glu Arg Gly Leu Gln His Arg Lys Thr Lys
            420                 425                 430

Lys Val Gly Gly Asn Leu His Cys Ile Ile Ala Phe Gln Arg Leu Asn
        435                 440                 445

Trp Gln Arg Phe Gly Pro Trp Asn Ile Pro Phe Gly Ser Val Arg Gln
    450                 455                 460

Asp Lys Gln Ser Gln Thr Gln Gly Gln Gly Ile Ala Lys Ser Glu Ser
465                 470                 475                 480

Glu Asp Asn Ile Ser Lys Lys Gln His Gly Arg Leu Gly Arg Ser Phe
                485                 490                 495

Ser Ala Gly Phe His Gln Glu Ser Thr Trp Lys Lys Ser Ser Leu Arg
            500                 505                 510

Glu Arg Arg Asn Ser Gly Tyr Gln Ser Tyr Asn Asp Tyr Asp Gly Asp
        515                 520                 525

Asp
```

<210> SEQ ID NO 10
<211> LENGTH: 1946
<212> TYPE: DNA
<213> ORGANISM: Danio rerio
<220> FEATURE:
<221> NAME/KEY: misc_feature
<222> LOCATION: (165)..(167)
<223> OTHER INFORMATION: Translation initiation codon (ATG)
<220> FEATURE:
<221> NAME/KEY: misc_feature
<222> LOCATION: (1671)..(1673)
<223> OTHER INFORMATION: Translation termination codon (TAA)

<400> SEQUENCE: 10

```
cgttgaaaca gctaggcagt cagagaggtc gcgcagcgca ttttatataa aatattcttg     60

ctgaacttgc gagtcggtgg attattttgg gactgagtca tcatatctgc ggtacacctg    120

acctgttggt tattctctta accatcatcc cagttctcca ttcaatgcct aacactgtgg    180

aaagtgaagg cgccaaggta tccgctagta cagatcagga ggccccatca cgggccccgg    240

gacgagagga tgaacgtgag cgcagcttcc tgagccccat gatgcgagat gctctgcggg    300

tacgacgggc ctccagcgca gagctccagc ttccatggac gtgccctgta acccactcca    360

gggagaagtt ctacaccgtc tgctcggact atgccctgct caaccgagct cgaccagtta    420

tcacatccga agatgcatca cagaccaatc ctgacagcgg gacatcatta gccaagagca    480

acacagcaac atcttctcag agtcactcag gggaataag cgtatcttta gatgggaact     540

gtgatatgga ggttgtgtcc tccagcaaca agcctgtgct ggcctgggag attgacacct    600

cagatttcga tgccgtttta acccggaaag ccagaacaag taatttgaag aaattcaaca    660

ctaagaaaat gaaatcatct gacaggccaa gcagaaacct gcaagatgtc ccgccacaag    720
```

-continued

```
cctctctaga tgaaatcaaa cagagaaaag tgctggacct ccgtagatgg tactgcatca    780

gccgaccaca gtataaaaca tcatgtggaa tctcttcact tgtttcttgc tggaactttc    840

tctacagtac tctcggagca ggcagtctcc cacctatttc tcaagaagaa gctctgcata    900

tacttggatt tcagcctccg tttgaagata tcaaatttgg accatttact ggcaatgcca    960

ctttaatgag atggttcaga caaatcaatg ataattttcg tgttcggggt tgctcatata   1020

ttctgtacaa gcctcatggg aagcacaaga cagcaggaga gacagccgag gggcgctca   1080

tgaagcttac acagggtctt aaagacgaat ccatggccta catttatcac tgtcagaatc   1140

actacttctg tcctgtgggc tatgaagcta ctccactgaa agcagccaaa gcatacaggg   1200

gaccactgcc tcttaatgag atggagcact ggattctcat tggtgaacca agccggaaac   1260

atcctgcaat ccactgtaaa aaatgggcag acatcgtgac ggacctaaat actcagaacc   1320

cagaatactt agacattcgc catattgaga gaggcataca gtatcgcaaa accaagaagg   1380

ttggaggcaa tctgcattgc atcatggcct tccagagagt gaactggcaa aaattgggac   1440

catgggcgct gaatctggaa aacctgaggc atgatctcca tcatcaggct ccagaacaca   1500

gaggccaagc ttcaacagag gacagttctg aggagcgaac ggtgaaacgc ctgggtaggt   1560

ctctcagcac ggggaacaag cctgaaaatg cctggaagcg tttgtccaac acagccgagt   1620

acaggcacag aggctctcca gacagtgacc tggatgaaga catcactgac taaatatgaa   1680

gggccaggtg ggtttcgaca cttttattca agattattaa ccttccaggt tattagctat   1740

agttaaaggt tacaatccgg tatgaggttg tgatgtaaga gttagtgctc agactggtaa   1800

acttaaaaat ggaagtttga cgccaataag aatatgggaa agagctcttg tggaggacat   1860

ctgtgtaata ctgacagcaa tgtgaattaa gttacactgg ctttggtgat gtgccgataa   1920

ataaaggttt aaaatactaa aaaaaa                                         1946
```

<210> SEQ ID NO 11
<211> LENGTH: 502
<212> TYPE: PRT
<213> ORGANISM: Danio rerio

<400> SEQUENCE: 11

```
Met Pro Asn Thr Val Glu Ser Glu Gly Ala Lys Val Ser Ala Ser Thr
1               5                   10                  15

Asp Gln Glu Ala Pro Ser Arg Ala Pro Gly Arg Glu Asp Glu Arg Glu
            20                  25                  30

Arg Ser Phe Leu Ser Pro Met Met Arg Asp Ala Leu Arg Val Arg Arg
        35                  40                  45

Ala Ser Ser Ala Glu Leu Gln Leu Pro Trp Thr Cys Pro Val Thr His
    50                  55                  60

Ser Arg Glu Lys Phe Tyr Thr Val Cys Ser Asp Tyr Ala Leu Leu Asn
65                  70                  75                  80

Arg Ala Arg Pro Val Ile Thr Ser Glu Asp Ala Ser Gln Thr Asn Pro
                85                  90                  95

Asp Ser Gly Thr Ser Leu Ala Lys Ser Asn Thr Ala Thr Ser Ser Gln
            100                 105                 110

Ser His Ser Gly Gly Ile Ser Val Ser Leu Asp Gly Asn Cys Asp Met
        115                 120                 125

Glu Val Val Ser Ser Ser Asn Lys Pro Val Leu Ala Trp Glu Ile Asp
    130                 135                 140

Thr Ser Asp Phe Asp Ala Val Leu Thr Arg Lys Ala Arg Thr Ser Asn
```

-continued

```
145                 150                 155                 160

Leu Lys Lys Phe Asn Thr Lys Lys Met Lys Ser Ser Asp Arg Pro Ser
                165                 170                 175

Arg Asn Leu Gln Asp Val Pro Pro Gln Ala Ser Leu Asp Glu Ile Lys
            180                 185                 190

Gln Arg Lys Val Leu Asp Leu Arg Arg Trp Tyr Cys Ile Ser Arg Pro
        195                 200                 205

Gln Tyr Lys Thr Ser Cys Gly Ile Ser Ser Leu Val Ser Cys Trp Asn
    210                 215                 220

Phe Leu Tyr Ser Thr Leu Gly Ala Gly Ser Leu Pro Pro Ile Ser Gln
225                 230                 235                 240

Glu Glu Ala Leu His Ile Leu Gly Phe Gln Pro Pro Phe Glu Asp Ile
                245                 250                 255

Lys Phe Gly Pro Phe Thr Gly Asn Ala Thr Leu Met Arg Trp Phe Arg
            260                 265                 270

Gln Ile Asn Asp Asn Phe Arg Val Arg Gly Cys Ser Tyr Ile Leu Tyr
        275                 280                 285

Lys Pro His Gly Lys His Lys Thr Ala Gly Glu Thr Ala Glu Gly Ala
    290                 295                 300

Leu Met Lys Leu Thr Gln Gly Leu Lys Asp Glu Ser Met Ala Tyr Ile
305                 310                 315                 320

Tyr His Cys Gln Asn His Tyr Phe Cys Pro Val Gly Tyr Glu Ala Thr
                325                 330                 335

Pro Leu Lys Ala Ala Lys Ala Tyr Arg Gly Pro Leu Pro Leu Asn Glu
            340                 345                 350

Met Glu His Trp Ile Leu Ile Gly Glu Pro Ser Arg Lys His Pro Ala
        355                 360                 365

Ile His Cys Lys Lys Trp Ala Asp Ile Val Thr Asp Leu Asn Thr Gln
    370                 375                 380

Asn Pro Glu Tyr Leu Asp Ile Arg His Ile Glu Arg Gly Ile Gln Tyr
385                 390                 395                 400

Arg Lys Thr Lys Lys Val Gly Gly Asn Leu His Cys Ile Met Ala Phe
                405                 410                 415

Gln Arg Val Asn Trp Gln Lys Leu Gly Pro Trp Ala Leu Asn Leu Glu
            420                 425                 430

Asn Leu Arg His Asp Leu His His Gln Ala Pro Glu His Arg Gly Gln
        435                 440                 445

Ala Ser Thr Glu Asp Ser Ser Glu Glu Arg Thr Val Lys Arg Leu Gly
    450                 455                 460

Arg Ser Leu Ser Thr Gly Asn Lys Pro Glu Asn Ala Trp Lys Arg Leu
465                 470                 475                 480

Ser Asn Thr Ala Glu Tyr Arg His Arg Gly Ser Pro Asp Ser Asp Leu
                485                 490                 495

Asp Glu Asp Ile Thr Asp
            500
```

<210> SEQ ID NO 12
<211> LENGTH: 2062
<212> TYPE: DNA
<213> ORGANISM: Strongylocentrotus purpuratus
<220> FEATURE:
<221> NAME/KEY: misc_feature
<222> LOCATION: (164)..(166)
<223> OTHER INFORMATION: translation initiation codon (ATG)

<400> SEQUENCE: 12

-continued

```
gcagtttgtg tgtgattctc aatctcattg tgcgcattat aggcctatag ctttcgggaa     60
aacagacaga ttagtgcttt gcaaaccttg catacattga ggcaaccaga aagttgggct    120
caactttcag ataacctttg acctttcctg ggcctgaggt ataatgggta actggccttc    180
agttctctct ggtgagggaa gtgaggacag cagcagcgag agcaacaacg aaagcaacaa    240
ccaggaaacc agtgatcagg aaaacacaag acatcatctc tgtggctcag aggagagcta    300
cttctccgag gaggaactcc ttcccattgt ctaccctgat gatgatgatg atgctgctgc    360
tcgtgatgac gtgttgggag acttcttgtc cgttaaagaa gatggagagt ttacaactga    420
cgaggttgat gggtctcgat atgacctagc acccgagtat taccccacct ctcttcatga    480
agacgtcact gcgagattct cagatcttgc ctcacctgta gatcgcaaag aaagcagcta    540
cagcagcact gacgactatg atgacaatga cagtgatgat gaggaggagg aggaggatga    600
ccactattac caaagaagga ggaatgataa atattcccta atgaaggaag acgatgatga    660
taatgagctc tccagcattc cactgccacc tccctcatca ctgtatgaag ttgcatcagc    720
tgagcagatg caaggggtca cagcttacct gaatgctgac cgacctgaca cactccaaga    780
aaccatcgtc ccttttgaga gtcgtgcaga agagtgcagt gcccctgaga gggtggttgc    840
atgggagata gacgtcagcg acatgacggg atccaagaag actaagaaga gaccacccaa    900
taaactttca aaggcaaaat caaggaaaag ttcatcgaaa ggtagcatgg atagtgccta    960
tatcccgcca actgtatcaa caacacctga gctcctagca cagagaaagt gcttggacca   1020
aaagagatgg ttttgtgtga gtagacccca gtacagcaag tcatgtggcc tatcgtcctt   1080
ggtttcttgc tggaactacc tgttcagtac cctaggaggg ggcaccatgc cccccatcac   1140
ccaggagcaa gcccttaacg tcctggggtt ccaaccaccc ttcggtgaga tccgttttgg   1200
gcctttcaca gggaatgcca ccctcatgag gtggttcaag cagctgaatg atcactacag   1260
agtgagagga agggcatact tccagtacaa accccatggc aggagtagaa cagtgggaag   1320
aacatctgcc caaggtttac atctgttacg acaagggttg aaggatccta acatggcttt   1380
catataccac tgccataacc actacttctg ccccattgga tacgaagatg tgcctctgaa   1440
ggctgtagat gcatacaggg atcctttaaa ccttgatgag gtagagacat ggatactgat   1500
cggtgatcct agtagaaagc aaccaggaat ccactgtttc aaatgggaag acatcagcac   1560
agatctgaac tgccagaacc ctgactatct caacatccgc aagctacggc ttggagtgca   1620
gcagaggagg acaaagagaa ccggtggcaa cttgcactgc atcatggcct tctgtcgcag   1680
tgcaggcttt ctcaccagac caaccaagag caagaaagag ggtgcaatga aggacacttc   1740
tagtaacagc aagagtagga agtctggctc cgttcggatg tcaggacgta aggttggcga   1800
gagtaagagt gaggggatgg tggggcgtcc agctccagga gggagtgtgc catgtctgca   1860
gactggcaaa gcggacagta gcgatatcat cgagcacttt gcttttgaga ctgtgagttg   1920
cgaccatagc agtgagggcc gaagctgtag atcagaagtt gttaaaaaga ctaaaagtga   1980
atctcaggtt ggcagacgaa gggcaaaggc atctgttgta aagcaggagg ataaggagat   2040
cagagtgaag agttctgagg ca                                            2062
```

<210> SEQ ID NO 13
<211> LENGTH: 633
<212> TYPE: PRT
<213> ORGANISM: Strongylocentrotus purpuratus

<400> SEQUENCE: 13

-continued

```
Met Gly Asn Trp Pro Ser Val Leu Ser Gly Glu Gly Ser Glu Asp Ser
1               5                   10                  15

Ser Ser Glu Ser Asn Asn Glu Ser Asn Asn Gln Glu Thr Ser Asp Gln
            20                  25                  30

Glu Asn Thr Arg His His Leu Cys Gly Ser Glu Glu Ser Tyr Phe Ser
        35                  40                  45

Glu Glu Glu Leu Leu Pro Ile Val Tyr Pro Asp Asp Asp Asp Asp Ala
    50                  55                  60

Ala Ala Arg Asp Asp Val Leu Gly Asp Phe Leu Ser Val Lys Glu Asp
65                  70                  75                  80

Gly Glu Phe Thr Thr Asp Glu Val Asp Gly Ser Arg Tyr Asp Leu Ala
                85                  90                  95

Pro Glu Tyr Tyr Pro Thr Ser Leu His Glu Asp Val Thr Ala Arg Phe
            100                 105                 110

Ser Asp Leu Ala Ser Pro Val Asp Arg Lys Glu Ser Ser Tyr Ser Ser
        115                 120                 125

Thr Asp Asp Tyr Asp Asp Asn Asp Ser Asp Asp Glu Glu Glu Glu Glu
    130                 135                 140

Asp Asp His Tyr Tyr Gln Arg Arg Arg Asn Asp Lys Tyr Ser Leu Met
145                 150                 155                 160

Lys Glu Asp Asp Asp Asp Asn Glu Leu Ser Ser Ile Pro Leu Pro Pro
                165                 170                 175

Pro Ser Ser Leu Tyr Glu Val Ala Ser Ala Glu Gln Met Gln Gly Val
            180                 185                 190

Thr Ala Tyr Leu Asn Ala Asp Arg Pro Asp Thr Leu Gln Glu Thr Ile
        195                 200                 205

Val Pro Phe Glu Ser Arg Ala Glu Glu Cys Ser Ala Pro Glu Arg Val
    210                 215                 220

Val Ala Trp Glu Ile Asp Val Ser Asp Met Thr Gly Ser Lys Lys Thr
225                 230                 235                 240

Lys Lys Arg Pro Pro Asn Lys Leu Ser Lys Ala Lys Ser Arg Lys Ser
                245                 250                 255

Ser Ser Lys Gly Ser Met Asp Ser Ala Tyr Ile Pro Pro Thr Val Ser
            260                 265                 270

Thr Thr Pro Glu Leu Leu Ala Gln Arg Lys Cys Leu Asp Gln Lys Arg
        275                 280                 285

Trp Phe Cys Val Ser Arg Pro Gln Tyr Ser Lys Ser Cys Gly Leu Ser
    290                 295                 300

Ser Leu Val Ser Cys Trp Asn Tyr Leu Phe Ser Thr Leu Gly Gly Gly
305                 310                 315                 320

Thr Met Pro Pro Ile Thr Gln Glu Gln Ala Leu Asn Val Leu Gly Phe
                325                 330                 335

Gln Pro Pro Phe Gly Glu Ile Arg Phe Gly Pro Phe Thr Gly Asn Ala
            340                 345                 350

Thr Leu Met Arg Trp Phe Lys Gln Leu Asn Asp His Tyr Arg Val Arg
        355                 360                 365

Gly Arg Ala Tyr Phe Gln Tyr Lys Pro His Gly Arg Ser Arg Thr Val
    370                 375                 380

Gly Arg Thr Ser Ala Gln Gly Leu His Leu Leu Arg Gln Gly Leu Lys
385                 390                 395                 400

Asp Pro Asn Met Ala Phe Ile Tyr His Cys His Asn His Tyr Phe Cys
                405                 410                 415

Pro Ile Gly Tyr Glu Asp Val Pro Leu Lys Ala Val Asp Ala Tyr Arg
```

-continued

```
        420                 425                 430

Asp Pro Leu Asn Leu Asp Glu Val Glu Thr Trp Ile Leu Ile Gly Asp
        435                 440                 445

Pro Ser Arg Lys Gln Pro Gly Ile His Cys Phe Lys Trp Glu Asp Ile
    450                 455                 460

Ser Thr Asp Leu Asn Cys Gln Asn Pro Asp Tyr Leu Asn Ile Arg Lys
465                 470                 475                 480

Leu Arg Leu Gly Val Gln Gln Arg Arg Thr Lys Arg Thr Gly Gly Asn
                485                 490                 495

Leu His Cys Ile Met Ala Phe Cys Arg Ser Ala Gly Phe Leu Thr Arg
            500                 505                 510

Pro Thr Lys Ser Lys Lys Glu Gly Ala Met Lys Asp Thr Ser Ser Asn
        515                 520                 525

Ser Lys Ser Arg Lys Ser Gly Ser Val Arg Met Ser Gly Arg Lys Val
    530                 535                 540

Gly Glu Ser Lys Ser Glu Gly Met Val Gly Arg Pro Ala Pro Gly Gly
545                 550                 555                 560

Ser Val Pro Cys Leu Gln Thr Gly Lys Ala Asp Ser Ser Asp Ile Ile
                565                 570                 575

Glu His Phe Ala Phe Glu Thr Val Ser Cys Asp His Ser Ser Glu Gly
            580                 585                 590

Arg Ser Cys Arg Ser Glu Val Val Lys Lys Thr Lys Ser Glu Ser Gln
        595                 600                 605

Val Gly Arg Arg Arg Ala Lys Ala Ser Val Val Lys Gln Glu Asp Lys
    610                 615                 620

Glu Ile Arg Val Lys Ser Ser Glu Ala
625                 630


<210> SEQ ID NO 14
<211> LENGTH: 2031
<212> TYPE: DNA
<213> ORGANISM: Giardia lamblia
<220> FEATURE:
<221> NAME/KEY: misc_feature
<222> LOCATION: (230)..(232)
<223> OTHER INFORMATION: Translation initiation codon (ATG)
<220> FEATURE:
<221> NAME/KEY: misc_feature
<222> LOCATION: (1040)..(1042)
<223> OTHER INFORMATION: Translation termination codon (TAG)

<400> SEQUENCE: 14

gcacatcttg caggtcaaaa cgaacacccc ctccttcgat atcctctcag accctacact     60

ctcaattgtg ttacagaccg ggcatgggaa gaacttgcta cggccggctt tcttaggggg    120

cgccgccctt gtcctcttct tctttcccat cctcctgtcc tctttttgtg actgtttgtg    180

actagacgcc gtttctaaca aaattgccaa gcatgtatgc aaaattaaaa tggaaagata    240

ccccagacaa cggttagacg acggcaggtg gcagtgcgtg gcagcgcagt acagatactc    300

ctgcgccatc tcatgccttg tgagcatatt caatcatctc ttcaacagag acatgaccct    360

ggacgagtgt attgctattc tctttccaga cctgaaagaa gacccacgac actatgattt    420

tggacctcag gcttctaaca gtgctgttca aagctggttc aagaccctct gcatgcacta    480

tggcctttct ggcacctctt gcacgatata caaggagcag ggcagaacga gaactgcgtg    540

tagcaagcaa gaggcactta agaatatcat cactgctttg aatacgccaa gatgtgcgtt    600

actgtatcac tgcttgaacc attactgcat aatcgtaggc tatataataa gtccatctac    660
```

-continued

```
gcctaataga ccaagtaatc attgcgtctt cagcggggat gatggatgca ccctcaagct    720

cctgtgtgca gacggcacag aagccgagga cgtggacgat agtaatattt ggttaatagt    780

ggcagactgt gggaaaggaa ctgctcccct taggtcactg acctgggaat ttgtacataa    840

agatatatct acccgacctc cgtatgcata taacgctagg tgccctgaga gaggactgct    900

aaggaaaaca gaatcaaagg gatatatacc agttgagata gactcagtgc ttgttaacag    960

cacgggagta tccacctgtg ttagatctgg tggcgtcatc aagggatcgt cgcactgcat   1020

cattggattt gttagtgact agagccccgt ttattactcc cggacgaaag tataactatt   1080

aacaccacaa gcacaacgat agctccagta gagcagagcc gaagcacttg aggcagcgag   1140

gcctccaaat acccacatag aacgtcacag atgatagctg tccatgtcgc aattgacaag   1200

gttaacggga aggttgaaac aggcgagggc gtccatctgg tacgttgtac tttggttgtt   1260

gaatattgaa ctgttgtaag tgttgatttg ctgggtatat ctattgctta tgtaccgaaa   1320

aagggcattg caaacgtcat atattgcatc tatctgatga acacagaccc cagtttttg    1380

aagatttgca agtcttcttt gtggtggggc attcatatat gaataagagc agacttctcc   1440

gcaggcaaag gacatggact gaatggcatg ctcgtaacca gttaggtcca gtgctttggt   1500

tcgtgcatag tatttaaaga ccttctgaag aaggatggtt tgaaataggg tcgtcctgtc   1560

cacacagtcc aggcagttta tccgcggata gcacttctga acaaagtcag gaagagcaac   1620

tccgacatca ccgctaggaa ctagaactgt gcttgtggct atgtcatctg ctaactggtg   1680

atactctgtg ttgctgtgtc tacgtatgtt gtagttcatc aacttaacgt tgagggagtt   1740

cttgcggcga gaatcagcag tttttctcat agactcggta aagaacgccg tcagagccgc   1800

tcatcggcgg tctcaaggct tttcttttca ctggcagcaa tggagtcatc caaaagatcg   1860

acttcatttt tgaggaggtt gacgataagt atctctgcgt ctgcagtcac taagttaccc   1920

aatagaaggc ttatatgcct ttgcaagaga ctactaaact gagcgaggcc ctgctcttca   1980

tgagccccat ctgggaagcg tatggcagga gtgaacttgt aagtaaaaaa a            2031
```

<210> SEQ ID NO 15
<211> LENGTH: 270
<212> TYPE: PRT
<213> ORGANISM: Giardia lamblia

<400> SEQUENCE: 15

```
Met Glu Arg Tyr Pro Arg Gln Arg Leu Asp Asp Gly Arg Trp Gln Cys
1               5                   10                  15

Val Ala Ala Gln Tyr Arg Tyr Ser Cys Ala Ile Ser Cys Leu Val Ser
            20                  25                  30

Ile Phe Asn His Leu Phe Asn Arg Asp Met Thr Leu Asp Glu Cys Ile
        35                  40                  45

Ala Ile Leu Phe Pro Asp Leu Lys Glu Asp Pro Arg His Tyr Asp Phe
    50                  55                  60

Gly Pro Gln Ala Ser Asn Ser Ala Val Gln Ser Trp Phe Lys Thr Leu
65                  70                  75                  80

Cys Met His Tyr Gly Leu Ser Gly Thr Ser Cys Thr Ile Tyr Lys Glu
                85                  90                  95

Gln Gly Arg Thr Arg Thr Ala Cys Ser Lys Gln Glu Ala Leu Lys Asn
            100                 105                 110

Ile Ile Thr Ala Leu Asn Thr Pro Arg Cys Ala Leu Leu Tyr His Cys
        115                 120                 125

Leu Asn His Tyr Cys Ile Ile Val Gly Tyr Ile Ile Ser Pro Ser Thr
```

-continued

```
    130                 135                 140

Pro Asn Arg Pro Ser Asn His Cys Val Phe Ser Gly Asp Asp Gly Cys
145                 150                 155                 160

Thr Leu Lys Leu Leu Cys Ala Asp Gly Thr Glu Ala Glu Asp Val Asp
                165                 170                 175

Asp Ser Asn Ile Trp Leu Ile Val Ala Asp Cys Gly Lys Gly Thr Ala
            180                 185                 190

Pro Leu Arg Ser Leu Thr Trp Glu Phe Val His Lys Asp Ile Ser Thr
        195                 200                 205

Arg Pro Pro Tyr Ala Tyr Asn Ala Arg Cys Pro Glu Arg Gly Leu Leu
    210                 215                 220

Arg Lys Thr Glu Ser Lys Gly Tyr Ile Pro Val Glu Ile Asp Ser Val
225                 230                 235                 240

Leu Val Asn Ser Thr Gly Val Ser Thr Cys Val Arg Ser Gly Gly Val
                245                 250                 255

Ile Lys Gly Ser Ser His Cys Ile Ile Gly Phe Val Ser Asp
            260                 265                 270


<210> SEQ ID NO 16
<211> LENGTH: 196
<212> TYPE: DNA
<213> ORGANISM: Branchiostoma floridae

<400> SEQUENCE: 16

tgatttgtgg ttccggcaga tcaatgatca tttccatgta aaaggatgct cctatgttct      60

gtataagccg catggcaaga acaagacagc aggagaaact gctgttgggg cactatcaga     120

gttaacacaa gggttaaaag aagacccaac agcctacgtc tatcattgcc agaaccacta     180

cttctgcccc aatccc                                                     196


<210> SEQ ID NO 17
<211> LENGTH: 65
<212> TYPE: PRT
<213> ORGANISM: Branchiostoma floridae

<400> SEQUENCE: 17

Asp Leu Trp Phe Arg Gln Ile Asn Asp His Phe His Val Lys Gly Cys
1               5                   10                  15

Ser Tyr Val Leu Tyr Lys Pro His Gly Lys Asn Lys Thr Ala Gly Glu
            20                  25                  30

Thr Ala Val Gly Ala Leu Ser Glu Leu Thr Gln Gly Leu Lys Glu Asp
        35                  40                  45

Pro Thr Ala Tyr Val Tyr His Cys Gln Asn His Tyr Phe Cys Pro Asn
    50                  55                  60

Pro
65


<210> SEQ ID NO 18
<211> LENGTH: 382
<212> TYPE: DNA
<213> ORGANISM: Mus musculus
<220> FEATURE:
<221> NAME/KEY: 5'UTR
<222> LOCATION: (1)..(382)
<223> OTHER INFORMATION: Exon A - untranslated

<400> SEQUENCE: 18

ccccaactac tttcgtccct tccctccgtc cctcactctc cctcctcctt tctccccccc      60
```

-continued

```
taccttcctt tctacttctt ttttcaactt tggagcacgg ctttctggca accttaaata    120

ctacagttgc gcaactagca tgtctggagt cacagcaaag atttcccaac ttatattttg    180

ttcaaggtat ccaccgcaaa tggcaggtat atagtaaacg ctgaaaggga ggctaggtgt    240

tatcaatgat acccagtcac tcggtgctat tcttgtgcgc tcaatgggac gaaagattct    300

gggccttggg taggagactt ggagatgcaa gatctggtgt tgccttccag caccagagtt    360

ccgggaccca acaggaacag ag                                              382


<210> SEQ ID NO 19
<211> LENGTH: 42
<212> TYPE: DNA
<213> ORGANISM: Mus musculus
<220> FEATURE:
<221> NAME/KEY: 5'UTR
<222> LOCATION: (1)..(42)
<223> OTHER INFORMATION: Exon B - untranslated

<400> SEQUENCE: 19

ccctggaagg atctgggtcg agctgagtct ctgaggagag at                         42


<210> SEQ ID NO 20
<211> LENGTH: 311
<212> TYPE: DNA
<213> ORGANISM: Mus musculus
<220> FEATURE:
<221> NAME/KEY: 5'UTR
<222> LOCATION: (1)..(311)
<223> OTHER INFORMATION: Exon C - untranslated

<400> SEQUENCE: 20

ttttcttccg gctgggagtg agggagcagg ccgggaggag gttacaaggc tttagatctg     60

gtcttggcca gtggggacta gggacgcctg gcactgggtt ggccaccgca ggacagtagt    120

gggaacccgg cacagtagcg ctgcagcagt tgcacttgca acatccctgc tctcccggtt    180

ctcctccacc tgcacctttg tcaccttcag gtgcttcgga gcctcaaaga gggggcagtg    240

ggaagtctcc tggctcctca gagtctgaac tccagagggc atcatgtgct gcatgaatct    300

catactcaca g                                                         311


<210> SEQ ID NO 21
<211> LENGTH: 601
<212> TYPE: DNA
<213> ORGANISM: Mus musculus
<220> FEATURE:
<221> NAME/KEY: 5'UTR
<222> LOCATION: (1)..(125)
<223> OTHER INFORMATION: Exon 1 - untranslated
<220> FEATURE:
<221> NAME/KEY: misc_feature
<222> LOCATION: (126)..(128)
<223> OTHER INFORMATION: Translation initiation codon (ATG)

<400> SEQUENCE: 21

gatcccattt gtcagctctc aagccttttt agaatcctgt gaacatttgc caaagttgct     60

tttttttttt ttaaagagag ggttgcggct tcttcctagg aacagagaca tctgcatttg    120

ctctcatgcc taacgccact gaagctggaa aagccactga tcctggacat ggtgagcaca    180

catctgagaa caagtcacca gaagagggtc tacaaggtgc tgtaccatct ttctacacaa    240

gtgcctcaga agcacccata gcgcccagag gagatgggca ttatccatcg agttgtccag    300

tgactcacac tcgagagaaa atttatgcga tctgctcaga ttatgccttc ctcaaccagg    360

caacatcagt ctacaaaact cctagcctaa cccgctctgc ttgcctccct gataacacct    420
```

```
ctctttctgc tggaaatact acaagatata ttggaatttc aactagtaca tcagaaataa    480

tctataatga aggaaaataa cttggaaaac ttgtccactg gcatgggcaa gctacctctt    540

gcatgggaga ttgataaatc tgaatttgat ggggtgacta caaatttgat acataagtca    600

g                                                                    601


<210> SEQ ID NO 22
<211> LENGTH: 912
<212> TYPE: DNA
<213> ORGANISM: Mus musculus
<220> FEATURE:
<221> NAME/KEY: misc_feature
<222> LOCATION: (1)..(912)
<223> OTHER INFORMATION: Alternative BIVM 5' end clone (6359)
<220> FEATURE:
<221> NAME/KEY: misc_feature
<222> LOCATION: (1)..(210)
<223> OTHER INFORMATION: Alternatively spliced exon A
<220> FEATURE:
<221> NAME/KEY: misc_feature
<222> LOCATION: (211)..(311)
<223> OTHER INFORMATION: Alternatively spliced exon C
<220> FEATURE:
<221> NAME/KEY: misc_feature
<222> LOCATION: (312)..(912)
<223> OTHER INFORMATION: Exon 1
<220> FEATURE:
<221> NAME/KEY: misc_feature
<222> LOCATION: (437)..(439)
<223> OTHER INFORMATION: Translation initiation codon

<400> SEQUENCE: 22

atattttgtt caaggtatcc accgcaaatg gcaggtatat agtaaacgct gaaagggagg     60

ctaggtgtta tcaatgatac ccagtcactc ggtgctattc ttgtgcgctc aatgggacga    120

aagattctgg gccttgggta ggagacttgg agatgcaaga tctggtgttg ccttccagca    180

ccagagttcc gggacccaac aggaacagag gtgcttcgga gcctcaaaga gggggcagtg    240

ggaagtctcc tggctcctca gagtctgaac tccagagggc atcatgtgct gcatgaatct    300

catactcaca ggatcccatt tgtcagctct caagcctttt tagaatcctg tgaacatttg    360

ccaaagttgc tttttttttt tttaaagaga gggttgcggc ttcttcctag gaacagagac    420

atctgcattt gctctcatgc ctaacgccac tgaagctgga aaagccactg atcctggaca    480

tggtgagcac acatctgaga acaagtcacc agaagagggt ctacaaggtg ctgtaccatc    540

tttctacaca agtgcctcag aagcacccat agcgcccaga ggagatgggc attatccatc    600

gagttgtcca gtgactcaca ctcgagagaa aatttatgcg atctgctcag attatgcctt    660

cctcaaccag gcaacatcag tctacaaaac tcctagccta acccgctctg cttgcctccc    720

tgataacacc tctctttctg ctggaaatac tacaagatat attggaattt caactagtac    780

atcagaaata atctataatg aaggaaaata acttggaaaa cttgtccact ggcatgggca    840

agctacctct tgcatgggag attgataaat ctgaatttga tggggtgact acaaatttga    900

tacataagtc ag                                                        912


<210> SEQ ID NO 23
<211> LENGTH: 912
<212> TYPE: DNA
<213> ORGANISM: Mus musculus
<220> FEATURE:
<221> NAME/KEY: misc_feature
<222> LOCATION: (1)..(912)
<223> OTHER INFORMATION: Alternative BIVM 5' end clone (6358)
<220> FEATURE:
```

-continued

<221> NAME/KEY: misc_feature
<222> LOCATION: (1)..(311)
<223> OTHER INFORMATION: Exon C
<220> FEATURE:
<221> NAME/KEY: misc_feature
<222> LOCATION: (312)..(912)
<223> OTHER INFORMATION: Exon 1
<220> FEATURE:
<221> NAME/KEY: misc_feature
<222> LOCATION: (437)..(439)
<223> OTHER INFORMATION: Translation initiation codon

<400> SEQUENCE: 23

```
ttttcttccg gctgggagtg agggagcagg ccgggaggag gttacaaggc tttagatctg     60

gtcttggcca gtggggacta gggacgcctg gcactgggtt ggccaccgca ggacagtagt    120

gggaacccgg cacagtagcg ctgcagcagt tgcacttgca acatccctgc tctcccggtt    180

ctcctccacc tgcacctttg tcaccttcag gtgcttcgga gcctcaaaga gggggcagtg    240

ggaagtctcc tggctcctca gagtctgaac tccagagggc atcatgtgct gcatgaatct    300

catactcaca ggatcccatt tgtcagctct caagcctttt tagaatcctg tgaacatttg    360

ccaaagttgc tttttttttt tttaaagaga gggttgcggc ttcttcctag gaacagagac    420

atctgcattt gctctcatgc ctaacgccac tgaagctgga aaagccactg atcctggaca    480

tggtgagcac acatctgaga acaagtcacc agaagagggt ctacaaggtg ctgtaccatc    540

tttctacaca agtgcctcag aagcacccat agcgcccaga ggagatgggc attatccatc    600

gagttgtcca gtgactcaca ctcgagagaa aatttatgcg atctgctcag attatgcctt    660

cctcaaccag gcaacatcag tctacaaaac tcctagccta acccgctctg cttgcctccc    720

tgataacacc tctctttctg ctggaaatac tacaagatat attggaattt caactagtac    780

atcagaaata atctataatg aaggaaaata acttggaaaa cttgtccact ggcatgggca    840

agctacctct tgcatgggag attgataaat ctgaatttga tggggtgact acaaatttga    900

tacataagtc ag                                                         912
```

<210> SEQ ID NO 24
<211> LENGTH: 888
<212> TYPE: DNA
<213> ORGANISM: Mus musculus
<220> FEATURE:
<221> NAME/KEY: misc_feature
<222> LOCATION: (1)..(888)
<223> OTHER INFORMATION: Alternative BIVM 5' end clone (6356)
<220> FEATURE:
<221> NAME/KEY: misc_feature
<222> LOCATION: (1)..(186)
<223> OTHER INFORMATION: Alternatively spliced exon A
<220> FEATURE:
<221> NAME/KEY: misc_feature
<222> LOCATION: (187)..(287)
<223> OTHER INFORMATION: Alternatively spliced exon C
<220> FEATURE:
<221> NAME/KEY: misc_feature
<222> LOCATION: (288)..(888)
<223> OTHER INFORMATION: Exon 1
<220> FEATURE:
<221> NAME/KEY: misc_feature
<222> LOCATION: (413)..(415)
<223> OTHER INFORMATION: Translation initiation codon (ATG)

<400> SEQUENCE: 24

```
ccccaactac tttcgtccct tccctccgtc cctcactctc cctcctcctt tctccccccc     60

taccttcctt tctacttctt ttttcaactt tggagcacgg ctttctggca accttaaata    120

ctacagttgc gcaactagca tgtctggagt cacagcaaag atttcccaac ttatattttg    180
```

-continued

```
ttcaaggtgc ttcggagcct caaagagggg gcagtgggaa gtctcctggc tcctcagagt    240

ctgaactcca gagggcatca tgtgctgcat gaatctcata ctcacaggat cccatttgtc    300

agctctcaag ccttttaga atcctgtgaa catttgccaa agttgctttt ttttttttta    360

aagagagggt tgcggcttct tcctaggaac agagacatct gcatttgctc tcatgcctaa    420

cgccactgaa gctggaaaag ccactgatcc tggacatggt gagcacacat ctgagaacaa    480

gtcaccagaa gagggtctac aaggtgctgt accatctttc tacacaagtg cctcagaagc    540

acccatagcg cccagaggag atgggcatta tccatcgagt tgtccagtga ctcacactcg    600

agagaaaatt tatgcgatct gctcagatta tgccttcctc aaccaggcaa catcagtcta    660

caaaactcct agcctaaccc gctctgcttg cctccctgat aacacctctc tttctgctgg    720

aaatactaca agatatattg gaatttcaac tagtacatca gaaataatct ataatgaagg    780

aaaataactt ggaaaacttg tccactggca tgggcaagct acctcttgca tgggagattg    840

ataaatctga atttgatggg gtgactacaa atttgataca taagtcag                888
```

<210> SEQ ID NO 25
<211> LENGTH: 668
<212> TYPE: DNA
<213> ORGANISM: Mus musculus
<220> FEATURE:
<221> NAME/KEY: misc_feature
<222> LOCATION: (1)..(668)
<223> OTHER INFORMATION: Alternative BIVM 5' end clone (cDNA)
<220> FEATURE:
<221> NAME/KEY: misc_feature
<222> LOCATION: (1)..(42)
<223> OTHER INFORMATION: Exon B
<220> FEATURE:
<221> NAME/KEY: misc_feature
<222> LOCATION: (43)..(143)
<223> OTHER INFORMATION: Alternatively spliced Exon C
<220> FEATURE:
<221> NAME/KEY: misc_feature
<222> LOCATION: (144)..(668)
<223> OTHER INFORMATION: Alternatively spliced Exon 1
<220> FEATURE:
<221> NAME/KEY: misc_feature
<222> LOCATION: (193)..(193)
<223> OTHER INFORMATION: Translation initiation codon (ATG)

<400> SEQUENCE: 25

```
ccctggaagg atctgggtcg agctgagtct ctgaggagag atgtgcttcg gagcctcaaa     60

gagggggcag tgggaagtct cctggctcct cagagtctga actccagagg gcatcatgtg    120

ctgcatgaat ctcatactca cagagagggt tgcggcttct tcctaggaac agagacatct    180

gcatttgctc tcatgcctaa cgccactgaa gctggaaaag ccactgatcc tggacatggt    240

gagcacacat ctgagaacaa gtcaccagaa gagggtctac aaggtgctgt accatctttc    300

tacacaagtg cctcagaagc acccatagcg cccagaggag atgggcatta tccatcgagt    360

tgtccagtga ctcacactcg agagaaaatt tatgcgatct gctcagatta tgccttcctc    420

aaccaggcaa catcagtcta caaaactcct agcctaaccc gctctgcttg cctccctgat    480

aacacctctc tttctgctgg aaatactaca agatatattg gaatttcaac tagtacatca    540

gaaataatct ataatgaagg aaaataactt ggaaaacttg tccactggca tgggcaagct    600

acctcttgca tgggagattg ataaatctga atttgatggg gtgactacaa atttgataca    660

taagtcag                                                             668
```

<210> SEQ ID NO 26

-continued

<211> LENGTH: 3312
<212> TYPE: DNA
<213> ORGANISM: Mus musculus
<220> FEATURE:
<221> NAME/KEY: misc_feature
<222> LOCATION: (1)..(209)
<223> OTHER INFORMATION: Exon A
<220> FEATURE:
<221> NAME/KEY: misc_feature
<222> LOCATION: (210)..(309)
<223> OTHER INFORMATION: Exon C
<220> FEATURE:
<221> NAME/KEY: misc_feature
<222> LOCATION: (310)..(911)
<223> OTHER INFORMATION: Exon 1
<220> FEATURE:
<221> NAME/KEY: misc_feature
<222> LOCATION: (437)..(439)
<223> OTHER INFORMATION: Translation initiation codon
<220> FEATURE:
<221> NAME/KEY: misc_feature
<222> LOCATION: (912)..(1038)
<223> OTHER INFORMATION: Exon 2
<220> FEATURE:
<221> NAME/KEY: misc_feature
<222> LOCATION: (1039)..(1134)
<223> OTHER INFORMATION: Exon 3
<220> FEATURE:
<221> NAME/KEY: misc_feature
<222> LOCATION: (1135)..(1239)
<223> OTHER INFORMATION: Exon 4
<220> FEATURE:
<221> NAME/KEY: misc_feature
<222> LOCATION: (1240)..(1334)
<223> OTHER INFORMATION: Exon 5
<220> FEATURE:
<221> NAME/KEY: misc_feature
<222> LOCATION: (1335)..(1467)
<223> OTHER INFORMATION: Exon 6
<220> FEATURE:
<221> NAME/KEY: misc_feature
<222> LOCATION: (1468)..(1554)
<223> OTHER INFORMATION: Exon 7
<220> FEATURE:
<221> NAME/KEY: misc_feature
<222> LOCATION: (1555)..(1651)
<223> OTHER INFORMATION: Exon 8
<220> FEATURE:
<221> NAME/KEY: misc_feature
<222> LOCATION: (1652)..(3312)
<223> OTHER INFORMATION: Exon 9
<220> FEATURE:
<221> NAME/KEY: misc_feature
<222> LOCATION: (1943)..(1945)
<223> OTHER INFORMATION: Translation termination codon (TGA)

<400> SEQUENCE: 26
atattttgtt caaggtatcc accgcaaatg gcaggtatat agtaaacgct gaaagggagg 60
ctaggtgtta tcaatgatac ccagtcactc ggtgctattc ttgtgcgctc aatgggacga 120
aagattctgg gccttgggta ggagacttga ggatgcagat ctggtgttgc cttccagcac 180
cagagttccg ggacccaaca ggaacagagg tgcttcggag cctcaaagag gggcagtggg 240
aagtctcctg gctcctcaga gtctgaactc cagagggcat catgtgctgc atgaatctca 300
tactcacagg atcccatttg tcagctctca agccttttta gaatcctgtg aacatttgcc 360
aaagttgctt ttttttttt tttaaagaga gggttgcggc ttcttcctag gaacagagac 420
atctgcattt gctctcatgc ctaacgccac tgaagctgga aaagccactg atcctggaca 480
tggtgagcac acatctgaga acaagtcacc agaagagggt ctacaaggtg ctgtaccatc 540
tttctataca agtgcctcag aagcacccat agcgcccaga ggagatgggc attatccatc 600
gagttgtcca gtgactcaca ctcgagagaa aatttatgcg atctgctcag attatgcctt 660

-continued

```
cctcaaccag gcaacatcag tctacaaaac tcctagccta acccgctctg cttgcctccc    720
tgataacacc tctctttctg ctggaaatac tacaagatat attggaattt caactagtac    780
atcagaaata atctataatg aagaaaataa cttggaaaac ttgtccactg gcatgggcaa    840
gctacctctt gcatgggaga ttgataaatc tgaatttgat ggggtgacta caaatttgat    900
acataagtca ggcaatgtaa agaaacaatt ttccaagaag aaaacgtcgg ataaaaaagg    960
gcggcatcag agggagtgtc tccactattc tcctcttgat gatgttaaac aacgcaaagt   1020
gttagacctt aggcgatggt actgcataag ccgaccacag tacaagactt catgtggtat   1080
ctcctcattg atttcttgtt ggaatttctt atacagcata atgggagctg ggaatctccc   1140
acctattacc caagaagagg cattacatat tttgggcttc caaccccccat ttgaagatat   1200
taggtttggc cctttcactg gaaatacaac actcatgaga tggtttagac aaattaatga   1260
ccactttcat gtgaaaggat gctcttatgt tctatataag ccccatggga agaacaaaac   1320
agctggagaa actgctccag ggccttatc aaagttgacc cgaggattga aagatgagtc   1380
actggcttat atctatcatt gccaaaatca ctatttctgt ccaattggct ttgaagcaac   1440
ccctgtgaaa gctaataaag cattcagcag gggcccctc tcttcacaag aagtagaata   1500
ctggatttta attggagagt caagtagaaa acatcctgcc attcactgta aaagatgggc   1560
agatattgtc actgatctaa acactcaaaa tccagaattc ttagatatcc gacatctaga   1620
gagggggctg cagttccgga aaataaagaa ggttggagga aatttgcatt gcatcatagc   1680
attccagaga ctcagttggc agagatttgg cttttggaac tttccatttg gaaccattac   1740
acaagaatca caacatccca cacatgtccc gggaattgcc aaatctgaga gtgaggacaa   1800
tatctctaag aagcagcatg ggcgcctggg caggtccttc agtgcgagtt tccatcagga   1860
ctcggcatgg aagaacatgt ctagcatcca cgagaggagg aacagtggct accacagctt   1920
tagagattat aatggcaatg actgaccatg ccaaaactta gccactggtg ttacccacac   1980
agctgttatg tacaggactg cattaggaca tcagctggtt ttattaagtc tgtcaatagg   2040
aacagatttt gtggtacaaa acacaccctg tagttctcta gtaaaaaagc ctacatagga   2100
ttactatggt tggcttcaaa tatacaggca ggtaagcaca gaaccccgcc cttctaaagt   2160
taaaagtaga taagcaatct ggacaaaggg tttcacaaaa tccaatacaa tcaaaacggc   2220
ttcaaagcaa aaacacaaat gcatttaatt tgaaaagcat cgaaacttga actacttaag   2280
catgaagcga cttattgata cttgatccct agcatttatt acaacacttt aattcctaag   2340
gcatcatctg tccttaaaaa atgggggcag tcaaggtcta gtttttgctc atggttaaaa   2400
ctaatttaaa attatctttc tagtctagtt gttctttcag tgctaacagt atccacctcc   2460
catcgttgct ttcctgaata actctcagga ttctccaaaa agcagcagaa actactccag   2520
gaactgacct tttctctagg tgcagatagg tgacttaggt cattgatcct gatactcttg   2580
acttggcacg tggttgtgaa atagctacaa gaagaatata ggtctggagc gaagtctgat   2640
gttctagaac aaaccttgtt tcagggatat agttagagag cacttggcat ccaaagtttc   2700
cttatccacg gtaacatgtg ctgtgagatg tcacatttga cttgtctctt aatggagtca   2760
tgtgttaaca acagcactga tgtcatgttg gcaatgtcca gctcactctg aggaagactt   2820
tgtattttca actctgagcc gtttcctttt gtgaaacctc caagcaatta ggtgttggaa   2880
gtgtgagtta catattctgg aagtgtgagt tcaatacttg agctcctctt tagcggctct   2940
tgttttcctt ttgctgccaa ggtgtgactc atagccgtct atgatgctgc tctttcacgt   3000
```

-continued

```
cgtaggttta ttccaggatt caaatcagta acttggtgat tacaaggtgc tgagtatgtt   3060

ggaaccattg caatacacct caaagggagg tgtcggattt tgacttttta aaaaaaattt   3120

tcatttttct cttgaatttc atatccatct atccactcat atatgtttag cctacagaat   3180

tacaaactag tcctgtttct gaagaggttc tttagcttga aatgtaaagg actgaaagat   3240

ttgtaggtgt tcttttgtta cttcacactg gaactttgaa aatgttttca tcaaataaag   3300

ttttgttttc ta                                                       3312
```

<210> SEQ ID NO 27
<211> LENGTH: 502
<212> TYPE: PRT
<213> ORGANISM: Mus musculus

<400> SEQUENCE: 27

```
Met Pro Asn Ala Thr Glu Ala Gly Lys Ala Thr Asp Pro Gly His Gly
1               5                   10                  15

Glu His Thr Ser Glu Asn Lys Ser Pro Glu Glu Gly Leu Gln Gly Ala
            20                  25                  30

Val Pro Ser Phe Tyr Thr Ser Ala Ser Glu Ala Pro Ile Ala Pro Arg
        35                  40                  45

Gly Asp Gly His Tyr Pro Ser Ser Cys Pro Val Thr His Thr Arg Glu
    50                  55                  60

Lys Ile Tyr Ala Ile Cys Ser Asp Tyr Ala Phe Leu Asn Gln Ala Thr
65                  70                  75                  80

Ser Val Tyr Lys Thr Pro Ser Leu Thr Arg Ser Ala Cys Leu Pro Asp
                85                  90                  95

Asn Thr Ser Leu Ser Ala Gly Asn Thr Thr Arg Tyr Ile Gly Ile Ser
            100                 105                 110

Thr Ser Thr Ser Glu Ile Ile Tyr Asn Glu Glu Asn Asn Leu Glu Asn
        115                 120                 125

Leu Ser Thr Gly Met Gly Lys Leu Pro Leu Ala Trp Glu Ile Asp Lys
    130                 135                 140

Ser Glu Phe Asp Gly Val Thr Thr Asn Leu Ile His Lys Ser Gly Asn
145                 150                 155                 160

Val Lys Lys Gln Phe Ser Lys Lys Lys Thr Ser Asp Lys Lys Gly Arg
                165                 170                 175

His Gln Arg Glu Cys Leu His Tyr Ser Pro Leu Asp Asp Val Lys Gln
            180                 185                 190

Arg Lys Val Leu Asp Leu Arg Arg Trp Tyr Cys Ile Ser Arg Pro Gln
        195                 200                 205

Tyr Lys Thr Ser Cys Gly Ile Ser Ser Leu Ile Ser Cys Trp Asn Phe
    210                 215                 220

Leu Tyr Ser Ile Met Gly Ala Gly Asn Leu Pro Pro Ile Thr Gln Glu
225                 230                 235                 240

Glu Ala Leu His Ile Leu Gly Phe Gln Pro Pro Phe Glu Asp Ile Arg
                245                 250                 255

Phe Gly Pro Phe Thr Gly Asn Thr Thr Leu Met Arg Trp Phe Arg Gln
            260                 265                 270

Ile Asn Asp His Phe His Val Lys Gly Cys Ser Tyr Val Leu Tyr Lys
        275                 280                 285

Pro His Gly Lys Asn Lys Thr Ala Gly Glu Thr Ala Pro Gly Ala Leu
    290                 295                 300

Ser Lys Leu Thr Arg Gly Leu Lys Asp Glu Ser Leu Ala Tyr Ile Tyr
305                 310                 315                 320
```

-continued

His Cys Gln Asn His Tyr Phe Cys Pro Ile Gly Phe Glu Ala Thr Pro
325 330 335

Val Lys Ala Asn Lys Ala Phe Ser Arg Gly Pro Leu Ser Ser Gln Glu
340 345 350

Val Glu Tyr Trp Ile Leu Ile Gly Glu Ser Ser Arg Lys His Pro Ala
355 360 365

Ile His Cys Lys Arg Trp Ala Asp Ile Val Thr Asp Leu Asn Thr Gln
370 375 380

Asn Pro Glu Phe Leu Asp Ile Arg His Leu Glu Arg Gly Leu Gln Phe
385 390 395 400

Arg Lys Ile Lys Lys Val Gly Gly Asn Leu His Cys Ile Ile Ala Phe
405 410 415

Gln Arg Leu Ser Trp Gln Arg Phe Gly Phe Trp Asn Phe Pro Phe Gly
420 425 430

Thr Ile Thr Gln Glu Ser Gln His Pro Thr His Val Pro Gly Ile Ala
435 440 445

Lys Ser Glu Ser Glu Asp Asn Ile Ser Lys Lys Gln His Gly Arg Leu
450 455 460

Gly Arg Ser Phe Ser Ala Ser Phe His Gln Asp Ser Ala Trp Lys Asn
465 470 475 480

Met Ser Ser Ile His Glu Arg Arg Asn Ser Gly Tyr His Ser Phe Arg
485 490 495

Asp Tyr Asn Gly Asn Asp
500

<210> SEQ ID NO 28
<211> LENGTH: 34562
<212> TYPE: DNA
<213> ORGANISM: Mus musculus
<220> FEATURE:
<221> NAME/KEY: misc_feature
<222> LOCATION: (349)..(554)
<223> OTHER INFORMATION: KDEL exon
<220> FEATURE:
<221> NAME/KEY: misc_feature
<222> LOCATION: (1630)..(2075)
<223> OTHER INFORMATION: KDEL exon
<220> FEATURE:
<221> NAME/KEY: misc_feature
<222> LOCATION: (2300)..(2681)
<223> OTHER INFORMATION: Exon A
<220> FEATURE:
<221> NAME/KEY: misc_feature
<222> LOCATION: (2794)..(2835)
<223> OTHER INFORMATION: Exon B
<220> FEATURE:
<221> NAME/KEY: misc_feature
<222> LOCATION: (3269)..(3579)
<223> OTHER INFORMATION: Exon C
<220> FEATURE:
<221> NAME/KEY: misc_feature
<222> LOCATION: (9571)..(10171)
<223> OTHER INFORMATION: Exon 1
<220> FEATURE:
<221> NAME/KEY: misc_feature
<222> LOCATION: (9696)..(9698)
<223> OTHER INFORMATION: Translation initiation codon (ATG)
<220> FEATURE:
<221> NAME/KEY: misc_feature
<222> LOCATION: (10945)..(11071)
<223> OTHER INFORMATION: Exon 2
<220> FEATURE:
<221> NAME/KEY: misc_feature
<222> LOCATION: (12030)..(12125)
<223> OTHER INFORMATION: Exon 3
<220> FEATURE:

-continued

<221> NAME/KEY: misc_feature
<222> LOCATION: (12562)..(12666)
<223> OTHER INFORMATION: Exon 4
<220> FEATURE:
<221> NAME/KEY: misc_feature
<222> LOCATION: (12885)..(12979)
<223> OTHER INFORMATION: Exon 5
<220> FEATURE:
<221> NAME/KEY: misc_feature
<222> LOCATION: (16786)..(16962)
<223> OTHER INFORMATION: n = a, c, g, or t; length of "nnnnnnnnnn" nucleotides is undetermined.
<220> FEATURE:
<221> NAME/KEY: misc_feature
<222> LOCATION: (20099)..(20231)
<223> OTHER INFORMATION: Exon 6
<220> FEATURE:
<221> NAME/KEY: misc_feature
<222> LOCATION: (21686)..(21772)
<223> OTHER INFORMATION: Exon 7
<220> FEATURE:
<221> NAME/KEY: misc_feature
<222> LOCATION: (24881)..(24977)
<223> OTHER INFORMATION: Exon 8
<220> FEATURE:
<221> NAME/KEY: misc_feature
<222> LOCATION: (25952)..(27613)
<223> OTHER INFORMATION: Exon 9
<220> FEATURE:
<221> NAME/KEY: misc_feature
<222> LOCATION: (26243)..(26245)
<223> OTHER INFORMATION: Translation termination codon (TGA)

<400> SEQUENCE: 28
ccagacttgg tcctttgcaa gtgcttttca ctgccgagcc atctctctag cttttttttt 60 ttttttttt ctctctagct ttttaagttg attattctca caggtgtgtc ctcaaggagc 120
aacttttcta gtaatgtttc ttggtcttta gtgaattata atccccatgt aaataatcaa 180
tatctctctt ttgccaagtt gcctaattta gttttcaatt agaaaaacat ctagtttttt 240
tttccattta gtgaaaaaag tatgctaagt ttttgataga attcttattg atggaatgac 300
atgccttttt gtatacaaat cctaccataa atttttgttt caaaatacct cttaaaacat 360
aaggagactc ggcaacatgt tgcccatggt gtttaacctc tatcttcaga tttctgtagc 420
tggcatacat tctgtatctt actatgaagg aaccgtcctt tcgatctaaa acctggacac 480
caactctcgt gaactgctca tcgggtgctg agattttaac ctggaacacc ttttcacctg 540
gagaagatgt aaacctgtta tggaaaacaa tgagagatga gggttatttt taagatcaaa 600
tgcacgctac ttattctctt taatgtgtaa aggttggacc ttctgcttta tcctgatttt 660
aagatattgt tgttcgatta ctctcttagg cttttaggac cagaaccaat atgatagaac 720
aaagataaaa aagaaaacaa taataacata aaataatttc attagatagt tgccaggaga 780
taacacttaa gactagcaat ctatttagca taccaaatag agcactatca gtgtactatt 840
attaattcat aaccaacaca gctggcaatt tgtcatttgt aacatgttta cttcaaggga 900
tgaccttatt tgaaaaattg ttcttaatgg cttaaaatac aatccagtac tgtggggcta 960
gggagatagc tgaatggttt agagcattta ccattatgta aaagacttag ttcagttcct 1020
agtatccatt gtccttaagg ctcacaacta tctgcagttt cagctcaagg agattcaagg 1080
ccctcttctg gcttcctcca gcacttgggt gtgagtatac accctaccca catcatgtaa 1140
ttaaaatatt actactaata aaagtctaac aaatatacca gtactctaaa ttatgtttag 1200
ttatggggga aatcaaaata actggtcatc atgttagtaa cacaagtgtt ttggactgaa 1260
tattcctgca ttttgaatgc atttagtttc tagtgtttag ttttcccatt taaaaataac 1320

-continued

```
ggagatttgt ttagcctcaa ttcccatcta aacagccaag aagagagctg ttattttagc   1380
aatattattt acactataca tatttcagaa ttattaagtc acagagaaaa gttgattttg   1440
aaggaaaagt ctattataac cagatgtaga cagcactcga gaattctgga atgtaaatgg   1500
acagcagtaa agacgagtcg gggcatataa agatgaagga caaaaccaaa ataaacaaca   1560
ggaacaaaaa cccctcgagt tattttaaac cgcgatctca aatagttgag gagtcatttc   1620
tccacttact gttcccctga ggtatccacc gcccgaatgt acgaaatagc gggcaggaag   1680
gaccacgtgt gcttttagcc cgggtcccat atttcgctct tctctgggct cagctcctct   1740
ctccgccggt ctgggcaagt gctggcacag tccccagaaa aaggcaggaa agcagcgaaa   1800
tgctgaacat ttacaagacc gagtcttgga agatccacga ataaatgcaa acgtgctaag   1860
tggacggagc tagcctgggt aggtaggagg acggtggtca gtcctagcag cagtcaaagt   1920
ccctaaagtg tcgcttgacg tgcggggtcc gccgtgggac tatgctgtgc ccaagaatgt   1980
cacaacccga gcggtggcat gtccaggaga aggatgccac acgttctgct gaacctggtt   2040
aagaaccgca ggctccactt tctccggaca atgacaaact tgtgttactc ttgccactag   2100
agcatcactt tgggaacgaa tccgtcgcaa gttctagcca aggtgagagg agaaggattg   2160
gcctgcgctg tgaccagtct tagtaaagtc ttctgctagt ggatgagtgg gtcagagtgg   2220
aaaacgcgtc ccgggcccct tagcttcctg ggatatgtag tccgccatag gactagcgga   2280
aatcctgcca ggagttcacc cccaactact ttcgtccctt ccctccgtcc ctcactctcc   2340
ctcctccttt ctcccccccct accttccttt ctacttcttt tttcaacttt ggagcacggc   2400
tttctggcaa ccttaaatac tacagttgcg caactagcat gtctggagtc acagcaaaga   2460
tttcccaact tatattttgt tcaaggtatc caccgcaaat ggcaggtata tagtaaacgc   2520
tgaaagggag gctaggtgtt atcaatgata cccagtcact cggtgctatt cttgtgcgct   2580
caatgggacg aaagattctg ggccttgggt aggagacttg gagatgcaag atctggtgtt   2640
gccttccagc accagagttc cgggacccaa caggaacaga ggtattcccc agcggagggc   2700
ctagcccagg cactgcggtg cgctccgcct ctccgtagcg ccgtcactgc ctcgttgcag   2760
acaaccccca cccccacccc caccccgccg cgcccctgga aggatctggg tcgagctgag   2820
tctctgagga gagatgtaag ggatagaaat caccagaaga aagctcggcc tgaggggggt   2880
gcatccgtgg gtatccctgt actctcttca ggagcgggtc ttcccvtgcg ctagcggatc   2940
ccaggcaccc ggcctgcagt ggccatcctc tctttgcacc ctcgcttctc ggccagtgag   3000
gtcaagagga gtagcaggct ttgtcctcct ccacggggta aggggcgtgg aaaacataga   3060
cggcctggtt gtgagcccaa ggcaagggga ttctttttcc ccctgccccc ccccccccgct   3120
attgttatta ttggtgatat aatcattcat cgcggcctcc cctcccagct ctcaggctgt   3180
cactgtctgc gtgccaccag cctctccagt ccctagcgcg taggaagcgg ccccccttcag   3240
gcctgcgcgc tccccctcct ggcgagcctt ttcttccggc tgggagtgag ggagcaggcc   3300
gggaggaggt tacaaggctt tagatctggt cttggccagt ggggactagg gacgcctggc   3360
actgggttgg ccaccgcagg acagtagtgg gaacccggca cagtagcgct gcagcagttg   3420
cacttgcaac atccctgctc tcccggttct cctccacctg cacctttgtc accttcaggt   3480
gcttcggagc ctcaaagagg gggcagtggg aagtctcctg gctcctcaga gtctgaactc   3540
cagagggcat catgtgctgc atgaatctca tactcacagg taggcctccc aggtctggtc   3600
tggtagtcta ggcaagggcg ctgatagaaa agggggggcgg tgggggcacc tggctgctgt   3660
cttagcagct cttatcaatc ctcagcaaaa cacttttctg ggtctcagtt gctttctatg   3720
```

-continued

```
cagaatattg attatactgt ttgtgatatg tggaaggctt tactgagatt ttattggatg   3780
tctagctctc tactgaatgt gatacttcag catgtagaca cgaaaggcac ataaatggaa   3840
aagaataaac tcaggcaatc gatatcggtt ttgcaaacag tatgtttatt tgacagaatt   3900
gttcattcca aagactttca taagtcattc ctctagtgcc gtcctagaag cttggggttt   3960
atattgctta tgagatactg tgaataaatt gagtggtatt ccgcaagtcc taatatgtta   4020
atcaaaacga gggagaacaa tttcaataat gcctagtgca ttgtagacac ctaaaaatgt   4080
ttgttagacc tggcttctac aagactaggc ctggagatgc aatttcagga aaactagact   4140
ttcaggagtt aaccatttgt gtacacacac acacacacac acacacacac acacacattt   4200
agaaagctta atcatattct agaaagaaaa gttcctcact atggataggg tatctggcct   4260
agttagaaca gcaaaaaaaa aaaaaaaaat tcttcagaaa gtgacatttg agtataactt   4320
tgaaagatgg atgagaatga ataattagta aggggctaca ggaagacaac attcagaaaa   4380
ccaaaaagta atgtggaagg acagaagaag gtatgtaggg taaggagttg atcttttgct   4440
tcaatagctg agggccttag gcagaaaatt tctatgagga tatatatgta gcagacttta   4500
ctctttgatg tctatgcagg gatcagacta gaaagaacag ctcaaagggt gggtggcatg   4560
aagttataag cataaagata aaagcagata taaaccccag atagctgcag atacagtgct   4620
ggacaatcaa tcagccttca taactccgtt ttccctgaga ctaccattgc atcttactag   4680
aataatctat gcctgtaatg gtcttgtttc cagtagttgt ggctttcttc attctaagaa   4740
agcaggctct gagtgaagtc ctaaggatac catagcagaa gcccttcaga gtttaactac   4800
aaagggtgga gatgcagatc agtcacggga tgcaaagaag tagagtgcca gcatgggttc   4860
tgggtcattc tttttcattt tctgtgaata tcttctgata tttcataatt ttctacaata   4920
tactttgtgt catcaaacct ataaatatat gtattttcag agatattcac ataaaacagt   4980
ggttcaaatg aggaaatgtt gatatctttc attttcagtg acaactatgt aaaatcttca   5040
ggtagatggc aggtttgttt gttttttttt aagataaaat gagagcaaag agattatttt   5100
tattcagtga ccattgctta aagcatacaa tccaaaacca gatggttgca tgttttataa   5160
atcaagtgtt ttactcttaa cagcttcatc tcctagcaat ttccattgta tttttttcatt   5220
cataaatgaa cctgtttccc ttggcaatgt tatttggtta gctttggtta tttgagctag   5280
ggtcttgccc ggtgtgtact gggctagatc agaagtagct gtgtagttta gtctagagta   5340
gatcttgcag cagctctctt gtatctgcat cttgagtctt ggaattacag aaatgggcta   5400
ccacgttcta ttttgaccat acttttttttt ctttccatat gttccaaatg agcataaaac   5460
catcaaactc tggtacattg tactagtccc ataggcaaaa ttatattcaa ggtgagcgag   5520
gcagtgatgg caaggtgagg ttaatgtcgg gttgtgatct acaaaaggta gagcctgggg   5580
tgcctgggat gtactgaatc aagctttccc actgccccag ctgaccatct gttgtttcct   5640
atcgttccac acccaaccac agacacatta taccccctcta ccacacagct tttaaagaag   5700
aacgtgagca tcacagacag gaagtgggca atggagaagt ggagaaactc agtgctcaga   5760
ggaaaggaag cagtgtggtc tgcaagcctc atgcactgta catcctttga gtcttcttcc   5820
actgtcacca tcacaccgca cacagaatga ggacaaagga gagagctcag acactacttg   5880
tacacacact aagacctttt taccaaacag tatttgaaag gaaagcactg cagatgccag   5940
ctttggtgat aatgtacttg catcctgtga gccactgtta actgaagatg agaaaaaagc   6000
ggacgggaag ttgtgagaag gtgcatctca taaggggagc tcactctgca cagataggag   6060
```

-continued

```
ttccttccta ggactgtttc cccttagatt ccataatggt gaaagtgcct tcacccccttc   6120
cattcagaag atactggaga ttccggttta tcatcacatc tgttcgttag agactcagac   6180
aggcttgtgc cattcaattc ttttataatg gttattaaac aaatcataat ctgtgattat   6240
tttcatttct gatgaggaga gagattaata atggatgggt ttagtctctc atgcactgcg   6300
cggtcactgg agcctggaaa ggcagatctc gccctgcatt tggtggttgg tgaaggtgat   6360
ttgaactgtg gaagcctggc tctagaggtt tcagagaaga attttaatat gtagccataa   6420
tattttggtg aagaatgtgg ctgctttttt gcccttgtct gaagagtcta ccggaggcta   6480
aggtgaagag atttagatta attcctttgt taaaggaaat ctcaagacat cctgatataa   6540
attctgttga gtggttacta aacttctctc ttacaaagac tgttttaatg aaaagaagca   6600
agctgagaaa ggaataatat aaaatatatg gttgcagtat taaaaggggc accaggaagt   6660
gaaatggagc tgaatcctgt gttcatggat attaaattga attaatgggg tggtgacttt   6720
gaggcaagag tccatccagc taaatttagg tccaggcatg gtagtataca agcctttaat   6780
cccaggagtc aaggcaagca ggtctctgag tttaaggcca gcctaggaca gagcaagttc   6840
taggtgaaga aaatcttaag tgcaggcatg gtggcatata cctttaattt caggagacat   6900
ctctgagttc aaaatcaatc tacagaacaa gttccaggac agccaagctt aggaagtgaa   6960
ggagttggaa aacaaaaagc tggtaataga atatgggggg aggggggggaa gggggccatg   7020
ttctaatccc agcatgcagc agaactcagc agctttgacc atgtggctct ggctttagag   7080
tccagaatag aagggactac tggaacaatt gatgctcgtt agctggagct aagacattag   7140
tgatgattaa gaagagaccg gtatcactga ggtgtaatct ggcgttttct gagagcacaa   7200
agaagctgtg ttccagagat agccaatgtt gtccctcgtg ctgcagctgg acttggtagt   7260
gtgtaagaac cacccaagtt gtactggttt tgaaggtatg gaggagtcat ggagagcagc   7320
cgaggctgct gtgagaggcc atgggaagcc actggtgaag gtgcagcatt agttgtagtt   7380
gatggcccag gactgaaggg gccatgcaaa gaagttgagg cttgactcca tgaagagagc   7440
ctacgagagg ctattggtga atcctagttg cagtggaaga ccccagggta ttggagatgc   7500
cactaccatg gggatgatca ccaagaacag cagcagcagt ggagtagagt caaccagagc   7560
ctagagtgct acagagagca gagctggaga tatgacccaa gccctttgaa ggagtccaga   7620
agatcatgtg tggatcccag acattggaaa gagaagctgt aatgttgaag tggccttgga   7680
taccctaaga tgttcgagat tgcagagctg tggaatacct gtcaaggaaa gctgctaaca   7740
gggagtggaa tcacccagga gaaaaaacct tgttgcagtc agtaaagatg aaaagggagt   7800
agagatatga agacagcttt gacatagaca tggagatgaa gagtttggat tttgcccagc   7860
tggtgtcctg tcttgttttg gggattacag ttaagtgatt ggatgaatgt cagaagagac   7920
tttgaccttt ggacttttaa cattgttgag actgctgtag actatgggga ctttggaagt   7980
tggagtaagt gtagtttttt attatgctgt atttaggtat ggccctatag actcatatgt   8040
ttgaacgagc ctatgggtcc atggagtaga atgtagtggt ttgagtattc ctagctcagg   8100
gagtggcact attaggaggt gtggtcttgt tggagtaact ttgtcactgt gggtgtgggc   8160
tttaataccc tagtcctagt tgcctagaag ccagtcttct cctagcagct ttcagatgaa   8220
tatgtagaac tctcagcttc tcctgcacca tgcctgcctg gatgctgcca tgctcttgcc   8280
ttgatcataa tgcattgaaa cttggaacct gtaagccagc ctcatttaaa tgtcatcttt   8340
ttaacagttt cctttgttat ggtgtctgtt cgcagcagta aaaccctaag taagacacac   8400
gctataaatc actcattaca atgtataatg tacaaaaagc tcatcttgtt gaacctttca   8460
```

-continued

```
tcccaaggca actgctaagg tgtattgtag acttgtccct cctggaggtc ctgggctgtt   8520
aggggaccag ctcctttgtg attggcatgt ttccaaagtc cattcacgtt gtatcatgac   8580
cagtagttct ttttattgca aagtagaatt ttaccaaatg catgtggcac ttttatccat   8640
aattcagttg ctaggctttg ggttgtttcc actttttgcc attcatgggc atggtttaat   8700
gttttctgta tgtatctaga acagcaattt ccatattaca tgggaagtgt tgaaatgtat   8760
gaaaactgct ctgtaaccct atatcatttt atatccttga aagcagctta tgaaggatct   8820
gattcgccac acattttcta atgctctttg ttatcgatgt cttttttttt tttttttttaa   8880
agatagggtt tctctgtgta gccctggctg tcctggaact cactctgtag accaggctgg   8940
cctcgaactc agagatctgc ctgcctctgc ttcccgagtg ctggtattaa aggcatgtgt   9000
caccactgcc cggctttatg tctttttatt atagacatct tggtgggtat gagttggcaa   9060
accattgagg ttcggattgt gtttccatag caacttatga tgaggaactt cttttcatgc   9120
aatcattgtt catctctgta gcatctttac agatgtgact tcccctttta actaggttat   9180
gtatattttc tccttataat ttgttttaaa ctaatttttg tgtgtatgtg tttatgtgta   9240
tatgtggtgt gtgttttcct gcctctcttt acccagagct ggcattatgg tttacacagc   9300
ttcttattga tctattgttt aatgtgggtg ctggagatcc agttcagatc ctcatatttg   9360
catgacaccc ccttaaccaa ctaagccata ttccccatcc gcaagctcat ctttaatgta   9420
agatagatgg ttagtaatca taactcagga tgtatggtca taaaatcaat atgcattgag   9480
tgcaggtata tgaatcatac aataatgttt attgccattc atcatgcctg ctggatagtc   9540
aatcagtctt tcttctctgt cttttcttag gatcccattt gtcagctctc aagccttttt   9600
agaatcctgt gaacatttgc caaagttgct tttttttttt ttaaagagag ggttgcggct   9660
tcttcctagg aacagagaca tctgcatttg ctctcatgcc taacgccact gaagctggaa   9720
aagccactga tcctggacat ggtgagcaca catctgagaa caagtcacca gaagagggtc   9780
tacaaggtgc tgtaccatct ttctacacaa gtgcctcaga agcacccata gcgcccagag   9840
gagatgggca ttatccatcg agttgtccag tgactcacac tcgagagaaa atttatgcga   9900
tctgctcaga ttatgccttc ctcaaccagg caacatcagt ctacaaaact cctagcctaa   9960
cccgctctgc ttgcctccct gataacacct ctctttctgc tggaaatact acaagatata  10020
ttggaatttc aactagtaca tcagaaataa tctataatga aggaaaataa cttggaaaac  10080
ttgtccactg gcatgggcaa gctacctctt gcatgggaga ttgataaatc tgaatttgat  10140
ggggtgacta caaatttgat acataagtca ggtaagaagg agctatgaag tttacaggta  10200
acaacaatca gaaacgaatg ctatctattg ctaagtcttc caatgaaatg tttttttgttg  10260
ctaagccagc agcatcattg ccatcttatc tgtcattgca gtttttggtt ttgttttgtt  10320
tctttcgtaa gtaaccctag atatggttag tctctgactg tgttgcccat ggaaacttct  10380
aatatcatat gtgcatttga gcagctttga aaatcaaaaa gaacaaaata taagtattaa  10440
agataataca gtagcttcaa aaaggctact gacataacta gaatattacc attatcttac  10500
agttttgcag agatgtgata atattttcta attcaggagg tattaagaca tttttgtttt  10560
gaaaaaattt gagttaaaaa agaacattca ttttgatcaa agtcttgatt ttatttaaag  10620
ctacaattat gtggctctct tttctaaacc atattctaaa gtccatttta tttctcatgt  10680
tattttaacc cgctctaaga gtctagctct ggacttggat acaatcttga taggaatacc  10740
gtttctgatg gttcaaattg ttttaaattc tcttcctgct ttctctctag agaagagtag  10800
```

-continued

```
tattctagaa agcacaggta ttactttgag acatttgcag ataccatttt cagaatgcat  10860
ggccagtcct ctaattctgt tgtaacttct ggcacgggtt ttactttatc tgaacatttc  10920
ttgtattact tctttgttct gtaggcaatg taaagaaaca attttccaag aagaaaacgt  10980
cagataaaaa agggcggcat cagagggagt gtctccatta ttctcctctt gatgatgtta  11040
aacaacgcaa agtgttagac cttaggcgat ggtatgtggc catgtcagtt tttacttttt  11100
ccaatcttaa aaatatgtaa tttgacatta attttcctga gtataggtta ataaattata  11160
ttaactataa acactgttag ttccaaaatt atgtctagat actttaggta tatctccgat  11220
tttggaagta gtctagttta gctcagcctg gctgtcagtc tcattcagtg atccctctta  11280
atgttaagcc acattggctg acacttaaag tcggaatagt cattcacctg gttgttcttt  11340
gtgactaatt ctataggcag tgatggtagc ttacagctat tttaattatt gccataccta  11400
gtaaaatgaa caatatttcc tgtatgtata ctttcagact aaattgacac tttcctttct  11460
agattgttct aaaagttcat catatgcgtg cttgtttgtc atggcccgtg agtttcaatt  11520
tagagtttcc agctttcttt ctttgtctcc gtctctccct ggaggatttg tgttttcctt  11580
ttaggtcccc agtgacagtt ctgttctggg gatttctgcc caggggttca tgggatgtgc  11640
ttagcctgag gagaatctct gaatctcttg acaaaaggag agcggtttgc tttgcttctc  11700
cagtatttca gaagctgcag aggatgcctg gcccactcaa atgagaattc acatagacat  11760
ttgagtcgtt gccatcaaaa tttcttggtt tgaataagac atactttagt aggttgctgg  11820
ccataatgta gctcatcttg ataaaacatg atttttatgc tcatgcattt tttatgtgtt  11880
taataggtag gggatacttt aaacaaaaaa tgagttacac tgcattgaag tttgtattat  11940
ggtcacgttt taaatcaccc ataaactata tatttctgtt ctgcatgttt tgtattcatt  12000
cgagtgaaga atactgtttg atttcccagg tactgcataa gccgaccaca gtacaagact  12060
tcatgtggta tctcctcatt gatttcttgt tggaatttct tatacagcat aatgggagct  12120
gggaagtaag tatgccagtt tactgctgac accaaactcc atctttgaaa gtagtgtcaa  12180
ggaaactgag tatagtgatg cacaccttta atcccagcac tcgggaggca gagtgaggca  12240
gatcactgtg agttggaaat cagactggtc tacagaatag attctaggac atctagggct  12300
acatagagac cctgtctaat tttaaggtac ctgtgttata atggaaagtc tctgagagtt  12360
gactttgtac aaactgagaa aaattgtgtg tattgttaca agcctttcag gttaaaatat  12420
ttgcatgtat tcttttcaat aaaataaatg aaaaatattg ctaaaatgtt tctaagctaa  12480
gcctatatat tactaacact ggggcatatt ttatttgcat atgactggaa ctgtgaaatg  12540
aaaggaatgt ttcttttata gtctcccacc tattacccaa gaagaggcat tacatatttt  12600
gggcttccaa cccccatttg aagatattag gtttggccct ttcactggaa atacaacact  12660
catgaggtac ggagctgcca cttagggatt acatacgcct tcctttaatt ctgtgaagtg  12720
ataactatgt agtgtttggg gacggtacaa gatagacttt gctgctgggt cgcaggctcc  12780
ctaagatatg ccatgtgtgg gctgtgcttg ggtttctgtg caattaggac agtagcctgt  12840
gttatgaaac tattgctatg agcaaatctt cttcttaatt tcacatggtt tagacaaatt  12900
aatgaccact ttcatgtgaa aggatgctct tatgttctat ataagcccca tgggaagaac  12960
aaaacagctg gagaaactgg taggtgaaaa tacacacaaa cacacaaaca cacacacaca  13020
cacacacaca cacacacaca cacacacaca caccccaaac tttcaggttg agtacatcgc  13080
agaaattggc cacgttgttt cctgggatat caaattaact cttaatagtc tgatgttttc  13140
atacctcttt aagaggaaaa tcatgatagt aatatataga gcactttcaa tattcaattc  13200
```

-continued

```
cattttcacc cctttctgat attttctatg taaatgttac aaatttaaag cattgtctat  13260
aaacactgtc tcttaacaca ttgttttgtc tgggtttagg acttgttata tttgcggtgc  13320
gcatgttgtt tgtgcgtgtg tccaccttct acgcaaaaac cttgaattta cagtttattt  13380
taaaacagag tgagagcact tgaggacatg tgatgttgga ctggcatcaa gtgaatacac  13440
agaacagcag agtaacaaac tgggaagtga caacactctg ttggttttaa catactcatt  13500
aatgaagttg aatttaagga ttatttgtta tctattagtt gaattatttg tattgtttaa  13560
tgatttcact tataaatggt cacaataaac tttgaaattt atggagcagg ctgctgtaag  13620
gtcctgctgt taaagaagaa acttttcgga ctatcctgga aacgggagac tttatctaag  13680
gttgttacag tggggtgttg tgataaggat taaagattaa cctcggcttc aaaggtgata  13740
aaggtggctg taaaggcaga tggataattg atgcgaaaga atacagggta ttgagaaact  13800
ataggtagta atgcaaattt aacaacattc tcaaagtata aaaatataaa acaattaata  13860
aaatgtagta aaacaacaaa agggctcctg agtgttagct taggattagt attcagaaat  13920
tttatgattt tttttttga tcaattgtgc tgtccagtat gttttggagc ataatttgtt  13980
agagatttta gtgtatggat ctttagaaca acagtacttg gtttactttc aaatggtcct  14040
ggttcgtaca attctccctg agttatttat aaaatgagtg gaaggatatg aatgctgtta  14100
tccagtttcc taacggacta ggatatgcta ggctgcttgg caccgacagg cacactctga  14160
tttcgtttac ctctgtttaa acatccttca acatatgcac agtcttttac ttatagaatg  14220
gaataaagtg ttttccttta caaggtttaa aatgacatat atgcatgtgt ttatttcatg  14280
tgtgatcaaa ggacagcctg agggatttgg ttctctcctt tcaccatttg ggccctgggg  14340
atcaagcttg ggcaagaggg taccgttact tccaaagcca tcttcctaag cccctccctt  14400
tttatctctc tttttatgca aaggcaagat ggtagtttct tcagatttct tcaaatacag  14460
tttaatgaca tcttttacca attgtggtct ccccaacccc cttccacctc cacagcctgg  14520
caccatttct gaaatgtccc tggacagtct agccccagga tcctattatc tcatgtactt  14580
ctatccattg gccccagaat cctattagct catgtactac ttactatcca ttggcctctg  14640
tcaggtgggg tttgggatgg actatcatga cttttatctt tttaatgtaa atgtcttgct  14700
cagtgcccat agtcaccatc tgaagtagcg ctttgatgct ttgattctgt gtatgataca  14760
catcagcgat agttacactc aggtcggcag agcactgata ttctgcttcc tgtcctcatt  14820
ttgtccatac tctctcttat agaagagctg ccaagaggag ctttcttcaa tggtttcgga  14880
tcttcaatgg ttaaaaccat ggccagctgg tattgcttat ttagtaacta ctcggaaact  14940
tccctcccca ccccccaccc ccctttgagg tagatctgat tttcacagtg tgctttcagt  15000
gttcttggta cttgcacaac ctggatttag taactcaggt tcttgaatgg cagtgccatg  15060
gccctcaata gtcactgtaa atgaagcagc tcatagagtt taaaaaaaca aacaaacctg  15120
tgcacatctc aggtgtacag cacactggta ctgttttcct catctccagt gcttttcgag  15180
ttcatattga gccgttttct ttaacctgca gtgtggttat gcccctttcc acctcgggag  15240
ctctcgaggt ttgcgtacag accaagcttc atagtgttga tagcatgtgg agccaacatc  15300
aactggactc atgtgcctgc tgtatttaaa aggtatcaaa tggatagggg ccttgcagga  15360
caatgccatg ttgcttgact acttaccata gttccagaat cttcccttga ctttcaatgt  15420
ataaagatgt gctctcagtt ctctaaggct cttctgcaga aggactggtt aatactaaac  15480
catcttgaag aatgtacggt gctgacagtg tattggagtg agagctataa tgccaaaggt  15540
```

-continued

```
ggccgaaccc attgacagct caagttgtcc actcctttca actctgaacc taattcttat  15600
cgctttttcc acatccatcc tgtctgtttg ctgtacagct gtggaggtag tggctttgtg  15660
acttggcttt taggtttcct ctgttattgg gtgaactata ctctgaacct cgtttctctt  15720
agcaacacat ttgtcttctt atcacagatc atttcctttg gtaactgcct tctgagtaat  15780
gctgcattgt cttttatttt agaaggtgat cttttctctg attttgtcct gaaattgtgg  15840
aggctttctc tgttttactc tacattctta cctagtgtct tgatgtatgt tcccctgtgg  15900
atttgcctct ccttatactc cttcctctgt ctagattgct aaaaccctcg ctcctcatta  15960
agttccatct tgaatgccat cccttcttga ttcctctgat ttctataccc atttgtgatg  16020
ccttaacatt agctctttca tctttcacgc tagagcttgt cttgcttcca tatggtatct  16080
gacagagtta ctaggtactc atgagttaaa tcaaaatctc catttaatct aaactagctg  16140
ctttcaaaat actgtccctg gatgcatcac ctgataactt gttaacaatg caaattctta  16200
gttcccaacc acagacctat aaggccagcc actcagactg ggctctagta agactttatt  16260
gaagtcttaa caacgagatg gtatgtagcc tctttaccag gagtttgatt ttgcattgag  16320
agaagatgca gtcattttct aattgtgttc agatgaaacc tgaggattcc ttttaaaggc  16380
ctgaaaggga ggtgatagaa gagaactgtg cacacactta ttttagctac agcagctctg  16440
ctttaagaat aagtttgctg atcttgaaaa catatgaaga atgttatgta ccttggagaa  16500
acaagagcaa acatcccatt actagaaatc atgtgtatag atgttatata tcgtatttaa  16560
caatgctaga agcattactt catagaagaa aacccatgtc atggcatttg gaaaactagg  16620
acatggtaaa agagtgtttg cagcagacaa aattatgtga ttgccaagga gggcagactt  16680
tgttatccat ttcatctgcc tctagaatcc ttacttctcc tcccctatgt gattgccaag  16740
gagggcagac tttgttatcc atttcatctg cctctagaat ccttannnnn nnnnnnnnnn  16800
nnnnnnnnnn nnnnnnnnnn nnnnnnnnnn nnnnnnnnnn nnnnnnnnnn nnnnnnnnnn  16860
nnnnnnnnnn nnnnnnnnnn nnnnnnnnnn nnnnnnnnnn nnnnnnnnnn nnnnnnnnnn  16920
nnnnnnnnnn nnnnnnnnnn nnnnnnnnnn nnnnnnnnnn nncatgatgt gattcaggct  16980
agcctgaact tgtctatggc cttacatctc tgttttttta aaatttaatt taatttttaa  17040
tttgtttttt ccactccata ttccattcct ctybbyyycc cccaccccca tccaccctct  17100
gactgctcca catcccacac ctcctcccca ctccaccctg tctccatgtg ggtactccta  17160
ccccccaccc cacctgatct ttaaactccc tggggccgcc agtctcttga ggttaggtgc  17220
atcatcttaa aattaattta atttttaatt tgtttttttcc actccatatt ccattcctct  17280
cgcccccccc ccccatccac cctctgactg ctccacatcc cacacctcct ccccactcca  17340
ccctgtctcc atgtgggtac tcctaccccc caccccacct gatctttaaa ctccctgggg  17400
cctccagtct cttgagggtt aggtgcatca tttctgaatg tacacagacg gaagtcctct  17460
actgtatgtg tgttgggggc cgcatatcag atggtgtgtg ctgtctgttt ggtggtccag  17520
tgtttgagag atctcggagg tccacattaa ttgagactgc tggtcctcct acaggatcac  17580
ccttctcctc agcttctttt agccttctct aattcaacca cagggtcagc tgcttctgtc  17640
cattgattgg gtgcaaatat ctgcatctga ctctttcagc tgcttgttgg atctttcaga  17700
gggcagtcat gatagatccc tttttgtgag cgctccatag cctcagtaat agtgtcagac  17760
cttgggacct ccccttgagc tggatcccac tttgggcctg tctttggacc ttgtttggat  17820
caggctctct ccatttccat ccctgtaatt ctttcagaca ggaacaatta tctgtcagag  17880
atgtgactgt ggggtggaac cccatccctc acttgatgtc ctgtcttcct gctggaggtg  17940
```

-continued ggctctatac gttccctctt cctactgtca gccttacatc tctgaatgag ttcaatcttg 18000
cctgatccta aaaggtctag cctgattaat acttgggaga aagagtgaga ttctgtcttc 18060
aagagtcaat tactggaact tacactgtat tcagtggtag agcttgcctg acataactaa 18120
aggctttgag tacaagtatt attgcaaaac agtattttca gttatctgag aaagcttctc 18180
attgattaat ttaaatttaa agagatttca ggagtttttc tatggcaatg gtggtaatag 18240
tcatctttta caatgttttc atctacagag tacagttaac tgaatccacc atctggaatc 18300
tatttacagt catgctcttt tatggaaatt aaagactgtt ctgaatttat tcctaaaaat 18360
tctttatcta aactgccaag gtgggggtca gtttttaaga tgtgaaggaa tacaactcaa 18420
tcctggggag tagctagtca tgactggtct ttgtgaagta gagattttag tagagaggac 18480
tccctgtctg tgctgatcta cctggaagtg aaagcttatg tggaatgcct tgatggaact 18540
tcagagtaga gaccagacac attaacttat gcataggcag agctcccacc cccaaaccct 18600
tgtgaggcag tcaggttgcc tctgtggagc tgctgcacac actgactagc agatctcaat 18660
ggtcatcagc tatttcagtg gtcagaaaat cgatcgctgt gaacatacca tgcaggcttt 18720
cagcttgctt tttttagggt tcccagtttt aatggactac ttgttaatga ataatttaag 18780
ttcttccagg aatggaagtt aatgaaatct cagttaatgg ctttgagtac tgagtgctga 18840
taaaattgtg tctcttacgc taatactttg gaaatcattt gacagctatt acaatgatgg 18900
gcaacagatg aggagaaaca gttgtgtaac tccagcccga ctgcagagct gatgcctttg 18960
atgtgtgtga tgcaggtgta gaaagacaat tttcttagtg tttctattgc tgtgatgaaa 19020
accatgacca aagcaactta gggaggcatt tggctggtgt gtcctgaatc ccagtccatt 19080
gagcaaagtc aaagcaggaa ctcgacaggg taggaacctg gaggcaggac ctgatgtaga 19140
gaccatagag aaatgctgct tactggcctg ctccacatgg gttgctcaga ctacttttta 19200
atggaatcca gaaccagtag cccagagatg gcactgccca caatgggctg agtcctccca 19260
catcaattac taattaagga aatgctctac aggctcccct acagccaaat cttatgaaag 19320
tattttctaa atcaatgttt cctcctttca aatgactgta gcttgtggga gttgacacaa 19380
aaatgagcca atataatgat aatatttgtt atgtggcagg tgtgagtgtt attgtgtggc 19440
aggtacactc aagtgcatgc atgtgtgtgt gtgtgtacga gtgtgtgtgt gtatgcatgc 19500
acaccattgt tgaggtttgt tgttatttaa ggtttgtgtt tattcatatg cattaataaa 19560
ctttaagttg gatgtagatg ttggatgtta tttaaggttt atgtttattc atatgcatta 19620
ataaacttta agttggatgt agatccagac attagaatgt ctataattta acctaattta 19680
aggttctttt gttaattctt ttgtagactt agtttatatg tgagcgttta tagacacatg 19740
tttcacttgg gcatgcttat tcagacgctg gtagtgaggg atgcccacag cagaaaagct 19800
aagacggtga ttgtgcaatt actgggtttt acacaatcat tgaatatctt agacaacttg 19860
gtatattctt agaaagttct gataagcaag gacatttgtt ttactactga gtttatctaa 19920
aactaaaagt aaattaattc atgtttttgc ccacattggt agcgtctcat tcattccctc 19980
gatggaactc agaatttcag tgtattccaa attctgtctt ttagtcctta actagtcctc 20040
tgcattaaat gtggacatcg ctttgtgttc ctcaggttgt ctggttttgt ctttgtagct 20100
ccaggggcct tatcaaagtt gacccgagga ttgaaagatg agtcactggc ttatatctat 20160
cattgccaaa atcactattt ctgtccaatt ggctttgaag caacccctgt gaaagccaat 20220
aaagcattca ggtaagcatt ccatacttga taaaggcaca gcactaggaa aatttgatat 20280

-continued

```
acaaagtaat tttgggaatt aaacaaattc tagtctctta gaaattggga agcatggtaa  20340
tgtgttttat tcaaaccaag tgtgcatatg ttttgcagga ctgattgcac ttcagagctg  20400
ttgctcagtc attgtaagaa aaagccatct gatgtaccac ttttatgatt agtatacaca  20460
gatgcagggg ccttcccatg ttattccctg tgtcctctcc gttgccatac atgtccttgt  20520
gtcaagagtg ctacaactaa gtacattaag aagcaccttc tatgctcata gtgaagaact  20580
aaggaattgt taggattttt ctccaaggga gctcaggacc agtttcatct ctaatcttct  20640
tggttatatt tgcctcttgc ttttcttaat ccagtttctg tctttttgaa caacgtgctt  20700
ttacacacac ataaacttgg gtctctttga aggagatgct tatgtgctga gaggttgccg  20760
agtttgaatg ttattctctt taccaagttc ctcataaggg acctgaaaac agaggttagg  20820
tttaagaaca ggtggcgtga ctgtcttacc ccgctgctct gctggttgat gcacccttgg  20880
attgctgaga ttggtgatta gggaggatga aaagattggg aggctcttgg aagttatctc  20940
ttaggtgaag gcccagattc tggctgaaga acaggcttgg cctttaggac tggagggttt  21000
ttatgtactg gaggtcatgg atccctggag tcccactcaa aggtccttgg atgtggtgcc  21060
taggggaacc tggaacagag gagcagaagt tggaggactt aggaggctgg atactacttg  21120
tgtagaagga gcaagagtaa cactgctttc tctccaactg ctgatgtgct cggttcactt  21180
tctggagtga ggggcacttt tgcacttctt tgatggctcc aacctctgcc tttaccttcc  21240
ttcaggtacc tatcaaatgt aaaacatgcg ttgacttcta ctgctctgct cctttaatag  21300
ttaggcttcc ccagtgaatg cctgtgccta tgaaccatct gattttttt cttaaaaatt  21360
atgtaaatct ccaggctcct ctccagactt gaattagagt ttctggggat gggaccgaaa  21420
cattgtgtgt ttaaaatcat catcatctcc tctgatccaa gggggtgata tgttaaaatg  21480
cttataaccc tagattttga atatggaagt aataaagctc aaacctaatt caaggatttc  21540
tagaatggga ccaaacctaa gtgctcatat ccatcctaga ttaacaaagc catctttgag  21600
tatcagtgta ttttagttca aacagcattc tctgggggag tgaatgccat ttatcaagct  21660
gattgtgaac gtattttctt tttagcaggg ggcccctctc ttcacaagaa gtagaatact  21720
ggattttaat tggagagtca agtagaaaac accctgccat tcactgtaaa aggtatgttt  21780
tagtagcctt tatgttttct ttaattggta atagttccgt caccgaaaga acagatcaaa  21840
attgtgtaac tagatgcatg tagataaatg tgcacacttg tgtggtctgt actctgtaca  21900
gtcttgccac agaaagttct gcattctact tctctccaat ctcacagcta accggttatg  21960
tttcccatta ccacagaagt cattttcttc tctctctctc tctctctctc tctgctttcc  22020
catataagta acatattaag aactttttct ctaaaaataa ttagaattgg ttcatttctg  22080
ctaaaagtcc tgatgcatac ttgattaaaa taaaatcttc aggactggtg tggtggctta  22140
ccaggtacag gtgcttgcat gcagtcccga tgatctgagt tagattccag gagtcaacat  22200
ggtagaatga cagaaccaat agttctcttc caaactccag acatacagaa tggcatgtgc  22260
atgcatgcgc ctgtctgtcc tccctccctc cctgttagtc tctttctctc ccctactctg  22320
tttccccaca cctgctgaga gctcctggcc cagagagggt agagacaggg catagagtag  22380
gactctggtg tggctttaaa gactgcagat ctccagacag tctagctctc taactgtact  22440
aaaatgctgg agataccttc tgaagtccta caagctttct tgctaattct gagagtaaaa  22500
agctgttggc ttaggtgatt gacacctgta gcctgcagtg ggggattagg taaagtggcc  22560
ttttcctatc tcagcaggaa ctgcacagct ctaactttca gcctgctagt agaagtccca  22620
ggaagaaaaa gggactcttt gaaaagtgtt tatagcattt attactaagt tgtaaaaagt  22680
```

-continued

```
tacccatgaa agctatctag gagaatgggg ggtagcagga agatcctaag tggggcaggg  22740
aataatttc cctttggatc aataaacttc tattgaacca ggagacaaga ataatgcttg  22800
cagaaggaaa aactttacat aagcaaatat gcataaatgc acatgaattc atatgcagat  22860
tcacacatac acatttatac atatccattc aaaccagtta gatccagctt gcattcattc  22920
ccacaattac acacacacac acacacacac acacacacac acacacacac acacagatcc  22980
atacttacat atgcatttga aacaaaagac caagcaccag tccagaaaga actcacttat  23040
tctggatgaa aaatgagctc caatctttat tgcataggga gagaaaaggc ttctaccatt  23100
tgaatgccaa atgaattaaa ctcatgtttg taagaagaaa gctttattcc ttttaatagt  23160
actaagcttg ccttaagagt agacctgttc tgttgcatgc taagaagcct gcctgcttct  23220
tctgctctct cttaagtttt gtttatatct gactaaaaaa tgttttgtct aaaaagattc  23280
tcctcagttc agttatgact cttctctttg acctcagctc tgaaacacct ttcaggatac  23340
atggctacac gattaaaagt tcaccacaag tttacacaaa ttcaaatcat aactagaata  23400
ggaagtttac gacagagaat gtttacatgt atatccatta ggagtaatta tctggctaac  23460
catttgccac ctgtcacagc tccacaggtt cactggaagt taaaaactgt aactgtgaag  23520
gtttgtatag atttaccctg tcaaaatgtt atcttctctc ctaccaccta taataaattg  23580
ttagttccct ttttatgacc gtagttaatg gttgtagaaa gtctggttac tatctagctg  23640
gcgacacaat ggaagactgg cagagttctc attgcagttt tgacaatcag aagagaccta  23700
atagcacttc cactataaaa gagcttagta aatactgata taattttagg aattcttata  23760
gggtcatcat taagaattaa gaagtcattt atttgtctat atagcattac tacaagacag  23820
tacatctttg tagatcggca gaaagctact caaaagggtg ggctaatatc tagtgattgt  23880
tgtatatgtt taataataac aggagaaata tattaatagc aggaatcttt cctaaaatga  23940
ttttcccctg ggccttgcct atgggatcaa atctgtcatg gattacaatc cgaggcagac  24000
cgtctcagga agatcacctg ctagttatta gcttgtccta tgatggctcc tgacacacac  24060
ccttgctctt tttcactatt gcctgtgcat acacacagac tgacacaatc tgaggattca  24120
tggtgtagtt aagggagtac tgacatcata atgacatgga ctcttacaag ctaacatcaa  24180
ggactctatc accacatact cagaacttta atttccttta gcactgattt tgatttttca  24240
aaaaaaaact cataatgtcc tttaaatgat ttttcctatt gtaaattaat ttaaaaattt  24300
cattttatgt tattgctggt aatataaaga aaaagaactc cccgatttta ctatatagac  24360
cttgattttc acatctttgc caaatttact tattatttgt ataaaatgtg ctttgatttt  24420
tctccacaag cattttatta gtatattgtt tattagtaat tctgacagaa tgtggcacat  24480
agtggcacac tggtaaatga agcaaaagga tcctgtaaac caaggggttc aaggccagct  24540
tatacaacat acaaaaccat accccattgc tgcccccccc ataagaaaat aaattaacga  24600
gtataacaga aagtgtagta tgccactgct ttagcctgcc aggtattatc tggtatgttg  24660
acatataaga ataggaccag ttataaactg agaacattga cagtaattgg ataatcataa  24720
ctgtcactta cacacaaaaa agaagctttt aaagtctagt tgatggaaca atgctgacct  24780
aagagaaaaa tcaccaatta ttgtggcagc ttgctcatgg aaaaagctta ctaaagtggt  24840
actttgaacc tgaagaaaac tgtccttttt cttactatag atgggcagat attgtcactg  24900
atctaaacac tcaaaatcca gaattcttag atatccgaca tctagagagg gggctgcagt  24960
tccggaaaac aaagaaggta agaatactat tacattggaa gtaacttgtc gaatgaccag  25020
```

-continued

```
attgcaatat tttattaata atcttgtctt ggtaaataac agaaaccaag ttcaaactac  25080
cttagtcagg aaagtaagat tattttaagg attcaggcta actttaagct tccagctaag  25140
gatagtcata aggaaatgac acacagcact gcagtaatgg tagaatggct tatgtaggct  25200
gtgctgtact aagtgcttta tctgaatgta aatttcttga gcaataactt tcaacttttt  25260
attctcaggt gtagattgag acttaacatg ccttggttga gctccatagt cttggcctaa  25320
gttgggtaaa ttatggtcac aagacagagc caggtgttca agcatgacta cagaaagaag  25380
ctttcagaaa cagatatagt atagattgag taggcaagct tttgctataa atgaagctgg  25440
gagtggtagc acatgcttgt aatctcagct cttaggcgag aggattttca tgctatctta  25500
aactattgag attattatct caaaagtctt gtgtaaacat acacacacac acacacacac  25560
acacacacac acacacacac acatgcgtgc gtgtgcacgt gggagggaat aagataggat  25620
tttagtagaa tggaggagag gagactacac acacagcaaa ggaaaagcat gattttaatt  25680
tgtgagtcag gaatatgtgg atatgactat gccgactcta ggctgtggag gggcatatgg  25740
gacacagtgc tctggtccct aagggcttta ttataatgta aaggcaggtg ttgggaaagg  25800
tgagtatgtt aaagtgttct gataaagcag agtagtagtg ttttcagaca tgtggaagaa  25860
taccaccatc acctcaaggg agtcaataag agccctaaaa acttacaaac ttattttctc  25920
tttattgtct tcatcttttt tcccttctca ggttggagga aatttgcatt gcatcatagc  25980
attccagaga ctcagttggc agagatttgg cttttggaac tttccatttg gaaccattac  26040
acaagaatca caacatccca cacatgtccc gggaattgcc aaatctgaga gtgaggacaa  26100
tatctctaag aagcagcatg ggcgcctggg caggtccttc agtgcgagtt tccatcagga  26160
ctcggcatgg aagaacatgt ctagcatcca cgagaggagg aacagtggct accacagctt  26220
tagagattat aatggcaatg actgaccatg ccaaaactta gccactggtg ttacccacac  26280
agctgttatg tacaggactg cattaggaca tcagctggtt ttattaagtc tgtcaatagg  26340
aacagatttt gtggtacaaa acacaccctg tagttctcta gtaaaaaagc ctacatagga  26400
ttactatggt tggcttcaaa tatacaggca ggtaagcaca gaaccccgcc cttctaaagt  26460
taaaagtaga taagcaatct ggacaaaggg tttcacaaaa tccaatacaa tcaaaacggc  26520
ttcaaagcaa aaacacaaat gcatttaatt tgaaaagcat cgaaacttga actacttaag  26580
catgaagcga cttattgata cttgatccct agcatttatt acaacacttt aattcctaag  26640
gcatcatctg tccttaaaaa atgggggcag tcaaggtcta gtttttgctc atggttaaaa  26700
ctaatttaaa attatctttc tagtctagtt gttctttcag tgctaacagt atccacctcc  26760
catcgttgct ttcctgaata actctcagga ttctccaaaa agcagcagaa actactccag  26820
aaactgacct tttctctagg tgcagatagg tgacttaggt cattgatcct gatactcttg  26880
acttggcacg tggttgtgaa atagctacaa gaagaatata ggtctggagc gaagtctgat  26940
gttctagaac aaaccttgtt tcagggatat agttagagag cacttggcat ccaaagtttc  27000
cttatccacg gtaacatgtg ctgtgagatg tcacatttga cttgtctctt aatggagtca  27060
tgtgttaaca acagcactga tgtcatgttg gcaatgtcca gctcactctg aggaagactt  27120
tgtattttca actctgagcc gtttcctttt gtgaaacctc caagcaatta ggtgttggaa  27180
gtgtgagtta catattctgg aagtgtgagt tcaatacttg agctcctctt tagcggctct  27240
tgttttcctt ttgctgccaa ggtgtgactc atagccgtct atgatgctgc tctttcacgt  27300
cgtaggttta ttccaggatt caaatcagta acttggtgat tacaaggtgc tgagtatgtt  27360
ggaaccattg caatacacct caaagggagg tgtcggattt tgacttttta aaaaaaattt  27420
```

-continued

```
tcatttttct cttgaatttc atatccatct atccactcat atatgtttag cctacagaat  27480
tacaaactag tcctgtttct gaagaggttc tttagcttga aatgtaaagg actgaaagat  27540
ttgtaggtgt tgcttttgtt acttcacact ggaactttga aaatgttttc atcaaataaa  27600
gttttgtttt ctacttttaa tcctatgaat tttaatgtct atgtttaagt tagcgtgtat  27660
tcttgtaact gtgtgaagca gatgataatt tgctaattcc atgtaatcag tgttataaga  27720
aacatcttac aatttttata atcaccggaa caatgtgaaa agccaataac ttccattcca  27780
tgcttgctac ttttcaagta cttgagcact gattctctaa tccttcacaa cgtgatttag  27840
gaattttctt atattaatta aaaaaaaaag gttggaattt ttgtggttca ggcatatttt  27900
caatataaac tgcttttaat agttcaattg agtatttcaa agcaataggt ttgaagagct  27960
aagaggaaag aatacaaatg caaaataaga tgtaaacctt aagaacaaag tgacagctgg  28020
gaaaataaga tgagtttatt tcctgtacac taatcatatg ctttattgaa atcactgaca  28080
gacatctgac cacttaaaac ttaagcttac agatttaaag atgacttaga gcacagaatg  28140
tttgaattca gtgggagttt tttttttttt tttttttttt tttttcaggg tatgtaggta  28200
agaggtcctg caaagtccct tttgaaaact agtaatattc ctatttgatt tgttagtcaa  28260
cctgtcttag aaattgtcat agatcttcta aggaaggata ctgattggct cagaagttac  28320
aagttgtctc acctgtgaga ttatgtcctc tttggtagtg atgtggaaga acggttacgc  28380
taatgagcat ggtatttata atagtagttg aaaagctatt taaatgcttg ctataattat  28440
tattttgaaa atgtgttctt aattgattag tctgttatca gcatggcaac ctgcaggcag  28500
gcatggcact ggagaaggag ctgagagtcc tacatcctga tcggaaggca gccaggagag  28560
gacagtcttc cacaggcatc caggaagaag gttcttttcc acacgaggag gagcttgaga  28620
ataggacctc aaagctcacc cctggtgatg aacttcctct gacaagggca cacctcctaa  28680
gagtaccact tcccatgggc caagtatttt gaaaccacca catttataga acctgttaat  28740
cctttatgca ctactacagt tacaggggta tatcccatca tagaaagcag gtatagcaac  28800
tgaagtgttt ctcaagttgc tttgttacag ccatggagtg agcctaggca accactccag  28860
aacctatggc attatttaac tcagtttcac tcttagcatt tctaccctgc caatctttca  28920
cttaaaaaaa aaaataaaga caaaacaaaa gccctgatct ctatgccatc actttctagg  28980
tgctttcata ggaaaatcag aacagcaccc cagctgttgg tggtagtgac gtgtgccagc  29040
taaaactgag gtttgcattg gtggagcatc ttgcctacgt ttatagagat tcttagtttg  29100
ctagagcttt cataataaag tactcaggtt gcttaaaaac aagtttgttt ttgtttcgtt  29160
tttttttcc ctcacagtta catagaccaa gacaaggtct ggcacatttg gtttcttatc  29220
ttttggactt gaagctggtc accctttttg tcctcccatg gcctttcctg tatttgtggg  29280
catactttat gatgttccca ctccttctta ttagtataac cgttatactg gattagaggc  29340
caccctgata gtctctctgt atatcaatgg tgaggtagaa atcacatcca tggacttaga  29400
cgtatcttca tgtttgtgat ctattactga ccatgactct gtcagacaca gaaatggttt  29460
tgttaagttc tggttcatgt gcccttaggt gcctaatggc cttattgttt tgacaatcat  29520
tttctaaaaa tcactttgaa tacaggcaca ttgtgcagta cttatattca acacgtgaat  29580
tttgaattct acatggatac tgacctgaat acatagtaat tccgcggtcc agccaagatc  29640
tgaactatca tctgcatgac ctctactcca aatattttcc acaggatgca aaatgtcctg  29700
gggagcatca gacctgagac ttgagaggtc acttaagcaa cattgacgaa ctcccgctat  29760
```

-continued

```
gcactactaa ggaaggggtg taacactcat caagattgat accagtttca acatgtttac  29820
agtctactgc tggaagtgat aaaaattaaa caggcaatta aattgccttc agtaaaatac  29880
gactttacta aaatgcaaaa gtccgtaatt ttacacattg agggaatgct aaactgtaaa  29940
ccacctgttt ggacatagat acgtttttgc taaaatttga cttctgatag acttcagctg  30000
taaatgaatt tttttcccca gaaattatct acttctatcc cttccttttt tttttttttc  30060
ttagacaagg ccatgtgagt cttgagcttg tgatattcct gcccatctcc cagatatttg  30120
tgccaccatg tcgggctatc tattgtttct tatcaatctt tttactgggt ttgaataatt  30180
acaataccgt ccatcaaaat tgagccattg tatgctaagt gctttgccca tattcactct  30240
gctcggtaaa agattgttct tttgtactgc ttacagatga cggagaagaa attctgaaga  30300
aacgtaatct ccacagagct aactctatag taaggcctca aagggctgca ttcgatttag  30360
aatgtgcata tcgtgtcttt tcctggctct actctgcccc aagtcatttt tcccaattgt  30420
ggaactcaaa gtttcagatg ctggaggaaa ttcaaagtta agcactgcgt tgtactgcca  30480
tccagttact gcacgttgtg aaaatatttg ccttcaccaa agtcaagatg ctcatctttc  30540
cgttcttttc ttgtcgaacc caatacttgg cgccaaatcg gcaaagctgg ggaggcaatg  30600
gggagactga tactgaaaat gcacaaagga gacctcactc cattaagaaa gccaatatgt  30660
gcaaacactt tttgcgccta acagtcagcc gaacagaggc acagattcaa aaccgaatcg  30720
ccacacacac tgacttcggg agtgctcggg cgtgggattt acgtgtcaag tgtcaacgcg  30780
ggaatcccaa ccctcgcgtt cacttggaag ccaagaggtt tcatcgtttg gtcagcggga  30840
gaaatcactc gcgaccggag gaaggctcgg cgctggcgtc accggtgctg cttctcagta  30900
cttttaggcg tgccagtact ggggctgaaa cctttctgct cctcccacca catttaaatt  30960
ccgctgttct ttcgggagac cgggtccgct ccggaagtgc gtcagcgccg tgttcctcct  31020
tcaagccctg gtgacagcgg gttccaggcg gagagcggtg ggctctgcgt gagttggtgg  31080
cgctgcgtgc tggtgcgggg cgcgtccttt atcctaacgg gaaacaaagg ccccgcgagc  31140
ccggccgaga gagagcgcct gcgccatggg agtgcagggg ctgtggaagc tgctggagtg  31200
ctcgggccac cgggtcagcc cggaggcgct ggagggcaag gtgctggccg tgggtatcct  31260
tcaaggcggc tccggagcgc cggatgagcg cctgctcggc gactgggctt cgtccgggac  31320
ttggtgctgg gggtcgattg ggtgtctgtc tatctagagt gcaggcctgc gctccttagg  31380
ccggcccatt ttgtgccccc tatgctttag ttctcacagc agagtggcta cagagttgtc  31440
gcggagaata aggagattta aatgataaaa tttggtatag cgtcaggctc cgtagtactg  31500
tacatctgag aagtcattct gtcagagtag aggggggggaa aaaaaagaag agttccgaac  31560
cctcccaccc tcctttttga atagttacct cttgtttgtt ggaataaaaa aagttcatac  31620
ggtgtatagt gaattagttt cctccagctt ctgtgatggg tgtgtgcatt ttagttttgt  31680
gtcattggag ttttgttttt ctcccacttt gaaaatgtga taccaatttt gaagttttgt  31740
ttacgtttat ctgttccacg gcccgtttca cagtgcctct tttatcttag aaggtacttt  31800
tacatagttt tcttaatgaa aactagaaat tcctgtaaat agttgctgaa tgtgcgtaca  31860
tgcctggacg tgtgtccgta ggtggtggca tgccatgcca ttctgtaaac tatgtcagtt  31920
cttcacgatg tgcccagctt ataattaatg gagaacttgc agttttgaaa aatcacattt  31980
tatgccaaat acatcaatga caaaaattaa aaatttgtct tacaagtctt tgcacagggt  32040
accataaacc ctagtggttt ctcggcgtca ctgctgttta aggatttctt cattatttat  32100
gatggaagaa caatttttag tgagggggtt cttaaattct catcaaaggg ttttagtagt  32160
```

-continued

```
ggtagagcac tttcttagta tgtatgataa accagagttc cattcacatc tttgtgagaa  32220
agtattgctg acaacaccat caaggagtta cgttattttc tcttccagcc cttataaaca  32280
attaggaagt taagcatcct agcattcagg gttgtcaaat gaaaagtaat ccatgtagat  32340
tattcataaa tggctgtgtt ccatttgggg tgtgaagtta tgtttatgag gttattaagc  32400
tcttctgaaa taatggatcg tttaaagaaa atcgtgaggg attttgccta cactcacatg  32460
taatctggtt acttctgtaa tttaattttc tgtgtttcat catgagaatt ctgatatctg  32520
aaatttaggt gttagaaatt tattcggttt gctaataaat aaatcatcca caattatctc  32580
aggtttgtaa tttacatact tttccaaata aactgtttgg gttttagacc atgtgaatag  32640
ctgagtgtat tatttaaaca gtttatgtct gtgtcaaaaa aatgttagga aataacagat  32700
tagtttttcc tcattattga ccttaacatc tgttagtgca ttggcagtat taagcagata  32760
gtaccctcac tggacacatg aacaacatgg attaacttag tctccagtca cctaattcca  32820
ggactaagga aaattcccat ttattttcag atgttattgg ttctttgagt ttaaattcta  32880
aagcaagttt tgactttgcc tttgcttcat tctttaattc ttctaaccct tgaggagttt  32940
agttttgcca catttgtgtt gaagcttgac taatcaaact gtgtaaattc tttcagccta  33000
tctgatttta tctgtttttt tttttgtttt ttgtttttttg ttttttttta actaagagtt  33060
tcatgttgga actctcggcc ttccatgaga agtggtaagc tgtggttaat ttaaatgtga  33120
aaaggaatta tttcagtgtg atttagtgtt ttaggaacat ggggtttaat cttttctcag  33180
aagctgtagg ccctagactc atatatatga gttaagaggt atcttaactc tgaaattgag  33240
ttttctcaat tctaaagtca aaagtgattg attgtataga cacttttgat ggcagtgtag  33300
caagcagaaa tggaccaagt atgagtagct gtccagagta gaactgagac tgcagaaggc  33360
ttgctctaag ctggatcctg gacctgatca ctcatgtctg agacctacca tcactatcat  33420
ctcctttcat gtgggctgct ggaacattct tttttttttt tttttgttat atggattttc  33480
atacttcttc tttcttgtat tagatatttt ctttatatac atttcaaatg ctatcctgaa  33540
agttccctat accctcccct actgctgtaa cattcttaaa actactctcc ttgcagttga  33600
tttttacatg tctcctaagg cccgaagtca ttctggaaac tgctcagatg tgtatattgt  33660
atatcagctt ccatacccaa gtgccccacc cctgcgccca ccacagggaa ctgtgtagac  33720
gtggctctgc cctaggcgtt tgtatttgct gcgtctcgtc tcccttctgt aactagagtg  33780
ctaaactcat aactactctc ctgacctatt atttcttggc acttaatgtg tcaattcttt  33840
taggatatgt gcatctcaga catagggtg catttgtctt gctcacaaat acaatgttta  33900
atgtatctcc gtagggtctt ggatttactt ttacatggga gctctttaac atatagggat  33960
ggagatacac acacacacac acacacacac acacacacac acacacacac acatattgtc  34020
aacttggcat ggcatgagag tcatcaagag tcaattgaga aaattccttt ggaagaccaa  34080
gcaagactat agggcttttc ctaattagcc attaatggga gagggcccag ccaattgtgg  34140
atggtgccac ccctgggctt gtgtcctggg ttctataagc aggcaagctg agtaagccat  34200
gaggagcaag cagctaagca gctcctgtac ccaagttcct gctctcttgg agtcgctgcc  34260
ttgattttcc tcagtgatgg actgtgatgt ggatgtgtaa gccaaataaa ctccccagtt  34320
tgcttttggt tatggtgttt tatcatagca agtagaaatc ctaagatatt ggcttaaaac  34380
acaaaataca ctagcaactt ttgcagtagt aaatgaataa ctgtacatta atttttattt  34440
atttattttc ccttaatttt tttattattt aaatgcattt tatacatcaa ccatattaat  34500
```

-continued

```
aatattgagt atttttataa tacataaaaa tgttcaactt ttatattcat atcctttcag  34560

ac                                                                 34562


<210> SEQ ID NO 29
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon A1 splice donor sequence

<400> SEQUENCE: 29

cggccccagg gtaac                                                      15


<210> SEQ ID NO 30
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon A2 splice donor sequence

<400> SEQUENCE: 30

tgtgatccag gtccg                                                      15


<210> SEQ ID NO 31
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon A3 splice donor sequence

<400> SEQUENCE: 31

caggccagag gtacc                                                      15


<210> SEQ ID NO 32
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon B splice acceptor sequence

<400> SEQUENCE: 32

ttccctaaag gaatc                                                      15


<210> SEQ ID NO 33
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon B splice donor sequence

<400> SEQUENCE: 33

tttctgtcag gtgat                                                      15


<210> SEQ ID NO 34
<211> LENGTH: 15
<212> TYPE: DNA
<213> ORGANISM: Homo sapiens
```

-continued

<220> FEATURE:
<221> NAME/KEY: misc_feature
<222> LOCATION: (1)..(15)
<223> OTHER INFORMATION: BIVM Exon 1 splice acceptor sequence

<400> SEQUENCE: 34
ttcctcttag gagct 15

<210> SEQ ID NO 35
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 1 splice donor sequence

<400> SEQUENCE: 35
cacaaatcag gtaag 15

<210> SEQ ID NO 36
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 2 splice acceptor sequence

<400> SEQUENCE: 36
tgtattctag gcaat 15

<210> SEQ ID NO 37
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 2 splice donor sequence

<400> SEQUENCE: 37
tcagacgatg gtgat 15

<210> SEQ ID NO 38
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 3 splice acceptor sequence

<400> SEQUENCE: 38
gtgttctcag gtact 15

<210> SEQ ID NO 39
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 3 splice donor sequence

<400> SEQUENCE: 39
gagctggaaa gtaag 15

-continued

<210> SEQ ID NO 40
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 4 splice acceptor sequence

<400> SEQUENCE: 40
tcttttgtag ccttc 15

<210> SEQ ID NO 41
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 4 splice donor sequence

<400> SEQUENCE: 41
cacttatgag gtatg 15

<210> SEQ ID NO 42
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 5 splice acceptor sequence

<400> SEQUENCE: 42
ttactttcag gtggt 15

<210> SEQ ID NO 43
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 5 splice donor sequence

<400> SEQUENCE: 43
ggagaaactg gtagg 15

<210> SEQ ID NO 44
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 6 splice acceptor sequence

<400> SEQUENCE: 44
tttttaatag cttca 15

<210> SEQ ID NO 45
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 6 splice donor sequence -continued

<400> SEQUENCE: 45
aagcattcag gtaag 15

<210> SEQ ID NO 46
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 7 splice acceptor sequence

<400> SEQUENCE: 46
ttatatttag caggg 15

<210> SEQ ID NO 47
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 7 splice donor sequence

<400> SEQUENCE: 47
actgtaaaaa gtatg 15

<210> SEQ ID NO 48
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 8 splice acceptor sequence

<400> SEQUENCE: 48
ttaactatag atggg 15

<210> SEQ ID NO 49
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 8 splice donor sequence

<400> SEQUENCE: 49
aacaaagaag gtaag 15

<210> SEQ ID NO 50
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 9 splice acceptor sequence

<400> SEQUENCE: 50
ttcttctcag gttgg 15

<210> SEQ ID NO 51
<211> LENGTH: 30
<212> TYPE: DNA

-continued

<213> ORGANISM: Artificial Sequence
<220> FEATURE:
<223> OTHER INFORMATION: HSMAP5 primer

<400> SEQUENCE: 51
ccatgcctct ctactactca ctcccaacac 30

<210> SEQ ID NO 52
<211> LENGTH: 30
<212> TYPE: DNA
<213> ORGANISM: Artificial Sequence
<220> FEATURE:
<223> OTHER INFORMATION: HSMAP6 primer

<400> SEQUENCE: 52
ggtaagaaga acaccattgt gtttgaaggc 30

<210> SEQ ID NO 53
<211> LENGTH: 30
<212> TYPE: DNA
<213> ORGANISM: Artificial Sequence
<220> FEATURE:
<223> OTHER INFORMATION: zfbivmMAPF1 primer

<400> SEQUENCE: 53
caatgcctaa cactgtggaa agtgaaggcg 30

<210> SEQ ID NO 54
<211> LENGTH: 29
<212> TYPE: DNA
<213> ORGANISM: Artificial Sequence
<220> FEATURE:
<223> OTHER INFORMATION: zfbivmMAPR1 primer

<400> SEQUENCE: 54
gataactgtc gagctcggtt gagcagggc 29

<210> SEQ ID NO 55
<211> LENGTH: 8
<212> TYPE: PRT
<213> ORGANISM: Artificial Sequence
<220> FEATURE:
<223> OTHER INFORMATION: M1 amino acid motif
<220> FEATURE:
<221> NAME/KEY: MISC_FEATURE
<222> LOCATION: (2)..(7)
<223> OTHER INFORMATION: Xaa = any amino acid

<400> SEQUENCE: 55

Gly Xaa Xaa Xaa Xaa Xaa Xaa Cys
1               5

<210> SEQ ID NO 56
<211> LENGTH: 4
<212> TYPE: PRT
<213> ORGANISM: Artificial Sequence
<220> FEATURE:
<223> OTHER INFORMATION: M2 amino acid motif
<220> FEATURE:
<221> NAME/KEY: MISC_FEATURE
<222> LOCATION: (2)..(2)
<223> OTHER INFORMATION: Xaa = Tyr or Phe
<220> FEATURE:
<221> NAME/KEY: MISC_FEATURE
<222> LOCATION: (4)..(4)
<223> OTHER INFORMATION: Xaa = Gln or His

<400> SEQUENCE: 56

-continued

Trp Xaa Arg Xaa
1

<210> SEQ ID NO 57
<211> LENGTH: 3
<212> TYPE: PRT
<213> ORGANISM: Artificial Sequence
<220> FEATURE:
<223> OTHER INFORMATION: M3a amino acid motif

<400> SEQUENCE: 57

Tyr Phe Cys
1

<210> SEQ ID NO 58
<211> LENGTH: 3
<212> TYPE: PRT
<213> ORGANISM: Artificial Sequence
<220> FEATURE:
<223> OTHER INFORMATION: M3b amino acid motif

<400> SEQUENCE: 58

Tyr His Cys
1

<210> SEQ ID NO 59
<211> LENGTH: 5
<212> TYPE: PRT
<213> ORGANISM: Artificial Sequence
<220> FEATURE:
<223> OTHER INFORMATION: BIVM N-terminus region of homology
<220> FEATURE:
<221> NAME/KEY: MISC_FEATURE
<222> LOCATION: (3)..(3)
<223> OTHER INFORMATION: Xaa = Val or Cys

<400> SEQUENCE: 59

Arg Lys Xaa Leu Asp
1 5

<210> SEQ ID NO 60
<211> LENGTH: 6
<212> TYPE: PRT
<213> ORGANISM: Artificial Sequence
<220> FEATURE:
<223> OTHER INFORMATION: BIVM C-terminus region of homology

<400> SEQUENCE: 60

Gly Gly Asn Leu His Cys
1 5

<210> SEQ ID NO 61
<211> LENGTH: 9
<212> TYPE: PRT
<213> ORGANISM: Artificial Sequence
<220> FEATURE:
<223> OTHER INFORMATION: BIVM amino acid motif 1

<400> SEQUENCE: 61

Gly Asn Thr Thr Leu Met Trp Arg Phe
1 5

<210> SEQ ID NO 62
<211> LENGTH: 9
<212> TYPE: PRT
<213> ORGANISM: Artificial Sequence
<220> FEATURE:
<223> OTHER INFORMATION: BIVM amino acid motif 2

-continued

```
<400> SEQUENCE: 62

Tyr Phe Cys Pro Ile Gly Phe Glu Ala
1               5


<210> SEQ ID NO 63
<211> LENGTH: 9
<212> TYPE: PRT
<213> ORGANISM: Artificial Sequence
<220> FEATURE:
<223> OTHER INFORMATION: BIVM amino acid motif 3

<400> SEQUENCE: 63

Trp Phe Arg Gln Ile Asn Asp His Phe
1               5


<210> SEQ ID NO 64
<211> LENGTH: 10
<212> TYPE: PRT
<213> ORGANISM: Artificial Sequence
<220> FEATURE:
<223> OTHER INFORMATION: BIVM amino acid motif 4

<400> SEQUENCE: 64

Tyr Arg His Gln Asn His Tyr Phe Cys Pro
1               5                   10


<210> SEQ ID NO 65
<211> LENGTH: 5
<212> TYPE: PRT
<213> ORGANISM: BIVM N-terminus region of homology
<220> FEATURE:
<221> NAME/KEY: misc_feature
<222> LOCATION: (3)..(3)
<223> OTHER INFORMATION: Xaa = Val or Cys

<400> SEQUENCE: 65

Arg Lys Xaa Leu Asp
1               5
```

BIVM (BASIC, IMMUNOGLOBULIN-LIKE VARIABLE MOTIF-CONTAINING) GENE, TRANSCRIPTIONAL PRODUCTS, AND USES THEREOF

CROSS REFERENCE TO RELATED APPLICATIONS

The application is a divisional of U.S. application Ser. No. 10/417,476, filed Apr. 16, 2003, now U.S. Pat. No. 7,038,030, which claims priority to U.S. Provisional Application Ser. No. 60/373,146, filed Apr. 16, 2002, the disclosures of which are hereby incorporated by reference in their entireties, including all figures, nucleic acid sequences, amino acid sequences, and tables.

The subject invention was made with government support under a research project supported by the National Institutes of Health Grant No. AI23338. The government may have certain rights in this invention.

The Sequence Listing for this application is labeled "Seq-List-replace.txt and was created on Jun. 4, 2008, and is 251 KB. The entire contents of the sequence listing is incorporated herein by reference in its entirety.

BACKGROUND OF INVENTION

Considerable uncertainty remains with regards to the total number of human genes. Initial interpretations of genomic sequences resulted in estimates that placed the numbers of genes in man in the range of 30,000 to 40,000 (Lander, E. S., et al. [2001] "Initial Sequencing and Analysis of the Human Genome," *Nature,* 409:860-921; Ventner, J. C., et al. [2001] "The Sequence of the Human Genome," *Science,* 291:1304-51). Subsequent re-examination of the sequence data suggests the number of genes in the human genome is likely to be between 65,000 and 75,000 (Wright, F. A., et al. [2001] "A Draft Annotation and Overview of the Human Genome," *Genome Biology* 2:1.1-1.39). Predictions of 35,000 to 120,000 genes have been projected on the basis of EST sequences (Ewing, B., et al. [2000] "Analysis of Expressed Sequence Tags Indicates 35,000 Human Genes," *Nature Genet.* 25:232-234; Liang, F., et al. [2000], "Gene Index Analysis of the Human Genome Estimates Approximately 120,000 Genes," *Nature Genet.* 25:239-240). New genes continue to be recognized through inspection of genomic sequences as well as through a variety of different biochemical, immunological and other directed approaches.

The immunoglobulin superfamily (IgSF) represents a particularly large and extensively diversified family of genes (Barclay, A. N., et al. [1997] *The Leucocyte Antigen Facts-Book*, Academic Press, San Diego). Each IgSF member encodes at least one Ig that consists of ~100 amino acid residues that are arranged in two β sheets, which are comprised of anti-parallel β strands that are linked by an intrachain disulfide. Although the majority of genes in the IgSF function in the immune response, other IgSF genes are involved with cell-adhesion or growth factor recognition. IgSF domains are the most abundant domain type found in leukocyte membrane proteins.

In the course of an electronic EST database search for novel human genes encoding Ig domains, we identified an anonymous EST (IMAGE 785450; GenBank AA449273) (Hawke, N. A., et al. [1999] "Expanding Our Understanding of Immunoglobulin, T-cell Antigen Receptor, and Novel Immune-Type Receptor Genes: a Subset of the Immunoglobulin Gene Superfamily," *Immunogenetics* 50:124-133) and cloned the corresponding full-length cDNA. The predicted structure of the protein encoded by this gene, which is termed BIVM (basic, immunoglobulin-like variable motif-containing), includes short peptide motifs characteristic of an Ig variable (V) region, one of the subtypes of Ig domains. However, it lacks significant sequence identity to any group of proteins heretofore described.

We have determined the sequence of BIVM cDNA in species representative of critical points in phylogeny, examined the intracellular distribution of a recombinant form of BIVM, characterized its expression patterns in various tissues at different times in development, and defined other features of the gene that further emphasize its unique character. In addition, we have identified a BIVM-like gene in the protozoan parasite, *Giardia lamblia.*

BRIEF SUMMARY

The subject invention provides polynucleotide sequences, designated BIVM, and transcriptional/translational products obtained from the polynucleotide sequences of the invention (SEQ ID Nos:1-28). The subject invention also provides methods of detecting the presence of BIVM nucleic acids, transcriptional products, or polypeptides in samples suspected of containing BIVM genes. These methods are also useful for the detection of BIVM orthologs. Other embodiments provide polypeptide and/or nucleic acid vaccines for the induction of an immune response. Kits for detecting the presence of BIVM genes, orthologs thereof, BIVM polypeptides, or BIVM transcriptional products obtained from the polynucleotide sequences are also provided.

BRIEF DESCRIPTION OF THE TABLES AND DRAWINGS

The file of this patent contains at least one drawing executed in color. Copies of this patent with color drawings will be provided by the Patent and Trademark Office upon request and payment of the necessary fee.

Table I. Exon-intron organization of human BIVM. Three alternative splice donors in the 5' untranslated region are designated $A_1$, $A_2$, and $A_3$. Nucleotide positions are relative to FIG. 1, intron length and splice donor/acceptor sequences are shown. Coding sequence is in upper case.

FIG. 1. Human BIVM. The nucleotide sequence (SEQ ID NO: 1) and predicted amino acid translation product (SEQ ID NO: 2) of a human BIVM transcript. Translational start and stop codons are in reverse text. RNA splice junctions are underlined (see Table I). Nucleotides at 5' ends, defined by analyses of RACE products, are boxed. Nucleotide numbering is on the right; amino acid numbering is on the left. The M1 ($GX_6C$), M2 (WFRQ), M3a and M3b (YFC and YHC) motifs are shaded. The Alu sequence in the 3' untranslated region is in lower case.

FIG. 2. Predicted genomic organization of human BIVM. BIVM consists of nine coding exons (exons 1-9) and two 5' untranslated region exons (A and B). Alternative splice donor sites are present within exon A (see Table I); transcripts have been identified that include exon A, but not exon B. The CpG island is denoted by a solid bar, the Alu sequence is denoted by a hatched bar, and the location of the sequence-tagged site (STS) marker, WI-5740, is indicated (see also FIG. 1A).

FIG. 3. BIVM is well conserved among deuterostomes. ClustalW alignment of the human BIVM peptide sequence (BIVM.Hs; (SEQ ID NO: 2)) with orthologous sequences from mouse (BIVM.Mm; (SEQ ID NO: 27)), chicken (BIVM.Gg; (SEQ ID NO: 8)), *Xenopus* (XBIVM; (SEQ ID NO: 5)), zebrafish (BIVM.Dr; (SEQ ID NO: 11)), and sea urchin (SpBIVM; (SEQ ID NO: 13)). The sea urchin sequence lacks a stop codon and therefore is predicted to encode a longer polypeptide (indicated by . . . ). The M1, M2, M3a and M3b motifs are indicated. The highly conserved domain within BIVM is indicated with arrowheads. Identical residues are shown in reverse text (black), similarities are shaded (gray). Gaps introduced to maintain/maximize alignment are indicated with (-).

Figure 4:
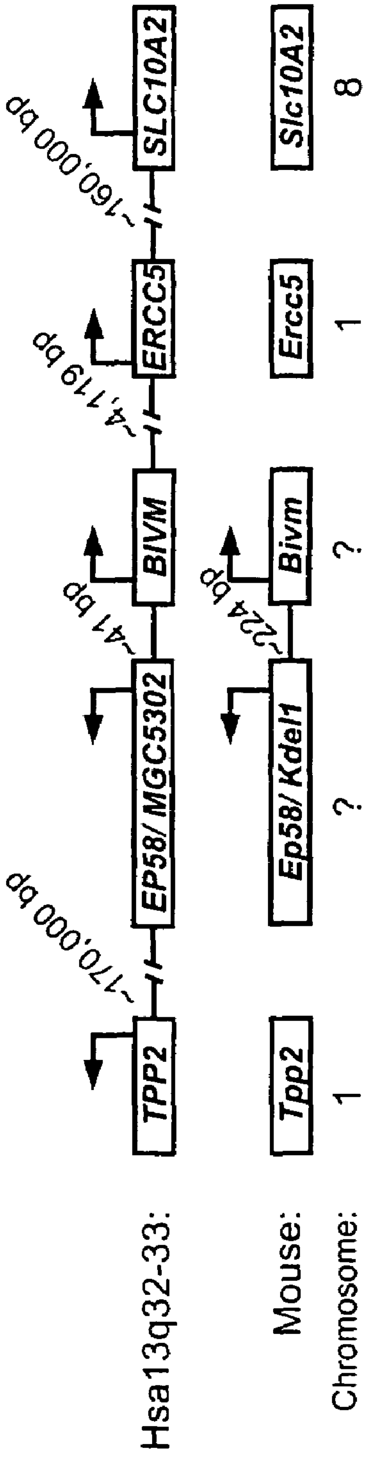

FIG. 4. Syntenic relationship between the human BIVM region and the mouse genome. The relative locations of human BIVM and flanking genes on chromosome 13q32-33; known corresponding chromosomal map positions are indicated for mouse. Transcription direction is indicated with arrows. Approximate distances between genes (if known) are indicated.

FIG. 5. Expression of BIVM. RNA blots of BIVM expression from (A) human tissues and cell lines, (B) mouse embryos and somatic tissues, (C) *Xenopus* embryos and kidney, and (D) sea urchin embryos. Approximately 2 μg of polyA+ RNA/track was analyzed in human and mouse; ~10 μg of total RNA/track was analyzed in *Xenopus* and sea urchin. Actin is used as a loading control with human and mouse blots; 18S ribosomal RNA is used as a loading control with *Xenopus* and sea urchin blots. Real time PCR analysis of BIVM expression in (E), developing zebrafish embryos and adult tissues, and in (F) chicken bursa at various stages of embryonic development. The quantity of BIVM (designated on the left) is relative and normalized (see Methods). Note that the level of zebrafish BIVM expression in the 0 hpf embryo is approximately 10 times the level detected at 6 hpf. Time points in the analysis of bursa are days of embryonic life (e.g. E12) and chicken embryonic fibroblasts (CEFs) were included as a control. Days post coitus=dpc, stage=st., hour post fertilization=hpf, days post fertilization=dpf and intestine=intest.

FIG. 6. BIVM localizes to the nucleus and the cytoplasm. (A) Western analysis of whole cell lysates from pIRES2-EGFP (EGFP), pBIVM-N2/EGFP (N2/EGFP) and pBIVM-K1/EGFP (K1/EGFP) transfected Cos-7 cells. Recombinant BIVM is detected with an anti-V5 antibody. EGFP is shown as a transfection and loading control. Note that only a single protein corresponding to the 5' ATG is generated from the endogenous transcript (pBIVM-N2); protein synthesis is increased by modification of the translational start site (pBIVMK1). Size standards are indicated. (B) Western analysis of nuclear and cytoplasmic fractions from pBIVM-K1/EGFP transfected Cos-7 cells. OCT-1 (Pombo, A., et al. [1998] "Regional and Temporal Specialization in the Nucleus: A Transcriptionally-Active Nuclear Domain Rich in PTF, Oct1 and PIKA Antigens Associated with Specific Chromosomes Early in the Cell Cycle," *EMBO J.* 1768) and HSP90 (Perdew, G. H., et al. [1991] "Evidence that the 90-kDa Heatshock Protein (HSP90) Exists in Cytosol in Heteromeric Complexes Containing HSP70 and Three Other Proteins with Mr 63,000, 56,000, and 50,000," *J Biol Chem* 6708) are nuclear and cytoplasmic markers, respectively. (C-J) Immunocytochemical localization of BIVM. Cos7 cells transiently transfected with pBIVM-K1 were analyzed by conventional fluorescent microscopy. Recombinant BIVM (green), actin (red), nuclei (blue), and overlayered images are shown. Note that levels of nuclear BIVM vary (compare C to G).

FIG. 7. *Giardia* BIVM-like sequence. (A) The nucleotide sequence (SEQ ID NO: 14) and predicted amino acid translation product (SEQ ID NO: 15) of a *Giardia lamblia* BIVM-like (BIVML) transcript. Translational start and stop codons are in reverse text. Numbering is as in FIG. 1. Grey shading indicates conserved motifs. A sequence resembling predicted giardial initiator regions is boxed. A classic giardial polyadenylation signal sequence is underlined. (B) Alignment of the predicted BIVML protein (SEQ ID NO: 15) with the C-terminal region of human BIVM (SEQ ID NO: 2). Labeling is as in FIG. 3. (C)RNA blot (10 μg/track) probed for BIVML in vegetative-stage (veg) and 21 hr encysting *Giardia*. Calmodulin is shown as loading control.

Figure 8:
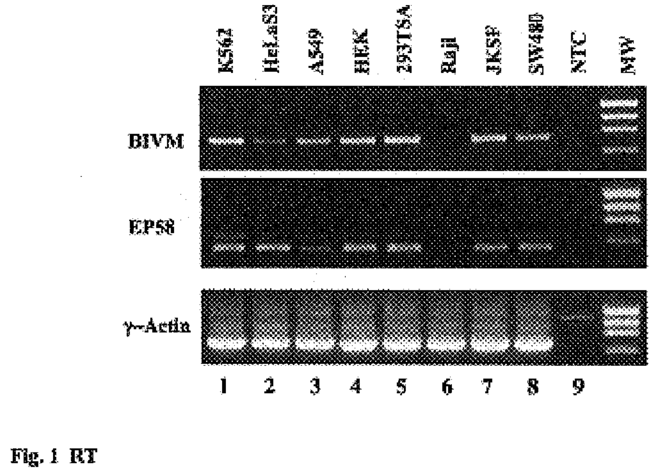

FIG. 8. RT-PCR analysis of extracts from BIVM expressing and non-expressing human cell lines indicated that EP58/MGC5302 was expressed in all cell lines that express BIVM but not in a BIVM non-expressing cell line.

Figure 9:
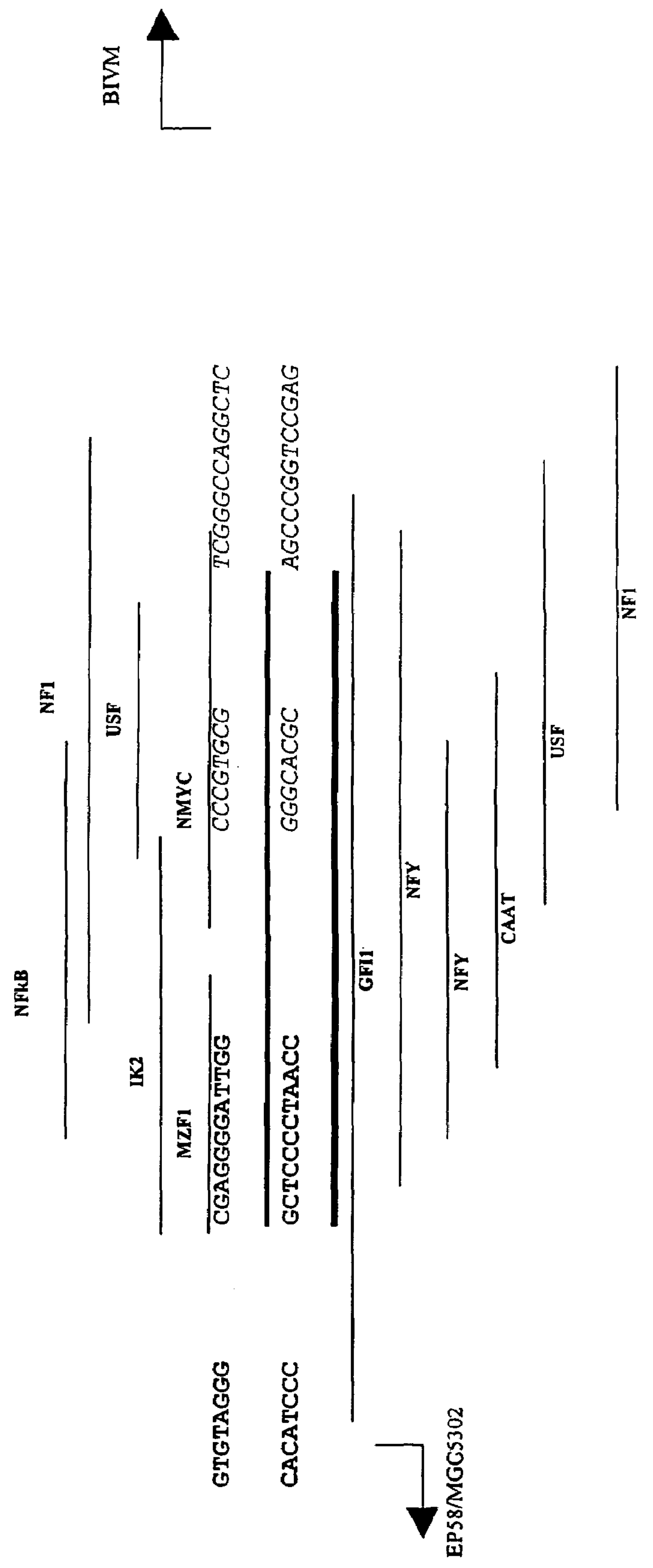

FIG. 9. Potential binding sites contained in the 41 bp region separating the BIVM and EP58/MGC5302 genes revealed sites for cell type specific factors such as the myeloid zinc finger-1 (MZF-1), the hematopoietic-expressed Ikaros-2 (IK2) factor, and the ubiquitously expressed transcription factors NF1, USF, NFκB, and NMYC.

Figure 10:
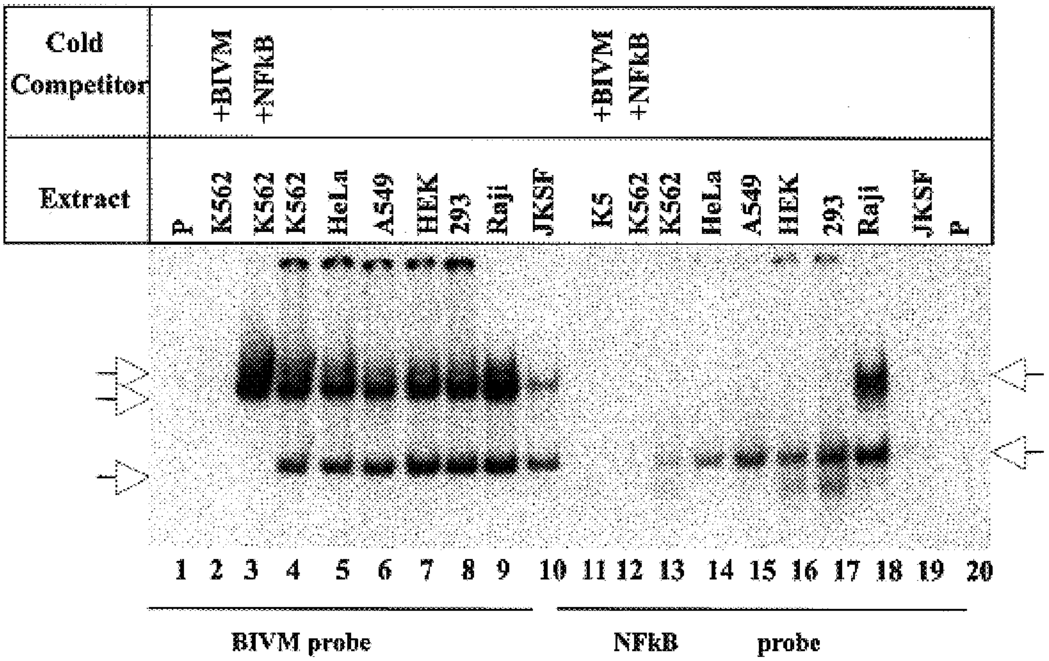

FIG. 10. Detection of bands representing NFκB-specific binding constitutively present in nuclear extracts.

Figure 11:
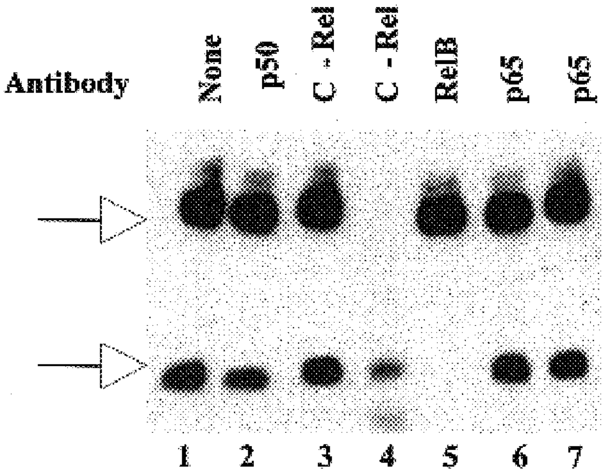

FIG. 11. Binding of the 41 bp intergenic region by NFκB complexes containing c-Rel and RelB factors, which are constitutively present in the nuclear extracts from the BIVM expressing K562 cell line.

Figure 12:
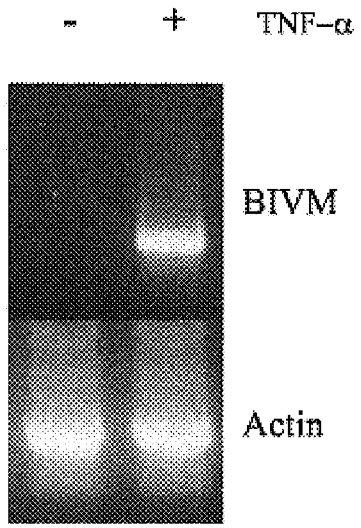

FIG. 12. TNF-α activated NFκB increases the expression of BIVM in the BIVM-expressing HeLa cell line (DNS). A cell line devoid of basal BIVM expression, the Raji Burkitt's lymphoma line, is induced to express BIVM by TNF-α.

Figure 13A:
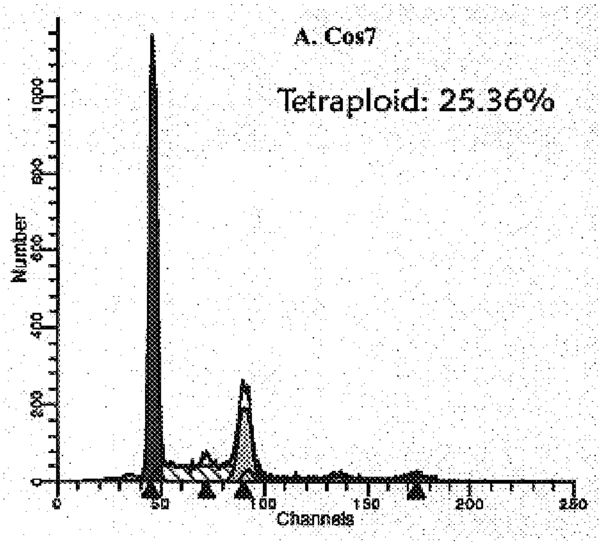
Figure 13B:
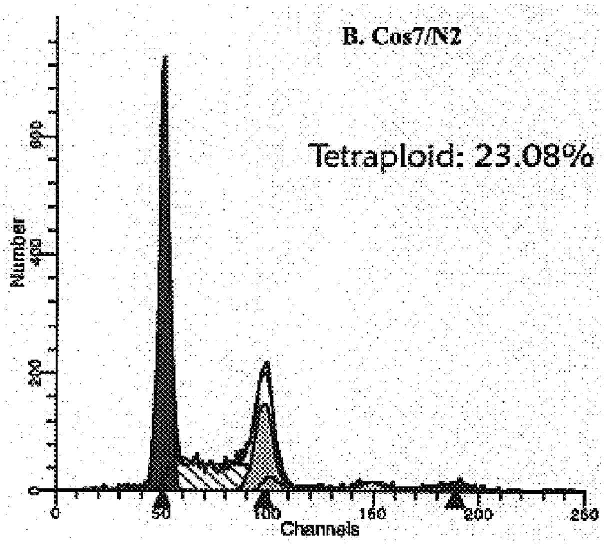
Figure 13C:
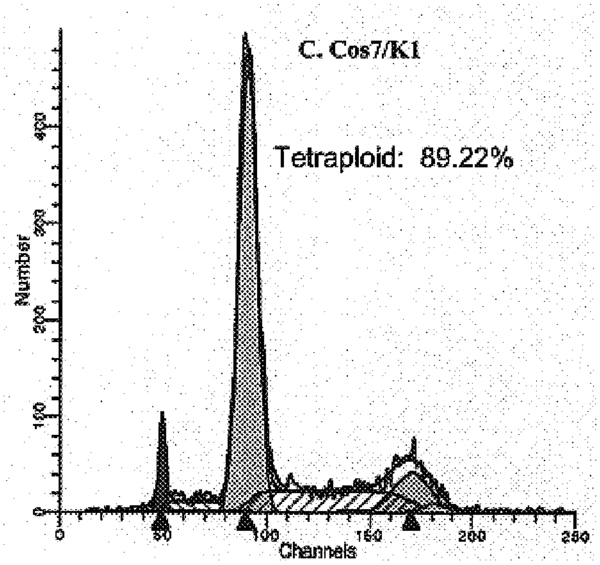

FIG. 13. Flow cytometer analyses of cells stained with propidium iodide.

BRIEF DESCRIPTION OF THE SEQUENCES

SEQ ID NO: 1—human BIVM cDNA

SEQ ID NO: 2—human BIVM amino acid sequence

SEQ ID NO: 3—human BIVM gemonic sequence with upstream partial sequence of MGC5302 gene and downstream partial sequence of ERCC5 gene SEQ ID NO: 4—*Xenopus* BIVM open reading frame SEQ ID NO: 5—*Xenopus* BIVM amino acid sequence SEQ ID NO: 6—Chicken BIVM open reading frame SEQ ID NO: 7—Alternatively spliced chicken BIVM open reading frame SEQ ID NO: 8—Chicken BIVM amino acid sequence SEQ ID NO: 9—Alternatively splice chicken BIVM amino acid sequence SEQ ID NO: 10—Zebrafish BIVM open reading frame SEQ ID NO: 11—Zebrafish BIVM amino acid sequence SEQ ID NO: 12—Sea urchin BIVM partial coding sequence SEQ ID NO: 13—Sea urchin BIVM partial amino acid sequence SEQ ID NO: 14—*Giardia* BIVM-like open reading frame SEQ ID NO: 15—*Giardia* BIVM-like amino acid sequence SEQ ID NO: 16—Lancelet BIVM partial coding sequence SEQ ID NO: 17—Lancelet BIVM partial amino acid sequence SEQ ID NO: 18—Mouse BIVM exon A nucleotide sequence SEQ ID NO: 19—Mouse BIVM exon B nucleotide sequence SEQ ID NO: 20—Mouse BIVM exon C nucleotide sequence SEQ ID NO: 21—Mouse BIVM exon 1 nucleotide sequence SEQ ID NO: 22—Alternative mouse BIVM 5' end clone (6359)

SEQ ID NO: 23—Alternative mouse BIVM 5' end clone (6358)

SEQ ID NO: 24—Alternative mouse BIVM 5' end clone (6356)

SEQ ID NO: 25—Alternative mouse BIVM 5' end clone (cDNA)

SEQ ID NO: 26—Mouse BIVM cDNA with clone 6359 5' end

SEQ ID NO: 27—Mouse BIVM amino acid sequence

SEQ ID NO: 28—Mouse BIVM genomic sequence with upstream partial sequence of KDEL gene SEQ ID NO: 29—Human BIVM exon $A^1$ splice donor sequence SEQ ID NO: 30—Human BIVM exon $A^2$ splice donor sequence SEQ ID NO: 31—Human BIVM exon $A^3$ splice donor sequence SEQ ID NO: 32—Human BIVM exon B splice acceptor sequence SEQ ID NO: 33—Human BIVM exon B splice donor sequence SEQ ID NO: 34—Human BIVM exon 1 splice acceptor sequence SEQ ID NO: 35—Human BIVM exon 1 splice donor sequence SEQ ID NO: 36—Human BIVM exon 2 splice acceptor sequence SEQ ID NO: 37—Human BIVM exon 2 splice donor sequence SEQ ID NO: 38—Human BIVM exon 3 splice acceptor sequence SEQ ID NO: 39—Human BIVM exon 3 splice donor sequence SEQ ID NO: 40—Human BIVM exon 4 splice acceptor sequence SEQ ID NO: 41—Human BIVM exon 4 splice donor sequence SEQ ID NO: 42—Human BIVM exon 5 splice acceptor sequence SEQ ID NO: 43—Human BIVM exon 5 splice donor sequence SEQ ID NO: 44—Human BIVM exon 6 splice acceptor sequence SEQ ID NO: 45—Human BIVM exon 6 splice donor sequence SEQ ID NO: 46—Human BIVM exon 7 splice acceptor sequence SEQ ID NO: 47—Human BIVM exon 7 splice donor sequence SEQ ID NO: 48—Human BIVM exon 8 splice acceptor sequence SEQ ID NO: 49—Human BIVM exon 8 splice donor sequence SEQ ID NO: 50—Human BIVM exon 9 splice acceptor sequence SEQ ID NO: 51—HSMAP5 primer SEQ ID NO: 52—HSMAP6 primer SEQ ID NO: 53—xfbivmMAPF1 primer SEQ ID NO: 54—xfbivmMAPR1 primer SEQ ID NO: 55—M1 amino acid motif SEQ ID NO: 56—M2 amino acid motif SEQ ID NO: 57—M3a amino acid motif SEQ ID NO: 58—M3b amino acid motif SEQ ID NO: 59—BIVM N-terminus region of homology SEQ ID NO: 60—BIVM C-terminus region of homology SEQ ID NO: 61—BIVM amino acid motif 1

SEQ ID NO: 62—BIVM amino acid motif 2

SEQ ID NO: 63—BIVM amino acid motif 3

SEQ ID NO: 64—BIVM amino acid motif 4

DETAILED DISCLOSURE OF THE INVENTION

The subject invention provides isolated and/or purified nucleotide sequences comprising: a) a polynucleotide sequence, or fragment thereof, or a polynucleotide encoding an amino acid sequence, or fragment of said amino acid sequence, of a sequence selected from the group consisting of SEQ ID NOs: 1-64 (or the complements of said polynucleotide sequences or fragments thereof); b) a polynucleotide sequence, or fragment thereof, comprising a sequence having at least about 20% to 99.99% identity to a polynucleotide selected from the group consisting of SEQ ID NOs:1-28; c) a polynucleotide sequence encoding a polypeptide comprising a sequence selected from the group consisting of SEQ ID NOs: 2, 5, 7, 8, 9, 11, 13, 15, 17, or 27; d) splice variants of SEQ ID NOs: 1-3 or 6-9; or e) a polynucleotide sequence encoding a polypeptide fragment of SEQ ID NOs: 2, 5, 7, 8, 9, 11, 13, 15, 17, or 27, wherein said fragment has substantially the same biological or serologic activity as the native (or intact) polypeptide.

Nucleotide, polynucleotide, or nucleic acid sequence(s) are understood to mean, according to the present invention, either a double-stranded DNA, a single-stranded DNA, or products of transcription of the said DNAs (e.g., RNA molecules). It should also be understood that the present invention does not relate to the genomic nucleotide sequences encoding BIVM in their natural/native environment or natural/native state. The nucleic acid, polynucleotide, or nucleotide sequences of the invention have been isolated, purified (or partially purified), by separation methods including, but not limited to, ion-exchange chromatography, molecular size exclusion chromatography, affinity chromatography, or by genetic engineering methods such as amplification, cloning, or subcloning.

Optionally, the polynucleotide sequences of the instant invention can also contain one or more polynucleotides encoding heterologous polypeptide sequences (e.g., tags that facilitate purification of the polypeptides of the invention (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli," J. of Experimental Biology* 203:19-28, The Co. of Biologists, Ltd., G. B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. of Chromatography A.* 707:3-22, Elsevier Science B. V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: the Strep-tag", *Biomolecular Engineering* 16:79-86, Elsevier Science, B. V.; Smith [1998] "Cookbook for Eukaryotic Protein Expression: Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology,* 139:49-57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.).

signals for termination of translation, and appropriate regions for regulation of transcription. In certain embodiments, the vectors can be stably maintained in the host cell and can, optionally, contain signal sequences directing the secretion of translated protein. Other embodiments provide vectors that are not stable in transformed host cells. Vectors can integrate into the host genome or be autonomously-replicating vectors.

In a specific embodiment, a vector comprises a promoter operably linked to a protein or peptide-encoding nucleic acid sequence, one or more origins of replication, and, optionally, one or more selectable markers (e.g., an antibiotic resistance gene). Non-limiting exemplary vectors for the expression of the polypeptides of the invention include pBr-type vectors, pET-type plasmid vectors (Promega), pBAD plasmid vectors

TABLE I

Splice variants of BIVM (SEQ ID NOs:29-50)

| Seq ID No. | Exon | Splice Donor | Splice Acceptor | Position | Intron (bp) |
|---|---|---|---|---|---|
| 29 | $A^1$ | CGGCCCCAGGgtaac | — | 1-415 | — |
| 30 | $A^2$ | TGTGATCCAGgtccg | — | 1-365 | — |
| 31 | $A^3$ | CAGGCCAGAGgtacc | — | 1-473 | — |
| 33/32 | B | TTTCTGTCAGgtgat | ttccctaaagGAATC | 474-557 | 5785 |
| 35/34 | 1 | CACAAATCAGgtaag | ttcctcttagGAGCT | 558-1157 | 1754 |
| 37/36 | 2 | TCAGACGATGgtgat | tgtattctagGCAAT | 1158-1284 | 8682 |
| 39/38 | 3 | GAGCTGGAAAgtaag | gtgttctcagGTACT | 1285-1380 | 4481 |
| 41/40 | 4 | CACTTATGAGgtatg | tcttttgtagCCTTC | 1381-1485 | 609 |
| 43/42 | 5 | GGAGAAACTGgtagg | ttactttcagGTGGT | 1486-1580 | 216 |
| 45/44 | 6 | AAGCATTCAGgtaag | tttttaatagCTTCA | 1581-1713 | 9405 |
| 49/48 | 7 | AACAAAGAAGgtaag | ttaactatagATGGG | 1714-1800 | 2768 |
| 50 | 8 | — | ttcttctcagGTTGG | 1801-1897 | 4089 |
| 50 | 9 | — | ttcttctcagGTTGG | 1898-3029 | 832 |

Other aspects of the invention provide vectors containing one or more of the polynucleotides of the invention. The vectors can be vaccine, replication, or amplification vectors. In some embodiments of this aspect of the invention, the polynucleotides are operably associated with regulatory elements capable of causing the expression of the polynucleotide sequences. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations of the aforementioned vector sources, such as those derived from plasmid and bacteriophage genetic elements (e.g., cosmids and phagemids).

As indicated above, vectors of this invention can also comprise elements necessary to provide for the expression and/or the secretion of a polypeptide encoded by the nucleotide sequences of the invention in a given host cell. The vector can contain one or more elements selected from the group consisting of a promoter, signals for initiation of translation, (Invitrogen) or those provided in the examples below. Furthermore, vectors according to the invention are useful for transforming host cells for the cloning or expression of the nucleotide sequences of the invention.

Promoters which may be used to control expression include, but are not limited to, the CMV promoter, the SV40 early promoter region (Bernoist and Chambon [1981] *Nature* 290:304-310), the promoter contained in the 3' long terminal repeat of Rous sarcoma virus (Yamamoto, et al. [1980] *Cell* 22:787-797), the herpes thymidine kinase promoter (Wagner et al. [1981] *Proc. Natl. Acad. Sci. USA* 78:1441-1445), the regulatory sequences of the metallothionein gene (Brinster et al. [1982] *Nature* 296:39-42); prokaryotic vectors containing promoters such as the β-lactamase promoter (Villa-Kamaroff, et al. [1978] *Proc. Natl. Acad. Sci. USA* 75:3727-3731), or the tac promoter (DeBoer, et al. [1983] *Proc. Natl. Acad. Sci. USA* 80:21-25); see also, "Useful Proteins from Recombinant Bacteria" in *Scientific American,* 1980, 242:74-94; plant expression vectors comprising the nopaline synthetase promoter region (Herrera-Estrella et al. [1983] *Nature* 303: 209-213) or the cauliflower mosaic virus 35S RNA promoter (Gardner, et al. [1981] *Nucl. Acids Res.* 9:2871), and the promoter of the photosynthetic enzyme ribulose biphosphate carboxylase (Herrera-Estrella et al. [1984] *Nature* 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The subject invention also provides for "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acid to the polynucleotides of the invention provide for "homologous" or "modified" nucleotide sequences. In various embodiments, "homologous" or "modified" nucleic acid sequences have substantially the same biological or serological activity as the native (naturally occurring) BIVM polypeptides. A "homologous" or "modified" nucleotide sequence will also be understood to mean a splice variant of the polynucleotides of the instant invention (see Table I) or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% or higher. The aforementioned range of percent identity is to be taken as including, and providing written description and support for, any fractional percentage, in intervals of 0.01%, between 20.00% and 99.99% or higher. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman [1988] *Proc. Natl. Acad. Sci. USA* 85(8):2444-2448; Altschul et al. [1990] *J. Mol. Biol.* 215(3): 403-410; Thompson et al. [1994] *Nucleic Acids Res.* 22(2): 4673-4680; Higgins et al. [1996] *Methods Enzymol.* 266:383-402; Altschul et al. [1990] *J. Mol. Biol.* 215(3):403-410; Altschul et al. [1993] *Nature Genetics* 3:266-272).

The subject invention also provides nucleotide sequences complementary to any of the polynucleotide sequences disclosed herein. Thus, the invention is understood to include any DNA whose nucleotides are complementary to those of the sequence of the invention, and whose orientation is reversed (e.g., an antisense sequence).

The present invention further provides fragments of the polynucleotide sequences provided herein. Representative fragments of the polynucleotide sequences according to the invention will be understood to mean any nucleotide fragment having at least 8 or 9 successive nucleotides, preferably at least 12 successive nucleotides, and still more preferably at least 15 or at least 20 successive nucleotides of the sequence from which it is derived. In other embodiments, fragments contain from one nucleotide less than the full length polynucleotide sequence to fragments comprising up to, and including 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or 255 consecutive nucleotides of a particular sequence disclosed herein. Yet other embodiments provide fragments (or detection probes) comprising nucleotides 1446 to 1697 or 1447 to 1698 of FIG. 1 (SEQ ID NO:1). It is to be understood that such fragments refer only to portions of the disclosed polynucleotide sequences that are not listed in a publicly available database or prior art references.

Among these representative fragments, those capable of hybridizing under stringent conditions with a nucleotide sequence according to the invention are preferred. Conditions of high or intermediate stringency are provided infra and are chosen to allow for hybridization between two complementary DNA fragments. Hybridization conditions for a polynucleotide of about 300 bases in size will be adapted by persons skilled in the art for larger- or smaller-sized oligonucleotides, according to methods well known in the art (see, for example, Sambrook et al. [1989]).

The subject invention also provides detection probes (e.g., fragments of the disclosed polynucleotide sequences) for hybridization with a target sequence or an amplicon generated from the target sequence. Such a detection probe will advantageously have as sequence a sequence of at least 9, 12, 15, 20, 25, 30, 35, 40, 45, 50, 55, 60, 65, 70, 75, 80, 85, 90, 95, or 100 nucleotides. Alternatively, detection probes can comprise 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or 255 consecutive nucleotides of the disclosed nucleic acids. The detection probes can also be used as labeled probe or primer in the subject invention. Labeled probes or primers are labeled with a radioactive compound or with another type of label. Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromodeoxyuridine, or fluorescein to provide probes that can be used in numerous applications.

The nucleotide sequences according to the invention may also be used in analytical systems, such as DNA chips. DNA chips and their uses are well known in the art and (see for example, U.S. Pat. Nos. 5,561,071; 5,753,439; 6,214,545; Schena et al. [1996] *BioEssays* 18:427-431; Bianchi et al. [1997] *Clin. Diagn. Virol.* 8:199-208; each of which is hereby incorporated by reference in their entireties) and/or are provided by commercial vendors such as Affymetrix, Inc. (Santa Clara, Calif.).

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak [1987] *DNA Probes*, Stockton Press, New York, N.Y., pp. 169-170.

By way of example, hybridization of immobilized DNA on Southern blots with $^{32}P$-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20-25° C. below the melting temperature (Tm) of the DNA hybrid in 6×SSPE, 5× Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$T_m$=81.5° C.+16.6 Log[Na+]+0.41(% G+C)−0.61(% formamide)−600/length of duplex in base pairs.

Washes are typically carried out as follows:

(1) twice at room temperature for 15 minutes in 1×SSPE, 0.1% SDS (low stringency wash);

(2) once at $T_m$−20° C. for 15 minutes in 0.2×SSPE, 0.1% SDS (moderate stringency wash).

For oligonucleotide probes, hybridization can be carried out overnight at 10-20° C. below the melting temperature ($T_m$) of the hybrid in 6×SSPE, 5× Denhardt's solution, 0.1% SDS, 0.1 mg/ml denatured DNA. $T_m$ for oligonucleotide probes can be determined by the following formula:

$T_m$(° C.)=2(number T/A base pairs)+4(number G/C base pairs) (Suggs et al. [1981] *ICN-UCLA Symp. Dev. Biol. Using Purified Genes*, D. D. Brown [ed.], Academic Press, New York, 23:683-693).

Washes can be carried out as follows:

(1) twice at room temperature for 15 minutes 1×SSPE, 0.1% SDS (low stringency wash;

2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C., the preferred hybridization temperature, in pre-hybridization mixture containing 100 μg/ml denatured salmon sperm DNA and 5-20×$10^6$ cpm of $^{32}P$-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art (see, for example, Sambrook et al. [1989] *Molecular Cloning, A Laboratory Manual, Second Edition*, Cold Spring Harbor Press, N.Y., pp. 9.47-9.57; and Ausubel et al. [1989] *Current Protocols in Molecular Biology*, Green Publishing Associates and Wiley Interscience, N.Y., each incorporated herein in its entirety).

A further non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art (see, for example, Sambrook et al. [1989] *Molecular Cloning, A Laboratory Manual, Second Edition*, Cold Spring Harbor Press, N.Y., pp. 9.47-9.57; and Ausubel et al. [1989] *Current Protocols in Molecular Biology*, Green Publishing Associates and Wiley Interscience, N.Y., each of which is incorporated herein in its entirety).

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006-13512. The nucleic acid sequences of the subject invention can also be used as molecular weight markers in nucleic acid analysis procedures.

The invention also provides host cells transformed by a polynucleotide according to the invention and the production of BIVM (or BIVM ortholog) polypeptides by the transformed host cells. In some embodiments, transformed cells comprise an expression vector containing BIVM, or BIVM ortholog, polynucleotide sequences. Other embodiments provide for host cells transformed with nucleic acids. Yet other embodiments provide transformed cells comprising an expression vector containing fragments of BIVM, or BIVM ortholog, polynucleotide sequences. Transformed host cells according to the invention are cultured under conditions allowing the replication and/or the expression of the nucleotide sequences of the invention. Expressed polypeptides are recovered from culture media and purified, for further use, according to methods known in the art.

The host cell may be chosen from eukaryotic or prokaryotic systems, for example bacterial cells (Gram negative or Gram positive), yeast cells, animal cells, plant cells, and/or insect cells using baculovirus vectors. In some embodiments, the host cell for expression of the polypeptides include, and are not limited to, those taught in U.S. Pat. Nos. 6,319,691; 6,277,375; 5,643,570; 5,565,335; Unger [1997] *The Scientist* 11(17):20; or Smith [1998] *The Scientist* 12(22):20, each of which is incorporated by reference in its entirety, including all references cited within each respective patent or reference. Other exemplary, and non-limiting, host cells include *Staphylococcus* spp., *Enterococcus* spp., *E. coli*, and *Bacillus subtilis*; fungal cells, such as *Streptomyces* spp., *Aspergillus* spp., *S. cerevisiae, Schizosaccharomyces pombe, Pichia pastoris, Hansela polymorpha, Kluveromyces lactis*, and *Yarrowia lipolytica*; insect cells such as *Drosophila* S2 and *Spodoptera* Sf9 cells; animal cells such as CHO, COS, HeLa, C127, 3T3, BHK, 293 and Bowes melanoma cells; and plant cells. A great variety of expression systems can be used to produce the polypeptides of the invention and polynucleotides can be modified according to methods known in the art to provide optimal codon usage for expression in a particular expression system.

Furthermore, a host cell strain may be chosen that modulates the expression of the inserted sequences, modifies the gene product, and/or processes the gene product in the specific fashion. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product whereas expression in yeast will produce a glycosylated product. Expression in mammalian cells can be used to provide "native" glycosylation of a heterologous protein. Furthermore, different vector/host expression systems may effect processing reactions to different extents.

Nucleic acids and/or vectors can be introduced into host cells by well-known methods, such as, calcium phosphate transfection, DEAE-dextran mediated transfection, transfection, microinjection, cationic lipid-mediated transfection, electroporation, transduction, scrape loading, ballistic introduction and infection (see, for example, Sambrook et al. [1989] *Molecular Cloning: A Laboratory Manual,* $2^{nd}$ Ed., Cold Spring Harbor Laboratory Press, Cold Spring Harbor, N.Y.).

The subject invention also provides for the expression of a polypeptide, derivative, or a variant (e.g., a splice variant) encoded by a polynucleotide sequence disclosed herein. Alternatively, the invention provides for the expression of a polypeptide fragment obtained from a polypeptide, derivative, or a variant encoded by a polynucleotide fragment derived from the polynucleotide sequences disclosed herein. In either embodiment, the disclosed sequences can be regulated by a second nucleic acid sequence so that the polypeptide or fragment is expressed in a host transformed with a recombinant DNA molecule according to the subject invention. For example, expression of a protein or peptide may be controlled by any promoter/enhancer element known in the art.

The subject invention also provides nucleic acid based methods for the identification of the presence of the BIVM gene, or orthologs thereof, in a sample. These methods can utilize the nucleic acids of the subject invention and are well known to those skilled in the art (see, for example, Sambrook et al. [1989] or Abbaszadega [2001] "Advanced Detection of Viruses and Protozoan Parasites in Water," *Reviews in Biology and Biotechnology,* 1(2):21-26). Among the techniques useful in such methods are enzymatic gene amplification (or PCR), Southern blots, Northern blots, or other techniques utilizing nucleic acid hybridization for the identification of polynucleotide sequences in a sample. Thus, the subject invention can provide nucleic acid based methodologies for the identification of *G. lamblia* in environmental or biological samples and provides sensitive assays for the diagnosis of *G. lamblia* infections. Alternatively, the nucleic acids can be used to screen individuals for cancers, tumors, or malignancies associated with dysregulation of the BIVM gene or its transcriptional products.

The subject invention also provides polypeptides encoded by nucleotide sequences of the invention. The subject invention also provides fragments of at least 5 amino acids of a polypeptide encoded by the polynucleotides of the instant invention. In some embodiments, the polypeptide fragments are reactive with antibodies found in the serum of an individual infected with *G. lamblia.*

In the context of the instant invention, the terms polypeptide, peptide and protein are used interchangeably. Likewise, the terms variant and homologous are also used interchangeably. It should be understood that the invention does not relate to the polypeptides in natural form or native environment. Peptides and polypeptides according to the invention have been isolated or obtained by purification from natural sources (or their native environment), chemically synthesized, or obtained from host cells prepared by genetic manipulation (e.g., the polypeptides, or fragments thereof, are recombinantly produced by host cells). Polypeptides according to the instant invention may also contain non-natural amino acids, as will be described below.

"Variant" or "homologous" polypeptides will be understood to designate the polypeptides containing, in relation to the native polypeptide, modifications such as deletion, addition, or substitution of at least one amino acid, truncation, extension, or the addition of chimeric heterologous polypeptides. Optionally, "variant" or "homologous" polypeptides can contain a mutation or post-translational modifications. Among the "variant" or "homologous" polypeptides, those whose amino acid sequence exhibits 20.00% to 99.99% (inclusive) identity to the native polypeptide sequence are preferred. The aforementioned range of percent identity is to be taken as including, and providing written description and support for, any fractional percentage, in intervals of 0.01%, between 50.00% and, up to, including 99.99%. These percentages are purely statistical and differences between two polypeptide sequences can be distributed randomly and over the entire sequence length.

"Variant" or "homologous" polypeptide sequences exhibiting a percentage identity with the polypeptides of the present invention can, alternatively, have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 91, 82, 83, 84, 85, 86, 87, 88, 89, 90, 91, 92, 93, 94, 95, 96, 97, 98, or 99 percent identity with the polypeptide sequences of the instant invention. The expression equivalent amino acid is intended here to designate any amino acid capable of being substituted for one of the amino acids in the basic structure without, however, essentially modifying the biological activities of the corresponding peptides and as provided below.

By way of example, amino acid substitutions can be carried out without resulting in a substantial modification of the biological activity of the corresponding modified polypeptides; for example, the replacement of leucine with valine or isoleucine; aspartic acid with glutamic acid; glutamine with asparagine; arginine with lysine; and the reverse substitutions can be performed without substantial modification of the biological activity of the polypeptides.

In other embodiments, homologous polypeptides according to the subject invention also include various splice variants identified within the BIVM coding sequence (see Table I).

The subject invention also provides biologically active fragments of a polypeptide according to the invention and includes those peptides capable of eliciting an immune response. In one embodiment, an immune response directed against *G. lamblia* is provided. The immune response can provide components (either antibodies or components of the cellular immune response (e.g., B-cells, helper, cytotoxic, and/or suppressor T-cells)) reactive with the biologically active fragment of a polypeptide, the intact, full length, unmodified polypeptide disclosed herein, or both the biologically active fragment of a polypeptide and the intact, full length, unmodified polypeptides disclosed herein. Biologically active fragments according to the invention comprise from five (5) amino acids to one amino acid less than the full length of any polypeptide sequence provided herein. Alternatively, fragments comprising 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or 255 consecutive amino acids of a disclosed polypeptide sequence are provided herein.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector containing nucleic acids encoding polypeptide fragments according to the invention. The transformed host cells contain a nucleic acid and are cultured according to well-known methods; thus, the invention allows for the expression of these fragments, under the control of appropriate elements for regulation and/or expression of the polypeptide fragments.

Modified polypeptides according to the invention are understood to designate a polypeptide obtained by variation in the splicing of transcriptional products of the BIVM gene, genetic recombination, or by chemical synthesis as described below. Modified polypeptides contain at least one modification in relation to the normal polypeptide sequence. These modifications can include the addition, substitution, deletion of amino acids contained within the polypeptides of the invention.

In order to extend the life of the polypeptides of the invention, it may be advantageous to use non-natural amino acids, for example in the D form, or alternatively amino acid analogs, such as sulfur-containing forms of amino acids. Alternative means for increasing the life of polypeptides can also be used in the practice of the instant invention. For example, polypeptides of the invention, and fragments thereof, can be recombinantly modified to include elements that increase the plasma, or serum half-life of the polypeptides of the invention. These elements include, and are not limited to, antibody constant regions (see for example, U.S. Pat. No. 5,565,335, hereby incorporated by reference in its entirety, including all references cited therein), or other elements such as those disclosed in U.S. Pat. No. 6,319,691; 6,277,375; or 5,643,570, each of which is incorporated by reference in its entirety, including all references cited within each respective patent. Alternatively, the polynucleotides and genes of the instant invention can be recombinantly fused to elements that are useful in the preparation of immunogenic constructs for the purposes of vaccine formulation or elements useful for the isolation of the polypeptides of the invention.

The polypeptides, fragments, and immunogenic fragments of the invention may further contain linkers that facilitate the attachment of the fragments to a carrier molecule for the stimulation of an immune response or diagnostic purposes. The linkers can also be used to attach fragments according to the invention to solid support matrices for use in affinity purification protocols. In this aspect of the invention, the linkers specifically exclude, and are not to be considered anticipated, where the fragment is a subsequence of another peptide, polypeptide, or protein as identified in a search of protein sequence databases as indicated in the preceding paragraph. In other words, the non-identical portions of the other peptide, polypeptide, of protein is not considered to be a "linker" in this aspect of the invention. Non-limiting examples of "linkers" suitable for the practice of the invention include chemical linkers (such as those sold by Pierce, Rockford, Ill.), peptides which allow for the connection of the immunogenic fragment to a carrier molecule (see, for example, linkers disclosed in U.S. Pat. Nos. 6,121,424; 5,843,464; 5,750,352; and 5,990,275, hereby incorporated by reference in their entirety). In various embodiments, the linkers can be up to 50 amino acids in length, up to 40 amino acids in length, up to 30 amino acids in length, up to 20 amino acids in length, up to 10 amino acids in length, or up to 5 amino acids in length.

In other specific embodiments, the polypeptides, peptides, derivatives, or analogs thereof may be expressed as a fusion, or chimeric protein product (comprising the protein, fragment, analog, or derivative joined via a peptide bond to a heterologous protein sequence (e.g., a different protein)). Such a chimeric product can be made by ligating the appropriate nucleic acid sequences encoding the desired amino acid sequences to each other by methods known in the art, in the proper coding frame, and expressing the chimeric product by methods commonly known in the art (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli," J. of Experimental Biology* 203:19-28, The Co. of Biologists, Ltd., G. B.; Baneyx [1999] "Recombinant Protein Expression in *Escherichia coli," Biotechnology* 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. Chromatography A.* 707:3-22, Elsevier Science B. V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," *TibTech* 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: The Strep-tag", *Biomolecular Engineering* 16:79-86, Elsevier Science, B. V.; Smith [1998] "Cookbook for Eukaryotic Protein Expression: Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology,* 139:49-57; Unger [1997] "Show Me the Money: Prokaryotic Expression Vectors and Purification Systems," *The Scientist* 11(17):20, each of which is hereby incorporated by reference in their entireties). Alternatively, such a chimeric product may be made by protein synthetic techniques, e.g., by use of a peptide synthesizer.

Another embodiment of the subject invention provides for the use of polypeptides encoded by the polynucleotides of the subject invention for the induction of an immune response or protective immunity in a subject to which the polypeptides are administered. In this aspect of the invention, compositions containing polypeptide are administered to a subject in amounts sufficient to induce an immune response, and/or induce protective immunity. The composition administered to the subject may, optionally, contain an adjuvant and may be delivered to the subject in any manner known in the art for the delivery of immunogen to a subject. Compositions may be formulated in any carriers, including for example, carriers described in E. W. Martin's *Remington's Pharmaceutical Science*, Mack Publishing Company, Easton, Pa.

The expression of the BIVM gene or BIVM gene product (e.g., DNA, RNA, or polypeptide) is dysregulated in a variety of cancers, tumors, and/or malignancies. Non-limiting examples of such cancers, tumors, and/or malignancies include prostate cancer, breast cancer, melanoma, chronic myelogenous leukemia, cervical cancer, adenocarcinomas, lymphoblastic leukemia, colorectal cancer, and lung carcinoma. Accordingly, the present invention provides a method for screening, or aiding in the diagnosis of, an individual suspected of having a malignancy or cancer. The subject invention provides methods comprising the steps of determining the amount of BIVM in a biological sample obtained from said individual and comparing the measured amount of BIVM to the amount of BIVM found in the normal population. The presence of a significantly increased amount of BIVM is associated with an indication of a malignancy or cancer. BIVM gene product can be detected by well-known methodologies including, and not limited to, Western blots, enzyme linked immunoassays (ELISAs), radioimmunoassays (RIAs), Northern blots, Southern blots, PCR-based assays, or other assays for the quantification of gene product known to the skilled artisan. This information, in conjunction with other information available to the skilled practitioner, assists in making a diagnosis.

The terms "comprising", "consisting of" and "consisting essentially of" are defined according to their standard meaning and may be substituted for one another throughout the instant application in order to attach the specific meaning associated with each term.

Following examples illustrate procedures for practicing the invention. These examples should not be construed as limiting. All percentages are by weight and all solvent mixture proportions are by volume unless otherwise noted.

EXAMPLE 1

Identification of BIVM

Human BIVM was identified originally as an EST (IMAGE #785450; GenBank AA449273) that encodes the two short motifs WFRQ (motif 2 [M2]) and YFC (motif 3a [M3a]), which correspond to framework region 2 (FR2) and FR3 of an Ig V domain, respectively (Barclay, A. N., et al. [1997] *The Leucocyte Antigen FactsBook*, Academic Press, San Diego). The W in M2 and C in M3a correspond to $W^{41}$ and $C^{104}$ of the IMGT numbering system. Complete sequencing of this EST, overlapping ESTs (IMAGE #2184889, GenBank AI538125; IMAGE 136117, GenBank R33273; IMAGE 1060823, GenBank AA568610; and IMAGE 785450, GenBank AA449273) and RACE strategies were used to resolve the complete mRNA sequence.

Human BIVM mRNA is 3857 nucleotides and encodes a 503 amino acid protein (FIG. 1). No proteins with significant identities (E<0.01) to BIVM have been identified using BLAST analyses. Searches of current motif databases (BLOCKS, PRINTS, Conserved Domain Database, Domain Architecture Retrieval Tool, Simple Modular Architecture Research Tool) also failed to identify any additional significant motifs within the BIVM protein.

In addition to the shared M2 and M3a motifs, a second V domain FR3 motif, YHC (M3b), is located several residues amino terminal of M3a. Furthermore, a putative FR1 motif (M1), encoding the conserved V domain residues $G^{16}$ and $C^{23}$ (IMGT amino acid numbering), was identified by visual inspection of BIVM peptide sequences (FIG. 1).

The 42 amino acids between M1 and M2 in BIVM are inconsistent with the sequence relationship in a V region in which the corresponding motifs would be separated by no more than 12 residues. This increased distance between $C^{23}$ and $C^{104}$ of M1 and M3a (or M3b), which normally form a disulfide bridge and stabilize the Ig domain architecture, strongly suggests that BIVM is not a member of the IgSF. Since these peptide motifs are extremely short, it could be argued that their presence in BIVM may be a random occurrence. However, it should be emphasized that in the original search of the EST database, only 17 sequences were identified that encode W(Y/F)R(Q/H) and YFC that are correctly spaced and maintain an open reading frame. Of these 17 sequences, 16 were TCR cDNAs (encoding WYRQ) and one was BIVM (encoding WFRQ) (Hawke, N. A., et al. [1999] "Expanding Our Understanding of Immunoglobulin, T-cell Antigen Receptor, and Novel Immune-Type Receptor Genes: a Subset of the Immunoglobulin Gene Superfamily," *Immunogenetics* 50:124-133).

EXAMPLE 2

Genomic Organization of BIVM

GeneBridge 4 radiation hybrid panel mapping (Gyapay, G., et al. [1996] "A Radiation Hybrid Map of the Human Genome," *Hum Mol Genet* 5:339-346) localized BIVM on chromosome 13q32-33 (data not shown). Examination of the publicly available Human Genome Project database revealed the exon-intron structure of BIVM. A 5' truncated BIVM sequence (hypothetical protein FLJ20159) was initially placed on the publicly available human genome map at 13q14-q21. The 5' untranslated region of BIVM consists of two separate exons (designated exons A and B), followed by the coding region consisting of nine exons; the exon/intron boundaries are indicated in Table I.

Inspection of genomic sequence localizes BIVM between ERCC5 and "hypothetical protein" MGC5302, a human ortholog of the gene encoding the mouse protein Kdel1/EP58 (Kimata, Y., et al. [2000] "Identification of a Novel Mammalian Endoplasmicreticulum-Resident KDEL Protein Using an EST Database Motif Search," *Gene* 261:321-327). A CpG island is located in the 5' untranslated region of BIVM; the 3' untranslated region contains an Alu sequence (FIGS. 1 and 2). The Alu polyA sequence in the 3' untranslated region leads to the spurious production of 3' truncated cDNAs including many that are represented as ESTs.

Multiple 5' untranslated region splice variants were observed in analysis of 5' RACE products. Specifically, exon A has at least 3 splice donor sequences and exon B, which has a poor splice acceptor sequence, can be absent from the mature transcript (FIGS. 1 and 2; Table I). In addition, it is likely that multiple transcriptional start sites are present (FIG. 1).

EXAMPLE 3

BIVM is Highly Conserved within Deuterostome Species

BIVM orthologs were identified in: mouse, chicken, *Xenopus* and zebrafish in order to address its potential phylogenetic conservation, as well as to define conserved motifs potentially relevant to function. In addition, a partial sequence for a BIVM ortholog was identified in sea urchin. The identity of the human BIVM protein to these orthologs ranges from 35-87% overall and is consistent with the phylogenetic relationships of the species considered (FIG. 3; see below). The C-terminal region of BIVM shares the highest degree of interspecific sequence identity. The N-terminus of this peptide domain is RK(V/C)LD (SEQ ID NO: 65) and the C-terminus is GGNLHC (SEQ ID NO: 60. This region includes all of the V domain motifs, and is 220 amino acids in human (indicated by arrowheads in FIG. 3).

The corresponding domains in mouse, chicken, *Xenopus*, zebrafish and sea urchin are 97%, 91%, 91%, 87% and 64% identical to the human domain, respectively. In addition, BIVM ESTs have been identified from an ascidian, sea squirt (*Halocynthia roretzi*) (e.g., GenBank AV385966), and a BIVM cDNA fragment has been isolated from a protochordate (cephalochordate), lancelet (*Branchiostoma floridae*), using an RT-PCR strategy (Yoder and Litman, GenBank AF411393). Their sequences within this domain are highly conserved.

EXAMPLE 4

Close Physical Linkage of BIVM and EP58/MGC5302

Human BIVM maps between EP58/MGC5302 and ERCC5 on 13q. The human EP58 EST (that extends most 5'), places the transcriptional start sites of EP58 and BIVM only 41 bp apart. We identified a mouse BIVM genomic clone (from a ë FixII library), which also encodes the 5' end of Ep58/Kdel1 (FIG. 4). The mapping position of Ep58/Kdel1 and BIVM in mouse has not yet been determined. The tight physical linkage of the EP58 to BIVM (41 bp in human and 224 bp in mouse) is consistent with a shared regulatory control system that functions in opposite directions (FIG. 4). Notably, both Ep58 and BIVM appear to be ubiquitously expressed (FIG. 5) (Kimata, Y., et al. [2000] "Identification of a Novel Mammalian Endoplasmicreticulum-Resident KDEL Protein Using an EST Database Motif Search," *Gene* 261: 321-327). Finally, zebrafish BIVM has been mapped to linkage group 6 (LG6); however, its linkage relationship to kdel1 is unknown.

EXAMPLE 5

Expression of Human BIVM

Figure 5A:
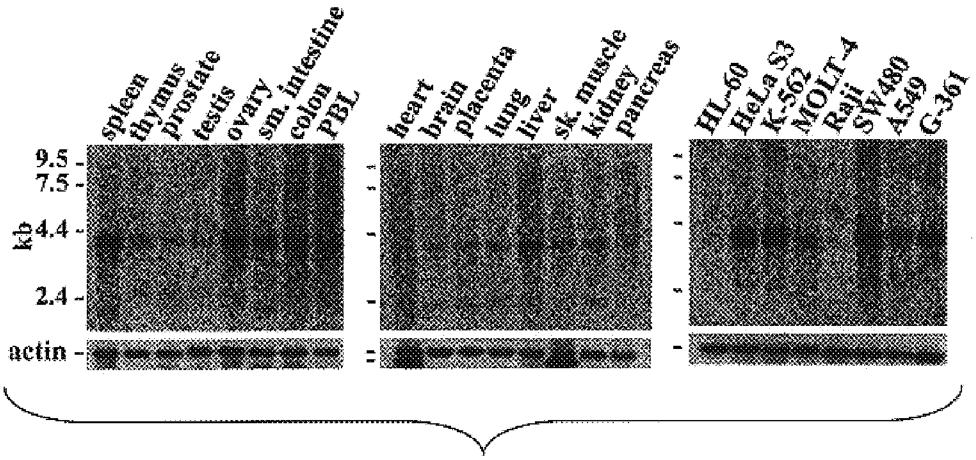

The human BIVM transcript is ~3.8 kb and appears to be expressed ubiquitously; the highest relative levels of expression are in spleen, ovary, small intestine, colon, peripheral leukocytes and liver (FIG. 5A). Additional RNA dot blot analyses indicate expression of BIVM in human testes, ovary, aorta, appendix, trachea, pituitary gland, bladder, uterus, spinal cord, salivary gland, stomach, mammary gland and bone marrow as well as in several fetal tissues (data not shown). Notably, BIVM expression was not detected in fetal spleen, adult thymus and certain cancer cell lines (e.g., promyelocytic leukemia, HL-60, and Burkitt's lymphoma Raji) while significant expression was evident in other lines (e.g., HeLa, S3, and colorectal adenocarcinoma, SW480).

EXAMPLE 6

Expression of BIVM in Other Species

Figure 5B:
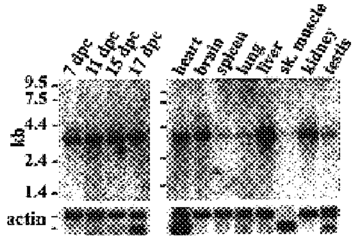

The predominant mouse BIVM transcript also is ~3.8 kb (FIG. 5B), of which ~3.3 kb have been sequenced. Comparisons of 5' mouse BIVM RACE products indicate that the 5' untranslated region undergoes alternative RNA splicing, which, like in the human gene, does not affect the coding sequences. The highest levels of expression of mouse BIVM are in heart, brain, liver and kidney (FIG. 5B).

Figure 5C:
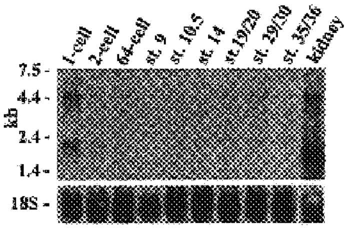
Figure 5D:
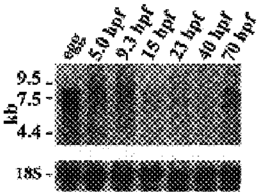

A major difference between the expression of human and mouse BIVM is observed in the spleen, in which expression is high in the human but appears to be minimal in the mouse. In the developing mouse embryo, BIVM expression is detected at a uniform level after gastrulation (FIG. 5B). An ~2.1 kb XBIVM cDNA was identified in *Xenopus* that is consistent with the length of the predominant transcript observed in RNA blotting (FIG. 5C). The broad, diffuse nature of the principal hybridizing band could reflect sequence heterogeneity. The nature of the larger transcript (~4.4 kb) is unknown. Northern blot analysis of sea urchin RNA detects two SpBIVM transcripts of ~7.4 and 8 kb (FIG. 5D), which are notably longer than the human and mouse forms. The additional sequence in these transcripts might be a result of additional 5' or 3' untranslated regions and/or could reflect polyadenylation effects. Extended 3' untranslated regions are encountered frequently with sea urchin mRNA.

Figure 5F:
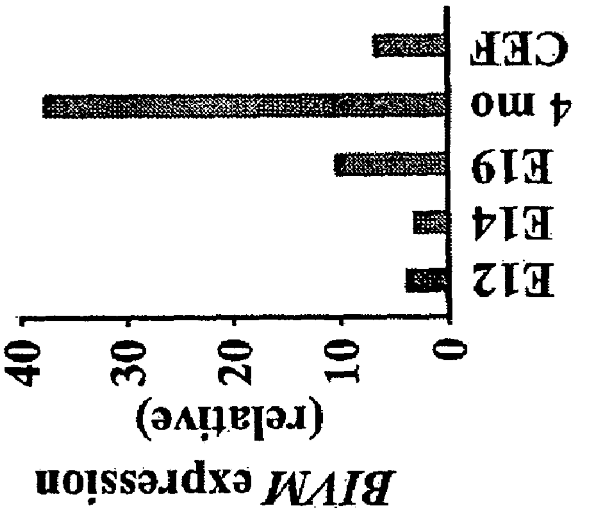
Figure 5E:
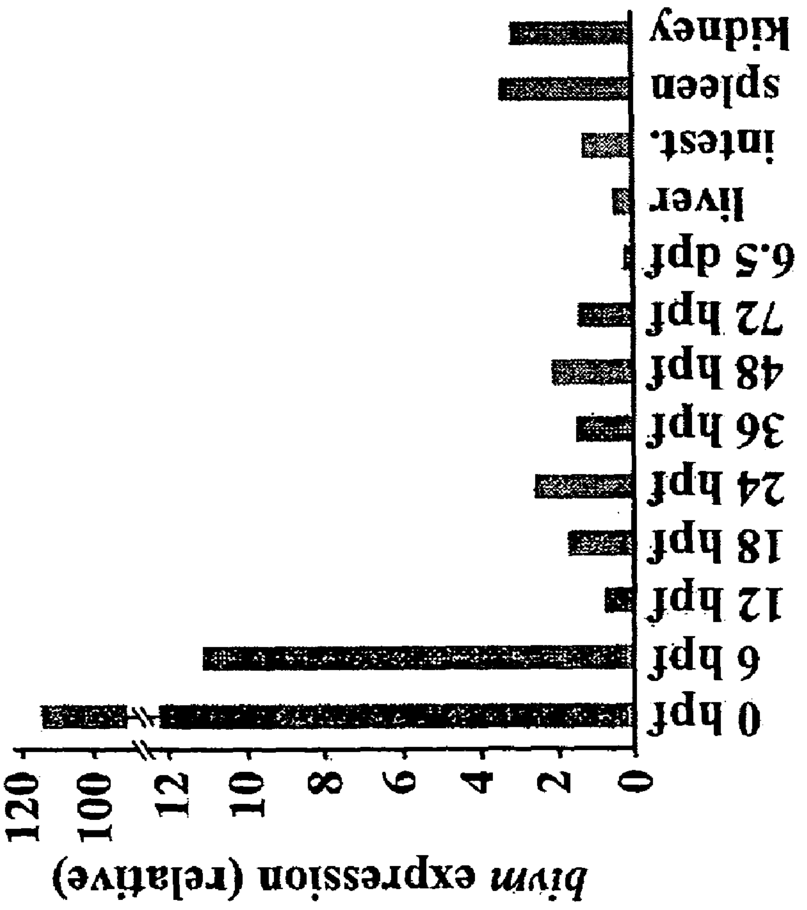

Real-time PCR was used to analyze BIVM expression levels throughout development in zebrafish (FIG. 5E). As observed in *Xenopus* and sea urchin, there is a large maternal store of BIVM transcript in the 1-cell embryo (0 hpf in zebrafish) which appears to be quickly lost after the initial cellular division(s). In zebrafish, the level of BIVM expression drops by ~90% within the first 6 hours of life (midgastrula stage) and is comparatively undetectable by 12 hpf (post-gastrula stage). Although comparable stages of development were not examined in mouse (see above), it is likely that this early embryonic regulation of BIVM expression will be conserved.

We noted BIVM expression in chicken bursa, which serves as the primary site of B lymphocyte differentiation. BIVM expression in chicken bursa decreases slightly between embryonic day 12 and day 14, increases significantly at day 19, and is the highest in the 4 month old chicken bursa, in which levels are 6-fold greater than observed in embryonic fibroblasts (CEFs; FIG. 5F). Expression of BIVM in other tissues in chicken has not been characterized.

EXAMPLE 7

BIVM Encodes a Nuclear/Cytoplasmic Protein

Figure 6A:
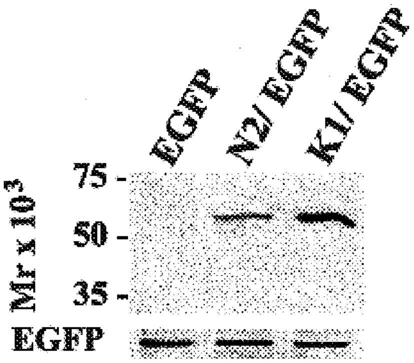
Figure 6B:
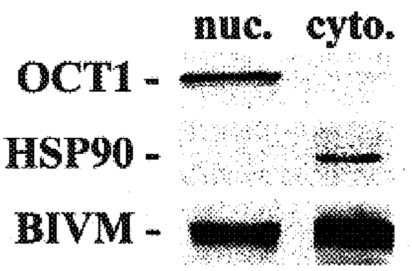
Figure 6C:
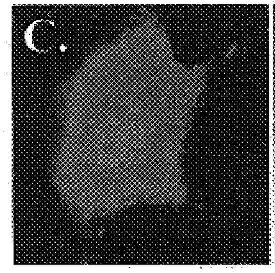
Figure 6D:
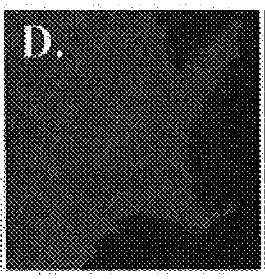
Figure 6E:
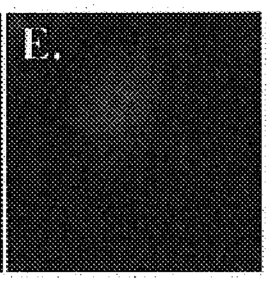
Figure 6F:
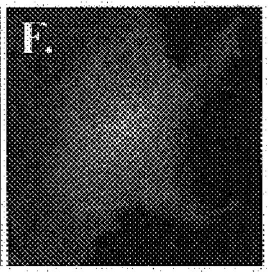
Figure 6G:
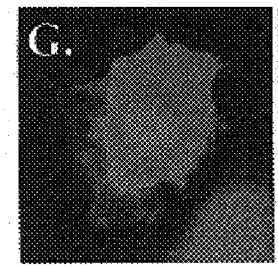
Figure 6H:
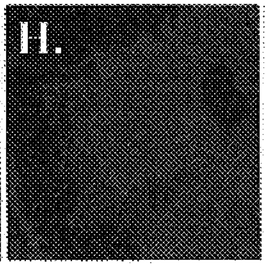
Figure 6I:
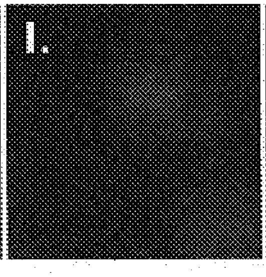
Figure 6J:
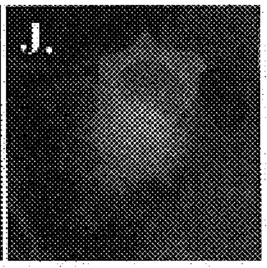

The relatively high predicted pI of BIVM (9.1) suggests that it may bind other proteins and/or DNA (or other nucleic acids). The levels of BIVM produced from the native pBIVM-N2 construct and modified pBIVM-K1 construct (see Methods) were compared in whole cells lysates from transiently transfected Cos7 cells. BIVM levels are higher in cells transfected with the modified pBIVM-K1 (FIG. 6A), which was used in all subsequent transfection experiments. It should be noted that the size of this recombinant protein (with C-terminal epitope tags) is ~61 KDa, whereas the native protein (without post-translational modifications) is predicted to be ~57 kDa. The observation that a single protein is generated from this transcript argues that translation does not begin at a more 3' ATG as suggested by the "hypothetical protein" FLJ20159 GenBank entries (which are predicted to encode a ~27 kDa protein). Western analysis using antibodies that recognize the V5 peptide sequence indicate that the epitope-tagged BIVM is present both in cytoplasmic and nuclear fractions (FIG. 6B). These results were confirmed by direct immunohistochemical localization of BIVM in the cytoplasm and nucleus (FIG. 6C-J). Variation in the relative amounts of BIVM in the nucleus was observed in individual cells. Thus, it is possible that the BIVM protein enters and exits the nucleus in a regulated or cell-cycle-dependent manner.

EXAMPLE 8

*Giardia* May Have Acquired a BIVM Ortholog by Horizontal Gene Transfer

Figure 7C:
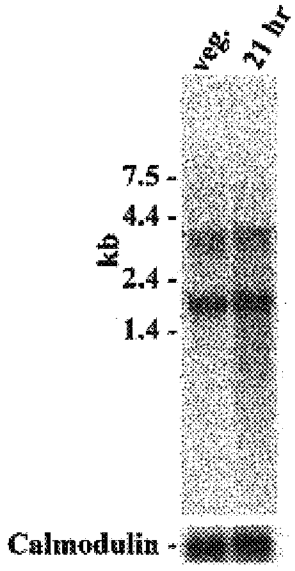

A tBLASTn search identified a BIVM-like gene (named BIVML) in the genome of the primitive protozoan parasite, *Giardia lamblia* (McArthur, A. G., et al. [2000] "The *Giardia* Genome Project Database," *FEMSMicrobiol Lett* 189:271-273). The 2045 nucleotide BIVML cDNA is predicted to encode a 270 amino acid protein (predicted MW ~30 kDa; Pi=7.56) with no predicted signal peptide, membrane spanning regions or nuclear localization signal; thus, it is likely to be cytosolic. BIVML contains 17 cysteine residues (6.2%) throughout the protein (FIG. 7A). Known giardial proteins that are secreted to the trophozite surface or the cyst wall are also highly cysteine rich. This sequence is 22-25% identical and 46-49% similar to the carboxyl-terminal region of all deuterostome BIVM peptides described here, correlates directly with the conserved domain described above, and includes the M2 and M3b motifs (FIG. 7B). Northern analysis detects an ~2.0 kb BIVML transcript as well as a larger transcript of unknown identity in both vegetatively growing and encysting cells (FIG. 7C).

BIVML is unusual in having long untranslated regions consistent with the size of the transcript. The 5' and 3' untranslated regions were determined by RACE and are 229 nucleotides and 983 nucleotides, respectively (FIG. 7A). most transcripts of giardial chromosomal genes characterized to date have very short (<20 nucleotides) untranslated regions, although exceptions are being noted.

The identification of a BIVM ortholog in such an early branching eukaryote was unexpected since tBLASTn searches of the currently available *S. cerevisiae* and *Drosophila* as well as *S. pombe* and *C. elegans* genome databases failed to identify any sequences exhibiting significant identity to BIVM. Furthermore, it has not been possible to identify BIVM-like sequences in the complete genomes of *Campylobacter jejuni* (Parkhill, J., et al. [2000] "Complete DNA Sequence of a Serogroup A Strain of *Neisseria Meningitidis* Z2491," *Nature* 404:502-506), *Mycobacterium leprae* (Cole, S. T., et al. [2001] "Massive Gene Decay in the Leprosy *Bacillus*," Nature 409:1007-11), *Mycobacterium tuberculosis* (Cole, S. T., et al. [1998] "Deciphering the Biology of *Mycobacterium Tuberculosis* from the Complete Genome Sequence," *Nature* 393:537-544), or *Neisseria menigitidis* (Parkhill, J., et al. [2000] "The Genome Sequence of the Food-Borne Pathogen *Campylobacter Jejuni* Reveals Hypervariable Sequences," *Nature* 403:665-668). In DNA hybridization studies, a *Giardia* BIVML probe failed to cross-hybridize to *Trichomonas foetus, Trichomonas vaginalis* or *Entamoeba histolytica* genomic DNA (data not shown).

The identification of a BIVM-like gene in the *Giardia* genome, but not in other similar proteostome genomes, taken together with the fact that *Giardia* is parasitic, suggests that BIVML may have been acquired via horizontal gene transfer from a higher eukaryotic host.

EXAMPLE 9

Physical Linkage of Human and Mouse BIVM to the EP58/MGC5302-EP58/Kdel1 Gene

The transcriptional start site of the human EP58/MGC5302 sequence (GenBank XM_015844) is only 41 bp from that of BIVM; BIVM and EP58 genes are in a head-to-head orientation, in opposite transcriptional orientation. The mouse EP58/Kdel1 and BIVM genes share the same physical orientation separated by 224 bp. This exceedingly tight physical linkage and close spacing of BIVM and EP58 suggests that common regulatory elements located in or near the intergenic region potentially control the expression of both genes. RT-PCR analysis of extracts from BIVM expressing and non-expressing human cell lines indicated that EP58/MGC5302 was expressed in all cell lines that express BIVM but not in the BIVM non-expressing cell line, Raji (FIG. 8). Based on these results, it is possible that these genes are co-regulated and that the transacting factors associated with the 41 bp intergenic region linking these genes control their expression.

EXAMPLE 10

DNA Binding Activity on the BIVM-EP58/MGC5302 41 bp Intergenic Region

A MatInspector V2.2 search for potential binding sites contained in the 41 bp region separating the BIVM and EP58/MGC5302 genes revealed sites for cell type specific factors such as the myeloid zinc finger-1 (MZF-1), the hematopoietic-expressed Ikaros-2 (IK2) factor, and the ubiquitously expressed transcription factors NF1, USF, NFκB, and NMYC (FIG. 9). Nearly identical sites also were predicted for the mouse 224 bp Bivm-Kdel1 intergenic region. MZF-1 and IK2 are expressed in the K562 human erythroleukemia cell line and IK2 is expressed in the Raji Burkitt's lymphoma cell line. Based on this information, electrophoretic mobility shift assays (EMSAs) were performed to compare protein binding to the 41 bp region in nuclear extracts from BIVM expressing and non-expressing cells (FIG. 10).

MZF-1 and IK2-specific binding would be expected to produce unique bands in the K562 and Raji nuclear extracts that are not observed in nuclear extracts from non-lymphoid cell lines. In addition, an NFκB consensus sequence was used as probe and competitor (Santa Cruz Biotechnology) to detect bands representing NFκB-specific binding that may be constitutively present in the nuclear extracts (FIG. 10). Significant DNA binding activity was observed with the 41 bp BIVM-specific probe in all extracts assayed, producing 1 minor band and two major bands (FIG. 10; Lanes 4-10), one of which was competed by the addition of cold NFκB-specific probe, indicating that NFκB complexes may be present (FIG.

10; Lane 3). One major band was detected with the NFκB consensus probe in the nuclear extracts from BIVM expressing lines (FIG. 10; Lanes 13-17) that was competed by the BIVM-specific probe (FIG. 10; Lane 11). An additional complex also was observed bound to the NFκB-specific probe in the extracts from a BIVM non-expressing line (FIG. 10; Lane 18). Together these results show that the 41 bp BIVM-EP58/MGC5302 intergenic region supports DNA binding activity and that the bound complexes include factors that also bind the NFκB consensus probe. Similar DNA binding activity was observed in the BIVM non-expressing Raji cell line as in the BIVM expressing cells and may result from constitutive nuclear NFκB factors and suggests either that additional flanking regions function in BIVM gene regulation or that protein co-factors or other mechanisms, such as methylation-dependent promoter silencing, could play a role in BIVM expression. The presence of a CpG island 5' of the BIVM gene, together with the lack of both BIVM and EP58/MGC5302 expression in the Raji cell lines, supports the latter hypothesis.

EXAMPLE 11

Regulation of BIVM Expression by TNF-A or Other Inducing Agents

As described above, the 41 bp intergenic region contains putative sites for ubiquitous transacting factors and an NFκB site that appears to be bound by NFκB complexes containing c-Rel and RelB factors, which are constitutively present in the nuclear extracts from the BIVM expressing K562 cell line (FIG. 11). NFκB comprises a large family of transcription factors, most of which are sequestered in the cytoplasm through inhibitor binding. Activation of the cell by various agents, such as the proinflammatory cytokine TNF-α, leads to phosphorylation-induced degradation of the inhibitor and nuclear translocation of additional NFκB transacting factors. Although constitutive factors may drive basal BIVM expression, TNF-α activated NFκB increases the expression of BIVM in the BIVM-expressing HeLa cell line (DNS). Furthermore, a cell line devoid of basal BIVM expression, the Raji Burkitt's lymphoma line, is induced to express BIVM by TNF-α (FIG. 12). The specific TNF-α activated factors associated with the BIVM promoter can be defined using antibody shift assays.

EXAMPLE 12

Characteristics of Recombinant BIVM Protein

The BIVM encoded protein has a high proportion of lysine and arginine residues and a predicted isoelectric point (pI) of 9.1. The net positive charge under physiological conditions suggests that BIVM may interact with other proteins and/or DNA. Western blot analysis and cytoimmunofluorescence studies utilizing transfected, epitope-tagged BIVM expression constructs revealed that BIVM is present in both cytoplasmic and nuclear fractions. Variation in the relative amounts of nuclear recombinant BIVM was observed in individual cells and may reflect regulated or cell cycle-dependent BIVM nuclear import/export. The Cos7 cells that have been transformed stably with BIVM exhibit a decreased cell doubling time compared to untransformed Cos7 cells, suggesting the potential role for BIVM in cell cycle regulation. Furthermore, preliminary studies of Cos7 BIVM stable transformants stained with a nuclear stain (DAPI) reveal a high proportion of cells containing multiple nuclei compared to untransformed cells. Flow cytometer analyses of these cells stained with propidium iodide indicate that ~90% of the cells contain tetraploid or greater DNA content, consistent with the presence of multiple nuclei (FIG. 13; Panel 3). This phenomenon was not observed in a G418-resistant, BIVM-revertant cell line, which has lost expression of recombinant BIVM and exhibits both a nuclear morphology and a diploid DNA content similar to that of the untransformed parental line (FIG. 13; Panels 1 & 2).

EXAMPLE 13

Identification of BIVM Protein Binding Partners

The high proportion of lysine and arginine residues and the net charge of the protein (pI 9.1) suggest that BIVM may interact with proteins and/or DNA (or other nucleosides). Specifically, protein-protein interactions are being assayed using the BacterioMatch two hybrid system (Stratagene). This system provides a rapid, selective approach to identify BIVM-specific protein interactions in vivo. Mouse Bivm has been utilized initially as we can take advantage of mouse cDNA libraries that are commercially available for this system (Stratagene) and because the results obtained can be used to complement concurrent BIVM knock out mice studies now underway in our laboratory. Although it is possible that BIVM may function differently in human and mouse, the 87% sequence conservation between human and mouse BIVM protein, strong synteny in BIVM flanking genes, and the tight physical linkage observed between the BIVM and EP58 genes, is consistent with functional equivalence.

EXAMPLE 14

Materials and Methods

Example 14A

General Methods

RNA was isolated with RNAzol B (Teltest, Friendswood, Tex.) or Trizol (Gibco BRL, Rockville, Md.). Mouse genomic DNA (ë FixII) and liver cDNA (ë ZAPII) libraries were screened using standard procedures (Strong, S. J., et al. [1999] "A Novel Multigene Family Encodes Diversified Variable Regions," *Proc Natl Acad Sci USA* 96:15080-15085). DNA sequencing and the analysis of DNA sequences were carried out as described previously (Rast, J. P. et al. [1994] "T Cell Receptor Gene Homologs are Present in the Most Primitive Jawed Vertebrates," *Proc. Natl. Acad. Sci. USA* 91:9248-9252). Alignments were constructed using ClustalW 1.8. Identity relationships were examined using BLAST and ALIGN software. Rapid amplification of cDNA ends (RACE) utilized a standard protocol (Mertineit, C., et al. [1998] "Sex-Specific Exons Control DNA Methyltransferase in Mammalian Germ Cells," *Development* 125:889-897) or the GeneRacer kit (Invitrogen, Carlsbad, Calif.). The RNA sources for RACE were: human HeLa cells, mouse liver, chicken bursa, *Xenopus laevis* liver, zebrafish (*Danio rerio*) liver, 15 hpf sea urchin (*Strongylocentotus purpuratus*) embryos, and vegetative-stage *Giardia lamblia*.

Example 14B

Genomic Mapping

Human BIVM was mapped using HSMAP5 (CCATGCCTCTCTACTACTCACTCCCAACAC) (SEQ ID NO: 51)

and HSMAP6 (GGTAAGAAGAACACCATTGT-GTTTGAAGGC) (SEQ ID NO: 52) intronic primers (which correspond to sequence between exon 8 and 9) and the GeneBridge 4 radiation hybrid (RH) panel (Gyapay, G., et al. [1996] "A Radiation Hybrid Map of the Human Genome," *Hum Mol Genet* 5:339-346) (Research Genetics, Huntsville, Ala.). Zebrafish BIVM (see below) was mapped using the zfBIVMMAPF1 (CAATGCCTAACACTGTGGAAAGT-GAAGGCG) (SEQ ID NO: 53) and zfBIVMMAPR1 (GATAACTGTCGAGCTCGGTTGAGCAGGGC) (SEQ ID NO: 54) primers and the T51 RH panel (Glusman, G., et al. [1996] "Sequence Analysis in the Olfactory Receptor Gene Cluster on Human Chromosome 17: Recombinatorial Events Affecting Receptor Diversity," *Genomics* 37:147-160) (Research Genetics). Additional gene mapping data were derived from the Human-Mouse Homology Map and the Mouse Genome Informatics Database (Blake, J. A., et al. and Mouse Genome Database Group [2001] "The Mouse Genome Database (MGD): Integration Nexus for the Laboratory Mouse," *Nucleic Acids Res* 29:91-94).

Example 14C

Identification of BIVM Orthologs

Mouse BIVM Partial sequence of the mouse BIVM gene was obtained by screening a mouse genomic library with a human BIVM cDNA probe. A mouse BIVM cDNA was recovered by screening a liver cDNA library with a probe corresponding to mouse exon 6.

Chicken BIVM tBLASTn searches using the human BIVM sequence identified a chicken (*Gallus gallus*) bursal EST (GenBank AJ399198) encoding an avian ortholog (BIVM). RACE strategies identified a complete open reading frame cDNA. A single RNA-splicing variant, which encodes an additional 23 amino acids, also has been sequenced (GenBank AF411388; data not shown).

*Xenopus* XBIVM Partial *Xenopus laevis* XBIVM sequence was identified as an oocyte EST (GenBank BF047666) using tBLASTn searches with the human BIVM sequence. RACE strategies resolved a complete open reading frame cDNA.

Zebrafish BIVM Touchdown PCR (Don, R. H., et al. [1991] "'Touchdown' PCR to Circumvent Spurious Priming During Gene Amplification," *Nucleic Acids Res* 19:4008) and nested degenerate primers, designed with CODE-HOP software (Rose, T. M., et al. [1998] "Consensus-Degenerate Hybrid Oligonucleotide Primers for Amplification of Distantly Related Sequences," *Nucleic Acids Res* 26:1628-35), were used to amplify BIVM cDNA fragments from zebrafish liver. Primers for the primary PCR were designed to amplify the coding sequence between the amino acid motifs GNTTLMWRF and YFCPIGFEA; primers for the nested PCR were designed to amplify the sequence between motifs WFRQINDHF and YRHQNHYFCP. PCR products of the expected size were gel purified, cloned and sequenced. Full-length clones were derived by RACE.

Sea urchin SpBIVM A fragment of the sea urchin SpBIVM cDNA was recovered from 20 hpf embryo cDNA using nested PCR as described for zebrafish. RACE strategies identified a 1,899 nucleotide coding region that corresponds to the complete open reading frame of BIVM from other species; as of yet it has not been possible to identify a stop codon.

*Giardia lamblia* BIVM-like The *Giardia lamblia* BIVML sequence was initially identified with a tBLASTn search of the High Throughput Genomic (HTGS) database with the human BIVM sequence. BIVML is encoded in four overlapping genomic clones (clone KJ1556, GenBank #AC049185; clone MJ4898, GenBank AC083097; clone EJ2770, GenBank #AC038625; and clone KI0613, GenBank #AC046875). RACE was used to identify the complete, 2,045 nucleotide cDNA.

Example 14D

Transient Transfections

The coding region of human BIVM was cloned into pcDNA3.1/V5-His TOPO (Invitrogen) in order to generate pBIVM-N2, which encodes a BIVM-V5 fusion protein (the V5 epitope is at the C terminus). A similar construct, pBIVM-K1, was generated in which the translational start sequence was modified in order to increase protein synthesis, as described in Kozak, M. [1996], "Interpreting cDNA Sequences: Some Insights from Studies on Translation," *Mamm. Genome* 7:563-574. Both of these constructs were then subcloned into pIRES2-EGFP (Clontech, Palo Alto, Calif.) to create pBIVM-N2/EGFP and pBIVM-K1/EGFP, which produced recombinant BIVM and EGFP from the same plasmid. Cos7 cells (~60% confluent) were transiently transfected with expression constructs using the GENEJAMMER™ transfection reagent according to manufacturer's instructions (Stratagene, La Jolla, Calif.).

Example 14E

Western Blots

Whole cell lysates were prepared from transfected cells in the presence of 1× Protease Inhibitor Cocktail Set III (Calbiochem, San Diego, Calif.) essentially as recommended by Santa Cruz Biotechnology. Nuclear and cytoplasmic extracts were prepared from transfected cells essentially as described in Yu, C. L., et al. [1995] "Enhanced DNA-Binding Activity of a Stat3-Related Protein in Cells Transformed by the Src Onco Protein," *Science* 269:81-83. Protein concentrations were determined using Protein Assay Reagent (Bio-Rad, Hercules, Calif.). Whole cell, nuclear, and cytoplasmic extracts were separated by SDS-polyacrylamide gel electrophoresis (10% polyacrylamide), transferred to Immobilon P filters (Millipore, Bedford, Mass.) and blocked prior to incubation with mouse anti-V5 monoclonal antibody (Invitrogen), anti-OCT1 polyclonal antibody (Santa Cruz) or anti-HSP90 monoclonal antibody (StressGen Biotechnologies Corp, Victoria, BC, Canada). Following incubation with alkaline phosphatase-conjugated secondary antibodies, reactive proteins were detected using Western Blue Stabilizer Substrate (Promega, Madison, Wis.).

Example 14F

Immunohistochemistry

Transfected Cos7 cells were fixed for 15 minutes with 3% paraformaldehyde, permeabilized in 1% Triton-X 100, incubated with primary antibodies, washed and incubated with secondary antibodies and 2 μg/ml Hoechst 33258. Primary antibodies included a mouse anti-V5 monoclonal antibody and an anti-actin polyclonal antibody (ICN Pharmaceuticals, Inc., Costa Mesa, Calif.) that were detected with a Cy2-conjugated, anti-mouse antibody (Jackson Immuno Research Laboratories, West Grove, Pa.) and a Cy3-conjugated, anti-rabbit antibody (Sigma, St. Louis, Mo.), respectively.

Example 14G

RNA Blots

Multiple Tissue Northern (MTN™) blots (human and mouse) were obtained from Clontech. In addition, 10 μg of *Xenopus*, sea urchin and *Giardia lamblia* total RNA were subjected to electrophoresis through 1.2% agarose, 2.2 M formaldehyde gels and transfer to nylon membranes (Zetaprobe™-GT; BioRad). RNA blots were hybridized with radiolabeled probes in Expresshyb™ (Clontech). The *Giardia* RNA blot was hybridized with single strand-specific probes as described in Knodler, L. A., et al. [1999] "Developmental Gene Regulation in *Giardia Lamblia*: First Evidence for an Encystation-Specific Promoter and Differential 5' mRNA Processing," *Mol Microbiol* 2:327-340. Blots were stripped and reprobed with actin, 18S rRNA or Calmodulin probes.

Example 14H

Quantitative PCR

Real time PCR analysis detected BIVM expression from chicken bursa and zebrafish embryos and tissues using a GeneAmp 5700 Sequence Detection System (PE Biosystems, Foster City, Calif.) with SYBR Green detection. Each PCR series was done in triplicate. The relative expression levels were determined for each transcript from plasmid standards that were included in each experiment and normalized to the expression of S17 rRNA (chicken bursa) or S26 rRNA (zebrafish) levels.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An isolated polynucleotide comprising SEQ ID NO: 14 or a polynucleotide sequence fully complementary thereto.

2. The isolated polynucleotide according to claim 1, further comprising a promoter operably linked to said polynucleotide.

3. The isolated polynucleotide according to claim 1, further comprising a detectable label.

4. The isolated polynucleotide according to claim 1, further comprising a heterologous polynucleotide sequence encoding a heterologous polypeptide sequence.

5. A vector comprising SEQ ID NO: 14.

6. A transformed host cell comprising a polynucleotide sequence comprising SEQ ID NO: 14.

7. The transformed host cell according to claim 6, wherein said host cell is selected from the group consisting of Gram negative bacterial cells, Gram positive bacterial cells, yeast cells, animal cells, plant cells, and insect cells.

8. A method of producing a polypeptide comprising culturing a transformed host cell comprising SEQ ID NO: 14 under conditions that allow for the expression of the polypeptide.

9. The method according to claim 8, further comprising the step of isolating or recovering the polypeptide.

* * * * *